US012636374B2

(12) United States Patent
Anderson et al.

(10) Patent No.: US 12,636,374 B2
(45) Date of Patent: May 26, 2026

(54) IMMUNOGENIC COMPOSITIONS COMPRISING CONJUGATED CAPSULAR SACCHARIDE ANTIGENS AND USES THEREOF

(71) Applicant: Pfizer Inc., New York, NY (US)

(72) Inventors: Annaliesa Sybil Anderson, Upper Saddle River, NJ (US); Caitlyn Gallagher, Ringwood, NJ (US); Jianxin Gu, Paramus, NJ (US); Isis Kanevsky, New York, NY (US); Jin-Hwan Kim, Suffern, NY (US); Justin Keith Moran, West Nyack, NY (US); Suddham Singh, Monroe, NY (US); Naveen Surendran, Dumont, NJ (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 17/824,293

(22) Filed: May 25, 2022

(65) Prior Publication Data

US 2022/0387613 A1 Dec. 8, 2022

Related U.S. Application Data

(60) Provisional application No. 63/228,763, filed on Aug. 3, 2021, provisional application No. 63/194,641, filed on May 28, 2021.

(51) Int. Cl.
*A61K 47/64* (2017.01)
*A61K 39/00* (2006.01)
(Continued)

(52) U.S. Cl.
CPC ............ *A61K 47/64* (2017.08); *A61K 39/092* (2013.01); *A61K 47/6415* (2017.08);
(Continued)

(58) Field of Classification Search
CPC .................. A61K 47/64; A61K 47/646; A61K 2039/627; A61K 47/6415;
(Continued)

(56) References Cited

U.S. PATENT DOCUMENTS

| | | | |
|---|---|---|---|
| 4,709,017 | A | 11/1987 | Collier et al. |
| 4,950,740 | A | 8/1990 | Greenfield et al. |

(Continued)

FOREIGN PATENT DOCUMENTS

| | | |
|---|---|---|
| CA | 2004810 | 6/1990 |
| CN | 103495161 | 1/2014 |

(Continued)

OTHER PUBLICATIONS

Tiwari, V.K., Cu-Catalyzed Click Reaction in Carbohydrate Chemistry, Chemical Reviews (2016) 116(5), 3086-3240 (Year: 2016).*

(Continued)

*Primary Examiner* — Daniel E Kolker
*Assistant Examiner* — Amelia Nicole Dickens

(57) ABSTRACT

The present invention relates to new conjugated capsular saccharide antigens (glycoconjugates), immunogenic compositions comprising said glycoconjugates and uses thereof.

22 Claims, 8 Drawing Sheets

Specification includes a Sequence Listing.

(51) Int. Cl.
*A61K 39/09* (2006.01)
*A61P 31/04* (2006.01)

(52) U.S. Cl.
CPC ............ *A61K 47/646* (2017.08); *A61P 31/04* (2018.01); *A61K 2039/6031* (2013.01); *A61K 2039/6037* (2013.01); *A61K 2039/6068* (2013.01); *A61K 2039/627* (2013.01)

(58) Field of Classification Search
CPC .... A61K 2039/6031; A61K 2039/6037; A61K 2039/6038; A61K 39/092; A61P 31/04
See application file for complete search history.

(56) References Cited

U.S. PATENT DOCUMENTS

| | | | | |
|---|---|---|---|---|
| 5,614,382 | A | 3/1997 | Metcalf | |
| 5,843,711 | A | 12/1998 | Collier et al. | |
| 5,917,017 | A | 6/1999 | Collier et al. | |
| 6,194,388 | B1 | 2/2001 | Krieg et al. | |
| 6,207,646 | B1 | 3/2001 | Krieg et al. | |
| 6,214,806 | B1 | 4/2001 | Krieg et al. | |
| 6,218,371 | B1 | 4/2001 | Krieg et al. | |
| 6,239,116 | B1 | 5/2001 | Krieg et al. | |
| 6,339,068 | B1 | 1/2002 | Krieg et al. | |
| 6,455,673 | B1 | 9/2002 | Collier | |
| 8,753,645 | B2 * | 6/2014 | Biemans | A61K 39/092 424/197.11 |
| 2006/0228380 | A1 | 10/2006 | Hausdorff et al. | |
| 2006/0228381 | A1 | 10/2006 | Bahler et al. | |
| 2007/0025398 | A1 | 2/2007 | Yonge et al. | |
| 2007/0184071 | A1 | 8/2007 | Hausdorff et al. | |
| 2007/0184072 | A1 | 8/2007 | Hausdorff et al. | |
| 2007/0231340 | A1 | 10/2007 | Hausdorff et al. | |
| 2008/0102498 | A1 | 5/2008 | Bahler et al. | |
| 2008/0268468 | A1 * | 10/2008 | Wong | G01N 33/533 435/71.1 |
| 2015/0314007 | A1 * | 11/2015 | Satomaa | C07K 9/001 435/375 |
| 2016/0346374 | A1 | 12/2016 | Seeberger et al. | |
| 2020/0054739 | A1 | 2/2020 | Fairman et al. | |
| 2020/0330579 | A1 * | 10/2020 | Forrest | A61K 47/26 |

FOREIGN PATENT DOCUMENTS

| | | | |
|---|---|---|---|
| EP | 0378881 | B1 | 6/1993 |
| EP | 0427347 | B1 | 2/1995 |
| EP | 0471177 | B1 | 10/1995 |
| EP | 0594610 | B1 | 9/1998 |
| EP | 0735898 | B1 | 3/1999 |
| EP | 0761231 | B1 | 1/2000 |
| EP | 0689454 | B1 | 2/2005 |
| WO | 91/01146 | A1 | 2/1991 |
| WO | 93/17712 | A2 | 9/1993 |
| WO | 94/03208 | A1 | 2/1994 |
| WO | 96/02555 | A1 | 2/1996 |
| WO | 97/01640 | A2 | 1/1997 |
| WO | 97/26008 | A1 | 7/1997 |
| WO | 98/18810 | A1 | 5/1998 |
| WO | 98/57659 | A1 | 12/1998 |
| WO | 98/58668 | A2 | 12/1998 |
| WO | 99/11241 | A1 | 3/1999 |
| WO | 99/52549 | A1 | 10/1999 |
| WO | 00/07621 | A2 | 2/2000 |
| WO | 00/23105 | A2 | 4/2000 |
| WO | 00/34487 | A1 | 6/2000 |
| WO | 00/37105 | A2 | 6/2000 |
| WO | 00/39299 | A2 | 7/2000 |
| WO | 00/56358 | A2 | 9/2000 |
| WO | 00/61761 | A2 | 10/2000 |
| WO | 00/62800 | A2 | 10/2000 |
| WO | 01/21152 | A1 | 3/2001 |
| WO | 01/21207 | A2 | 3/2001 |
| WO | 01/72337 | A1 | 10/2001 |
| WO | 01/98334 | A2 | 12/2001 |
| WO | 02/091998 | A2 | 11/2002 |
| WO | 03/024480 | A2 | 3/2003 |
| WO | 03/054007 | A2 | 7/2003 |
| WO | 2004/081515 | A2 | 9/2004 |
| WO | 2004/083251 | A2 | 9/2004 |
| WO | 2006/032499 | A1 | 3/2006 |
| WO | 2007/026190 | A2 | 3/2007 |
| WO | 2008/118752 | A2 | 10/2008 |
| WO | 2009/000826 | A1 | 12/2008 |
| WO | 2010/125480 | A1 | 11/2010 |
| WO | 2014/027302 | A1 | 2/2014 |
| WO | 2014/111344 | A1 | 7/2014 |
| WO | 2015/121783 | A1 | 8/2015 |
| WO | 2017/178664 | A1 | 10/2017 |

OTHER PUBLICATIONS

Anderson et al, "Immunization of 2-month-old infants with protein-coupled oligosaccharides derived from the capsule of Haemophilus influenzae type b", The Journal of Pediatrics 107(3):346-351 (1985).

Baraldo et al, "N19 Polyepitope as a Carrier for Enhanced Immunogenicity and Protective Efficacy of Meningococcal Conjugate Vaccines", Infection and Immunity 72(8):4884-4887 (2004).

Brown et al, "Structure of the *Streptococcal* cell wall C5a peptidase", PNAS 102(51):18391-18396 (2005).

Crooke and Bennett, "Progress in Antisense Oligonucleotide Therapeutics", Annu. Rev. Pharmacol. Toxicol. 36:107-129 (1996).

Douglas and Collier, "Exotoxin A of *Pseudomonas aeruginosa*: Substitution of Glutamic Acid 553 with Aspartic Acid Drastically Reduces Toxicity and Enzymatic Activity", Journal of Bacteriology 169(11):4968-4971 (1987).

Falugi et al., "Rationally designed strings of promiscuous CD4+ T cell epitopes provide help to Haemophilus Influenzae type b oligosaccharide: a model for new conjugate vaccines", Eur. J. Immunol. 31:3816-3824 (2001).

Gatchalian et al, "A Randomized, Placebo-Controlled Study to Evaluate the Immunogenicity of an 11-Valent Pneumococcal Protein D Conjugate Vaccine Administered as Primary Vaccination to Infants at 6, 10 and 14 Weeks of Age", 17th Annual Meeting of the Eur. Soc. Paed. Inf. Dis. (ESPID); Poster No. 4; PIA Poster Session 1; Istanbul, Turkey; Mar. 27, 2001.

Geno et al, "Pneumococcal Capsules and Their Types: Past, Present, and Future", Clinical Microbiology Reviews 28(3):871-899 (2015).

Goebel, "Studies on Antibacterial Immunity Induced by Artificial Antigens—I. Immunity to Experimental Pneumococcal Infection with an Antigen Containing Cellobiuronic Acid", Journal of Experimental Medicine 69(3):353-364 (1939).

Hu et al, "Approach to Validating and Opsonophagocytic Assay for *Streptococcus pneumoniae*", Clinical and Diagnostic Laboratory Immunology 12(2):287-295 (2005).

Hunziker and Leumann, "Nucleic Acid Analogues: Synthesis and Properties", Mod. Synth. Methods 7:331-417 (1995).

Insel and Anderson, "Oligosaccharide-Protein Conjugate Vaccines Induce and Prime for Oligoclonal IgG Antibody Responses to the Haemophilus influenzae b Capsular Polysaccharide in Human Infants", J. Exp. Med. 163:262-269 (1986).

Kuo et al, "Characterization of a Recombinant Pneumolysin and Its Use as a Protein Carrier for Pneumococcal Type 18C Conjugate Vaccines", Infection and Immunity 63(7):2706-2713 (1995).

Nurkka et al, "Immunogenicity and Safety of the Eleven Valent Pneumococcal Polysaccharide-Protein D Conjugate Vaccine in Infants", Pediatr Infect Dis J 23:1008-1014 (2004).

Prymula et al, "Pneumococcal capsular polysaccharides conjugated to protein D for prevention of acute otitis media caused by both *Streptococcus pneumoniae* and non-typable Haemophilus influenzae: a randomised double-blind efficacy study", Lancet 367:740-748 (2006).

Schneerson et al, "Serum Antibody Responses of Juvenile and Infant Rhesus Monkeys Injected with Haemophilus Influenzae Type b and Pneumococcus Type 6A Capsular Polysaccharide-Protein Conjugates", Infection and Immunity 45(3):582-591 (1984).

(56) References Cited

OTHER PUBLICATIONS

Uchida et al, "Mutation in the Structural Gene for Diphtheria Toxin carried by Temperate Phage β", Nature New Biology 233:8-11 (1971).
Uchida et al, "Diphtheria Toxin and Related Proteins—I. Isolation and Properties of Mutant Proteins Serologically Related to Diphtheria Toxin", The Journal of Biological Chemistry 248(11):3838-3844 (1973).
Uhlmann and Peyman, "Antisense Oligonucleotides: A New Therapeutic Principle", Chemical Reviews 90(4):543-584 (1990).
Miller et al, "Synthesis of Neoglycopeptides via Click Chemistry", International Journal of Peptide Research and Therapeutics 16(3):125-132 (2010).
PCT International Search Report and Written Opinion for International Application No. PCT/IB2022/054914 mailed on Feb. 9, 2023.
Stefanetti et al, "Click chemistry compared to thiol chemistry for the synthesis of site-selective glycoconjugate vaccines using CRM197 as carrier protein", Glycoconjugate Journal 37(5):611-622 (2020).
Macccalman, T., et al., "Glycoconjugate vaccines: some observations on carrier and production methods.", Biotechnology and Genetic Engineering Reviews, 2019, 35(2):93-125.
Núñez-Villanueva, D., et al., "Cap control: cyclic versus linear oligomerisation in covalent template-directed synthesis." RSC Advances, 2019, 9(51):29566-29569.
Pergolizzi, G., et al., "Contemporary glycoconjugation chemistry.", Carbohydr. Chem., 2017, 42:1-46.
Hu, Q-Y., et al., Towards the next generation of biomedicines by site selective conjugation, Chem. Soc. Rev., 2016, 45, 1691.
Richichi, B., et al., Conjugation Techniques and Linker Strategies for Carbohydrate-Based Vaccines, Editor(s): Joseph J. Barchi, Comprehensive Glycoscience (Second Edition), Elsevier, 2021, pp. 676-705.
Hein, C.D., et al., Click Chemistry, a Powerful Tool for Pharmaceutical Sciences, Pharm Res. 25(10): 2216-2230 (2008).
Peeters, J.M., et al., Comparison of four bifunctional reagents for coupling peptides to proteins and the effect of the three moieties on the immunogenicity of the conjugates, J. Immunol. Meths. 120:133-143 (1989).
Bartoloni, A., et al., Immunogenicity of meningococcal B polysaccharide conjugated to tetanus toxoid or CRM197 via adipic acid dihydrazide, Vaccine 13(5):463-470 (1995).
Agrahari, A.K., et al., Cu(I)-Catalyzed Click Chemistry in Glycoscience and Their Diverse Applications, Chemical Reviews (2021) 121(13), 7638-7956.
Tiwari, V.K., Cu-Catalyzed Click Reaction in Carbohydrate Chemistry, Chemical Reviews (2016) 116(5), 3086-3240.
Wu, D, et al., Development of pneumococcal polysaccharide conjugate vaccine with long spacer arm, Vaccine 31 (2013) 5623-5626.
Wan, Q, et al., A Potentially Valuable Advance in the Synthesis of Carbohydrate-Based Anticancer Vaccines through Extended Cycloaddition Chemistry, J. Org. Chem. 2006, 71, 8244-8249.
Wan, Q, et al., A Potentially Valuable Advance in the Synthesis of Carbohydrate-Based Anticancer Vaccines through Extended Cycloaddition Chemistry, J. Org. Chem. 2006, 71, 8244-8249 (Supporting Information).
Krechikova O. I. et al., "Isolation, identification and antimicrobial susceptibility testing of *Streptococcus pneumoniae*", Clinical microbiology and antimicrobial chemotherapy, 2000, v. 2, No. 1, pp. 88-98 (Russian with English.
Buskas, T., et al., "The Immunogenicity of the Tumor-Associated Antigen Lewis May Be Suppressed by a Bifunctional Cross-Linker Required for Coupling to a Carrier Protein", Chem. Eur. Journal, 2004, 10:3517-3524.
Costantino, P., et al., "The design of semi-synthetic and synthetic glycoconjugate vaccines", Expert Opinion on Drug Discovery, 2011, 6(10):1045-1066.
Cox, A.D., et al., "Investigating the candidacy of LPS-based glycoconjugates to prevent invasive meningococcal disease: immunology of glycoconjugates with high carbohydrate loading", Glycoconj Journal, 2010, 27:643-648.
Ju, T., et al., "The TN Antigen—Structural Simplicity and Biological Complexity", Angewandte Chemie International Edition, 2011, 50:1770-1791.
Lipinski, T., et al., "A structurally diversified linker enhances the immune response to a small carbohydrate hapten", Glycoconj Journal, 2011, 28:149-164.

* cited by examiner

[4)-β-D-Glc*p*-(1→3)-β-D-Glc*p*A-(1→]$_n$

SEQUENCE LISTING

```
<160> NUMBER OF SEQ ID NOS: 42

<210> SEQ ID NO 1
<211> LENGTH: 21
<212> TYPE: DNA
<213> ORGANISM: Artificial Sequence
<220> FEATURE:
<223> OTHER INFORMATION: "A class" CpG oligonucleotide

<400> SEQUENCE: 1

ggggacgacg tcgtgggggg g                                          21


<210> SEQ ID NO 2
<211> LENGTH: 21
<212> TYPE: DNA
<213> ORGANISM: Artificial Sequence
<220> FEATURE:
<223> OTHER INFORMATION: "A class" CpG oligonucleotide

<400> SEQUENCE: 2

ggggacgacg tcgtgggggg g                                          21


<210> SEQ ID NO 3
<211> LENGTH: 21
<212> TYPE: DNA
<213> ORGANISM: Artificial Sequence
<220> FEATURE:
<223> OTHER INFORMATION: "B class" CpG oligonucleotide
```

<400> SEQUENCE: 3
tcgtcgtttt tcggtgcttt t 21

<210> SEQ ID NO 4
<211> LENGTH: 21
<212> TYPE: DNA
<213> ORGANISM: Artificial Sequence
<220> FEATURE:
<223> OTHER INFORMATION: “B class” CpG oligonucleotide

<400> SEQUENCE: 4
tcgtcgtttt tcggtcgttt t 21

<210> SEQ ID NO 5
<211> LENGTH: 24
<212> TYPE: DNA
<213> ORGANISM: Artificial Sequence
<220> FEATURE:
<223> OTHER INFORMATION: “B class” CpG oligonucleotide

<400> SEQUENCE: 5
tcgtcgtttt gtcgttttgt cgtt 24

<210> SEQ ID NO 6
<211> LENGTH: 24
<212> TYPE: DNA
<213> ORGANISM: Artificial Sequence
<220> FEATURE:
<223> OTHER INFORMATION: “B class” CpG oligonucleotide

<400> SEQUENCE: 6
tcgtcgtttc gtcgttttgt cgtt 24

<210> SEQ ID NO 7
<211> LENGTH: 24
<212> TYPE: DNA
<213> ORGANISM: Artificial Sequence
<220> FEATURE:
<223> OTHER INFORMATION: “B class” CpG oligonucleotide

<400> SEQUENCE: 7
tcgtcgtttt gtcgtttttt tcga 24

<210> SEQ ID NO 8
<211> LENGTH: 21
<212> TYPE: DNA
<213> ORGANISM: Artificial Sequence
<220> FEATURE:
<223> OTHER INFORMATION: B-Class oligonucleotide

<400> SEQUENCE: 8
tcgtcgtttt tcggtgcttt t 21

<210> SEQ ID NO 9
<211> LENGTH: 21
<212> TYPE: DNA
<213> ORGANISM: Artificial Sequence
<220> FEATURE:
<223> OTHER INFORMATION: B-Class oligonucleotide

<400> SEQUENCE: 9
tcgtcgtttt tcggtcgttt t 21

<210> SEQ ID NO 10

-continued

<211> LENGTH: 24
<212> TYPE: DNA
<213> ORGANISM: Artificial Sequence
<220> FEATURE:
<223> OTHER INFORMATION: B-Class oligonucleotide

<400> SEQUENCE: 10
tcgtcgtttt gtcgttttgt cgtt 24

<210> SEQ ID NO 11
<211> LENGTH: 24
<212> TYPE: DNA
<213> ORGANISM: Artificial Sequence
<220> FEATURE:
<223> OTHER INFORMATION: B-Class oligonucleotide

<400> SEQUENCE: 11
tcgtcgtttc gtcgttttgt cgtt 24

<210> SEQ ID NO 12
<211> LENGTH: 24
<212> TYPE: DNA
<213> ORGANISM: Artificial Sequence
<220> FEATURE:
<223> OTHER INFORMATION: B-Class oligonucleotide

<400> SEQUENCE: 12
tcgtcgtttt gtcgtttttt tcga 24

<210> SEQ ID NO 13
<211> LENGTH: 22
<212> TYPE: DNA
<213> ORGANISM: Artificial Sequence
<220> FEATURE:
<223> OTHER INFORMATION: C class CpG Oligonucleotide

<400> SEQUENCE: 13
tcgcgtcgtt cggcgcgcgc cg 22

<210> SEQ ID NO 14
<211> LENGTH: 23
<212> TYPE: DNA
<213> ORGANISM: Artificial Sequence
<220> FEATURE:
<223> OTHER INFORMATION: C class CpG Oligonucleotide

<400> SEQUENCE: 14
tcgtcgacgt tcggcgcgcg ccg 23

<210> SEQ ID NO 15
<211> LENGTH: 21
<212> TYPE: DNA
<213> ORGANISM: Artificial Sequence
<220> FEATURE:
<223> OTHER INFORMATION: C class CpG Oligonucleotide

<400> SEQUENCE: 15
tcggacgttc ggcgcgcgcc g 21

<210> SEQ ID NO 16
<211> LENGTH: 19
<212> TYPE: DNA
<213> ORGANISM: Artificial Sequence
<220> FEATURE:
<223> OTHER INFORMATION: C class CpG Oligonucleotide

<400> SEQUENCE: 16
tcggacgttc ggcgcgccg 19

<210> SEQ ID NO 17
<211> LENGTH: 20
<212> TYPE: DNA
<213> ORGANISM: Artificial Sequence
<220> FEATURE:
<223> OTHER INFORMATION: C class CpG Oligonucleotide

<400> SEQUENCE: 17
tcgcgtcgtt cggcgcgccg 20

<210> SEQ ID NO 18
<211> LENGTH: 20
<212> TYPE: DNA
<213> ORGANISM: Artificial Sequence
<220> FEATURE:
<223> OTHER INFORMATION: C class CpG Oligonucleotide

<400> SEQUENCE: 18
tcgacgttcg gcgcgcgccg 20

<210> SEQ ID NO 19
<211> LENGTH: 18
<212> TYPE: DNA
<213> ORGANISM: Artificial Sequence
<220> FEATURE:
<223> OTHER INFORMATION: C class CpG Oligonucleotide

<400> SEQUENCE: 19
tcgacgttcg gcgcgccg 18

<210> SEQ ID NO 20
<211> LENGTH: 18
<212> TYPE: DNA
<213> ORGANISM: Artificial Sequence
<220> FEATURE:
<223> OTHER INFORMATION: C class CpG Oligonucleotide

<400> SEQUENCE: 20
tcgcgtcgtt cggcgccg 18

<210> SEQ ID NO 21
<211> LENGTH: 22
<212> TYPE: DNA
<213> ORGANISM: Artificial Sequence
<220> FEATURE:
<223> OTHER INFORMATION: C class CpG Oligonucleotide

<400> SEQUENCE: 21
tcgcgacgtt cggcgcgcgc cg 22

<210> SEQ ID NO 22
<211> LENGTH: 22
<212> TYPE: DNA
<213> ORGANISM: Artificial Sequence
<220> FEATURE:
<223> OTHER INFORMATION: C class CpG Oligonucleotide

<400> SEQUENCE: 22
tcgtcgtttt cggcgcgcgc cg 22

<210> SEQ ID NO 23
<211> LENGTH: 22
<212> TYPE: DNA

-continued

```
<213> ORGANISM: Artificial Sequence
<220> FEATURE:
<223> OTHER INFORMATION: C class CpG Oligonucleotide

<400> SEQUENCE: 23

tcgtcgtttt cggcggccgc cg                                          22


<210> SEQ ID NO 24
<211> LENGTH: 24
<212> TYPE: DNA
<213> ORGANISM: Artificial Sequence
<220> FEATURE:
<223> OTHER INFORMATION: C class CpG Oligonucleotide

<400> SEQUENCE: 24

tcgtcgtttt acggcgccgt gccg                                        24


<210> SEQ ID NO 25
<211> LENGTH: 23
<212> TYPE: DNA
<213> ORGANISM: Artificial Sequence
<220> FEATURE:
<223> OTHER INFORMATION: C class CpG Oligonucleotide

<400> SEQUENCE: 25

tcgtcgtttt cggcgcgcgc cgt                                         23


<210> SEQ ID NO 26
<211> LENGTH: 22
<212> TYPE: DNA
<213> ORGANISM: Artificial Sequence
<220> FEATURE:
<223> OTHER INFORMATION: C-Class oligonucleotides

<400> SEQUENCE: 26

tcgcgtcgtt cggcgcgcgc cg                                          22


<210> SEQ ID NO 27
<211> LENGTH: 23
<212> TYPE: DNA
<213> ORGANISM: Artificial Sequence
<220> FEATURE:
<223> OTHER INFORMATION: C-Class oligonucleotide

<400> SEQUENCE: 27

tcgtcgacgt tcggcgcgcg ccg                                         23


<210> SEQ ID NO 28
<211> LENGTH: 21
<212> TYPE: DNA
<213> ORGANISM: Artificial Sequence
<220> FEATURE:
<223> OTHER INFORMATION: C-Class oligonucleotide

<400> SEQUENCE: 28

tcggacgttc ggcgcgcgcc g                                           21


<210> SEQ ID NO 29
<211> LENGTH: 19
<212> TYPE: DNA
<213> ORGANISM: Artificial Sequence
<220> FEATURE:
<223> OTHER INFORMATION: C-Class oligonucleotide

<400> SEQUENCE: 29

tcggacgttc ggcgcgccg                                              19
```

<210> SEQ ID NO 30
<211> LENGTH: 20
<212> TYPE: DNA
<213> ORGANISM: Artificial Sequence
<220> FEATURE:
<223> OTHER INFORMATION: C-Class oligonucleotide

<400> SEQUENCE: 30
tcgcgtcgtt cggcgcgccg 20

<210> SEQ ID NO 31
<211> LENGTH: 20
<212> TYPE: DNA
<213> ORGANISM: Artificial Sequence
<220> FEATURE:
<223> OTHER INFORMATION: C-Class oligonucleotide

<400> SEQUENCE: 31
tcgacgttcg gcgcgcgccg 20

<210> SEQ ID NO 32
<211> LENGTH: 18
<212> TYPE: DNA
<213> ORGANISM: Artificial Sequence
<220> FEATURE:
<223> OTHER INFORMATION: C-Class oligonucleotide

<400> SEQUENCE: 32
tcgacgttcg gcgcgccg 18

<210> SEQ ID NO 33
<211> LENGTH: 18
<212> TYPE: DNA
<213> ORGANISM: Artificial Sequence
<220> FEATURE:
<223> OTHER INFORMATION: C-Class oligonucleotide

<400> SEQUENCE: 33
tcgcgtcgtt cggcgccg 18

<210> SEQ ID NO 34
<211> LENGTH: 22
<212> TYPE: DNA
<213> ORGANISM: Artificial Sequence
<220> FEATURE:
<223> OTHER INFORMATION: C-Class oligonucleotide

<400> SEQUENCE: 34
tcgcgacgtt cggcgcgcgc cg 22

<210> SEQ ID NO 35
<211> LENGTH: 22
<212> TYPE: DNA
<213> ORGANISM: Artificial Sequence
<220> FEATURE:
<223> OTHER INFORMATION: C-Class oligonucleotide

<400> SEQUENCE: 35
tcgtcgtttt cggcgcgcgc cg 22

<210> SEQ ID NO 36
<211> LENGTH: 22
<212> TYPE: DNA
<213> ORGANISM: Artificial Sequence
<220> FEATURE:

<223> OTHER INFORMATION: C-Class oligonucleotide

<400> SEQUENCE: 36
tcgtcgtttt cggcggccgc cg 22

<210> SEQ ID NO 37
<211> LENGTH: 24
<212> TYPE: DNA
<213> ORGANISM: Artificial Sequence
<220> FEATURE:
<223> OTHER INFORMATION: C-Class oligonucleotide

<400> SEQUENCE: 37
tcgtcgtttt acggcgccgt gccg 24

<210> SEQ ID NO 38
<211> LENGTH: 23
<212> TYPE: DNA
<213> ORGANISM: Artificial Sequence
<220> FEATURE:
<223> OTHER INFORMATION: C-Class oligonucleotide

<400> SEQUENCE: 38
tcgtcgtttt cggcgcgcgc cgt 23

<210> SEQ ID NO 39
<211> LENGTH: 23
<212> TYPE: DNA
<213> ORGANISM: Artificial Sequence
<220> FEATURE:
<223> OTHER INFORMATION: P class CpG oligonucleotide

<400> SEQUENCE: 39
tcgtcgacga tcggcgcgcg ccg 23

<210> SEQ ID NO 40
<211> LENGTH: 23
<212> TYPE: DNA
<213> ORGANISM: Artificial Sequence
<220> FEATURE:
<223> OTHER INFORMATION: P class CpG oligonucleotide

<400> SEQUENCE: 40
tcgtcgacga tcggcgcgcg ccg 23

<210> SEQ ID NO 41
<211> LENGTH: 950
<212> TYPE: PRT
<213> ORGANISM: Artificial Sequence
<220> FEATURE:
<223> OTHER INFORMATION: Enzymatically inactive fragment of SCP

<400> SEQUENCE: 41

Met Ala Lys Thr Ala Asp Thr Pro Ala Thr Ser Lys Ala Thr Ile Arg
1 5 10 15

Asp Leu Asn Asp Pro Ser Gln Val Lys Thr Leu Gln Glu Lys Ala Gly
20 25 30

Lys Gly Ala Gly Thr Val Val Ala Val Ile Ala Ala Gly Phe Asp Lys
35 40 45

Asn His Glu Ala Trp Arg Leu Thr Asp Lys Ala Lys Ala Arg Tyr Gln
50 55 60

Ser Lys Glu Asp Leu Glu Lys Ala Lys Lys Glu His Gly Ile Thr Tyr
65 70 75 80

-continued

```
Gly Glu Trp Val Asn Asp Lys Val Ala Tyr Tyr His Asp Tyr Ser Lys
                85                  90                  95

Asp Gly Lys Thr Ala Val Asp Gln Glu His Gly Thr His Val Ser Gly
            100                 105                 110

Ile Leu Ser Gly Asn Ala Pro Ser Glu Thr Lys Glu Pro Tyr Arg Leu
        115                 120                 125

Glu Gly Ala Met Pro Glu Ala Gln Leu Leu Leu Met Arg Val Glu Ile
    130                 135                 140

Val Asn Gly Leu Ala Asp Tyr Ala Arg Asn Tyr Ala Gln Ala Ile Arg
145                 150                 155                 160

Asp Ala Ile Asn Leu Gly Ala Lys Val Ile Asn Met Ser Phe Gly Asn
                165                 170                 175

Ala Ala Leu Ala Tyr Ala Asn Leu Pro Asp Glu Thr Lys Lys Ala Phe
            180                 185                 190

Asp Tyr Ala Lys Ser Lys Gly Val Ser Ile Val Thr Ser Ala Gly Asn
        195                 200                 205

Asp Ser Ser Phe Gly Gly Lys Thr Arg Leu Pro Leu Ala Asp His Pro
    210                 215                 220

Asp Tyr Gly Val Val Gly Thr Pro Ala Ala Ala Asp Ser Thr Leu Thr
225                 230                 235                 240

Val Ala Ser Tyr Ser Pro Asp Lys Gln Leu Thr Glu Thr Val Thr Val
                245                 250                 255

Lys Thr Ala Asp Gln Gln Asp Lys Glu Met Pro Val Leu Ser Thr Asn
            260                 265                 270

Arg Phe Glu Pro Asn Lys Ala Tyr Asp Tyr Ala Tyr Ala Asn Arg Gly
        275                 280                 285

Thr Lys Glu Asp Asp Phe Lys Asp Val Lys Gly Lys Ile Ala Leu Ile
    290                 295                 300

Glu Arg Gly Asp Ile Asp Phe Lys Asp Lys Ile Ala Lys Ala Lys Lys
305                 310                 315                 320

Ala Gly Ala Val Gly Val Leu Ile Tyr Asp Asn Gln Asp Lys Gly Phe
                325                 330                 335

Pro Ile Glu Leu Pro Asn Val Asp Gln Met Pro Ala Ala Phe Ile Ser
            340                 345                 350

Arg Lys Asp Gly Leu Leu Leu Lys Asp Asn Pro Gln Lys Thr Ile Thr
        355                 360                 365

Phe Asn Ala Thr Pro Lys Val Leu Pro Thr Ala Ser Gly Thr Lys Leu
    370                 375                 380

Ser Arg Phe Ser Ser Trp Gly Leu Thr Ala Asp Gly Asn Ile Lys Pro
385                 390                 395                 400

Asp Ile Ala Ala Pro Gly Gln Asp Ile Leu Ser Ser Val Ala Asn Asn
                405                 410                 415

Lys Tyr Ala Lys Leu Ser Gly Thr Ala Met Ser Ala Pro Leu Val Ala
            420                 425                 430

Gly Ile Met Gly Leu Leu Gln Glu Gln Tyr Glu Thr Gln Tyr Pro Asp
        435                 440                 445

Met Thr Pro Ser Glu Arg Leu Asp Leu Ala Lys Lys Val Leu Met Ser
    450                 455                 460

Ser Ala Thr Ala Leu Tyr Asp Glu Asp Glu Lys Ala Tyr Phe Ser Pro
465                 470                 475                 480

Arg Gln Gln Gly Ala Gly Ala Val Asp Ala Lys Lys Ala Ser Ala Ala
                485                 490                 495

Thr Met Tyr Val Thr Asp Lys Asp Asn Thr Ser Ser Lys Val His Leu
```

-continued

```
            500                 505                 510

Asn Asn Val Ser Asp Lys Phe Glu Val Thr Val Thr Val His Asn Lys
        515                 520                 525

Ser Asp Lys Pro Gln Glu Leu Tyr Tyr Gln Ala Thr Val Gln Thr Asp
    530                 535                 540

Lys Val Asp Gly Lys His Phe Ala Leu Ala Pro Lys Ala Leu Tyr Glu
545                 550                 555                 560

Thr Ser Trp Gln Lys Ile Thr Ile Pro Ala Asn Ser Ser Lys Gln Val
                565                 570                 575

Thr Val Pro Ile Asp Ala Ser Arg Phe Ser Lys Asp Leu Leu Ala Gln
            580                 585                 590

Met Lys Asn Gly Tyr Phe Leu Glu Gly Phe Val Arg Phe Lys Gln Asp
        595                 600                 605

Pro Lys Lys Glu Glu Leu Met Ser Ile Pro Tyr Ile Gly Phe Arg Gly
    610                 615                 620

Asp Phe Gly Asn Leu Ser Ala Leu Glu Lys Pro Ile Tyr Asp Ser Lys
625                 630                 635                 640

Asp Gly Ser Ser Tyr Tyr His Glu Ala Asn Ser Asp Ala Lys Asp Gln
                645                 650                 655

Leu Asp Gly Asp Gly Leu Gln Phe Tyr Ala Leu Lys Asn Asn Phe Thr
            660                 665                 670

Ala Leu Thr Thr Glu Ser Asn Pro Trp Thr Ile Ile Lys Ala Val Lys
        675                 680                 685

Glu Gly Val Glu Asn Ile Glu Asp Ile Glu Ser Ser Glu Ile Thr Glu
    690                 695                 700

Thr Ile Phe Ala Gly Thr Phe Ala Lys Gln Asp Asp Asp Ser His Tyr
705                 710                 715                 720

Tyr Ile His Arg His Ala Asn Gly Lys Pro Tyr Ala Ala Ile Ser Pro
                725                 730                 735

Asn Gly Asp Gly Asn Arg Asp Tyr Val Gln Phe Gln Gly Thr Phe Leu
            740                 745                 750

Arg Asn Ala Lys Asn Leu Val Ala Glu Val Leu Asp Lys Glu Gly Asn
        755                 760                 765

Val Val Trp Thr Ser Glu Val Thr Glu Gln Val Val Lys Asn Tyr Asn
    770                 775                 780

Asn Asp Leu Ala Ser Thr Leu Gly Ser Thr Arg Phe Glu Lys Thr Arg
785                 790                 795                 800

Trp Asp Gly Lys Asp Lys Asp Gly Lys Val Val Ala Asn Gly Thr Tyr
                805                 810                 815

Thr Tyr Arg Val Arg Tyr Thr Pro Ile Ser Ser Gly Ala Lys Glu Gln
            820                 825                 830

His Thr Asp Phe Asp Val Ile Val Asp Asn Thr Thr Pro Glu Val Ala
        835                 840                 845

Thr Ser Ala Thr Phe Ser Thr Glu Asp Arg Arg Leu Thr Leu Ala Ser
    850                 855                 860

Lys Pro Lys Thr Ser Gln Pro Val Tyr Arg Glu Arg Ile Ala Tyr Thr
865                 870                 875                 880

Tyr Met Asp Glu Asp Leu Pro Thr Thr Glu Tyr Ile Ser Pro Asn Glu
                885                 890                 895

Asp Gly Thr Phe Thr Leu Pro Glu Glu Ala Glu Thr Met Glu Gly Ala
            900                 905                 910

Thr Val Pro Leu Lys Met Ser Asp Phe Thr Tyr Val Val Glu Asp Met
        915                 920                 925
```

```
Ala Gly Asn Ile Thr Tyr Thr Pro Val Thr Lys Leu Leu Glu Gly His
    930                 935                 940

Ser Asn Lys Pro Glu Gln
945                 950


<210> SEQ ID NO 42
<211> LENGTH: 949
<212> TYPE: PRT
<213> ORGANISM: Artificial Sequence
<220> FEATURE:
<223> OTHER INFORMATION: Enzymatically inactive fragment of SCP

<400> SEQUENCE: 42

Ala Lys Thr Ala Asp Thr Pro Ala Thr Ser Lys Ala Thr Ile Arg Asp
1               5                   10                  15

Leu Asn Asp Pro Ser Gln Val Lys Thr Leu Gln Glu Lys Ala Gly Lys
            20                  25                  30

Gly Ala Gly Thr Val Val Ala Val Ile Ala Ala Gly Phe Asp Lys Asn
        35                  40                  45

His Glu Ala Trp Arg Leu Thr Asp Lys Ala Lys Ala Arg Tyr Gln Ser
    50                  55                  60

Lys Glu Asp Leu Glu Lys Ala Lys Lys Glu His Gly Ile Thr Tyr Gly
65                  70                  75                  80

Glu Trp Val Asn Asp Lys Val Ala Tyr Tyr His Asp Tyr Ser Lys Asp
                85                  90                  95

Gly Lys Thr Ala Val Asp Gln Glu His Gly Thr His Val Ser Gly Ile
            100                 105                 110

Leu Ser Gly Asn Ala Pro Ser Glu Thr Lys Glu Pro Tyr Arg Leu Glu
        115                 120                 125

Gly Ala Met Pro Glu Ala Gln Leu Leu Leu Met Arg Val Glu Ile Val
    130                 135                 140

Asn Gly Leu Ala Asp Tyr Ala Arg Asn Tyr Ala Gln Ala Ile Arg Asp
145                 150                 155                 160

Ala Ile Asn Leu Gly Ala Lys Val Ile Asn Met Ser Phe Gly Asn Ala
                165                 170                 175

Ala Leu Ala Tyr Ala Asn Leu Pro Asp Glu Thr Lys Lys Ala Phe Asp
            180                 185                 190

Tyr Ala Lys Ser Lys Gly Val Ser Ile Val Thr Ser Ala Gly Asn Asp
        195                 200                 205

Ser Ser Phe Gly Gly Lys Thr Arg Leu Pro Leu Ala Asp His Pro Asp
    210                 215                 220

Tyr Gly Val Val Gly Thr Pro Ala Ala Ala Asp Ser Thr Leu Thr Val
225                 230                 235                 240

Ala Ser Tyr Ser Pro Asp Lys Gln Leu Thr Glu Thr Val Thr Val Lys
                245                 250                 255

Thr Ala Asp Gln Gln Asp Lys Glu Met Pro Val Leu Ser Thr Asn Arg
            260                 265                 270

Phe Glu Pro Asn Lys Ala Tyr Asp Tyr Ala Tyr Ala Asn Arg Gly Thr
        275                 280                 285

Lys Glu Asp Asp Phe Lys Asp Val Lys Gly Lys Ile Ala Leu Ile Glu
    290                 295                 300

Arg Gly Asp Ile Asp Phe Lys Asp Lys Ile Ala Lys Ala Lys Lys Ala
305                 310                 315                 320

Gly Ala Val Gly Val Leu Ile Tyr Asp Asn Gln Asp Lys Gly Phe Pro
                325                 330                 335
```

-continued

```
Ile Glu Leu Pro Asn Val Asp Gln Met Pro Ala Ala Phe Ile Ser Arg
            340                 345                 350

Lys Asp Gly Leu Leu Leu Lys Asp Asn Pro Gln Lys Thr Ile Thr Phe
        355                 360                 365

Asn Ala Thr Pro Lys Val Leu Pro Thr Ala Ser Gly Thr Lys Leu Ser
    370                 375                 380

Arg Phe Ser Ser Trp Gly Leu Thr Ala Asp Gly Asn Ile Lys Pro Asp
385                 390                 395                 400

Ile Ala Ala Pro Gly Gln Asp Ile Leu Ser Ser Val Ala Asn Asn Lys
                405                 410                 415

Tyr Ala Lys Leu Ser Gly Thr Ala Met Ser Ala Pro Leu Val Ala Gly
            420                 425                 430

Ile Met Gly Leu Leu Gln Glu Gln Tyr Glu Thr Gln Tyr Pro Asp Met
        435                 440                 445

Thr Pro Ser Glu Arg Leu Asp Leu Ala Lys Lys Val Leu Met Ser Ser
    450                 455                 460

Ala Thr Ala Leu Tyr Asp Glu Asp Glu Lys Ala Tyr Phe Ser Pro Arg
465                 470                 475                 480

Gln Gln Gly Ala Gly Ala Val Asp Ala Lys Lys Ala Ser Ala Ala Thr
                485                 490                 495

Met Tyr Val Thr Asp Lys Asp Asn Thr Ser Ser Lys Val His Leu Asn
            500                 505                 510

Asn Val Ser Asp Lys Phe Glu Val Thr Val Thr Val His Asn Lys Ser
        515                 520                 525

Asp Lys Pro Gln Glu Leu Tyr Tyr Gln Ala Thr Val Gln Thr Asp Lys
    530                 535                 540

Val Asp Gly Lys His Phe Ala Leu Ala Pro Lys Ala Leu Tyr Glu Thr
545                 550                 555                 560

Ser Trp Gln Lys Ile Thr Ile Pro Ala Asn Ser Ser Lys Gln Val Thr
                565                 570                 575

Val Pro Ile Asp Ala Ser Arg Phe Ser Lys Asp Leu Leu Ala Gln Met
            580                 585                 590

Lys Asn Gly Tyr Phe Leu Glu Gly Phe Val Arg Phe Lys Gln Asp Pro
        595                 600                 605

Lys Lys Glu Glu Leu Met Ser Ile Pro Tyr Ile Gly Phe Arg Gly Asp
    610                 615                 620

Phe Gly Asn Leu Ser Ala Leu Glu Lys Pro Ile Tyr Asp Ser Lys Asp
625                 630                 635                 640

Gly Ser Ser Tyr Tyr His Glu Ala Asn Ser Asp Ala Lys Asp Gln Leu
                645                 650                 655

Asp Gly Asp Gly Leu Gln Phe Tyr Ala Leu Lys Asn Asn Phe Thr Ala
            660                 665                 670

Leu Thr Thr Glu Ser Asn Pro Trp Thr Ile Ile Lys Ala Val Lys Glu
        675                 680                 685

Gly Val Glu Asn Ile Glu Asp Ile Glu Ser Ser Glu Ile Thr Glu Thr
    690                 695                 700

Ile Phe Ala Gly Thr Phe Ala Lys Gln Asp Asp Asp Ser His Tyr Tyr
705                 710                 715                 720

Ile His Arg His Ala Asn Gly Lys Pro Tyr Ala Ala Ile Ser Pro Asn
                725                 730                 735

Gly Asp Gly Asn Arg Asp Tyr Val Gln Phe Gln Gly Thr Phe Leu Arg
            740                 745                 750
```

-continued

```
Asn Ala Lys Asn Leu Val Ala Glu Val Leu Asp Lys Glu Gly Asn Val
        755                 760                 765

Val Trp Thr Ser Glu Val Thr Glu Gln Val Val Lys Asn Tyr Asn Asn
    770                 775                 780

Asp Leu Ala Ser Thr Leu Gly Ser Thr Arg Phe Glu Lys Thr Arg Trp
785                 790                 795                 800

Asp Gly Lys Asp Lys Asp Gly Lys Val Val Ala Asn Gly Thr Tyr Thr
                805                 810                 815

Tyr Arg Val Arg Tyr Thr Pro Ile Ser Ser Gly Ala Lys Glu Gln His
            820                 825                 830

Thr Asp Phe Asp Val Ile Val Asp Asn Thr Thr Pro Glu Val Ala Thr
        835                 840                 845

Ser Ala Thr Phe Ser Thr Glu Asp Arg Arg Leu Thr Leu Ala Ser Lys
    850                 855                 860

Pro Lys Thr Ser Gln Pro Val Tyr Arg Glu Arg Ile Ala Tyr Thr Tyr
865                 870                 875                 880

Met Asp Glu Asp Leu Pro Thr Thr Glu Tyr Ile Ser Pro Asn Glu Asp
                885                 890                 895

Gly Thr Phe Thr Leu Pro Glu Glu Ala Glu Thr Met Glu Gly Ala Thr
            900                 905                 910

Val Pro Leu Lys Met Ser Asp Phe Thr Tyr Val Val Glu Asp Met Ala
        915                 920                 925

Gly Asn Ile Thr Tyr Thr Pro Val Thr Lys Leu Leu Glu Gly His Ser
    930                 935                 940

Asn Lys Pro Glu Gln
945
```

IMMUNOGENIC COMPOSITIONS COMPRISING CONJUGATED CAPSULAR SACCHARIDE ANTIGENS AND USES THEREOF

REFERENCE TO SEQUENCE LISTING

The instant application contains a Sequence Listing which has been submitted electronically in ASCII format and is hereby incorporated by reference in its entirety. Said ASCII copy, created on May 18, 2022, is named PC072675A_ST25.txt and is 25 KB in size.

FIELD OF THE INVENTION

The present invention relates to new conjugated capsular saccharide antigens (glycoconjugates), immunogenic compositions comprising said glycoconjugates and uses thereof. Immunogenic compositions of the present invention will typically comprise glycoconjugates, wherein the saccharides are derived from serotypes of *Streptococcus pneumoniae*. The invention also relates to vaccination of human subjects, in particular infants and elderly, against pneumococcal infections using said glycoconjugates.

BACKGROUND OF THE INVENTION

The approach to increasing immunogenicity of poorly immunogenic molecules by conjugating these molecules to "carrier" molecules has been utilized successfully for decades (see, e.g., Goebel et al. (1939) J. Exp. Med. 69: 53). For example, many immunogenic compositions have been described in which purified capsular polymers have been conjugated to carrier proteins to create more effective immunogenic compositions by exploiting this "carrier effect." Schneerson et al. (1984) Infect. Immun. 45: 582-591). Conjugation has also been shown to bypass the poor antibody response usually observed in infants when immunized with a free polysaccharide (Anderson et al. (1985) J. Pediatr. 107: 346; Insel et al. (1986) J. Exp. Med. 158: 294).

Conjugates have been successfully generated using various cross-linking or coupling reagents, such as homobifunctional, heterobifunctional, or zero-length crosslinkers. Many methods are currently available for coupling immunogenic molecules, such as saccharides, proteins, and peptides, to peptide or protein carriers. Most methods create amine, amide, urethane, isothiourea, or disulfide bonds, or in some cases thioethers. A disadvantage to the use of cross-linking or coupling reagents which introduce reactive sites into the side chains of reactive amino acid molecules on carrier and/or immunogenic molecules is that the reactive sites, if not neutralized, are free to react with any unwanted molecule either in vitro (thus potentially adversely affecting the functionality or stability of the conjugates) or in vivo (thus posing a potential risk of adverse events in persons or animals immunized with the preparations). Such excess reactive sites can be reacted or "capped", so as to inactivate these sites, utilizing various known chemical reactions, but these reactions may be otherwise disruptive to the functionality of the conjugates.

Thus, there remains a need for new glycoconjugates appropriately capped and methods to prepare said conjugates, such that the functionality is preserved and the conjugate retains the ability to elicit the desired immune response.

Pneumococcal polysaccharides, in particular capsular polysaccharides, are important immunogens found on the surface of the bacteria. This has led to them being an important component in the design of pneumococcal vaccines. They have proved useful in eliciting immune responses especially when linked to carrier proteins.

Some serotypes, in particular *Streptococcus pneumoniae* serotype 3, produce large and viscous polysaccharide chains (e.g., for Type 3, chains of glucose/glucuronic acid of 2-3 million Daltons). Its viscosity has made it difficult to handle.

Furthermore, significant immunogenicity with respect to serotype 3 polysaccharides has been difficult to obtain. For example, in a study of the immunogenicity and safety of an 11-valent pneumococcal protein D conjugate vaccine (11-Pn-PD), no priming effect was observed for serotype 3 in infants who had received three doses of the vaccine followed by a booster dose of either the same vaccine or a pneumococcal polysaccharide vaccine (Nurkka et al. (2004) Ped. Inf. Dis. J., 23:1008-1014). In another study, opsonophagocytic assay (OPA) results from infants who had received doses of 11-Pn-PD failed to show antibody responses for serotype 3 at levels comparable to other tested serotypes (Gatchalian et al., 17th annual Meeting of the Eur. Soc. Paed. Inf. Dis. (ESPID), Poster No. 4, PIA Poster Session 1, Istanbul Turkey, Mar. 27, 2001). In yet another study, which assessed the efficacy of an 11-Pn-PD in the prevention of acute otitis media, the vaccine did not provide protection against episodes caused by serotype 3 (Prymula et al. The Lancet, Vol. 367: 740-748 (Mar. 4, 2006)).

Thus, there is a need for antigens which are able to generate a more robust immune response to *Streptococcus pneumoniae* serotype 3.

The present invention provides in particular *Streptococcus pneumoniae* serotype 3 glycoconjugates which show improved immunogenicity. The present invention also provides a process (method of making) which generates *Streptococcus pneumoniae* serotype 3 glycoconjugate with improved conjugation yield.

SUMMARY OF THE INVENTION

In an aspect, the invention relates to a method of making a *Streptococcus pneumoniae* serotype 3 glycoconjugate, comprising the steps of:

(a) reacting an isolated *Streptococcus pneumoniae* serotype 3 capsular polysaccharide with a carbonic acid derivative and an azido linker in an aprotic solvent to produce an activated azido polysaccharide, (b) reacting a carrier protein with an agent bearing an N-Hydroxysuccinimide (NHS) moiety and an alkyne group where the NHS moiety reacts with the amino groups to form an amide linkage thereby obtaining an alkyne functionalized carrier protein, (c) reacting the activated azido polysaccharide of step (a) with the activated alkyne-carrier protein of step (b) by $Cu^{+1}$ mediated azide-alkyne cycloaddition reaction to form a glycoconjugate.

In a particular aspect, the isolated polysaccharide is sized to a weight average molecular weight between 100 kDa and 200 kDa before the activation step (a).

In an aspect, the carbonic acid derivative is 1,1'-carbonyldiimidazole (CDI).

In an aspect, the invention relates to a *Streptococcus pneumoniae* serotype 3 glycoconjugate produced according to said methods.

In an aspect, the invention relates to a *Streptococcus pneumoniae* serotype 3 glycoconjugate comprising a *Strep-*

*tococcus pneumoniae* serotype 3 saccharide covalently conjugated to a carrier protein (CP) through a spacer and having the general formula (VII):

(VII)

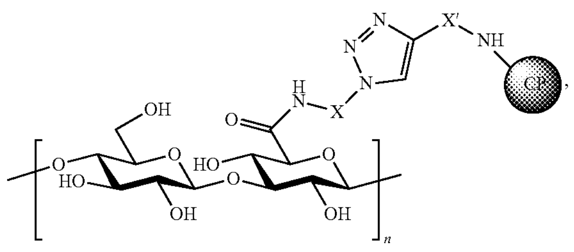

wherein X is selected from the group consisting of $CH_2(CH_2)_{n'}$, $(CH_2CH_2O)_mCH_2CH_2$, $NHCO(CH_2)_{n'}$, $NHCO(CH_2CH_2O)_mCH_2CH_2$, $OCH_2(CH_2)_{n'}$ and $O(CH_2CH_2O)_mCH_2CH_2$, where n' is selected from 1 to 10 and m is selected from 1 to 4, and wherein X is selected from the group consisting of $CH_2O(CH_2)_{n''}CH_2C{=}O$, $CH_2O(CH_2CH_2O)_{m'}(CH_2)_{n''}CH_2C{=}O$, where n" is selected from 0 to 10 and m' is selected from 0 to 4.

In yet a further aspect, the invention relates to an immunogenic composition comprising said *Streptococcus pneumoniae* serotype 3 glycoconjugate.

FIGURES

FIG. 1 shows a repeating polysaccharide structure of the *S. pneumoniae* serotype 3 capsular polysaccharide.

FIG. 2 shows a general scheme for the preparation of *Streptococcus pneumoniae* serotype 3 glycoconjugate of the invention prepared using click chemistry. Pn3 poly=*S. pneumoniae* serotype 3 capsular polysaccharide; CP=Carrier Protein, CDI=1,1'-carbonyldiimidazole.

Figure 7:
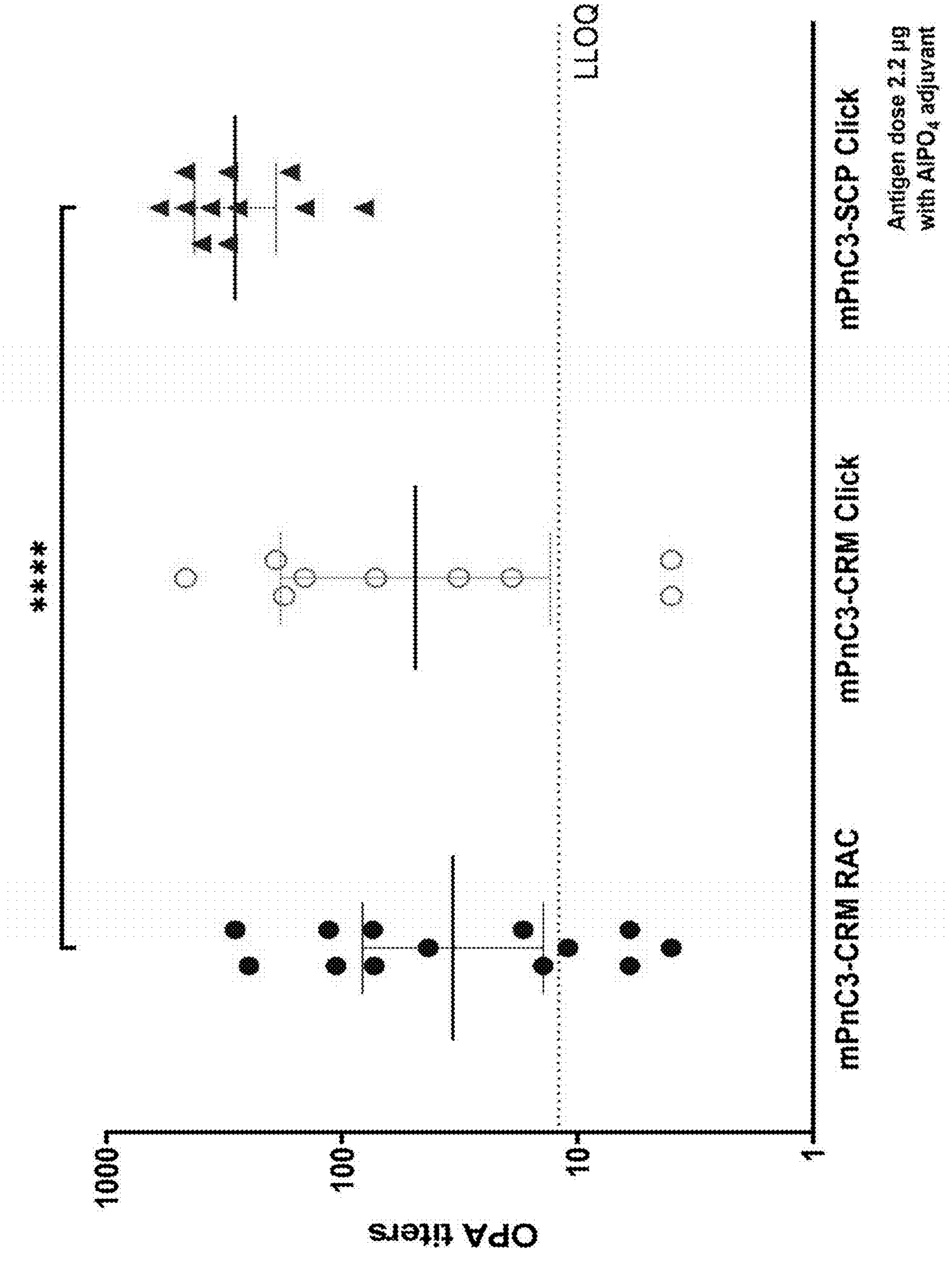

FIG. 7 shows Post dose 1 OPA titers in infant rhesus vaccinated with serotype 3 chemistry/carrier conjugates. Different chemistries have been used (Reductive Amination in aqueous (RAC/Aq.) or click chemistry (Click). Opsonophagocytic titers measured from sera collected at 4 weeks post dose 1 time point between different conjugation chemistries. Each dot represents individual animal and data expressed as geomean titers with 95% confidence interval. Statistical significance determined based on one-way ANOVA. Tukey's multiplicity adjusted p values are reported. ****=$p<0.0001$ LLOQ—lower limit of quantitation.

Figure 8:
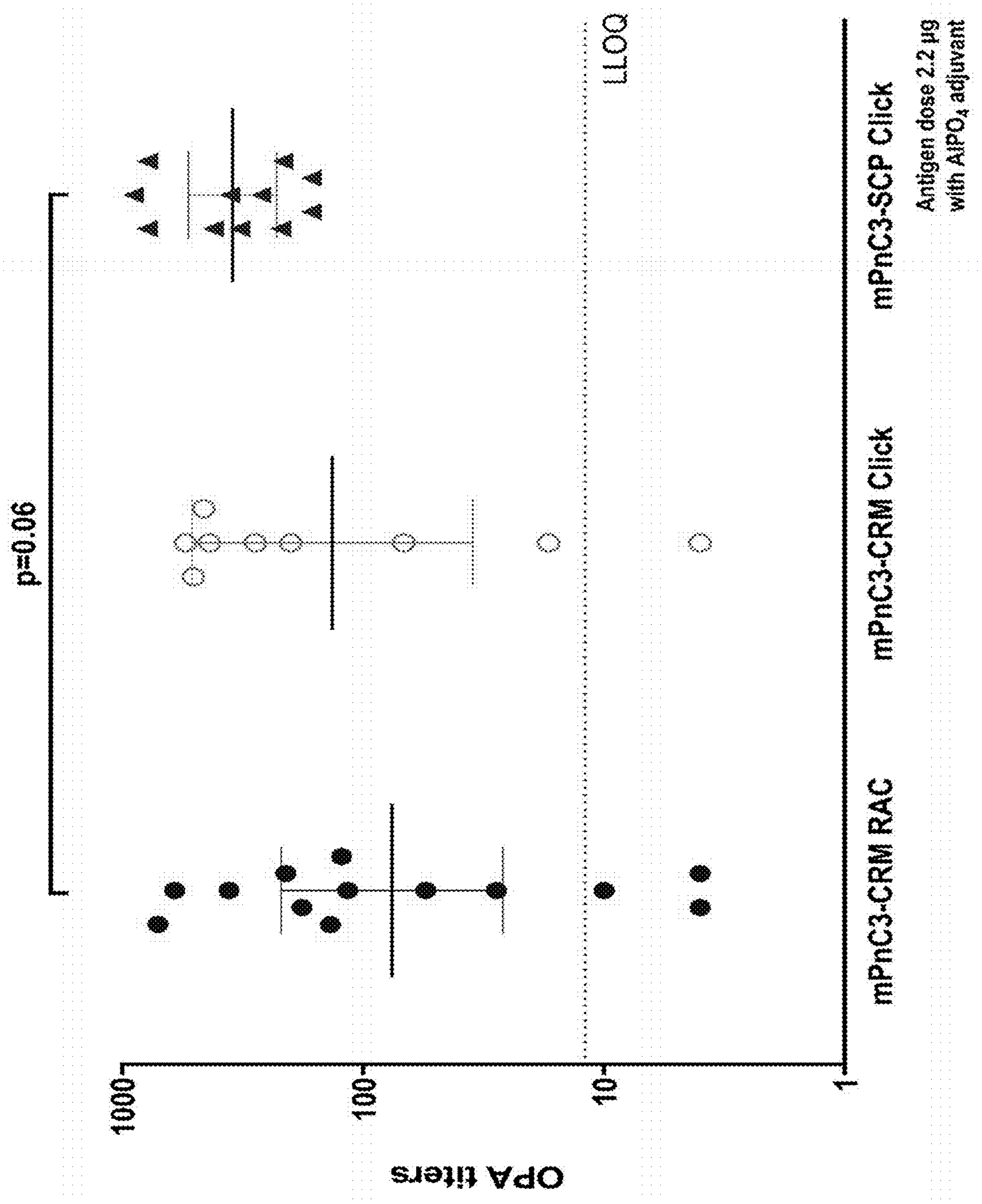

FIG. 8 shows Post dose 2 OPA response in infant rhesus macaques vaccinated with serotype 3 chemistry/carrier conjugates. Opsonophagocytic titers measured from sera collected at 4 weeks post dose 2 between different conjugation chemistries. Each dot represents individual animal and data expressed as geomean titers with 95% confidence interval. Statistical significance determined based on one-way ANOVA. Tukey's multiplicity adjusted p values are reported. LLOQ—lower limit of quantitation

1. GLYCOCONJUGATES OF THE INVENTION

The present invention is directed in part to conjugated capsular saccharide antigens (also named glycoconjugates), where saccharides are derived from serotypes of *S. pneumoniae*, in particular from serotype 3. For the purpose of the invention the term 'glycoconjugate' indicates a capsular saccharide linked covalently to a carrier protein. In one embodiment a capsular saccharide is linked directly to a carrier protein. In a second embodiment a bacterial saccharide is linked to a protein through a spacer/linker.

1.1 Pneumococcal Saccharide from *S. pneumoniae* Serotype 3

Figure 1:
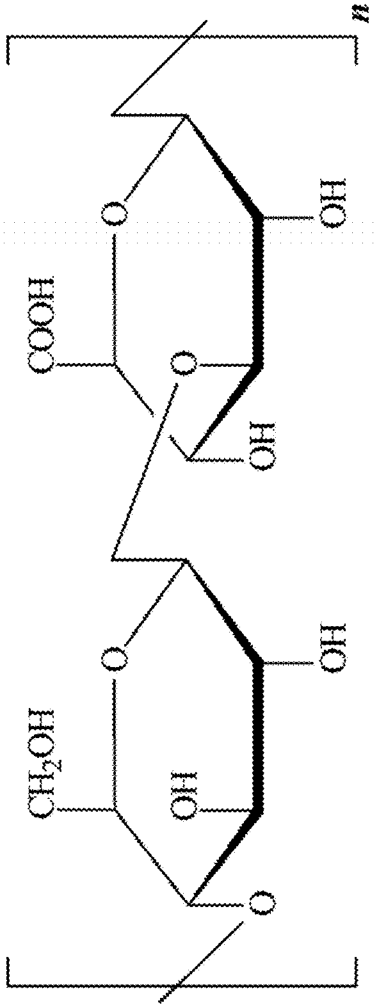

As shown at FIG. 1, the polysaccharide repeating unit of serotype 3 consists of a linear disaccharide unit with one glucopyranose (Glcp) and one glucuronic acid (GlcpA) (see e.g. Geno K et al. (2015) Clin Microbiol Rev Vol 28:3, p 871-899).

In an embodiment, the capsular *S. pneumoniae* serotype 3 saccharide used in the present invention is a synthetic carbohydrate. Preparation of a synthetic *Streptococcus pneumoniae* type 3 capsular saccharide can for example be conducted as disclosed in WO2017178664.

In a preferred embodiment though, the source of bacterial polysaccharide according to this invention can be *Streptococcus pneumoniae* serotype 3 bacterial cells. Bacterial strains which can be used as source of *Streptococcus pneumoniae* serotype 3 polysaccharides may be obtained from established culture collections (such as for example from the Streptococcal Reference Laboratory (Centers for Disease Control and Prevention, Atlanta, GA USA)) or clinical specimens.

Serotype 3 polysaccharides can be obtained directly from bacteria using isolation procedures known to one of ordinary skill in the art (see for example methods disclosed in US2006/0228380, US2006/0228381, US2007/0184071, US2007/0184072, US2007/0231340, and US2008/0102498 and WO2008/118752). They can also be produced using synthetic protocols known to the man skilled in the art. They can also be purchased (such as for example from the American Type Culture Collection (ATCC, Manassas, VA USA) (e.g., reference No. ATCC 172-X or ATCC 33-X)).

In case the serotype 3 polysaccharide is obtained directly from bacteria, the bacterial cells can be grown in a medium, preferably in a soy based medium. Following fermentation of bacterial cells that produce *S. pneumoniae* serotype 3 capsular polysaccharides, the bacterial cells can be lysed to produce a cell lysate. The serotype 3 polysaccharide may then be isolated from the cell lysate using purification techniques known in the art, including the use of centrifugation, depth filtration, precipitation, ultra-filtration, treatment with activate carbon, diafiltration and/or column chromatography (see, for example, US2006/0228380, US2006/0228381 and WO2008/118752). The purified serotype 3 capsular polysaccharide can then be used for the preparation of immunogenic conjugates.

The isolated serotype 3 capsular polysaccharide obtained by purification of serotype 3 polysaccharide from the *S. pneumoniae* lysate and optionally sizing of the purified polysaccharide can be characterized by different parameters including, for example the weight average molecular weight (Mw).

The molecular weight of the polysaccharide can be measured by Size Exclusion Chromatography (SEC) combined with Multiangle Laser Light Scattering detector (MALLS).

In a preferred embodiment, the isolated serotype 3 capsular polysaccharide (i.e. purified before further treatment) has a weight average molecular weight between 5 kDa and 5000 kDa. In an embodiment, the isolated serotype 3 capsular polysaccharide has a weight average molecular weight between 5 kDa and 4000 kDa. In an embodiment, the isolated serotype 3 capsular polysaccharide has a weight average molecular weight between 5 kDa and 3000 kDa. In an embodiment, the isolated serotype 3 capsular polysaccharide has a weight average molecular weight between 5 kDa and 2000 kDa. In an embodiment, the isolated serotype 3 capsular polysaccharide has a weight average molecular weight between 5 kDa and 1500 kDa. In an embodiment, the isolated serotype 3 capsular polysaccharide has a weight average molecular weight between 5 kDa and 1000 kDa. In an embodiment, the isolated serotype 3 capsular polysaccharide has a weight average molecular weight between 5 kDa and 500 kDa. In an embodiment, the isolated serotype 3 capsular polysaccharide has a weight average molecular weight between 5 kDa and 400 kDa. In an embodiment, the isolated serotype 3 capsular polysaccharide has a weight average molecular weight between 5 kDa and 300 kDa. In an embodiment, the isolated serotype 3 capsular polysaccharide has a weight average molecular weight between 5 kDa and 200 kDa. In an embodiment, the isolated serotype 3 capsular polysaccharide has a weight average molecular weight between 5 kDa and 100 kDa.

In an embodiment, the isolated serotype 3 capsular polysaccharide has a weight average molecular weight between 50 kDa and 5000 kDa. In an embodiment, the isolated serotype 3 capsular polysaccharide has a weight average molecular weight between 50 kDa and 4000 kDa. In an embodiment, the isolated serotype 3 capsular polysaccharide has a weight average molecular weight between 50 kDa and 3000 kDa. In an embodiment, the isolated serotype 3 capsular polysaccharide has a weight average molecular weight between 50 kDa and 2000 kDa. In an embodiment, the isolated serotype 3 capsular polysaccharide has a weight average molecular weight between 50 kDa and 1500 kDa. In an embodiment, the isolated serotype 3 capsular polysaccharide has a weight average molecular weight between 50 kDa and 1000 kDa. In an embodiment, the isolated serotype 3 capsular polysaccharide has a weight average molecular weight between 50 kDa and 500 kDa. In an embodiment, the isolated serotype 3 capsular polysaccharide has a weight average molecular weight between 50 kDa and 400 kDa. In an embodiment, the isolated serotype 3 capsular polysaccharide has a weight average molecular weight between 50 kDa and 300 kDa. In an embodiment, the isolated serotype 3 capsular polysaccharide has a weight average molecular weight between 50 kDa and 200 kDa. In an embodiment, the isolated serotype 3 capsular polysaccharide has a weight average molecular weight between 50 kDa and 100 kDa.

In an embodiment, the isolated serotype 3 capsular polysaccharide has a weight average molecular weight between 100 kDa and 5000 kDa. In an embodiment, the isolated serotype 3 capsular polysaccharide has a weight average molecular weight between 100 kDa and 4000 kDa. In an embodiment, the isolated serotype 3 capsular polysaccharide has a weight average molecular weight between 100 kDa and 3000 kDa. In an embodiment, the isolated serotype 3 capsular polysaccharide has a weight average molecular weight between 100 kDa and 2000 kDa. In an embodiment, the isolated serotype 3 capsular polysaccharide has a weight average molecular weight between 100 kDa and 1500 kDa. In an embodiment, the isolated serotype 3 capsular polysaccharide has a weight average molecular weight between 100 kDa and 1000 kDa. In an embodiment, the isolated serotype 3 capsular polysaccharide has a weight average molecular weight between 100 kDa and 500 kDa. In an embodiment, the isolated serotype 3 capsular polysaccharide has a weight average molecular weight between 100 kDa and 400 kDa. In an embodiment, the isolated serotype 3 capsular polysaccharide has a weight average molecular weight between 100 kDa and 300 kDa. In an embodiment, the isolated serotype 3 capsular polysaccharide has a weight average molecular weight between 100 kDa and 200 kDa.

In an embodiment, the isolated serotype 3 capsular polysaccharide has a weight average molecular weight between 150 kDa and 5000 kDa. In an embodiment, the isolated serotype 3 capsular polysaccharide has a weight average molecular weight between 150 kDa and 4000 kDa. In an embodiment, the isolated serotype 3 capsular polysaccharide has a weight average molecular weight between 150 kDa and 3000 kDa. In an embodiment, the isolated serotype 3 capsular polysaccharide has a weight average molecular weight between 150 kDa and 2000 kDa. In an embodiment, the isolated serotype 3 capsular polysaccharide has a weight average molecular weight between 150 kDa and 1500 kDa. In an embodiment, the isolated serotype 3 capsular polysaccharide has a weight average molecular weight between 150 kDa and 1000 kDa. In an embodiment, the isolated serotype 3 capsular polysaccharide has a weight average molecular weight between 150 kDa and 500 kDa. In an embodiment, the isolated serotype 3 capsular polysaccharide has a weight average molecular weight between 150 kDa and 400 kDa. In an embodiment, the isolated serotype 3 capsular polysaccharide has a weight average molecular weight between 150 kDa and 300 kDa. In an embodiment, the isolated serotype 3 capsular polysaccharide has a weight average molecular weight between 150 kDa and 200 kDa.

In an embodiment, the isolated serotype 3 capsular polysaccharide has a weight average molecular weight between 200 kDa and 5000 kDa. In an embodiment, the isolated serotype 3 capsular polysaccharide has a weight average molecular weight between 200 kDa and 4000 kDa. In an embodiment, the isolated serotype 3 capsular polysaccharide has a weight average molecular weight between 200 kDa and 3000 kDa. In an embodiment, the isolated serotype 3 capsular polysaccharide has a weight average molecular weight between 200 kDa and 2000 kDa. In an embodiment, the isolated serotype 3 capsular polysaccharide has a weight average molecular weight between 200 kDa and 1500 kDa. In an embodiment, the isolated serotype 3 capsular polysaccharide has a weight average molecular weight between 200 kDa and 1000 kDa. In an embodiment, the isolated serotype 3 capsular polysaccharide has a weight average molecular weight between 200 kDa and 500 kDa. In an embodiment, the isolated serotype 3 capsular polysaccharide has a weight average molecular weight between 200 kDa and 400 kDa. In an embodiment, the isolated serotype 3 capsular polysaccharide has a weight average molecular weight between 200 kDa and 300 kDa.

In an embodiment, the isolated serotype 3 capsular polysaccharide has a weight average molecular weight between 300 kDa and 5000 kDa. In an embodiment, the isolated serotype 3 capsular polysaccharide has a weight average molecular weight between 300 kDa and 4000 kDa. In an embodiment, the isolated serotype 3 capsular polysaccharide has a weight average molecular weight between 300 kDa and 3000 kDa. In an embodiment, the isolated serotype 3 capsular polysaccharide has a weight average molecular weight between 300 kDa and 2000 kDa. In an embodiment, the isolated serotype 3 capsular polysaccharide has a weight average molecular weight between 300 kDa and 1500 kDa. In an embodiment, the isolated serotype 3 capsular polysaccharide has a weight average molecular weight between 300 kDa and 1000 kDa. In an embodiment, the isolated serotype 3 capsular polysaccharide has a weight average molecular weight between 300 kDa and 500 kDa. In an embodiment, the isolated serotype 3 capsular polysaccharide has a weight average molecular weight between 300 kDa and 400 kDa.

In an embodiment, the isolated serotype 3 capsular polysaccharide has a weight average molecular weight between 400 kDa and 5000 kDa. In an embodiment, the isolated serotype 3 capsular polysaccharide has a weight average molecular weight between 400 kDa and 4000 kDa. In an embodiment, the isolated serotype 3 capsular polysaccharide has a weight average molecular weight between 400 kDa and 3000 kDa. In an embodiment, the isolated serotype 3 capsular polysaccharide has a weight average molecular weight between 400 kDa and 2000 kDa. In an embodiment, the isolated serotype 3 capsular polysaccharide has a weight average molecular weight between 400 kDa and 1500 kDa. In an embodiment, the isolated serotype 3 capsular polysaccharide has a weight average molecular weight between 400 kDa and 1000 kDa. In an embodiment, the isolated serotype 3 capsular polysaccharide has a weight average molecular weight between 400 kDa and 500 kDa.

In an embodiment, the isolated serotype 3 capsular polysaccharide has a weight average molecular weight between 500 kDa and 5000 kDa. In an embodiment, the isolated serotype 3 capsular polysaccharide has a weight average molecular weight between 500 kDa and 4000 kDa. In an embodiment, the isolated serotype 3 capsular polysaccharide has a weight average molecular weight between 500 kDa and 3000 kDa. In an embodiment, the isolated serotype 3 capsular polysaccharide has a weight average molecular weight between 500 kDa and 2000 kDa. In an embodiment, the isolated serotype 3 capsular polysaccharide has a weight average molecular weight between 500 kDa and 1500 kDa. In an embodiment, the isolated serotype 3 capsular polysaccharide has a weight average molecular weight between 500 kDa and 1000 kDa.

In an embodiment, the isolated serotype 3 capsular polysaccharide has a weight average molecular weight between 750 kDa and 5000 kDa. In an embodiment, the isolated serotype 3 capsular polysaccharide has a weight average molecular weight between 750 kDa and 4000 kDa. In an embodiment, the isolated serotype 3 capsular polysaccharide has a weight average molecular weight between 750 kDa and 3000 kDa. In an embodiment, the isolated serotype 3 capsular polysaccharide has a weight average molecular weight between 750 kDa and 2000 kDa. In an embodiment, the isolated serotype 3 capsular polysaccharide has a weight average molecular weight between 750 kDa and 1500 kDa. In an embodiment, the isolated serotype 3 capsular polysaccharide has a weight average molecular weight between 750 kDa and 1000 kDa.

In an embodiment, the isolated serotype 3 capsular polysaccharide has a weight average molecular weight between 1000 kDa and 5000 kDa. In an embodiment, the isolated serotype 3 capsular polysaccharide has a weight average molecular weight between 1000 kDa and 4000 kDa. In an embodiment, the isolated serotype 3 capsular polysaccharide has a weight average molecular weight between 1000 kDa and 3000 kDa. In an embodiment, the isolated serotype 3 capsular polysaccharide has a weight average molecular weight between 1000 kDa and 2000 kDa. In an embodiment, the isolated serotype 3 capsular polysaccharide has a weight average molecular weight between 1000 kDa and 1500 kDa.

In an embodiment, the isolated serotype 3 capsular polysaccharide has a weight average molecular weight between 1500 kDa and 5000 kDa. In an embodiment, the isolated serotype 3 capsular polysaccharide has a weight average molecular weight between 1500 kDa and 4000 kDa. In an embodiment, the isolated serotype 3 capsular polysaccharide has a weight average molecular weight between 1500 kDa and 3000 kDa. In an embodiment, the isolated serotype 3 capsular polysaccharide has a weight average molecular weight between 1500 kDa and 2000 kDa.

In an embodiment, the isolated serotype 3 capsular polysaccharide has a weight average molecular weight between 2000 kDa and 5000 kDa. In an embodiment, the isolated serotype 3 capsular polysaccharide has a weight average molecular weight between 2000 kDa and 4000 kDa. In an embodiment, the isolated serotype 3 capsular polysaccharide has a weight average molecular weight between 2000 kDa and 3000 kDa.

In an embodiment, the isolated serotype 3 capsular polysaccharide has a weight average molecular weight between 2500 kDa and 5000 kDa. In an embodiment, the isolated serotype 3 capsular polysaccharide has a weight average molecular weight between 2500 kDa and 4000 kDa. In an embodiment, the isolated serotype 3 capsular polysaccharide has a weight average molecular weight between 2500 kDa and 3000 kDa.

Any whole number integer within any of the above ranges is contemplated as an embodiment of the disclosure.

Preferably, in order to generate serotype 3 conjugates with advantageous filterability characteristics, immunogenicity and/or yields, sizing of the polysaccharide to a target molecular weight range is performed prior to the conjugation to a carrier protein.

Advantageously, the size of the purified serotype 3 polysaccharide is reduced while preserving critical features of the structure of the polysaccharide. Mechanical or chemical sizing maybe employed. In an embodiment, the size of the purified serotype 3 polysaccharide is reduced by chemical hydrolysis. Chemical hydrolysis maybe conducted using a mild acid (e.g. acetic acid, formic acid, propanoic acid). In an embodiment, chemical hydrolysis is conducted using formic acid. In an embodiment, chemical hydrolysis is conducted using propanoic acid. In a preferred embodiment, chemical hydrolysis is conducted using acetic acid. Chemical hydrolysis may also be conducted using a diluted strong acid (such as diluted hydrochloric acid, diluted sulfuric acid, diluted phosphoric acid, diluted nitric acid or diluted perchloric acid). In an embodiment, chemical hydrolysis is conducted using diluted hydrochloric acid. In an embodiment, chemical hydrolysis is conducted using diluted sulfuric acid. In an embodiment, chemical hydrolysis is conducted using diluted phosphoric acid. In an embodiment, chemical hydrolysis is conducted using diluted nitric acid. In an embodiment, chemical hydrolysis is conducted using diluted perchloric acid. The size of the purified serotype 3 polysaccharide can also be reduced by mechanical homogenization. In an embodiment, the size of the purified serotype 3 polysaccharide is reduced by high pressure homogenization. High pressure homogenization achieves high shear rates by pumping the process stream through a flow path with sufficiently small dimensions. The shear rate is increased by using a larger applied homogenization pressure, and exposure time can be increased by recirculating the feed stream through the homogenizer.

The high-pressure homogenization process can be appropriate for reducing the size of the purified serotype 3 polysaccharide while preserving the structural features of the polysaccharide.

In a preferred embodiment, the isolated serotype 3 capsular polysaccharide is sized to a weight average molecular weight between 5 kDa and 1000 kDa. In an embodiment, the isolated serotype 3 capsular polysaccharide is sized to a weight average molecular weight between 5 kDa and 900 kDa. In an embodiment, the isolated serotype 3 capsular polysaccharide is sized to a weight average molecular weight between 5 kDa and 800 kDa. In an embodiment, the isolated serotype 3 capsular polysaccharide is sized to a weight average molecular weight between 5 kDa and 700 kDa. In an embodiment, the isolated serotype 3 capsular polysaccharide is sized to a weight average molecular weight between 5 kDa and 600 kDa. In an embodiment, the isolated serotype 3 capsular polysaccharide is sized to a weight average molecular weight between 5 kDa and 500 kDa. In an embodiment, the isolated serotype 3 capsular polysaccharide is sized to a weight average molecular weight between 5 kDa and 450 kDa. In an embodiment, the isolated serotype 3 capsular polysaccharide is sized to a weight average molecular weight between 5 kDa and 400 kDa. In an embodiment, the isolated serotype 3 capsular polysaccharide is sized to a weight average molecular weight between 5 kDa and 350 kDa. In an embodiment, the isolated serotype 3 capsular polysaccharide is sized to a weight average molecular weight between 5 kDa and 300 kDa. In an embodiment, the isolated serotype 3 capsular polysaccharide is sized to a weight average molecular weight between 5 kDa and 250 kDa. In an embodiment, the isolated serotype 3 capsular polysaccharide is sized to a weight average molecular weight between 5 kDa and 200 kDa. In an embodiment, the isolated serotype 3 capsular polysaccharide is sized to a weight average molecular weight between 5 kDa and 150 kDa. In an embodiment, the isolated serotype 3 capsular polysaccharide is sized to a weight average molecular weight between 5 kDa and 100 kDa. In an embodiment, the isolated serotype 3 capsular polysaccharide is sized to a weight average molecular weight between 5 kDa and 50 kDa.

In an embodiment, the isolated serotype 3 capsular polysaccharide is sized to a weight average molecular weight between 50 kDa and 1000 kDa. In an embodiment, the isolated serotype 3 capsular polysaccharide is sized to a weight average molecular weight between 50 kDa and 900 kDa. In an embodiment, the isolated serotype 3 capsular polysaccharide is sized to a weight average molecular weight between 50 kDa and 800 kDa. In an embodiment, the isolated serotype 3 capsular polysaccharide is sized to a weight average molecular weight between 50 kDa and 700 kDa. In an embodiment, the isolated serotype 3 capsular polysaccharide is sized to a weight average molecular weight between 50 kDa and 600 kDa. In an embodiment, the isolated serotype 3 capsular polysaccharide is sized to a weight average molecular weight between 50 kDa and 500 kDa. In an embodiment, the isolated serotype 3 capsular polysaccharide is sized to a weight average molecular weight between 50 kDa and 450 kDa. In an embodiment, the isolated serotype 3 capsular polysaccharide is sized to a weight average molecular weight between 50 kDa and 400 kDa. In an embodiment, the isolated serotype 3 capsular polysaccharide is sized to a weight average molecular weight between 50 kDa and 350 kDa. In an embodiment, the isolated serotype 3 capsular polysaccharide is sized to a weight average molecular weight between 50 kDa and 300 kDa. In an embodiment, the isolated serotype 3 capsular polysaccharide is sized to a weight average molecular weight between 50 kDa and 250 kDa. In an embodiment, the isolated serotype 3 capsular polysaccharide is sized to a weight average molecular weight between 50 kDa and 200 kDa. In an embodiment, the isolated serotype 3 capsular polysaccharide is sized to a weight average molecular weight between 50 kDa and 150 kDa. In an embodiment, the isolated serotype 3 capsular polysaccharide is sized to a weight average molecular weight between 50 kDa and 100 kDa.

In an embodiment, the isolated serotype 3 capsular polysaccharide is sized to a weight average molecular weight between 100 kDa and 1000 kDa. In an embodiment, the isolated serotype 3 capsular polysaccharide is sized to a weight average molecular weight between 100 kDa and 900 kDa. In an embodiment, the isolated serotype 3 capsular polysaccharide is sized to a weight average molecular weight between 100 kDa and 800 kDa. In an embodiment, the isolated serotype 3 capsular polysaccharide is sized to a weight average molecular weight between 100 kDa and 700 kDa. In an embodiment, the isolated serotype 3 capsular polysaccharide is sized to a weight average molecular weight between 100 kDa and 600 kDa. In an embodiment, the isolated serotype 3 capsular polysaccharide is sized to a weight average molecular weight between 100 kDa and 500 kDa. In an embodiment, the isolated serotype 3 capsular polysaccharide is sized to a weight average molecular weight between 100 kDa and 450 kDa. In an embodiment, the isolated serotype 3 capsular polysaccharide is sized to a weight average molecular weight between 100 kDa and 400 kDa. In an embodiment, the isolated serotype 3 capsular polysaccharide is sized to a weight average molecular weight between 100 kDa and 350 kDa. In an embodiment, the isolated serotype 3 capsular polysaccharide is sized to a weight average molecular weight between 100 kDa and 300 kDa. In an embodiment, the isolated serotype 3 capsular polysaccharide is sized to a weight average molecular weight between 100 kDa and 250 kDa. In an embodiment, the isolated serotype 3 capsular polysaccharide is sized to a weight average molecular weight between 100 kDa and 200 kDa. In an embodiment, the isolated serotype 3 capsular polysaccharide is sized to a weight average molecular weight between 100 kDa and 150 kDa.

In an embodiment, the isolated serotype 3 capsular polysaccharide is sized to a weight average molecular weight between 110 kDa and 150 kDa. In an embodiment, the isolated serotype 3 capsular polysaccharide is sized to a weight average molecular weight between 120 kDa and 150 kDa. In an embodiment, the isolated serotype 3 capsular polysaccharide is sized to a weight average molecular weight between 110 kDa and 150 kDa. In an embodiment, the isolated serotype 3 capsular polysaccharide is sized to a weight average molecular weight between 130 kDa and 150 kDa. In an embodiment, the isolated serotype 3 capsular polysaccharide is sized to a weight average molecular weight between 120 kDa and 150 kDa. In an embodiment, the isolated serotype 3 capsular polysaccharide is sized to a weight average molecular weight between 120 kDa and 140 kDa. In an embodiment, the isolated serotype 3 capsular polysaccharide is sized to a weight average molecular weight between 120 kDa and 130 kDa. In an embodiment, the isolated serotype 3 capsular polysaccharide is sized to a weight average molecular weight between 130 kDa and 150 kDa. In an embodiment, the isolated serotype 3 capsular polysaccharide is sized to a weight average molecular weight between 130 kDa and 140 kDa.

In an embodiment, the isolated serotype 3 capsular polysaccharide is sized to a weight average molecular weight between 150 kDa and 1000 kDa. In an embodiment, the isolated serotype 3 capsular polysaccharide is sized to a weight average molecular weight between 150 kDa and 900 kDa. In an embodiment, the isolated serotype 3 capsular polysaccharide is sized to a weight average molecular weight between 150 kDa and 800 kDa. In an embodiment, the isolated serotype 3 capsular polysaccharide is sized to a weight average molecular weight between 150 kDa and 700 kDa. In an embodiment, the isolated serotype 3 capsular polysaccharide is sized to a weight average molecular weight between 150 kDa and 600 kDa. In an embodiment, the isolated serotype 3 capsular polysaccharide is sized to a weight average molecular weight between 150 kDa and 500 kDa. In an embodiment, the isolated serotype 3 capsular polysaccharide is sized to a weight average molecular weight between 150 kDa and 450 kDa. In an embodiment, the isolated serotype 3 capsular polysaccharide is sized to a weight average molecular weight between 150 kDa and 400 kDa. In an embodiment, the isolated serotype 3 capsular polysaccharide is sized to a weight average molecular weight between 150 kDa and 350 kDa. In an embodiment, the isolated serotype 3 capsular polysaccharide is sized to a weight average molecular weight between 150 kDa and 300 kDa. In an embodiment, the isolated serotype 3 capsular polysaccharide is sized to a weight average molecular weight between 150 kDa and 250 kDa. In an embodiment, the isolated serotype 3 capsular polysaccharide is sized to a weight average molecular weight between 150 kDa and 200 kDa.

In an embodiment, the isolated serotype 3 capsular polysaccharide is sized to a weight average molecular weight between 200 kDa and 1000 kDa. In an embodiment, the isolated serotype 3 capsular polysaccharide is sized to a weight average molecular weight between 200 kDa and 900 kDa. In an embodiment, the isolated serotype 3 capsular polysaccharide is sized to a weight average molecular weight between 200 kDa and 800 kDa. In an embodiment, the isolated serotype 3 capsular polysaccharide is sized to a weight average molecular weight between 200 kDa and 700 kDa. In an embodiment, the isolated serotype 3 capsular polysaccharide is sized to a weight average molecular weight between 200 kDa and 600 kDa. In an embodiment, the isolated serotype 3 capsular polysaccharide is sized to a weight average molecular weight between 200 kDa and 500 kDa. In an embodiment, the isolated serotype 3 capsular polysaccharide is sized to a weight average molecular weight between 200 kDa and 450 kDa. In an embodiment, the isolated serotype 3 capsular polysaccharide is sized to a weight average molecular weight between 200 kDa and 400 kDa. In an embodiment, the isolated serotype 3 capsular polysaccharide is sized to a weight average molecular weight between 200 kDa and 350 kDa. In an embodiment, the isolated serotype 3 capsular polysaccharide is sized to a weight average molecular weight between 200 kDa and 300 kDa. In an embodiment, the isolated serotype 3 capsular polysaccharide is sized to a weight average molecular weight between 200 kDa and 250 kDa.

In an embodiment, the isolated serotype 3 capsular polysaccharide is sized to a weight average molecular weight between 250 kDa and 1000 kDa. In an embodiment, the isolated serotype 3 capsular polysaccharide is sized to a weight average molecular weight between 250 kDa and 900 kDa. In an embodiment, the isolated serotype 3 capsular polysaccharide is sized to a weight average molecular weight between 250 kDa and 800 kDa. In an embodiment, the isolated serotype 3 capsular polysaccharide is sized to a weight average molecular weight between 250 kDa and 700 kDa. In an embodiment, the isolated serotype 3 capsular polysaccharide is sized to a weight average molecular weight between 250 kDa and 600 kDa. In an embodiment, the isolated serotype 3 capsular polysaccharide is sized to a weight average molecular weight between 250 kDa and 500 kDa. In an embodiment, the isolated serotype 3 capsular polysaccharide is sized to a weight average molecular weight between 250 kDa and 450 kDa. In an embodiment, the isolated serotype 3 capsular polysaccharide is sized to a weight average molecular weight between 250 kDa and 400 kDa. In an embodiment, the isolated serotype 3 capsular polysaccharide is sized to a weight average molecular weight between 250 kDa and 350 kDa. In an embodiment, the isolated serotype 3 capsular polysaccharide is sized to a weight average molecular weight between 250 kDa and 300 kDa.

In an embodiment, the isolated serotype 3 capsular polysaccharide is sized to a weight average molecular weight between 300 kDa and 1000 kDa. In an embodiment, the isolated serotype 3 capsular polysaccharide is sized to a weight average molecular weight between 300 kDa and 900 kDa. In an embodiment, the isolated serotype 3 capsular polysaccharide is sized to a weight average molecular weight between 300 kDa and 800 kDa. In an embodiment, the isolated serotype 3 capsular polysaccharide is sized to a weight average molecular weight between 300 kDa and 700 kDa. In an embodiment, the isolated serotype 3 capsular polysaccharide is sized to a weight average molecular weight between 300 kDa and 600 kDa. In an embodiment, the isolated serotype 3 capsular polysaccharide is sized to a weight average molecular weight between 300 kDa and 500 kDa. In an embodiment, the isolated serotype 3 capsular polysaccharide is sized to a weight average molecular weight between 300 kDa and 450 kDa. In an embodiment, the isolated serotype 3 capsular polysaccharide is sized to a weight average molecular weight between 300 kDa and 400 kDa. In an embodiment, the isolated serotype 3 capsular polysaccharide is sized to a weight average molecular weight between 300 kDa and 350 kDa.

In an embodiment, the isolated serotype 3 capsular polysaccharide is sized to a weight average molecular weight between 350 kDa and 1000 kDa. In an embodiment, the isolated serotype 3 capsular polysaccharide is sized to a weight average molecular weight between 350 kDa and 900 kDa. In an embodiment, the isolated serotype 3 capsular polysaccharide is sized to a weight average molecular weight between 350 kDa and 800 kDa. In an embodiment, the isolated serotype 3 capsular polysaccharide is sized to a weight average molecular weight between 350 kDa and 700 kDa. In an embodiment, the isolated serotype 3 capsular polysaccharide is sized to a weight average molecular weight between 350 kDa and 600 kDa. In an embodiment, the isolated serotype 3 capsular polysaccharide is sized to a weight average molecular weight between 350 kDa and 500 kDa. In an embodiment, the isolated serotype 3 capsular polysaccharide is sized to a weight average molecular weight between 350 kDa and 450 kDa. In an embodiment, the isolated serotype 3 capsular polysaccharide is sized to a weight average molecular weight between 350 kDa and 400 kDa.

In an embodiment, the isolated serotype 3 capsular polysaccharide is sized to a weight average molecular weight between 400 kDa and 1000 kDa. In an embodiment, the isolated serotype 3 capsular polysaccharide is sized to a weight average molecular weight between 400 kDa and 900 kDa. In an embodiment, the isolated serotype 3 capsular polysaccharide is sized to a weight average molecular weight between 400 kDa and 800 kDa. In an embodiment, the isolated serotype 3 capsular polysaccharide is sized to a weight average molecular weight between 400 kDa and 700 kDa. In an embodiment, the isolated serotype 3 capsular polysaccharide is sized to a weight average molecular weight between 400 kDa and 600 kDa. In an embodiment, the isolated serotype 3 capsular polysaccharide is sized to a weight average molecular weight between 400 kDa and 500 kDa. In an embodiment, the isolated serotype 3 capsular polysaccharide is sized to a weight average molecular weight between 400 kDa and 450 kDa.

In an embodiment, the isolated serotype 3 capsular polysaccharide is sized to a weight average molecular weight between 450 kDa and 1000 kDa. In an embodiment, the isolated serotype 3 capsular polysaccharide is sized to a weight average molecular weight between 450 kDa and 900 kDa. In an embodiment, the isolated serotype 3 capsular polysaccharide is sized to a weight average molecular weight between 450 kDa and 800 kDa. In an embodiment, the isolated serotype 3 capsular polysaccharide is sized to a weight average molecular weight between 450 kDa and 700 kDa. In an embodiment, the isolated serotype 3 capsular polysaccharide is sized to a weight average molecular weight between 450 kDa and 600 kDa. In an embodiment, the isolated serotype 3 capsular polysaccharide is sized to a weight average molecular weight between 450 kDa and 500 kDa.

In an embodiment, the isolated serotype 3 capsular polysaccharide is sized to a weight average molecular weight between 500 kDa and 1000 kDa. In an embodiment, the isolated serotype 3 capsular polysaccharide is sized to a weight average molecular weight between 500 kDa and 900 kDa. In an embodiment, the isolated serotype 3 capsular polysaccharide is sized to a weight average molecular weight between 500 kDa and 800 kDa. In an embodiment, the isolated serotype 3 capsular polysaccharide is sized to a weight average molecular weight between 500 kDa and 700 kDa. In an embodiment, the isolated serotype 3 capsular polysaccharide is sized to a weight average molecular weight between 500 kDa and 600 kDa.

In an embodiment, the isolated serotype 3 capsular polysaccharide is sized to a weight average molecular weight between 500 kDa and 1000 kDa. In an embodiment, the isolated serotype 3 capsular polysaccharide is sized to a weight average molecular weight between 500 kDa and 900 kDa. In an embodiment, the isolated serotype 3 capsular polysaccharide is sized to a weight average molecular weight between 500 kDa and 800 kDa. In an embodiment, the isolated serotype 3 capsular polysaccharide is sized to a weight average molecular weight between 500 kDa and 700 kDa. In an embodiment, the isolated serotype 3 capsular polysaccharide is sized to a weight average molecular weight between 500 kDa and 600 kDa.

In an embodiment, the isolated serotype 3 capsular polysaccharide is sized to a weight average molecular weight between 600 kDa and 1000 kDa. In an embodiment, the isolated serotype 3 capsular polysaccharide is sized to a weight average molecular weight between 600 kDa and 900 kDa. In an embodiment, the isolated serotype 3 capsular polysaccharide is sized to a weight average molecular weight between 600 kDa and 800 kDa. In an embodiment, the isolated serotype 3 capsular polysaccharide is sized to a weight average molecular weight between 600 kDa and 700 kDa.

In an embodiment, the isolated serotype 3 capsular polysaccharide is sized to a weight average molecular weight between 700 kDa and 1000 kDa. In an embodiment, the isolated serotype 3 capsular polysaccharide is sized to a weight average molecular weight between 700 kDa and 900 kDa. In an embodiment, the isolated serotype 3 capsular polysaccharide is sized to a weight average molecular weight between 700 kDa and 800 kDa.

In an embodiment, the isolated serotype 3 capsular polysaccharide is sized to a weight average molecular weight between 800 kDa and 1000 kDa. In an embodiment, the isolated serotype 3 capsular polysaccharide is sized to a weight average molecular weight between 800 kDa and 900 kDa.

In an embodiment, the isolated serotype 3 capsular polysaccharide is sized to a weight average molecular weight between 900 kDa and 1000 kDa.

In an embodiment, the isolated serotype 3 capsular polysaccharide is sized to a weight average molecular weight of about 5 kDa. In an embodiment, the isolated serotype 3 capsular polysaccharide is sized to a weight average molecular weight of about 50 kDa.

In an embodiment, the isolated serotype 3 capsular polysaccharide is sized to a weight average molecular weight of about 100 kDa. In an embodiment, the isolated serotype 3 capsular polysaccharide is sized to a weight average molecular weight of about 110 kDa.

In an embodiment, the isolated serotype 3 capsular polysaccharide is sized to a weight average molecular weight of about 120 kDa. In an embodiment, the isolated serotype 3 capsular polysaccharide is sized to a weight average molecular weight of about 130 kDa.

In an embodiment, the isolated serotype 3 capsular polysaccharide is sized to a weight average molecular weight of about 140 kDa. In an embodiment, the isolated serotype 3 capsular polysaccharide is sized to a weight average molecular weight of about 150 kDa.

In an embodiment, the isolated serotype 3 capsular polysaccharide is sized to a weight average molecular weight of about 160 kDa. In an embodiment, the isolated serotype 3 capsular polysaccharide is sized to a weight average molecular weight of about 170 kDa.

In an embodiment, the isolated serotype 3 capsular polysaccharide is sized to a weight average molecular weight of about 180 kDa. In an embodiment, the isolated serotype 3 capsular polysaccharide is sized to a weight average molecular weight of about 190 kDa.

In an embodiment, the isolated serotype 3 capsular polysaccharide is sized to a weight average molecular weight of about 200 kDa. In an embodiment, the isolated serotype 3 capsular polysaccharide is sized to a weight average molecular weight of about 250 kDa.

In an embodiment, the isolated serotype 3 capsular polysaccharide is sized to a weight average molecular weight of about 300 kDa. In an embodiment, the isolated serotype 3 capsular polysaccharide is sized to a weight average molecular weight of about 350 kDa.

In an embodiment, the isolated serotype 3 capsular polysaccharide is sized to a weight average molecular weight of about 400 kDa. In an embodiment, the isolated serotype 3 capsular polysaccharide is sized to a weight average molecular weight of about 450 kDa.

In an embodiment, the isolated serotype 3 capsular polysaccharide is sized to a weight average molecular weight of about 500 kDa. In an embodiment, the isolated serotype 3 capsular polysaccharide is sized to a weight average molecular weight of about 550 kDa.

In an embodiment, the isolated serotype 3 capsular polysaccharide is sized to a weight average molecular weight of about 600 kDa. In an embodiment, the isolated serotype 3 capsular polysaccharide is sized to a weight average molecular weight of about 700 kDa.

In an embodiment, the isolated serotype 3 capsular polysaccharide is sized to a weight average molecular weight of about 800 kDa. In an embodiment, the isolated serotype 3 capsular polysaccharide is sized to a weight average molecular weight of about 900 kDa.

In an embodiment, the isolated serotype 3 capsular polysaccharide is sized to a weight average molecular weight of about 1000 kDa.

In an embodiment, the isolated serotype 3 capsular polysaccharide is not sized.

The isolated serotype 3 capsular polysaccharide described above may be activated (e.g., chemically activated) to make them capable of reacting (e.g. with a linker or directly with the carrier protein) and then incorporated into glycoconjugates, as further described herein.

For the purposes of the invention the term 'glycoconjugate' indicates a saccharide covalently linked to a carrier protein. In one embodiment a saccharide is linked directly to a carrier protein. In a second embodiment a saccharide is linked to a carrier protein through a spacer/linker.

In general, covalent conjugation of saccharides to carriers enhances the immunogenicity of saccharides as it converts them from T-independent antigens to T-dependent antigens, thus allowing priming for immunological memory. Conjugation is particularly useful for pediatric vaccines.

1.2 *Streptococcus pneumoniae* Serotype 3 Glycoconjugates of the Invention

In some embodiments, the serotype 3 glycoconjugate of the present invention comprises a serotype 3 capsular polysaccharide wherein the weight average molecular weight (Mw) of said polysaccharide before conjugation is between 10 kDa and 2,000 kDa.

The weight average molecular weight (Mw) of the saccharide before conjugation refers to the Mw before the activation of the polysaccharide (i.e. after an eventual sizing step but before reacting the polysaccharide with an activating agent). In the context of the present invention the Mw of the polysaccharide is not substantially modified by the activation step and the Mw of the polysaccharide incorporated in the conjugate is similar to the Mw of the polysaccharide as measured before activation. In an embodiment, the polysaccharide is activated with a carbonic acid derivative (e.g. CDI or CDT) in combination with an azido linker (see sections 1.3 below). In an embodiment, the polysaccharide is activated with CDI in combination with an azido linker (see sections 1.3 below). In an embodiment, the polysaccharide is activated with CDT in combination with an azido linker (see sections 1.3 below).

In an embodiment, the serotype 3 glycoconjugate of the present invention comprises a serotype 3 capsular polysaccharide wherein the weight average molecular weight (Mw) of said polysaccharide before conjugation is between 50 kDa and 1,000 kDa. In an embodiment, the weight average molecular weight (Mw) is between 50 kDa and 750 kDa. In an embodiment, the weight average molecular weight (Mw) is between 50 kDa and 700 kDa. In an embodiment, the weight average molecular weight (Mw) is between 50 kDa and 600 kDa. In an embodiment, the weight average molecular weight (Mw) is between 50 kDa and 500 kDa. In an embodiment, the weight average molecular weight (Mw) is between 50 kDa and 400 kDa. In an embodiment, the weight average molecular weight (Mw) is between 50 kDa and 300 kDa. In an embodiment, the weight average molecular weight (Mw) is between 50 kDa and 200 kDa. In an embodiment, the weight average molecular weight (Mw) is between 50 kDa and 150 kDa. In an embodiment, the weight average molecular weight (Mw) is between 50 kDa and 140 kDa. In an embodiment, the weight average molecular weight (Mw) is between 50 kDa and 130 kDa. In an embodiment, the weight average molecular weight (Mw) is between 50 kDa and 120 kDa. In an embodiment, the weight average molecular weight (Mw) is between 50 kDa and 110 kDa.

In an embodiment, the serotype 3 glycoconjugate of the present invention comprises a serotype 3 capsular polysaccharide wherein the weight average molecular weight (Mw) of said polysaccharide before conjugation is between 75 kDa and 1,000 kDa. In an embodiment, the weight average molecular weight (Mw) is between 75 kDa and 750 kDa. In an embodiment, the weight average molecular weight (Mw) is between 75 kDa and 700 kDa. In an embodiment, the weight average molecular weight (Mw) is between 75 kDa and 600 kDa. In an embodiment, the weight average molecular weight (Mw) is between 75 kDa and 500 kDa. In an embodiment, the weight average molecular weight (Mw) is between 75 kDa and 400 kDa. In an embodiment, the weight average molecular weight (Mw) is between 75 kDa and 300 kDa. In an embodiment, the weight average molecular weight (Mw) is between 75 kDa and 200 kDa. In an embodiment, the weight average molecular weight (Mw) is between 75 kDa and 150 kDa. In an embodiment, the weight average molecular weight (Mw) is between 75 kDa and 140 kDa. In an embodiment, the weight average molecular weight (Mw) is between 75 kDa and 130 kDa. In an embodiment, the weight average molecular weight (Mw) is between 75 kDa and 120 kDa. In an embodiment, the weight average molecular weight (Mw) is between 75 kDa and 110 kDa.

In an embodiment, the serotype 3 glycoconjugate of the present invention comprises a serotype 3 capsular polysaccharide wherein the weight average molecular weight (Mw) of said polysaccharide before conjugation is between 100 kDa and 1,000 kDa. In an embodiment, the weight average molecular weight (Mw) is between 100 kDa and 750 kDa. In an embodiment, the weight average molecular weight (Mw) is between 100 kDa and 700 kDa. In an embodiment, the weight average molecular weight (Mw) is between 100 kDa and 600 kDa. In an embodiment, the weight average molecular weight (Mw) is between 100 kDa and 500 kDa. In an embodiment, the weight average molecular weight (Mw) is between 100 kDa and 400 kDa. In an embodiment, the weight average molecular weight (Mw) is between 100 kDa and 300 kDa. In an embodiment, the weight average molecular weight (Mw) is between 100 kDa and 200 kDa. In an embodiment, the weight average molecular weight (Mw) is between 100 kDa and 150 kDa. In an embodiment, the weight average molecular weight (Mw) is between 100 kDa and 140 kDa. In an embodiment, the weight average molecular weight (Mw) is between 100 kDa and 130 kDa. In an embodiment, the weight average molecular weight (Mw) is between 100 kDa and 120 kDa. In an embodiment, the weight average molecular weight (Mw) is between 100 kDa and 110 kDa.

In an embodiment, the serotype 3 glycoconjugate of the present invention comprises a serotype 3 capsular polysaccharide wherein the weight average molecular weight (Mw) of said polysaccharide before conjugation is between 125 kDa and 1,000 kDa. In an embodiment, the weight average molecular weight (Mw) is between 125 kDa and 750 kDa. In an embodiment, the weight average molecular weight (Mw) is between 125 kDa and 700 kDa. In an embodiment, the weight average molecular weight (Mw) is between 125 kDa and 600 kDa. In an embodiment, the weight average molecular weight (Mw) is between 125 kDa and 500 kDa. In an embodiment, the weight average molecular weight (Mw) is between 125 kDa and 400 kDa. In an embodiment, the weight average molecular weight (Mw) is between 125 kDa and 300 kDa. In an embodiment, the weight average molecular weight (Mw) is between 125 kDa and 200 kDa. In an embodiment, the weight average molecular weight (Mw) is between 125 kDa and 150 kDa. In an embodiment, the weight average molecular weight (Mw) is between 125 kDa and 140 kDa. In an embodiment, the weight average molecular weight (Mw) is between 125 kDa and 130 kDa.

In an embodiment, the serotype 3 glycoconjugate of the present invention comprises a serotype 3 capsular polysaccharide wherein the weight average molecular weight (Mw) of said polysaccharide before conjugation is between 130 kDa and 1,000 kDa. In an embodiment, the weight average molecular weight (Mw) is between 130 kDa and 750 kDa. In an embodiment, the weight average molecular weight (Mw) is between 130 kDa and 700 kDa. In an embodiment, the weight average molecular weight (Mw) is between 130 kDa and 600 kDa. In an embodiment, the weight average molecular weight (Mw) is between 130 kDa and 500 kDa. In an embodiment, the weight average molecular weight (Mw) is between 130 kDa and 400 kDa. In an embodiment, the weight average molecular weight (Mw) is between 130 kDa and 300 kDa. In an embodiment, the weight average molecular weight (Mw) is between 130 kDa and 200 kDa. In an embodiment, the weight average molecular weight (Mw) is between 130 kDa and 150 kDa. In an embodiment, the weight average molecular weight (Mw) is between 130 kDa and 140 kDa.

In an embodiment, the serotype 3 glycoconjugate of the present invention comprises a serotype 3 capsular polysaccharide wherein the weight average molecular weight (Mw) of said polysaccharide before conjugation is between 150 kDa and 1,000 kDa. In an embodiment, the weight average molecular weight (Mw) is between 150 kDa and 750 kDa. In an embodiment, the weight average molecular weight (Mw) is between 150 kDa and 700 kDa. In an embodiment, the weight average molecular weight (Mw) is between 150 kDa and 600 kDa. In an embodiment, the weight average molecular weight (Mw) is between 150 kDa and 500 kDa. In an embodiment, the weight average molecular weight (Mw) is between 150 kDa and 400 kDa. In an embodiment, the weight average molecular weight (Mw) is between 150 kDa and 300 kDa. In an embodiment, the weight average molecular weight (Mw) is between 150 kDa and 200 kDa.

In an embodiment, the serotype 3 glycoconjugate of the present invention comprises a serotype 3 capsular polysaccharide wherein the weight average molecular weight (Mw) of said polysaccharide before conjugation is between 200 kDa and 1,000 kDa. In an embodiment, the weight average molecular weight (Mw) is between 200 kDa and 750 kDa. In an embodiment, the weight average molecular weight (Mw) is between 200 kDa and 700 kDa. In an embodiment, the weight average molecular weight (Mw) is between 200 kDa and 600 kDa. In an embodiment, the weight average molecular weight (Mw) is between 200 kDa and 500 kDa. In an embodiment, the weight average molecular weight (Mw) is between 200 kDa and 400 kDa. In an embodiment, the weight average molecular weight (Mw) is between 200 kDa and 300 kDa.

In an embodiment, the serotype 3 glycoconjugate of the present invention comprises a serotype 3 capsular polysaccharide wherein the weight average molecular weight (Mw) of said polysaccharide before conjugation is between 300 kDa and 1,000 kDa. In an embodiment, the weight average molecular weight (Mw) is between 300 kDa and 750 kDa. In an embodiment, the weight average molecular weight (Mw) is between 300 kDa and 700 kDa. In an embodiment, the weight average molecular weight (Mw) is between 300 kDa and 600 kDa. In an embodiment, the weight average molecular weight (Mw) is between 300 kDa and 500 kDa. In an embodiment, the weight average molecular weight (Mw) is between 300 kDa and 400 kDa.

In an embodiment, the serotype 3 glycoconjugate of the present invention comprises a serotype 3 capsular polysaccharide wherein the weight average molecular weight (Mw) of said polysaccharide before conjugation is between 400 kDa and 1,000 kDa. In an embodiment, the weight average molecular weight (Mw) is between 400 kDa and 750 kDa. In an embodiment, the weight average molecular weight (Mw) is between 400 kDa and 700 kDa. In an embodiment, the weight average molecular weight (Mw) is between 400 kDa and 600 kDa. In an embodiment, the weight average molecular weight (Mw) is between 400 kDa and 500 kDa.

In an embodiment, the serotype 3 glycoconjugate of the present invention comprises a serotype 3 capsular polysaccharide wherein the weight average molecular weight (Mw) of said polysaccharide before conjugation is between 500 kDa and 1,000 kDa. In an embodiment, the weight average molecular weight (Mw) is between 500 kDa and 750 kDa. In an embodiment, the weight average molecular weight (Mw) is between 500 kDa and 700 kDa. In an embodiment, the weight average molecular weight (Mw) is between 500 kDa and 600 kDa.

In an embodiment, the serotype 3 glycoconjugate of the present invention comprises a serotype 3 capsular polysaccharide wherein the weight average molecular weight (Mw) of said polysaccharide before conjugation is between 600 kDa and 1,000 kDa. In an embodiment, the weight average molecular weight (Mw) is between 600 kDa and 750 kDa. In an embodiment, the weight average molecular weight (Mw) is between 600 kDa and 700 kDa.

In an embodiment, the serotype 3 glycoconjugate of the present invention comprises a serotype 3 capsular polysaccharide wherein the weight average molecular weight (Mw) of said polysaccharide before conjugation is between 700 kDa and 1,000 kDa. In an embodiment, the weight average molecular weight (Mw) is between 700 kDa and 750 kDa.

In an embodiment, the serotype 3 glycoconjugate of the present invention comprises a serotype 3 capsular polysaccharide wherein the weight average molecular weight (Mw) of said polysaccharide before conjugation is between 750 kDa and 1,000 kDa.

Any whole number integer within any of the above ranges is contemplated as an embodiment of the disclosure.

In an embodiment, the serotype 3 glycoconjugate of the present invention comprises a serotype 3 capsular polysaccharide wherein the weight average molecular weight (Mw) of said polysaccharide before conjugation is about 1,000 kDa. In an embodiment, the weight average molecular weight (Mw) is about 750 kDa. In an embodiment, the weight average molecular weight (Mw) is about 700 kDa. In an embodiment, the weight average molecular weight (Mw) is about 600 kDa. In an embodiment, the weight average molecular weight (Mw) is about 500 kDa. In an embodiment, the weight average molecular weight (Mw) is about 400 kDa. In an embodiment, the weight average molecular weight (Mw) is about 300 kDa. In an embodiment, the weight average molecular weight (Mw) is about 200 kDa. In an embodiment, the weight average molecular weight (Mw) is about 150 kDa. In an embodiment, the weight average molecular weight (Mw) is about 140 kDa. In an embodiment, the weight average molecular weight (Mw) is about 130 kDa. In an embodiment, the weight average molecular weight (Mw) is about 120 kDa. In an embodiment, the weight average molecular weight (Mw) is about 110 kDa. In an embodiment, the weight average molecular weight (Mw) is about 100 kDa.

In some such embodiments, the serotype 3 glycoconjugates are prepared using click chemistry (see section 1.3).

In some embodiments, the serotype 3 glycoconjugate of the invention has a weight average molecular weight (Mw) of between 250 kDa and 20,000 kDa. In other embodiments, the serotype 3 glycoconjugate has a weight average molecular weight (Mw) of between 500 kDa and 15,000 kDa. In yet other embodiments, the serotype 3 glycoconjugate has a weight average molecular weight (Mw) of between 500 kDa and 10,000 kDa.

In other embodiments, the serotype 3 glycoconjugate has a weight average molecular weight (Mw) of between 250 kDa and 10,000 kDa. In other embodiments, the serotype 3 glycoconjugate has a weight average molecular weight (Mw) of between 250 kDa and 9,000 kDa. In other embodiments, the serotype 3 glycoconjugate has a weight average molecular weight (Mw) of between 250 kDa and 8,000 kDa. In still other embodiments, the serotype 3 glycoconjugate has a weight average molecular weight (Mw) of between 250 kDa and 7,000 kDa. In still other embodiments, the serotype 3 glycoconjugate has a weight average molecular weight (Mw) of between 250 kDa and 6,000 kDa. In still other embodiments, the serotype 3 glycoconjugate has a weight average molecular weight (Mw) of between 250 kDa and 5,000 kDa. In still other embodiments, the serotype 3 glycoconjugate has a weight average molecular weight (Mw) of between 250 kDa and 4,000 kDa. In still other embodiments, the serotype 3 glycoconjugate has a weight average molecular weight (Mw) of between 250 kDa and 3,000 kDa. In still other embodiments, the serotype 3 glycoconjugate has a weight average molecular weight (Mw) of between 250 kDa and 2,000 kDa. In still other embodiments, the serotype 3 glycoconjugate has a weight average molecular weight (Mw) of between 250 kDa and 1,500 kDa. In still other embodiments, the serotype 3 glycoconjugate has a weight average molecular weight (Mw) of between 250 kDa and 1,000 kDa. In still other embodiments, the serotype 3 glycoconjugate has a weight average molecular weight (Mw) of between 250 kDa and 750 kDa. In still other embodiments, the serotype 3 glycoconjugate has a weight average molecular weight (Mw) of between 250 kDa and 600 kDa. In still other embodiments, the serotype 3 glycoconjugate has a weight average molecular weight (Mw) of between 250 kDa and 500 kDa. In still other embodiments, the serotype 3 glycoconjugate has a weight average molecular weight (Mw) of between 250 kDa and 400 kDa.

In other embodiments, the serotype 3 glycoconjugate has a weight average molecular weight (Mw) of between 500 kDa and 10,000 kDa. In other embodiments, the serotype 3 glycoconjugate has a weight average molecular weight (Mw) of between 500 kDa and 9,000 kDa. In other embodiments, the serotype 3 glycoconjugate has a weight average molecular weight (Mw) of between 500 kDa and 8,000 kDa. In still other embodiments, the serotype 3 glycoconjugate has a weight average molecular weight (Mw) of between 500 kDa and 7,000 kDa. In still other embodiments, the serotype 3 glycoconjugate has a weight average molecular weight (Mw) of between 500 kDa and 6,000 kDa. In still other embodiments, the serotype 3 glycoconjugate has a weight average molecular weight (Mw) of between 500 kDa and 5,000 kDa. In still other embodiments, the serotype 3 glycoconjugate has a weight average molecular weight (Mw) of between 500 kDa and 4,000 kDa. In still other embodiments, the serotype 3 glycoconjugate has a weight average molecular weight (Mw) of between 500 kDa and 3,000 kDa. In still other embodiments, the serotype 3 glycoconjugate has a weight average molecular weight (Mw) of between 500 kDa and 2,000 kDa. In still other embodiments, the serotype 3 glycoconjugate has a weight average molecular weight (Mw) of between 500 kDa and 1,500 kDa. In still other embodiments, the serotype 3 glycoconjugate has a weight average molecular weight (Mw) of between 500 kDa and 1,000 kDa. In still other embodiments, the serotype 3 glycoconjugate has a weight average molecular weight (Mw) of between 500 kDa and 750 kDa. In still other embodiments, the serotype 3 glycoconjugate has a weight average molecular weight (Mw) of between 500 kDa and 600 kDa.

In other embodiments, the serotype 3 glycoconjugate has a weight average molecular weight (Mw) of between 750 kDa and 10,000 kDa. In other embodiments, the serotype 3 glycoconjugate has a weight average molecular weight (Mw) of between 750 kDa and 9,000 kDa. In other embodiments, the serotype 3 glycoconjugate has a weight average molecular weight (Mw) of between 750 kDa and 8,000 kDa. In still other embodiments, the serotype 3 glycoconjugate has a weight average molecular weight (Mw) of between 750 kDa and 7,000 kDa. In still other embodiments, the serotype 3 glycoconjugate has a weight average molecular weight (Mw) of between 750 kDa and 6,000 kDa. In still other embodiments, the serotype 3 glycoconjugate has a weight average molecular weight (Mw) of between 750 kDa and 5,000 kDa. In still other embodiments, the serotype 3 glycoconjugate has a weight average molecular weight (Mw) of between 750 kDa and 4,000 kDa. In still other embodiments, the serotype 3 glycoconjugate has a weight average molecular weight (Mw) of between 750 kDa and 3,000 kDa. In still other embodiments, the serotype 3 glycoconjugate has a weight average molecular weight (Mw) of between 750 kDa and 2,000 kDa. In still other embodiments, the serotype 3 glycoconjugate has a weight average molecular weight (Mw) of between 750 kDa and 1,500 kDa. In still other embodiments, the serotype 3 glycoconjugate has a weight average molecular weight (Mw) of between 750 kDa and 1,000 kDa.

In other embodiments, the serotype 3 glycoconjugate has a weight average molecular weight (Mw) of between 1,000 kDa and 10,000 kDa. In other embodiments, the serotype 3 glycoconjugate has a weight average molecular weight (Mw) of between 1,000 kDa and 9,000 kDa. In other embodiments, the serotype 3 glycoconjugate has a weight average molecular weight (Mw) of between 1,000 kDa and 8,000 kDa. In still other embodiments, the serotype 3 glycoconjugate has a weight average molecular weight (Mw) of between 1,000 kDa and 7,000 kDa. In still other embodiments, the serotype 3 glycoconjugate has a weight average molecular weight (Mw) of between 1,000 kDa and 6,000 kDa. In still other embodiments, the serotype 3 glycoconjugate has a weight average molecular weight (Mw) of between 1,000 kDa and 5,000 kDa. In still other embodiments, the serotype 3 glycoconjugate has a weight average molecular weight (Mw) of between 1,000 kDa and 4,000 kDa. In still other embodiments, the serotype 3 glycoconjugate has a weight average molecular weight (Mw) of between 1,000 kDa and 3,000 kDa. In still other embodiments, the serotype 3 glycoconjugate has a weight average molecular weight (Mw) of between 1,000 kDa and 2,000 kDa. In still other embodiments, the serotype 3 glycoconjugate has a weight average molecular weight (Mw) of between 1,000 kDa and 1,500 kDa.

In other embodiments, the serotype 3 glycoconjugate has a weight average molecular weight (Mw) of between 2,000 kDa and 10,000 kDa. In other embodiments, the serotype 3 glycoconjugate has a weight average molecular weight (Mw) of between 2,000 kDa and 9,000 kDa. In other embodiments, the serotype 3 glycoconjugate has a weight average molecular weight (Mw) of between 2,000 kDa and 8,000 kDa. In still other embodiments, the serotype 3 glycoconjugate has a weight average molecular weight (Mw) of between 2,000 kDa and 7,000 kDa. In still other embodiments, the serotype 3 glycoconjugate has a weight average molecular weight (Mw) of between 2,000 kDa and 6,000 kDa. In still other embodiments, the serotype 3 glycoconjugate has a weight average molecular weight (Mw) of between 2,000 kDa and 5,000 kDa. In still other embodiments, the serotype 3 glycoconjugate has a weight average molecular weight (Mw) of between 2,000 kDa and 4,000 kDa. In still other embodiments, the serotype 3 glycoconjugate has a weight average molecular weight (Mw) of between 2,000 kDa and 3,000 kDa. In still other embodiments, the serotype 3 glycoconjugate has a weight average molecular weight (Mw) of between 2,000 kDa and 3,500 kDa.

In still other embodiments, the serotype 3 glycoconjugate has a weight average molecular weight (Mw) of between 2,250 kDa and 3,500 kDa.

In other embodiments, the serotype 3 glycoconjugate has a weight average molecular weight (Mw) of between 3,000 kDa and 10,000 kDa. In other embodiments, the serotype 3 glycoconjugate has a weight average molecular weight (Mw) of between 3,000 kDa and 9,000 kDa. In other embodiments, the serotype 3 glycoconjugate has a weight average molecular weight (Mw) of between 3,000 kDa and 8,000 kDa. In still other embodiments, the serotype 3 glycoconjugate has a weight average molecular weight (Mw) of between 3,000 kDa and 7,000 kDa. In still other embodiments, the serotype 3 glycoconjugate has a weight average molecular weight (Mw) of between 3,000 kDa and 6,000 kDa. In still other embodiments, the serotype 3 glycoconjugate has a weight average molecular weight (Mw) of between 3,000 kDa and 5,000 kDa. In still other embodiments, the serotype 3 glycoconjugate has a weight average molecular weight (Mw) of between 3,000 kDa and 4,000 kDa.

In other embodiments, the serotype 3 glycoconjugate has a weight average molecular weight (Mw) of between 4,000 kDa and 10,000 kDa. In other embodiments, the serotype 3 glycoconjugate has a weight average molecular weight (Mw) of between 4,000 kDa and 9,000 kDa. In other embodiments, the serotype 3 glycoconjugate has a weight average molecular weight (Mw) of between 4,000 kDa and 8,000 kDa. In still other embodiments, the serotype 3 glycoconjugate has a weight average molecular weight (Mw) of between 4,000 kDa and 7,000 kDa. In still other embodiments, the serotype 3 glycoconjugate has a weight average molecular weight (Mw) of between 4,000 kDa and 6,000 kDa. In still other embodiments, the serotype 3 glycoconjugate has a weight average molecular weight (Mw) of between 4,000 kDa and 5,000 kDa.

In other embodiments, the serotype 3 glycoconjugate has a weight average molecular weight (Mw) of between 5,000 kDa and 10,000 kDa. In other embodiments, the serotype 3 glycoconjugate has a weight average molecular weight (Mw) of between 5,000 kDa and 9,000 kDa. In other embodiments, the serotype 3 glycoconjugate has a weight average molecular weight (Mw) of between 5,000 kDa and 8,000 kDa. In still other embodiments, the serotype 3 glycoconjugate has a weight average molecular weight (Mw) of between 5,000 kDa and 7,000 kDa. In still other embodiments, the serotype 3 glycoconjugate has a weight average molecular weight (Mw) of between 5,000 kDa and 6,000 kDa.

In other embodiments, the serotype 3 glycoconjugate has a weight average molecular weight (Mw) of between 6,000 kDa and 10,000 kDa. In other embodiments, the serotype 3 glycoconjugate has a weight average molecular weight (Mw) of between 6,000 kDa and 9,000 kDa. In other embodiments, the serotype 3 glycoconjugate has a weight average molecular weight (Mw) of between 6,000 kDa and 8,000 kDa. In still other embodiments, the serotype 3 glycoconjugate has a weight average molecular weight (Mw) of between 6,000 kDa and 7,000 kDa.

In other embodiments, the serotype 3 glycoconjugate has a weight average molecular weight (Mw) of between 7,000 kDa and 10,000 kDa. In other embodiments, the serotype 3 glycoconjugate has a weight average molecular weight (Mw) of between 7,000 kDa and 9,000 kDa. In other embodiments, the serotype 3 glycoconjugate has a weight average molecular weight (Mw) of between 7,000 kDa and 8,000 kDa.

In other embodiments, the serotype 3 glycoconjugate has a weight average molecular weight (Mw) of between 8,000 kDa and 10,000 kDa. In other embodiments, the serotype 3 glycoconjugate has a weight average molecular weight (Mw) of between 8,000 kDa and 9,000 kDa.

In other embodiments, the serotype 3 glycoconjugate has a weight average molecular weight (Mw) of between 9,000 kDa and 10,000 kDa.

Any whole number integer within any of the above ranges is contemplated as an embodiment of the disclosure.

In other embodiments, the serotype 3 glycoconjugate has a weight average molecular weight (Mw) of about 10,000 kDa. In other embodiments, the serotype 3 glycoconjugate has a weight average molecular weight (Mw) of about 9,000 kDa. In other embodiments, the serotype 3 glycoconjugate has a weight average molecular weight (Mw) of about 8,000 kDa. In still other embodiments, the serotype 3 glycoconjugate has a weight average molecular weight (Mw) of about 7,000 kDa. In still other embodiments, the serotype 3 glycoconjugate has a weight average molecular weight (Mw) of about 6,000 kDa. In still other embodiments, the serotype 3 glycoconjugate has a weight average molecular weight (Mw) of about 5,000 kDa. In still other embodiments, the serotype 3 glycoconjugate has a weight average molecular weight (Mw) of about 4,000 kDa. In still other embodiments, the serotype 3 glycoconjugate has a weight average molecular weight (Mw) of about 3,500 kDa. In still other embodiments, the serotype 3 glycoconjugate has a weight average molecular weight (Mw) of about 3,250 kDa. In still other embodiments, the serotype 3 glycoconjugate has a weight average molecular weight (Mw) of about 3,000 kDa. In still other embodiments, the serotype 3 glycoconjugate has a weight average molecular weight (Mw) of about 2,500 kDa. In still other embodiments, the serotype 3 glycoconjugate has a weight average molecular weight (Mw) of about 2,250 kDa. In still other embodiments, the serotype 3 glycoconjugate has a weight average molecular weight (Mw) of about 2,000 kDa. In still other embodiments, the serotype 3 glycoconjugate has a weight average molecular weight (Mw) of about 1,000 kDa. In still other embodiments, the serotype 3 glycoconjugate has a weight average molecular weight (Mw) of about 750 kDa. In still other embodiments, the serotype 3 glycoconjugate has a weight average molecular weight (Mw) of about 600 kDa. In still other embodiments, the serotype 3 glycoconjugate has a weight average molecular weight (Mw) of about 500 kDa. In still other embodiments, the serotype 3 glycoconjugate has a weight average molecular weight (Mw) of about 400 kDa.

The molecular weight of the polysaccharide can be measured by Size Exclusion Chromatography (SEC) combined with Multiangle Laser Light Scattering detector (MALLS).

Another way to characterize the serotype 3 glycoconjugates of the invention is by the number of lysine residues in the carrier protein (e.g., $CRM_{197}$ or SCP) that become conjugated to the saccharide which can be characterized as a range of conjugated lysines (degree of conjugation). The evidence for lysine modification of the carrier protein, due to covalent linkages to the polysaccharides, can be obtained by amino acid analysis using routine methods known to those of skill in the art. Conjugation results in a reduction in the number of lysine residues recovered compared to the carrier protein starting material used to generate the conjugate materials. In a preferred embodiment, the degree of conjugation of the serotype 3 glycoconjugate of the invention is between 2 and 15. In an embodiment, the degree of conjugation of the serotype 3 glycoconjugate of the invention is between 2 and 13. In an embodiment, the degree of conjugation of the serotype 3 glycoconjugate of the invention is between 2 and 10. In an embodiment, the degree of conjugation of the serotype 3 glycoconjugate of the invention is between 2 and 8. In an embodiment, the degree of conjugation of the serotype 3 glycoconjugate of the invention is between 2 and 6. In an embodiment, the degree of conjugation of the serotype 3 glycoconjugate of the invention is between 2 and 5. In an embodiment, the degree of conjugation of the serotype 3 glycoconjugate of the invention is between 2 and 4. In an embodiment, the degree of conjugation of the serotype 3 glycoconjugate of the invention is between 3 and 15. In an embodiment, the degree of conjugation of the serotype 3 glycoconjugate of the invention is between 3 and 13. In an embodiment, the degree of conjugation of the serotype 3 glycoconjugate of the invention is between 3 and 10. In an embodiment, the degree of conjugation of the serotype 3 glycoconjugate of the invention is between 3 and 8. In an embodiment, the degree of conjugation of the serotype 3 glycoconjugate of the invention is between 3 and 6. In an embodiment, the degree of conjugation of the serotype 3 glycoconjugate of the invention is between 3 and 5. In an embodiment, the degree of conjugation of the serotype 3 glycoconjugate of the invention is between 3 and 4. In an embodiment, the degree of conjugation of the serotype 3 glycoconjugate of the invention is between 5 and 15. In an embodiment, the degree of conjugation of the serotype 3 glycoconjugate of the invention is between 5 and 10. In an embodiment, the degree of conjugation of the serotype 3 glycoconjugate of the invention is between 8 and 15. In an embodiment, the degree of conjugation of the serotype 3 glycoconjugate of the invention is between 8 and 12. In an embodiment, the degree of conjugation of the serotype 3 glycoconjugate of the invention is between 10 and 15. In an embodiment, the degree of conjugation of the serotype 3 glycoconjugate of the invention is between 10 and 12.

In an embodiment, the degree of conjugation of the serotype 3 glycoconjugate of the invention is about 2.

In an embodiment, the degree of conjugation of the serotype 3 glycoconjugate of the invention is about 3. In an embodiment, the degree of conjugation of the serotype 3 glycoconjugate of the invention is about 4. In an embodiment, the degree of conjugation of the serotype 3 glycoconjugate of the invention is about 5. In an embodiment, the degree of conjugation of the serotype 3 glycoconjugate of the invention is about 6. In an embodiment, the degree of conjugation of the serotype 3 glycoconjugate of the invention is about 7. In an embodiment, the degree of conjugation of the serotype 3 glycoconjugate of the invention is about 8. In an embodiment, the degree of conjugation of the serotype 3 glycoconjugate of the invention is about 9. In an embodiment, the degree of conjugation of the serotype 3 glycoconjugate of the invention is about 10, about 11. In an embodiment, the degree of conjugation of the serotype 3 glycoconjugate of the invention is about 12.

In an embodiment, the degree of conjugation of the serotype 3 glycoconjugate of the invention is about 13. In an embodiment, the degree of conjugation of the serotype 3 glycoconjugate of the invention is about 14. In an embodiment, the degree of conjugation of the serotype 3 glycoconjugate of the invention is about 15. In a preferred embodiment, the degree of conjugation of the serotype 3 glycoconjugate of the invention is between 4 and 7. In some such embodiments, the carrier protein is $CRM_{197}$. In other such embodiments, the carrier protein is SCP.

The serotype 3 glycoconjugates of the invention may also be characterized by the ratio (weight/weight) of saccharide to carrier protein. In some embodiments, the ratio of serotype 3 polysaccharide to carrier protein in the glycoconjugate (w/w) is between 0.5 and 3.0. In other embodiments, the saccharide to carrier protein ratio (w/w) is between 0.5 and 2.0. In other embodiments, the saccharide to carrier protein ratio (w/w) is between 0.5 and 1.5. In other embodiments, the saccharide to carrier protein ratio (w/w) is between 0.8 and 1.2. In other embodiments, the saccharide to carrier protein ratio (w/w) is between 0.5 and 1.0. In other embodiments, the saccharide to carrier protein ratio (w/w) is between 1.0 and 1.5. In other embodiments, the saccharide to carrier protein ratio (w/w) is between 1.0 and 2.0. In further embodiments, the saccharide to carrier protein ratio (w/w) is between 0.8 and 1.2. In a preferred embodiment, the ratio of serotype 3 capsular polysaccharide to carrier protein in the conjugate is between 0.9 and 1.1.

In an embodiment, the saccharide to carrier protein ratio (w/w) is about 0.5. In other embodiments, the saccharide to carrier protein ratio (w/w) is about 0.6. In other embodiments, the saccharide to carrier protein ratio (w/w) is about 0.7. In other embodiments, the saccharide to carrier protein ratio (w/w) is about 0.8. In other embodiments, the saccharide to carrier protein ratio (w/w) is about 0.9. In other embodiments, the saccharide to carrier protein ratio (w/w) is about 1.0. In other embodiments, the saccharide to carrier protein ratio (w/w) is about 1.1. In other embodiments, the saccharide to carrier protein ratio (w/w) is about 1.2. In other embodiments, the saccharide to carrier protein ratio (w/w) is about 1.3. In other embodiments, the saccharide to carrier protein ratio (w/w) is about 1.4. In other embodiments, the saccharide to carrier protein ratio (w/w) is about 1.5. In other embodiments, the saccharide to carrier protein ratio (w/w) is about 1.6. In other embodiments, the saccharide to carrier protein ratio (w/w) is about 1.7. In other embodiments, the saccharide to carrier protein ratio (w/w) is about 1.8. In other embodiments, the saccharide to carrier protein ratio (w/w) is about 1.9. In other embodiments, the saccharide to carrier protein ratio (w/w) is about 2.0. In other embodiments, the saccharide to carrier protein ratio (w/w) is about 2.1. In other embodiments, the saccharide to carrier protein ratio (w/w) is about 2.2. In other embodiments, the saccharide to carrier protein ratio (w/w) is about 2.5. In other embodiments, the saccharide to carrier protein ratio (w/w) is about 2.8. In other embodiments, the saccharide to carrier protein ratio (w/w) is about 3.0. In some such embodiments, the carrier protein is $CRM_{197}$. In other such embodiments, the carrier protein is SCP.

The serotype 3 glycoconjugates of the invention may also be characterized by the number of covalent linkages between the carrier protein and the saccharide as a function of repeat units of the saccharide. In one embodiment, the serotype 3 glycoconjugate of the invention comprises at least one covalent linkage between the carrier protein and the polysaccharide for every 4 saccharide repeat units of the polysaccharide. In another embodiment, the covalent linkage between the carrier protein and the polysaccharide occurs at least once in every 10 saccharide repeat units of the polysaccharide. In another embodiment, the covalent linkage between the carrier protein and the polysaccharide occurs at least once in every 15 saccharide repeat units of the polysaccharide. In a further embodiment, the covalent linkage between the carrier protein and the polysaccharide occurs at least once in every 25 saccharide repeat units of the polysaccharide. In a further embodiment, the covalent linkage between the carrier protein and the polysaccharide occurs at least once in every 50 saccharide repeat units of the polysaccharide. In yet a further embodiment, the covalent linkage between the carrier protein and the polysaccharide occurs at least once in every 100 saccharide repeat units of the polysaccharide.

In other embodiments, the serotype 3 glycoconjugate of the invention comprises at least one covalent linkage between the carrier protein and the polysaccharide for every 5 to 10 saccharide repeat units of the polysaccharide.

In other embodiments, the serotype 3 glycoconjugate of the invention comprises at least one covalent linkage between the carrier protein and the polysaccharide for every 2 to 7 saccharide repeat units of the polysaccharide.

In other embodiments, the serotype 3 glycoconjugate of the invention comprises at least one covalent linkage between the carrier protein and the polysaccharide for every 6 to 11 saccharide repeat units of the polysaccharide.

In other embodiments, the serotype 3 glycoconjugate of the invention comprises at least one covalent linkage between the carrier protein and the polysaccharide for every 9 to 14 saccharide repeat units of the polysaccharide.

In other embodiments, the serotype 3 glycoconjugate of the invention comprises at least one covalent linkage between the carrier protein and the polysaccharide for every 10 to 20 saccharide repeat units of the polysaccharide.

In other embodiments, the serotype 3 glycoconjugate of the invention comprises at least one covalent linkage between the carrier protein and the polysaccharide for every 4 to 25 saccharide repeat units of the polysaccharide.

In frequent embodiments, the carrier protein is CRM197. In frequent embodiments, the carrier protein is SCP.

In some embodiments, the carrier protein is $CRM_{197}$ and the covalent linkage between the $CRM_{197}$ and the polysaccharide occurs at least once in every 4, 10, 15 or 25 saccharide repeat units of the polysaccharide. In frequent embodiments, the carrier protein is SCP and the covalent linkage between the SCP and the polysaccharide occurs at least once in every 4, 10, 15 or 25 saccharide repeat units of the polysaccharide.

The serotype 3 glycoconjugates and immunogenic compositions of the invention may contain free saccharide that is not covalently conjugated to the carrier protein but is nevertheless present in the glycoconjugate composition. The free saccharide may be noncovalently associated with (i.e., noncovalently bound to, adsorbed to, or entrapped in or with) the glycoconjugate.

In a preferred embodiment, the serotype 3 glycoconjugate comprises less than about 50% of free serotype 3 polysaccharide compared to the total amount of serotype 3 polysaccharide. In a preferred embodiment the serotype 3 glycoconjugate comprises less than about 40% of free serotype 3 polysaccharide compared to the total amount of serotype 3 polysaccharide. In a yet preferred embodiment, the serotype 3 glycoconjugate comprises less than about 25% of free serotype 3 polysaccharide compared to the total amount of serotype 3 polysaccharide. In an even preferred embodiment, the serotype 3 glycoconjugate comprises less than about 20% of free serotype 3 polysaccharide compared to the total amount of serotype 3 polysaccharide. In a yet preferred embodiment, the serotype 3 glycoconjugate comprises less than about 15% of free serotype 3 polysaccharide compared to the total amount of serotype 3 polysaccharide.

The serotype 3 glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to $K_d$ by the expression, $K_d=(V_e-V_0)/(V_i-V_0)$.

In a preferred embodiment, at least 30% of the serotype 3 glycoconjugate has a $K_d$ below or equal to 0.3 in a CL-4B column. In a preferred embodiment, at least 40% of the glycoconjugate has a $K_d$ below or equal to 0.3 in a CL-4B column. In a preferred embodiment, at least 45%, 50%, 55%, 60%, 65%, 70%, 75%, 80%, or 85% of the serotype 3 glycoconjugate has a $K_d$ below or equal to 0.3 in a CL-4B column. In a preferred embodiment, at least 60% of the serotype 3 glycoconjugate has a $K_d$ below or equal to 0.3 in a CL-4B column. In a preferred embodiment, between 50% and 80% of the serotype 3 glycoconjugate has a $K_d$ below or equal to 0.3 in a CL-4B column. In a preferred embodiment, between 65% and 80% of the serotype 3 glycoconjugate has a $K_d$ below or equal to 0.3 in a CL-4B column.

1.3 *Streptococcus pneumoniae* Serotype 3 Glycoconjugates of the Invention Prepared Using Click Chemistry In an embodiment, serotype 3 glycoconjugates of the present invention are prepared using click chemistry.

The invention also relates to a method of making a serotype 3 glycoconjugate, as disclosed herein.

According to the present invention, click chemistry comprises three steps, (a) reacting an isolated serotype 3 capsular polysaccharide with a carbonic acid derivative and an azido linker in an aprotic solvent to produce an activated azido polysaccharide (activation of the polysaccharide), (b) reacting a carrier protein with an agent bearing an N-Hydroxysuccinimide (NHS) moiety and an alkyne group where the NHS moiety reacts with the amino groups to form an amide linkage thereby obtaining an alkyne functionalized carrier protein (activation of the carrier protein), (c) reacting the activated azido polysaccharide of step (a) with the activated alkyne-carrier protein of step (b) by $Cu^{+1}$ mediated azide-alkyne cycloaddition reaction to form a glycoconjugate.

Following step (a) the polysaccharide is said to be activated and is referred to herein as “activated polysaccharide” or “activated azido polysaccharide”.

Following step (b) the carrier is said to be activated and is referred to as “activated carrier”.

As mentioned above, before the activation (a), sizing of the polysaccharide to a target molecular weight (MW) range can be performed.

Therefore, in an embodiment, the isolated polysaccharide is sized before activation with a carbonic acid derivative and an azido linker.

In an embodiment, the isolated polysaccharide is sized to any of the target molecular weight (MW) range defined above.

In an embodiment, said carbonic acid derivative is selected from the group consisting of 1,1'-carbonyldiimidazole (CDI), 1,1'-carbonyl-di-(1,2,4-triazole) (CDT), disuccinimidyl carbonate (DSC) and N-hydroxysuccinimidyl chloroformate.

In an embodiment, said carbonic acid derivative is 1,1'-carbonyldiimidazole (CDI). In an embodiment, said carbonic acid derivative is 1,1'-Carbonyl-di-(1,2,4-triazole) (CDT). In another embodiment, said carbonic acid derivative is disuccinimidyl carbonate (DSC). In yet a further embodiment, said carbonic acid derivative is N-hydroxysuccinimidyl chloroformate.

In an embodiment, said carbonic acid derivative is 1,1'-carbonyldiimidazole (CDI) or 1,1'-Carbonyl-di-(1,2,4-triazole) (CDT). Preferably, said carbonic acid derivative is 1,1'-carbonyldiimidazole (CDI).

In an embodiment, said azido linker is a compound of formula (I), $$H_2N—X—N_3 \qquad (I)$$

wherein X is selected from the group consisting of $CH_2(CH_2)_n$, $(CH_2CH_2O)_mCH_2CH_2$, $NHCO(CH_2)_n$, $NHCO(CH_2CH_2O)_mCH_2CH_2$, $OCH_2(CH_2)_n$ and $O(CH_2CH_2O)_mCH_2CH_2$, where n is selected from 1 to 10 and m is selected from 1 to 4.

In an embodiment, said azido linker is a compound of formula (I), wherein X is $CH_2(CH_2)_n$, and n is selected from 1 to 10. In an embodiment, n is selected from 1 to 5. In an embodiment, n is selected from 1 to 4. In an embodiment, n is selected from 1 to 3. In an embodiment, n is selected from 1 to 2. In a particular embodiment, n is 1. In another embodiment, n is 2. In yet another embodiment, n is 3. In yet a further embodiment, n is 4. In yet a further embodiment, n is 5. In yet a further embodiment, n is 6. In yet a further embodiment, n is 7. In yet a further embodiment, n is 8. In yet a further embodiment, n is 9. In yet a further embodiment, n is 10.

In an embodiment, said azido linker is a compound of formula (I), wherein X is $(CH_2CH_2O)_mCH_2CH_2$, wherein m is selected from 1 to 4. In an embodiment, m is selected from 1 to 3. In an embodiment, m is selected from 1 to 2. In a particular embodiment, m is 1. In another embodiment, m is 2. In yet another embodiment, m is 3. In yet a further embodiment, m is 4.

In an embodiment, said azido linker is a compound of formula (I), wherein X is $NHCO(CH_2)_n$, and n is selected from 1 to 10. In an embodiment, n is selected from 1 to 5. In an embodiment, n is selected from 1 to 4. In an embodiment, n is selected from 1 to 3. In an embodiment, n is selected from 1 to 2. In a particular embodiment, n is 1. In another embodiment, n is 2. In yet another embodiment, n is 3. In yet a further embodiment, n is 4. In yet a further embodiment, n is 5. In yet a further embodiment, n is 6. In yet a further embodiment, n is 7. In yet a further embodiment, n is 8. In yet a further embodiment, n is 9. In yet a further embodiment, n is 10.

In an embodiment, said azido linker is a compound of formula (I), wherein X is $NHCO(CH_2CH_2O)_mCH_2CH_2$, where m is selected from 1 to 4. In an embodiment, m is selected from 1 to 3. In an embodiment, m is selected from 1 to 2. In a particular embodiment, m is 1. In another embodiment, m is 2. In yet another embodiment, m is 3. In yet a further embodiment, m is 4.

In an embodiment, said azido linker is a compound of formula (I), wherein X is $OCH_2(CH_2)_n$, and n is selected from 1 to 10. In an embodiment, n is selected from 1 to 5. In an embodiment, n is selected from 1 to 4. In an embodiment, n is selected from 1 to 3. In an embodiment, n is selected from 1 to 2. In a particular embodiment, n is 1. In another embodiment, n is 2. In yet another embodiment, n is 3. In yet a further embodiment, n is 4. In yet a further embodiment, n is 5. In yet a further embodiment, n is 6. In yet a further embodiment, n is 7. In yet a further embodiment, n is 8. In yet a further embodiment, n is 9. In yet a further embodiment, n is 10.

In an embodiment, said azido linker is a compound of formula (I), wherein X is $O(CH_2CH_2O)_mCH_2CH_2$, where m is selected from 1 to 4. In an embodiment, m is selected from 1 to 3. In an embodiment, m is selected from 1 to 2. In a particular embodiment, m is 1. In another embodiment, m is 2. In yet another embodiment, m is 3. In yet a further embodiment, m is 4.

In an embodiment, said azido linker is a compound of formula (II), (II)

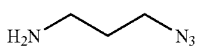

In an embodiment, said azido linker is 3-azido-propylamine.

In an embodiment, said agent bearing an N-Hydroxysuccinimide (NHS) moiety and an alkyne group is an agent bearing an N-Hydroxysuccinimide (NHS) moiety and a terminal alkyne.

In an embodiment, said agent bearing an N-Hydroxysuccinimide (NHS) moiety and an alkyne group is an agent bearing an N-Hydroxysuccinimide (NHS) moiety and a cycloalkyne.

In an embodiment, said agent bearing an N-Hydroxysuccinimide (NHS) moiety and an alkyne group is a compound of formula (III), (III)

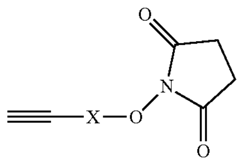

where X is selected from the group consisting of $CH_2O(CH_2)_nCH_2C{=}O$ and $CH_2O(CH_2CH_2O)_m(CH_2)_nCH_2C{=}O$, where n is selected from 0 to 10 and m is selected from 0 to 4.

In an embodiment, said agent bearing an N-Hydroxysuccinimide (NHS) moiety and an alkyne group is a compound of formula (III), wherein X is $CH_2O(CH_2)_nCH_2C{=}O$, where n is selected from 0 to 10. In an embodiment, n is selected from 0 to 5. In an embodiment, n is selected from 0 to 4. In an embodiment, n is selected from 0 to 3. In an embodiment, n is selected from 0 to 2. In a particular embodiment, n is 0. In a particular embodiment, n is 1. In another embodiment, n is 2. In yet another embodiment, n is 3. In yet a further embodiment, n is 4. In yet a further embodiment, n is 5. In yet a further embodiment, n is 6. In yet a further embodiment, n is 7. In yet a further embodiment, n is 8. In yet a further embodiment, n is 9. In yet a further embodiment, n is 10.

In an embodiment, said agent bearing an N-Hydroxysuccinimide (NHS) moiety and an alkyne group is a compound of formula (III), wherein X is $CH_2O(CH_2CH_2O)_m(CH_2)_nCH_2C{=}O$, where n is selected from 0 to 10 and m is selected from 0 to 4. In an embodiment, n is selected from 0 to 5. In an embodiment, n is selected from 0 to 4. In an embodiment, n is selected from 0 to 3. In an embodiment, n is selected from 0 to 2. In a particular embodiment, n is 0. In a particular embodiment, n is 1. In another embodiment, n is 2. In yet another embodiment, n is 3. In yet a further embodiment, n is 4. In yet a further embodiment, n is 5. In yet a further embodiment, n is 6. In yet a further embodiment, n is 7. In yet a further embodiment, n is 8. In yet a further embodiment, n is 9. In yet a further embodiment, n is 10. In an embodiment, m is selected from 0 to 3. In an embodiment, m is selected from 0 to 2. In a particular embodiment, m is 1. In a particular embodiment, m is 1. In another embodiment, m is 2.

In yet another embodiment, m is 3. In yet a further embodiment, m is 4.

In an embodiment, n is selected from 0 to 5 and m is selected from 0 to 3. In an embodiment, n is selected from 0 to 5 and m is selected from 0 to 2.

In an embodiment, n is selected from 0 to 4 and m is selected from 0 to 3. In an embodiment, n is selected from 0 to 4 and m is selected from 0 to 2.

In an embodiment, n is selected from 0 to 3 and m is selected from 0 to 3. In an embodiment, n is selected from 0 to 3 and m is selected from 0 to 2.

In an embodiment, n is selected from 0 to 2 and m is selected from 0 to 3. In an embodiment, n is selected from 0 to 2 and m is selected from 0 to 2.

In an embodiment, n is selected from 0 to 1 and m is selected from 0 to 3. In an embodiment, n is selected from 0 to 1 and m is selected from 0 to 2.

In an embodiment, n is 0 and m is 0. In an embodiment, n is 1 and m is 0. In an embodiment, n is 2 and m is 0. In an embodiment, n is 3 and m is 0. In an embodiment, n is 4 and m is 0. In an embodiment, n is 5 and m is 0. In an embodiment, n is 6 and m is 0. In an embodiment, n is 7 and m is 0. In an embodiment, n is 8 and m is 0. In an embodiment, n is 9 and m is 0. In an embodiment, n is 10 and m is 0.

In an embodiment, n is 0 and m is 1. In an embodiment, n is 1 and m is 1. In an embodiment, n is 2 and m is 1. In an embodiment, n is 3 and m is 1. In an embodiment, n is 4 and m is 1. In an embodiment, n is 5 and m is 1. In an embodiment, n is 6 and m is 1. In an embodiment, n is 7 and m is 1. In an embodiment, n is 8 and m is 1. In an embodiment, n is 9 and m is 1. In an embodiment, n is 10 and m is 1.

In an embodiment, n is 0 and m is 2. In an embodiment, n is 1 and m is 2. In an embodiment, n is 2 and m is 2. In an embodiment, n is 3 and m is 2. In an embodiment, n is 4 and m is 2. In an embodiment, n is 5 and m is 2. In an embodiment, n is 6 and m is 2. In an embodiment, n is 7 and m is 2. In an embodiment, n is 8 and m is 2. In an embodiment, n is 9 and m is 2. In an embodiment, n is 10 and m is 2.

In an embodiment, n is 0 and m is 3. In an embodiment, n is 1 and m is 3. In an embodiment, n is 2 and m is 3. In an embodiment, n is 3 and m is 3. In an embodiment, n is 4 and m is 3. In an embodiment, n is 5 and m is 3. In an embodiment, n is 6 and m is 3. In an embodiment, n is 7 and m is 3. In an embodiment, n is 8 and m is 3. In an embodiment, n is 9 and m is 3. In an embodiment, n is 10 and m is 3.

In an embodiment, n is 0 and m is 4. In an embodiment, n is 1 and m is 4. In an embodiment, n is 2 and m is 4. In an embodiment, n is 3 and m is 4. In an embodiment, n is 4 and m is 4. In an embodiment, n is 5 and m is 4. In an embodiment, n is 6 and m is 4. In an embodiment, n is 7 and m is 4. In an embodiment, n is 8 and m is 4. In an embodiment, n is 9 and m is 4. In an embodiment, n is 10 and m is 4.

In an embodiment, said agent bearing an N-Hydroxysuccinimide (NHS) moiety and an alkyne group is a compound of formula (IV):

(IV)

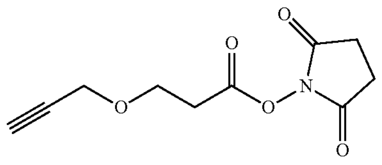

In an embodiment, step a) comprises reacting the polysaccharide with a carbonic acid derivative followed by reacting the carbonic acid derivative-activated polysaccharide with an azido linker in an aprotic solvent to produce an activated azido polysaccharide.

In one embodiment step a) comprises reacting the polysaccharide with an amount of carbonic acid derivative that is between 0.01-10 molar equivalent to the amount of serotype 3 capsular polysaccharide present in the reaction mixture.

In one embodiment step a) comprises reacting the polysaccharide with an amount of carbonic acid derivative that is between 0.05-10 molar equivalent to the amount of serotype 3 capsular polysaccharide present in the reaction mixture.

In one embodiment step a) comprises reacting the polysaccharide with an amount of carbonic acid derivative that is between 0.1-10 molar equivalent to the amount of serotype 3 capsular polysaccharide present in the reaction mixture.

In one embodiment step a) comprises reacting the polysaccharide with an amount of carbonic acid derivative that is between 0.2-10 molar equivalent to the amount of serotype 3 capsular polysaccharide present in the reaction mixture.

In one embodiment step a) comprises reacting the polysaccharide with an amount of carbonic acid derivative that is between 0.3-10 molar equivalent to the amount of serotype 3 capsular polysaccharide present in the reaction mixture.

In one embodiment step a) comprises reacting the polysaccharide with an amount of carbonic acid derivative that is between 0.4-10 molar equivalent to the amount of serotype 3 capsular polysaccharide present in the reaction mixture.

In one embodiment step a) comprises reacting the polysaccharide with an amount of carbonic acid derivative that is between 0.5-10 molar equivalent to the amount of serotype 3 capsular polysaccharide present in the reaction mixture.

In one embodiment step a) comprises reacting the polysaccharide with an amount of carbonic acid derivative that is between 0.8-10 molar equivalent to the amount of serotype 3 capsular polysaccharide present in the reaction mixture.

In one embodiment step a) comprises reacting the polysaccharide with an amount of carbonic acid derivative that is between 1-10 molar equivalent to the amount of serotype 3 capsular polysaccharide present in the reaction mixture.

In one embodiment step a) comprises reacting the polysaccharide with an amount of carbonic acid derivative that is between 2-10 molar equivalent to the amount of serotype 3 capsular polysaccharide present in the reaction mixture.

In one embodiment step a) comprises reacting the polysaccharide with an amount of carbonic acid derivative that is between 3-10 molar equivalent to the amount of serotype 3 capsular polysaccharide present in the reaction mixture.

In one embodiment step a) comprises reacting the polysaccharide with an amount of carbonic acid derivative that is between 5-10 molar equivalent to the amount of serotype 3 capsular polysaccharide present in the reaction mixture.

In one embodiment step a) comprises reacting the polysaccharide with an amount of carbonic acid derivative that is between 0.01-5 molar equivalent to the amount of serotype 3 capsular polysaccharide present in the reaction mixture.

In one embodiment step a) comprises reacting the polysaccharide with an amount of carbonic acid derivative that is between 0.05-5 molar equivalent to the amount of serotype 3 capsular polysaccharide present in the reaction mixture.

In one embodiment step a) comprises reacting the polysaccharide with an amount of carbonic acid derivative that is between 0.1-5 molar equivalent to the amount of serotype 3 capsular polysaccharide present in the reaction mixture.

In one embodiment step a) comprises reacting the polysaccharide with an amount of carbonic acid derivative that is between 0.2-5 molar equivalent to the amount of serotype 3 capsular polysaccharide present in the reaction mixture.

In one embodiment step a) comprises reacting the polysaccharide with an amount of carbonic acid derivative that is between 0.3-5 molar equivalent to the amount of serotype 3 capsular polysaccharide present in the reaction mixture.

In one embodiment step a) comprises reacting the polysaccharide with an amount of carbonic acid derivative that is between 0.4-5 molar equivalent to the amount of serotype 3 capsular polysaccharide present in the reaction mixture.

In one embodiment step a) comprises reacting the polysaccharide with an amount of carbonic acid derivative that is between 0.5-5 molar equivalent to the amount of serotype 3 capsular polysaccharide present in the reaction mixture.

In one embodiment step a) comprises reacting the polysaccharide with an amount of carbonic acid derivative that is between 0.8-5 molar equivalent to the amount of serotype 3 capsular polysaccharide present in the reaction mixture.

In one embodiment step a) comprises reacting the polysaccharide with an amount of carbonic acid derivative that is between 1-5 molar equivalent to the amount of serotype 3 capsular polysaccharide present in the reaction mixture.

In one embodiment step a) comprises reacting the polysaccharide with an amount of carbonic acid derivative that is between 2-5 molar equivalent to the amount of serotype 3 capsular polysaccharide present in the reaction mixture.

In one embodiment step a) comprises reacting the polysaccharide with an amount of carbonic acid derivative that is between 3-5 molar equivalent to the amount of serotype 3 capsular polysaccharide present in the reaction mixture.

In one embodiment step a) comprises reacting the polysaccharide with an amount of carbonic acid derivative that is between 0.01-3 molar equivalent to the amount of serotype 3 capsular polysaccharide present in the reaction mixture.

In one embodiment step a) comprises reacting the polysaccharide with an amount of carbonic acid derivative that is between 0.05-3 molar equivalent to the amount of serotype 3 capsular polysaccharide present in the reaction mixture.

In one embodiment step a) comprises reacting the polysaccharide with an amount of carbonic acid derivative that is between 0.1-3 molar equivalent to the amount of serotype 3 capsular polysaccharide present in the reaction mixture.

In one embodiment step a) comprises reacting the polysaccharide with an amount of carbonic acid derivative that is between 0.2-3 molar equivalent to the amount of serotype 3 capsular polysaccharide present in the reaction mixture.

In one embodiment step a) comprises reacting the polysaccharide with an amount of carbonic acid derivative that is between 0.3-3 molar equivalent to the amount of serotype 3 capsular polysaccharide present in the reaction mixture.

In one embodiment step a) comprises reacting the polysaccharide with an amount of carbonic acid derivative that is between 0.4-3 molar equivalent to the amount of serotype 3 capsular polysaccharide present in the reaction mixture.

In one embodiment step a) comprises reacting the polysaccharide with an amount of carbonic acid derivative that is between 0.5-3 molar equivalent to the amount of serotype 3 capsular polysaccharide present in the reaction mixture.

In one embodiment step a) comprises reacting the polysaccharide with an amount of carbonic acid derivative that is between 0.8-3 molar equivalent to the amount of serotype 3 capsular polysaccharide present in the reaction mixture.

In one embodiment step a) comprises reacting the polysaccharide with an amount of carbonic acid derivative that is between 1-3 molar equivalent to the amount of serotype 3 capsular polysaccharide present in the reaction mixture.

In one embodiment step a) comprises reacting the polysaccharide with an amount of carbonic acid derivative that is between 2-3 molar equivalent to the amount of serotype 3 capsular polysaccharide present in the reaction mixture.

In one embodiment step a) comprises reacting the polysaccharide with an amount of carbonic acid derivative that is between 0.01-2 molar equivalent to the amount of serotype 3 capsular polysaccharide present in the reaction mixture.

In one embodiment step a) comprises reacting the polysaccharide with an amount of carbonic acid derivative that is between 0.05-2 molar equivalent to the amount of serotype 3 capsular polysaccharide present in the reaction mixture.

In one embodiment step a) comprises reacting the polysaccharide with an amount of carbonic acid derivative that is between 0.1-2 molar equivalent to the amount of serotype 3 capsular polysaccharide present in the reaction mixture.

In one embodiment step a) comprises reacting the polysaccharide with an amount of carbonic acid derivative that is between 0.2-2 molar equivalent to the amount of serotype 3 capsular polysaccharide present in the reaction mixture.

In one embodiment step a) comprises reacting the polysaccharide with an amount of carbonic acid derivative that is between 0.3-2 molar equivalent to the amount of serotype 3 capsular polysaccharide present in the reaction mixture.

In one embodiment step a) comprises reacting the polysaccharide with an amount of carbonic acid derivative that is between 0.4-2 molar equivalent to the amount of serotype 3 capsular polysaccharide present in the reaction mixture.

In one embodiment step a) comprises reacting the polysaccharide with an amount of carbonic acid derivative that is between 0.5-2 molar equivalent to the amount of serotype 3 capsular polysaccharide present in the reaction mixture.

In one embodiment step a) comprises reacting the polysaccharide with an amount of carbonic acid derivative that is between 0.8-2 molar equivalent to the amount of serotype 3 capsular polysaccharide present in the reaction mixture.

In one embodiment step a) comprises reacting the polysaccharide with an amount of carbonic acid derivative that is between 1-2 molar equivalent to the amount of serotype 3 capsular polysaccharide present in the reaction mixture.

In one embodiment step a) comprises reacting the polysaccharide with an amount of carbonic acid derivative that is between 0.01-1 molar equivalent to the amount of serotype 3 capsular polysaccharide present in the reaction mixture.

In one embodiment step a) comprises reacting the polysaccharide with an amount of carbonic acid derivative that is between 0.05-1 molar equivalent to the amount of serotype 3 capsular polysaccharide present in the reaction mixture.

In one embodiment step a) comprises reacting the polysaccharide with an amount of carbonic acid derivative that is between 0.1-1 molar equivalent to the amount of serotype 3 capsular polysaccharide present in the reaction mixture.

In one embodiment step a) comprises reacting the polysaccharide with an amount of carbonic acid derivative that is between 0.2-1 molar equivalent to the amount of serotype 3 capsular polysaccharide present in the reaction mixture.

In one embodiment step a) comprises reacting the polysaccharide with an amount of carbonic acid derivative that is between 0.3-1 molar equivalent to the amount of serotype 3 capsular polysaccharide present in the reaction mixture.

In one embodiment step a) comprises reacting the polysaccharide with an amount of carbonic acid derivative that is between 0.4-1 molar equivalent to the amount of serotype 3 capsular polysaccharide present in the reaction mixture.

In one embodiment step a) comprises reacting the polysaccharide with an amount of carbonic acid derivative that is between 0.5-1 molar equivalent to the amount of serotype 3 capsular polysaccharide present in the reaction mixture.

In one embodiment step a) comprises reacting the polysaccharide with an amount of carbonic acid derivative that is between 0.8-1 molar equivalent to the amount of serotype 3 capsular polysaccharide present in the reaction mixture.

In one embodiment step a) comprises reacting the polysaccharide with an amount of carbonic acid derivative that is between 0.01-0.5 molar equivalent to the amount of serotype 3 capsular polysaccharide present in the reaction mixture.

In one embodiment step a) comprises reacting the polysaccharide with an amount of carbonic acid derivative that is between 0.05-0.5 molar equivalent to the amount of serotype 3 capsular polysaccharide present in the reaction mixture.

In one embodiment step a) comprises reacting the polysaccharide with an amount of carbonic acid derivative that is between 0.1-0.5 molar equivalent to the amount of serotype 3 capsular polysaccharide present in the reaction mixture.

In one embodiment step a) comprises reacting the polysaccharide with an amount of carbonic acid derivative that is between 0.2-0.5 molar equivalent to the amount of serotype 3 capsular polysaccharide present in the reaction mixture.

In one embodiment step a) comprises reacting the polysaccharide with an amount of carbonic acid derivative that is between 0.3-0.5 molar equivalent to the amount of serotype 3 capsular polysaccharide present in the reaction mixture.

In one embodiment step a) comprises reacting the polysaccharide with an amount of carbonic acid derivative that is between 0.4-0.5 molar equivalent to the amount of serotype 3 capsular polysaccharide present in the reaction mixture.

In one embodiment step a) comprises reacting the polysaccharide with an amount of carbonic acid derivative In one embodiment step a) comprises reacting the polysaccharide with an amount of carbonic acid derivative that is between 0.01-0.4 molar equivalent to the amount of serotype 3 capsular polysaccharide present in the reaction mixture.

In one embodiment step a) comprises reacting the polysaccharide with an amount of carbonic acid derivative that is between 0.05-0.4 molar equivalent to the amount of serotype 3 capsular polysaccharide present in the reaction mixture.

In one embodiment step a) comprises reacting the polysaccharide with an amount of carbonic acid derivative that is between 0.1-0.4 molar equivalent to the amount of serotype 3 capsular polysaccharide present in the reaction mixture.

In one embodiment step a) comprises reacting the polysaccharide with an amount of carbonic acid derivative that is between 0.2-0.4 molar equivalent to the amount of serotype 3 capsular polysaccharide present in the reaction mixture.

In one embodiment step a) comprises reacting the polysaccharide with an amount of carbonic acid derivative that is between 0.3-0.4 molar equivalent to the amount of serotype 3 capsular polysaccharide present in the reaction mixture.

In one embodiment step a) comprises reacting the polysaccharide with an amount of carbonic acid derivative that is between 0.01-0.3 molar equivalent to the amount of serotype 3 capsular polysaccharide present in the reaction mixture.

In one embodiment step a) comprises reacting the polysaccharide with an amount of carbonic acid derivative that is between 0.05-0.3 molar equivalent to the amount of serotype 3 capsular polysaccharide present in the reaction mixture.

In one embodiment step a) comprises reacting the polysaccharide with an amount of carbonic acid derivative that is between 0.1-0.3 molar equivalent to the amount of serotype 3 capsular polysaccharide present in the reaction mixture.

In one embodiment step a) comprises reacting the polysaccharide with an amount of carbonic acid derivative that is between 0.2-0.3 molar equivalent to the amount of serotype 3 capsular polysaccharide present in the reaction mixture.

In one embodiment step a) comprises reacting the polysaccharide with an amount of carbonic acid derivative of about 0.01 molar equivalent to the amount of serotype 3 capsular polysaccharide present in the reaction mixture.

In one embodiment step a) comprises reacting the polysaccharide with an amount of carbonic acid derivative of about 0.05 molar equivalent to the amount of serotype 3 capsular polysaccharide present in the reaction mixture.

In one embodiment step a) comprises reacting the polysaccharide with an amount of carbonic acid derivative of about 0.08 molar equivalent to the amount of serotype 3 capsular polysaccharide present in the reaction mixture.

In one embodiment step a) comprises reacting the polysaccharide with an amount of carbonic acid derivative of about 0.1 molar equivalent to the amount of serotype 3 capsular polysaccharide present in the reaction mixture.

In one embodiment step a) comprises reacting the polysaccharide with an amount of carbonic acid derivative of about 0.2 molar equivalent to the amount of serotype 3 capsular polysaccharide present in the reaction mixture.

In one embodiment step a) comprises reacting the polysaccharide with an amount of carbonic acid derivative of about 0.3 molar equivalent to the amount of serotype 3 capsular polysaccharide present in the reaction mixture.

In one embodiment step a) comprises reacting the polysaccharide with an amount of carbonic acid derivative of about 0.4 molar equivalent to the amount of serotype 3 capsular polysaccharide present in the reaction mixture.

In one embodiment step a) comprises reacting the polysaccharide with an amount of carbonic acid derivative of about 0.5 molar equivalent to the amount of serotype 3 capsular polysaccharide present in the reaction mixture.

In one embodiment step a) comprises reacting the polysaccharide with an amount of carbonic acid derivative of about 1 molar equivalent to the amount of serotype 3 capsular polysaccharide present in the reaction mixture.

In one embodiment step a) comprises reacting the polysaccharide with an amount of carbonic acid derivative of about 2 molar equivalent to the amount of serotype 3 capsular polysaccharide present in the reaction mixture.

In one embodiment step a) comprises reacting the polysaccharide with an amount of carbonic acid derivative of about 3 molar equivalent to the amount of serotype 3 capsular polysaccharide present in the reaction mixture.

In one embodiment step a) comprises reacting the polysaccharide with an amount of carbonic acid derivative of about 4 molar equivalent to the amount of serotype 3 capsular polysaccharide present in the reaction mixture.

In one embodiment step a) comprises reacting the polysaccharide with an amount of carbonic acid derivative of about 5 molar equivalent to the amount of serotype 3 capsular polysaccharide present in the reaction mixture.

In one embodiment step a) comprises reacting the polysaccharide with an amount of carbonic acid derivative of about 8 molar equivalent to the amount of serotype 3 capsular polysaccharide present in the reaction mixture.

In one embodiment step a) comprises reacting the polysaccharide with an amount of carbonic acid derivative of about 10 molar equivalent to the amount of serotype 3 capsular polysaccharide present in the reaction mixture.

In an embodiment, at step a) the isolated polysaccharide is reacted with a carbonic acid derivative in an aprotic solvent.

In one embodiment the isolated polysaccharide is reacted with a carbonic acid derivative in a solution consisting essentially of dimethylsulphoxide (DMSO) or dimethylformamide (DMF). In one embodiment the isolated polysaccharide is reacted with a carbonic acid derivative in a solution consisting essentially of dimethylformamide (DMF). In one embodiment the isolated polysaccharide is reacted with a carbonic acid derivative in a solution consisting essentially of dimethylsulphoxide (DMSO).

In an embodiment, the isolated polysaccharide is reacted with a carbonic acid derivative in a solution consisting essentially of dimethylacetamide. In an embodiment, the isolated polysaccharide is reacted with a carbonic acid derivative in a solution consisting essentially of N-methyl-2-pyrrolidone. In an embodiment, the isolated polysaccharide is reacted with a carbonic acid derivative in a solution consisting essentially of hexamethylphosphoramide (HMPA).

In a preferred embodiment the isolated polysaccharide is reacted with a carbonic acid derivative in a solution consisting essentially of dimethylsulphoxide (DMSO).

In one embodiment the isolated polysaccharide is reacted with a carbonic acid derivative in dimethylsulphoxide (DMSO) or dimethylformamide (DMF). In one embodiment the isolated polysaccharide is reacted with a carbonic acid derivative in dimethylformamide (DMF). In one embodiment the isolated polysaccharide is reacted with a carbonic acid derivative in dimethylsulphoxide (DMSO).

In an embodiment, the isolated polysaccharide is reacted with a carbonic acid derivative in dimethylacetamide. In an embodiment, the isolated polysaccharide is reacted with a carbonic acid derivative in N-methyl-2-pyrrolidone. In an embodiment, the isolated polysaccharide is reacted with a carbonic acid derivative in hexamethylphosphoramide (HMPA).

In a preferred embodiment the isolated polysaccharide is reacted with CDI in dimethylsulphoxide (DMSO). In an embodiment the isolated polysaccharide is reacted with CDI in anhydrous DMSO.

It has been surprisingly found that reacting the isolated polysaccharide with CDI in an environment with a moisture level of about 0.1% to 1% (v/v) allows to avoid side reactions.

Therefore, in one embodiment the isolated polysaccharide is reacted with CDI in an aprotic solvent comprising 0.1% to 1% (v/v) water. In one embodiment the isolated polysaccharide is reacted with CDI in an aprotic solvent comprising 0.1% to 0.8% (v/v) water. In one embodiment the isolated polysaccharide is reacted with CDI in an aprotic solvent comprising 0.1% to 0.5% (v/v) water. In one embodiment the isolated polysaccharide is reacted with CDI in an aprotic solvent comprising 0.1% to 0.4% (v/v) water. In one embodiment the isolated polysaccharide is reacted with CDI in an aprotic solvent comprising 0.1% to 0.3% (v/v) water. In one embodiment the isolated polysaccharide is reacted with CDI in an aprotic solvent comprising 0.1% to 0.2% (v/v) water.

In one embodiment the isolated polysaccharide is reacted with CDI in an aprotic solvent comprising 0.2% to 1% (v/v) water. In one embodiment the isolated polysaccharide is reacted with CDI in an aprotic solvent comprising 0.2% to 0.8% (v/v) water. In one embodiment the isolated polysaccharide is reacted with CDI in an aprotic solvent comprising 0.2% to 0.5% (v/v) water. In one embodiment the isolated polysaccharide is reacted with CDI in an aprotic solvent comprising 0.2% to 0.4% (v/v) water. In one embodiment the isolated polysaccharide is reacted with CDI in an aprotic solvent comprising 0.2% to 0.3% (v/v) water.

In one embodiment the isolated polysaccharide is reacted with CDI in an aprotic solvent comprising 0.3% to 0.8% (v/v) water. In one embodiment the isolated polysaccharide is reacted with CDI in an aprotic solvent comprising 0.3% to 0.5% (v/v) water. In one embodiment the isolated polysaccharide is reacted with CDI in an aprotic solvent comprising 0.3% to 0.4% (v/v) water.

In one embodiment the isolated polysaccharide is reacted with CDI in an aprotic solvent comprising about 0.1% (v/v) water. In one embodiment the isolated polysaccharide is reacted with CDI in an aprotic solvent comprising about 0.2% (v/v) water. In one embodiment the isolated polysaccharide is reacted with CDI in an aprotic solvent comprising about 0.3% (v/v) water. In one embodiment the isolated polysaccharide is reacted with CDI in an aprotic solvent comprising about 0.4% (v/v) water. In one embodiment the isolated polysaccharide is reacted with CDI in an aprotic solvent comprising about 0.5% (v/v) water. In one embodiment the isolated polysaccharide is reacted with CDI in an aprotic solvent comprising about 0.6% (v/v) water. In one embodiment the isolated polysaccharide is reacted with CDI in an aprotic solvent comprising about 0.7% (v/v) water. In one embodiment the isolated polysaccharide is reacted with CDI in an aprotic solvent comprising about 0.8% (v/v) water. In one embodiment the isolated polysaccharide is reacted with CDI in an aprotic solvent comprising about 0.9% (v/v) water.

In one embodiment the isolated polysaccharide is reacted with CDI in DMSO comprising 0.1% to 1% (v/v) water. In one embodiment the isolated polysaccharide is reacted with CDI in DMSO comprising 0.1% to 0.8% (v/v) water. In one embodiment the isolated polysaccharide is reacted with CDI in DMSO comprising 0.1% to 0.5% (v/v) water. In one embodiment the isolated polysaccharide is reacted with CDI in DMSO comprising 0.1% to 0.4% (v/v) water. In one embodiment the isolated polysaccharide is reacted with CDI in DMSO comprising 0.1% to 0.3% (v/v) water. In one embodiment the isolated polysaccharide is reacted with CDI in DMSO comprising 0.1% to 0.2% (v/v) water.

In one embodiment the isolated polysaccharide is reacted with CDI in DMSO comprising 0.2% to 1% (v/v) water. In one embodiment the isolated polysaccharide is reacted with CDI in DMSO comprising 0.2% to 0.8% (v/v) water. In one embodiment the isolated polysaccharide is reacted with CDI in DMSO comprising 0.2% to 0.5% (v/v) water. In one embodiment the isolated polysaccharide is reacted with CDI in DMSO comprising 0.2% to 0.4% (v/v) water. In one embodiment the isolated polysaccharide is reacted with CDI in DMSO comprising 0.2% to 0.3% (v/v) water.

In one embodiment the isolated polysaccharide is reacted with CDI in DMSO comprising 0.3% to 0.8% (v/v) water. In one embodiment the isolated polysaccharide is reacted with CDI in DMSO comprising 0.3% to 0.5% (v/v) water. In one embodiment the isolated polysaccharide is reacted with CDI in DMSO comprising 0.3% to 0.4% (v/v) water.

In one embodiment the isolated polysaccharide is reacted with CDI in DMSO comprising about 0.1% (v/v) water. In one embodiment the isolated polysaccharide is reacted with CDI in DMSO comprising about 0.2% (v/v) water. In one embodiment the isolated polysaccharide is reacted with CDI in DMSO comprising about 0.3% (v/v) water. In one embodiment the isolated polysaccharide is reacted with CDI in DMSO comprising about 0.4% (v/v) water. In one embodiment the isolated polysaccharide is reacted with CDI in DMSO comprising about 0.5% (v/v) water. In one embodiment the isolated polysaccharide is reacted with CDI in DMSO comprising about 0.6% (v/v) water. In one embodiment the isolated polysaccharide is reacted with CDI in DMSO comprising about 0.7% (v/v) water. In one embodiment the isolated polysaccharide is reacted with CDI in DMSO comprising about 0.8% (v/v) water. In one embodiment the isolated polysaccharide is reacted with CDI in DMSO comprising about 0.9% (v/v) water.

In one embodiment the free carbonic acid derivative is then quenched by the addition of water before the addition of the azido linker. Water can inactivate free CDI.

Therefore, in an embodiment, carbonic acid derivative activation is followed by the addition of water. In an embodiment, water is added to bring the total water content in the mixture to between about 1% to about 10% (v/v). In an embodiment, water is added to bring the total water content in the mixture to between about 1.2% to about 8% (v/v). In an embodiment, water is added to bring the total water content in the mixture to between about 1.5% to about 5% (v/v). In an embodiment, water is added to bring the total water content in the mixture to between about 1.5% to about 3% (v/v). In an embodiment, water is added to bring the total water content in the mixture to between about 1.5% to about 2.5% (v/v). In an embodiment, water is added to bring the total water content in the mixture to about 1% (v/v). In an embodiment, water is added to bring the total water content in the mixture to about 1.2% (v/v). In an embodiment, water is added to bring the total water content in the mixture to about 1.4% (v/v). In an embodiment, water is added to bring the total water content in the mixture to about 1.5% (v/v). In an embodiment, water is added to bring the total water content in the mixture to about 2% (v/v). In an embodiment, water is added to bring the total water content in the mixture to about 2.5% (v/v). In an embodiment, water is added to bring the total water content in the mixture to about 3% (v/v). In an embodiment, water is added to bring the total water content in the mixture to about 5% (v/v). In an embodiment, water is added to bring the total water content in the mixture to about 7% (v/v). In an embodiment, water is added to bring the total water content in the mixture to about 10% (v/v).

Once the polysaccharide has been reacted with carbonic acid derivative, and following an eventual quenching of carbonic acid derivative with water, the carbonic acid derivative-activated polysaccharide is reacted with an azido linker.

In one embodiment step a) further comprises reacting the carbonic acid derivative-activated polysaccharide with an amount of azido linker that is between 0.01-10 molar equivalent to the amount of polysaccharide Repeat Unit of the activated polysaccharide (molar equivalent of RU).

In one embodiment step a) further comprises reacting the carbonic acid derivative-activated polysaccharide with an amount of azido linker that is between 0.01-8 molar equivalent to the amount of polysaccharide repeat unit of the activated polysaccharide.

In one embodiment step a) further comprises reacting the carbonic acid derivative-activated polysaccharide with an amount of azido linker that is between 0.01-5 molar equivalent to the amount of polysaccharide repeat unit of the activated polysaccharide.

In one embodiment step a) further comprises reacting the carbonic acid derivative-activated polysaccharide with an amount of azido linker that is between 0.01-4 molar equivalent to the amount of polysaccharide repeat unit of the activated polysaccharide.

In one embodiment step a) further comprises reacting the carbonic acid derivative-activated polysaccharide with an amount of azido linker that is between 0.01-3 molar equivalent to the amount of polysaccharide repeat unit of the activated polysaccharide.

In one embodiment step a) further comprises reacting the carbonic acid derivative-activated polysaccharide with an amount of azido linker that is between 0.01-2 molar equivalent to the amount of polysaccharide repeat unit of the activated polysaccharide.

In one embodiment step a) further comprises reacting the carbonic acid derivative-activated polysaccharide with an amount of azido linker that is between 0.01-1 molar equivalent to the amount of polysaccharide repeat unit of the activated polysaccharide.

In one embodiment step a) further comprises reacting the carbonic acid derivative-activated polysaccharide with an amount of azido linker that is between 0.01-0.5 molar equivalent to the amount of polysaccharide repeat unit of the activated polysaccharide.

In one embodiment step a) further comprises reacting the carbonic acid derivative-activated polysaccharide with an amount of azido linker that is between 0.01-0.1 molar equivalent to the amount of polysaccharide repeat unit of the activated polysaccharide.

In one embodiment step a) further comprises reacting the carbonic acid derivative-activated polysaccharide with an amount of azido linker that is between 0.05-10 molar equivalent to the amount of polysaccharide repeat unit of the activated polysaccharide.

In one embodiment step a) further comprises reacting the carbonic acid derivative-activated polysaccharide with an amount of azido linker that is between 0.05-8 molar equivalent to the amount of polysaccharide repeat unit of the activated polysaccharide.

In one embodiment step a) further comprises reacting the carbonic acid derivative-activated polysaccharide with an amount of azido linker that is between 0.05-5 molar equivalent to the amount of polysaccharide repeat unit of the activated polysaccharide.

In one embodiment step a) further comprises reacting the carbonic acid derivative-activated polysaccharide with an amount of azido linker that is between 0.05-4 molar equivalent to the amount of polysaccharide repeat unit of the activated polysaccharide.

In one embodiment step a) further comprises reacting the carbonic acid derivative-activated polysaccharide with an amount of azido linker that is between 0.05-3 molar equivalent to the amount of polysaccharide repeat unit of the activated polysaccharide.

In one embodiment step a) further comprises reacting the carbonic acid derivative-activated polysaccharide with an amount of azido linker that is between 0.05-2 molar equivalent to the amount of polysaccharide repeat unit of the activated polysaccharide.

In one embodiment step a) further comprises reacting the carbonic acid derivative-activated polysaccharide with an amount of azido linker that is between 0.05-1 molar equivalent to the amount of polysaccharide repeat unit of the activated polysaccharide.

In one embodiment step a) further comprises reacting the carbonic acid derivative-activated polysaccharide with an amount of azido linker that is between 0.05-0.5 molar equivalent to the amount of polysaccharide repeat unit of the activated polysaccharide.

In one embodiment step a) further comprises reacting the carbonic acid derivative-activated polysaccharide with an amount of azido linker that is between 0.05-0.1 molar equivalent to the amount of polysaccharide repeat unit of the activated polysaccharide.

In one embodiment step a) further comprises reacting the carbonic acid derivative-activated polysaccharide with an amount of azido linker that is between 0.1-10 molar equivalent to the amount of polysaccharide repeat unit of the activated polysaccharide.

In one embodiment step a) further comprises reacting the carbonic acid derivative-activated polysaccharide with an amount of azido linker that is between 0.1-8 molar equivalent to the amount of polysaccharide repeat unit of the activated polysaccharide.

In one embodiment step a) further comprises reacting the carbonic acid derivative-activated polysaccharide with an amount of azido linker that is between 0.1-5 molar equivalent to the amount of polysaccharide repeat unit of the activated polysaccharide.

In one embodiment step a) further comprises reacting the carbonic acid derivative-activated polysaccharide with an amount of azido linker that is between 0.1-4 molar equivalent to the amount of polysaccharide repeat unit of the activated polysaccharide.

In one embodiment step a) further comprises reacting the carbonic acid derivative-activated polysaccharide with an amount of azido linker that is between 0.1-3 molar equivalent to the amount of polysaccharide repeat unit of the activated polysaccharide.

In one embodiment step a) further comprises reacting the carbonic acid derivative-activated polysaccharide with an amount of azido linker that is between 0.1-2 molar equivalent to the amount of polysaccharide repeat unit of the activated polysaccharide.

In one embodiment step a) further comprises reacting the carbonic acid derivative-activated polysaccharide with an amount of azido linker that is between 0.1-1 molar equivalent to the amount of polysaccharide repeat unit of the activated polysaccharide.

In one embodiment step a) further comprises reacting the carbonic acid derivative-activated polysaccharide with an amount of azido linker that is between 0.1-0.5 molar equivalent to the amount of polysaccharide repeat unit of the activated polysaccharide.

In one embodiment step a) further comprises reacting the carbonic acid derivative-activated polysaccharide with an amount of azido linker that is between 0.5-10 molar equivalent to the amount of polysaccharide repeat unit of the activated polysaccharide.

In one embodiment step a) further comprises reacting the carbonic acid derivative-activated polysaccharide with an amount of azido linker that is between 0.5-8 molar equivalent to the amount of polysaccharide repeat unit of the activated polysaccharide.

In one embodiment step a) further comprises reacting the carbonic acid derivative-activated polysaccharide with an amount of azido linker that is between 0.5-5 molar equivalent to the amount of polysaccharide repeat unit of the activated polysaccharide.

In one embodiment step a) further comprises reacting the carbonic acid derivative-activated polysaccharide with an amount of azido linker that is between 0.5-4 molar equivalent to the amount of polysaccharide repeat unit of the activated polysaccharide.

In one embodiment step a) further comprises reacting the carbonic acid derivative-activated polysaccharide with an amount of azido linker that is between 0.5-3 molar equivalent to the amount of polysaccharide repeat unit of the activated polysaccharide.

In one embodiment step a) further comprises reacting the carbonic acid derivative-activated polysaccharide with an amount of azido linker that is between 0.5-2 molar equivalent to the amount of polysaccharide repeat unit of the activated polysaccharide.

In one embodiment step a) further comprises reacting the carbonic acid derivative-activated polysaccharide with an amount of azido linker that is between 0.5-1 molar equivalent to the amount of polysaccharide repeat unit of the activated polysaccharide.

In one embodiment step a) further comprises reacting the carbonic acid derivative-activated polysaccharide with an amount of azido linker that is between 1-10 molar equivalent to the amount of polysaccharide repeat unit of the activated polysaccharide.

In one embodiment step a) further comprises reacting the carbonic acid derivative-activated polysaccharide with an amount of azido linker that is between 1-8 molar equivalent to the amount of polysaccharide repeat unit of the activated polysaccharide.

In one embodiment step a) further comprises reacting the carbonic acid derivative-activated polysaccharide with an amount of azido linker that is between 1-5 molar equivalent to the amount of polysaccharide repeat unit of the activated polysaccharide.

In one embodiment step a) further comprises reacting the carbonic acid derivative-activated polysaccharide with an amount of azido linker that is between 1-4 molar equivalent to the amount of polysaccharide repeat unit of the activated polysaccharide.

In one embodiment step a) further comprises reacting the carbonic acid derivative-activated polysaccharide with an amount of azido linker that is between 1-3 molar equivalent to the amount of polysaccharide repeat unit of the activated polysaccharide.

In one embodiment step a) further comprises reacting the carbonic acid derivative-activated polysaccharide with an amount of azido linker that is between 1-2 molar equivalent to the amount of polysaccharide repeat unit of the activated polysaccharide.

In one embodiment step a) further comprises reacting the carbonic acid derivative-activated polysaccharide with an amount of azido linker that is between 2-10 molar equivalent to the amount of polysaccharide repeat unit of the activated polysaccharide.

In one embodiment step a) further comprises reacting the carbonic acid derivative-activated polysaccharide with an amount of azido linker that is between 2-8 molar equivalent to the amount of polysaccharide repeat unit of the activated polysaccharide.

In one embodiment step a) further comprises reacting the carbonic acid derivative-activated polysaccharide with an amount of azido linker that is between 2-5 molar equivalent to the amount of polysaccharide repeat unit of the activated polysaccharide.

In one embodiment step a) further comprises reacting the carbonic acid derivative-activated polysaccharide with an amount of azido linker that is between 2-4 molar equivalent to the amount of polysaccharide repeat unit of the activated polysaccharide.

In one embodiment step a) further comprises reacting the carbonic acid derivative-activated polysaccharide with an amount of azido linker that is between 2-3 molar equivalent to the amount of polysaccharide repeat unit of the activated polysaccharide.

In one embodiment step a) further comprises reacting the carbonic acid derivative-activated polysaccharide with an amount of azido linker that is between 3-10 molar equivalent to the amount of polysaccharide repeat unit of the activated polysaccharide.

In one embodiment step a) further comprises reacting the carbonic acid derivative-activated polysaccharide with an amount of azido linker that is between 3-8 molar equivalent to the amount of polysaccharide repeat unit of the activated polysaccharide.

In one embodiment step a) further comprises reacting the carbonic acid derivative-activated polysaccharide with an amount of azido linker that is between 3-5 molar equivalent to the amount of polysaccharide repeat unit of the activated polysaccharide.

In one embodiment step a) further comprises reacting the carbonic acid derivative-activated polysaccharide with an amount of azido linker that is between 3-4 molar equivalent to the amount of polysaccharide repeat unit of the activated polysaccharide.

In one embodiment step a) further comprises reacting the carbonic acid derivative-activated polysaccharide with an amount of azido linker that is between 4-10 molar equivalent to the amount of polysaccharide repeat unit of the activated polysaccharide.

In one embodiment step a) further comprises reacting the carbonic acid derivative-activated polysaccharide with an amount of azido linker that is between 4-8 molar equivalent to the amount of polysaccharide repeat unit of the activated polysaccharide.

In one embodiment step a) further comprises reacting the carbonic acid derivative-activated polysaccharide with an amount of azido linker that is between 4-5 molar equivalent to the amount of polysaccharide repeat unit of the activated polysaccharide.

In one embodiment step a) further comprises reacting the carbonic acid derivative-activated polysaccharide with an amount of azido linker that is between 5-10 molar equivalent to the amount of polysaccharide repeat unit of the activated polysaccharide.

In one embodiment step a) further comprises reacting the carbonic acid derivative-activated polysaccharide with an amount of azido linker that is between 5-8 molar equivalent to the amount of polysaccharide repeat unit of the activated polysaccharide.

In one embodiment step a) further comprises reacting the carbonic acid derivative-activated polysaccharide with an amount of azido linker that is between 8-10 molar equivalent to the amount of polysaccharide repeat unit of the activated polysaccharide.

In one embodiment step a) further comprises reacting the carbonic acid derivative-activated polysaccharide with an amount of azido linker that is about 0.01 molar equivalent to the amount of polysaccharide repeat unit of the activated polysaccharide.

In one embodiment step a) further comprises reacting the carbonic acid derivative-activated polysaccharide with an amount of azido linker that is about 0.05 molar equivalent to the amount of polysaccharide repeat unit of the activated polysaccharide.

In one embodiment step a) further comprises reacting the carbonic acid derivative-activated polysaccharide with an amount of azido linker that is about 0.1 molar equivalent to the amount of polysaccharide repeat unit of the activated polysaccharide.

In one embodiment step a) further comprises reacting the carbonic acid derivative-activated polysaccharide with an amount of azido linker that is about 0.5 molar equivalent to the amount of polysaccharide repeat unit of the activated polysaccharide.

In one embodiment step a) further comprises reacting the carbonic acid derivative-activated polysaccharide with an amount of azido linker that is about 1 molar equivalent to the amount of polysaccharide repeat unit of the activated polysaccharide.

In one embodiment step a) further comprises reacting the carbonic acid derivative-activated polysaccharide with an amount of azido linker that is about 2 molar equivalents to the amount of polysaccharide repeat unit of the activated polysaccharide.

In one embodiment step a) further comprises reacting the carbonic acid derivative-activated polysaccharide with an amount of azido linker that is about 3 molar equivalents to the amount of polysaccharide repeat unit of the activated polysaccharide.

In one embodiment step a) further comprises reacting the carbonic acid derivative-activated polysaccharide with an amount of azido linker that is about 4 molar equivalents to the amount of polysaccharide repeat unit of the activated polysaccharide.

In one embodiment step a) further comprises reacting the carbonic acid derivative-activated polysaccharide with an amount of azido linker that is about 5 molar equivalents to the amount of polysaccharide repeat unit of the activated polysaccharide.

In one embodiment step a) further comprises reacting the carbonic acid derivative-activated polysaccharide with an amount of azido linker that is about 8 molar equivalents to the amount of polysaccharide repeat unit of the activated polysaccharide.

In one embodiment step a) further comprises reacting the carbonic acid derivative-activated polysaccharide with an amount of azido linker that is about 10 molar equivalents to the amount of polysaccharide repeat unit of the activated polysaccharide.

In the above embodiments, said carbonic acid derivative is preferably CDI. In another embodiment, said carbonic acid derivative is CDT.

In one embodiment the degree of activation of the activated polysaccharide following step a) is between 0.5 to 50%. The degree of activation of the azido polysaccharide being defined as the percentage of Repeating Unit linked to an azido linker.

In one embodiment the degree of activation of the activated polysaccharide following step a) is between 1 to 30%. In another embodiment the degree of activation of the activated polysaccharide following step a) is between 2 to 25%. In another embodiment the degree of activation of the activated polysaccharide following step a) is between 3 to 20%.

In another embodiment the degree of activation of the activated polysaccharide following step a) is between 3 to 15%. In another embodiment the degree of activation of the activated polysaccharide following step a) is between 4 to 15%. In an embodiment the degree of activation of the activated polysaccharide following step a) is between 1 to 6%.

In an embodiment the degree of activation of the activated polysaccharide following step a) is between 3 to 6%. In an embodiment the degree of activation of the activated polysaccharide following step a) is between 10 to 15%.

In an embodiment the degree of activation of the activated polysaccharide following step a) is about 1%. In an embodiment the degree of activation of the activated polysaccharide following step a) is about 2%. In an embodiment the degree of activation of the activated polysaccharide following step a) is about 3%. In an embodiment the degree of activation of the activated polysaccharide following step a) is about 4%. In an embodiment the degree of activation of the activated polysaccharide following step a) is about 5%. In an embodiment the degree of activation of the activated polysaccharide following step a) is about 6%. In an embodiment the degree of activation of the activated polysaccharide following step a) is about 7%. In an embodiment the degree of activation of the activated polysaccharide following step a) is about 8%. In an embodiment the degree of activation of the activated polysaccharide following step a) is about 9%. In an embodiment the degree of activation of the activated polysaccharide following step a) is about 10%. In an embodiment the degree of activation of the activated polysaccharide following step a) is about 11%. In an embodiment the degree of activation of the activated polysaccharide following step a) is about 12%. In an embodiment the degree of activation of the activated polysaccharide following step a) is about 13%. In an embodiment the degree of activation of the activated polysaccharide following step a) is about 14%. In an embodiment the degree of activation of the activated polysaccharide following step a) is about 15%. In an embodiment the degree of activation of the activated polysaccharide following step a) is about 16%. In an embodiment the degree of activation of the activated polysaccharide following step a) is about 17%. In an embodiment the degree of activation of the activated polysaccharide following step a) is about 18%. In an embodiment the degree of activation of the activated polysaccharide following step a) is about 19%. In an embodiment the degree of activation of the activated polysaccharide following step a) is about 20%.

In one embodiment step b) comprises reacting the carrier protein with an amount of agent bearing an N-Hydroxysuccinimide (NHS) moiety and an alkyne group that is 0.1-10 molar equivalents to the lysines on the carrier.

In one embodiment step b) comprises reacting the carrier protein with an amount of agent bearing an N-Hydroxysuccinimide (NHS) moiety and an alkyne group that is 0.5-10 molar equivalents to the lysines on the carrier.

In one embodiment step b) comprises reacting the carrier protein with an amount of agent bearing an N-Hydroxysuccinimide (NHS) moiety and an alkyne group that is 1-10 molar equivalents to the lysines on the carrier.

In one embodiment step b) comprises reacting the carrier protein with an amount of agent bearing an N-Hydroxysuccinimide (NHS) moiety and an alkyne group that is 1.5-10 molar equivalents to the lysines on the carrier.

In one embodiment step b) comprises reacting the carrier protein with an amount of agent bearing an N-Hydroxysuccinimide (NHS) moiety and an alkyne group that is 2-10 molar equivalents to the lysines on the carrier.

In one embodiment step b) comprises reacting the carrier protein with an amount of agent bearing an N-Hydroxysuccinimide (NHS) moiety and an alkyne group that is 2.5-10 molar equivalents to the lysines on the carrier.

In one embodiment step b) comprises reacting the carrier protein with an amount of agent bearing an N-Hydroxysuccinimide (NHS) moiety and an alkyne group that is 3-10 molar equivalents to the lysines on the carrier.

In one embodiment step b) comprises reacting the carrier protein with an amount of agent bearing an N-Hydroxysuccinimide (NHS) moiety and an alkyne group that is 5-10 molar equivalents to the lysines on the carrier.

In one embodiment step b) comprises reacting the carrier protein with an amount of agent bearing an N-Hydroxysuccinimide (NHS) moiety and an alkyne group that is 7.5-10 molar equivalents to the lysines on the carrier.

In one embodiment step b) comprises reacting the carrier protein with an amount of agent bearing an N-Hydroxysuccinimide (NHS) moiety and an alkyne group that is 0.1-7.5 molar equivalents to the lysines on the carrier.

In one embodiment step b) comprises reacting the carrier protein with an amount of agent bearing an N-Hydroxysuccinimide (NHS) moiety and an alkyne group that is 0.5-7.5 molar equivalents to the lysines on the carrier.

In one embodiment step b) comprises reacting the carrier protein with an amount of agent bearing an N-Hydroxysuccinimide (NHS) moiety and an alkyne group that is 1-7.5 molar equivalents to the lysines on the carrier.

In one embodiment step b) comprises reacting the carrier protein with an amount of agent bearing an N-Hydroxysuccinimide (NHS) moiety and an alkyne group that is 1.5-7.5 molar equivalents to the lysines on the carrier.

In one embodiment step b) comprises reacting the carrier protein with an amount of agent bearing an N-Hydroxysuccinimide (NHS) moiety and an alkyne group that is 2-7.5 molar equivalents to the lysines on the carrier.

In one embodiment step b) comprises reacting the carrier protein with an amount of agent bearing an N-Hydroxysuccinimide (NHS) moiety and an alkyne group that is 2.5-7.5 molar equivalents to the lysines on the carrier.

In one embodiment step b) comprises reacting the carrier protein with an amount of agent bearing an N-Hydroxysuccinimide (NHS) moiety and an alkyne group that is 3-7.5 molar equivalents to the lysines on the carrier.

In one embodiment step b) comprises reacting the carrier protein with an amount of agent bearing an N-Hydroxysuccinimide (NHS) moiety and an alkyne group that is 5-7.5 molar equivalents to the lysines on the carrier.

In one embodiment step b) comprises reacting the carrier protein with an amount of agent bearing an N-Hydroxysuccinimide (NHS) moiety and an alkyne group that is 0.1-5 molar equivalents to the lysines on the carrier.

In one embodiment step b) comprises reacting the carrier protein with an amount of agent bearing an N-Hydroxysuccinimide (NHS) moiety and an alkyne group that is 0.5-5 molar equivalents to the lysines on the carrier.

In one embodiment step b) comprises reacting the carrier protein with an amount of agent bearing an N-Hydroxysuccinimide (NHS) moiety and an alkyne group that is 1-5 molar equivalents to the lysines on the carrier.

In one embodiment step b) comprises reacting the carrier protein with an amount of agent bearing an N-Hydroxysuccinimide (NHS) moiety and an alkyne group that is 1.5-5 molar equivalents to the lysines on the carrier.

In one embodiment step b) comprises reacting the carrier protein with an amount of agent bearing an N-Hydroxysuccinimide (NHS) moiety and an alkyne group that is 2-5 molar equivalents to the lysines on the carrier.

In one embodiment step b) comprises reacting the carrier protein with an amount of agent bearing an N-Hydroxysuccinimide (NHS) moiety and an alkyne group that is 2.5-5 molar equivalents to the lysines on the carrier.

In one embodiment step b) comprises reacting the carrier protein with an amount of agent bearing an N-Hydroxysuccinimide (NHS) moiety and an alkyne group that is 3-5 molar equivalents to the lysines on the carrier.

In one embodiment step b) comprises reacting the carrier protein with an amount of agent bearing an N-Hydroxysuccinimide (NHS) moiety and an alkyne group that is 0.1-3 molar equivalents to the lysines on the carrier.

In one embodiment step b) comprises reacting the carrier protein with an amount of agent bearing an N-Hydroxysuccinimide (NHS) moiety and an alkyne group that is 0.5-3 molar equivalents to the lysines on the carrier.

In one embodiment step b) comprises reacting the carrier protein with an amount of agent bearing an N-Hydroxysuccinimide (NHS) moiety and an alkyne group that is 1-3 molar equivalents to the lysines on the carrier.

In one embodiment step b) comprises reacting the carrier protein with an amount of agent bearing an N-Hydroxysuccinimide (NHS) moiety and an alkyne group that is 1.5-3 molar equivalents to the lysines on the carrier.

In one embodiment step b) comprises reacting the carrier protein with an amount of agent bearing an N-Hydroxysuccinimide (NHS) moiety and an alkyne group that is 2-3 molar equivalents to the lysines on the carrier.

In one embodiment step b) comprises reacting the carrier protein with an amount of agent bearing an N-Hydroxysuccinimide (NHS) moiety and an alkyne group that is 2.5-3 molar equivalents to the lysines on the carrier.

In one embodiment step b) comprises reacting the carrier protein with an amount of agent bearing an N-Hydroxysuccinimide (NHS) moiety and an alkyne group that is 0.1-2.5 molar equivalents to the lysines on the carrier.

In one embodiment step b) comprises reacting the carrier protein with an amount of agent bearing an N-Hydroxysuccinimide (NHS) moiety and an alkyne group that is 0.5-2.5 molar equivalents to the lysines on the carrier.

In one embodiment step b) comprises reacting the carrier protein with an amount of agent bearing an N-Hydroxysuccinimide (NHS) moiety and an alkyne group that is 1-2.5 molar equivalents to the lysines on the carrier.

In one embodiment step b) comprises reacting the carrier protein with an amount of agent bearing an N-Hydroxysuccinimide (NHS) moiety and an alkyne group that is 1.5-2.5 molar equivalents to the lysines on the carrier.

In one embodiment step b) comprises reacting the carrier protein with an amount of agent bearing an N-Hydroxysuccinimide (NHS) moiety and an alkyne group that is 2-2.5 molar equivalents to the lysines on the carrier.

In one embodiment step b) comprises reacting the carrier protein with an amount of agent bearing an N-Hydroxysuccinimide (NHS) moiety and an alkyne group that is 0.1-2 molar equivalents to the lysines on the carrier.

In one embodiment step b) comprises reacting the carrier protein with an amount of agent bearing an N-Hydroxysuccinimide (NHS) moiety and an alkyne group that is 0.5-2 molar equivalents to the lysines on the carrier.

In one embodiment step b) comprises reacting the carrier protein with an amount of agent bearing an N-Hydroxysuccinimide (NHS) moiety and an alkyne group that is 1-2 molar equivalents to the lysines on the carrier.

In one embodiment step b) comprises reacting the carrier protein with an amount of agent bearing an N-Hydroxysuccinimide (NHS) moiety and an alkyne group that is 1.5-2 molar equivalents to the lysines on the carrier.

In one embodiment step b) comprises reacting the carrier protein with an amount of agent bearing an N-Hydroxysuccinimide (NHS) moiety and an alkyne group that is 0.1-1.5 molar equivalents to the lysines on the carrier.

In one embodiment step b) comprises reacting the carrier protein with an amount of agent bearing an N-Hydroxysuccinimide (NHS) moiety and an alkyne group that is 0.5-1.5 molar equivalents to the lysines on the carrier.

In one embodiment step b) comprises reacting the carrier protein with an amount of agent bearing an N-Hydroxysuccinimide (NHS) moiety and an alkyne group that is 1-1.5 molar equivalents to the lysines on the carrier.

In one embodiment step b) comprises reacting the carrier protein with an amount of agent bearing an N-Hydroxysuccinimide (NHS) moiety and an alkyne group that is 0.1-1 molar equivalents to the lysines on the carrier.

In one embodiment step b) comprises reacting the carrier protein with an amount of agent bearing an N-Hydroxysuccinimide (NHS) moiety and an alkyne group that is 0.5-1 molar equivalents to the lysines on the carrier.

In one embodiment step b) comprises reacting the carrier protein with an amount of agent bearing an N-Hydroxysuccinimide (NHS) moiety and an alkyne group that is 0.1-0.5 molar equivalents to the lysines on the carrier.

In one embodiment step b) comprises reacting the carrier protein with an amount of agent bearing an N-Hydroxysuccinimide (NHS) moiety and an alkyne group that is about 10 molar equivalents to the lysines on the carrier.

In one embodiment step b) comprises reacting the carrier protein with an amount of agent bearing an N-Hydroxysuccinimide (NHS) moiety and an alkyne group that is about 7.5 molar equivalents to the lysines on the carrier.

In one embodiment step b) comprises reacting the carrier protein with an amount of agent bearing an N-Hydroxysuccinimide (NHS) moiety and an alkyne group that is about 5 molar equivalents to the lysines on the carrier.

In one embodiment step b) comprises reacting the carrier protein with an amount of agent bearing an N-Hydroxysuccinimide (NHS) moiety and an alkyne group that is about 3 molar equivalents to the lysines on the carrier.

In one embodiment step b) comprises reacting the carrier protein with an amount of agent bearing an N-Hydroxysuccinimide (NHS) moiety and an alkyne group that is about 2.5 molar equivalents to the lysines on the carrier.

In one embodiment step b) comprises reacting the carrier protein with an amount of agent bearing an N-Hydroxysuccinimide (NHS) moiety and an alkyne group that is about 2 molar equivalents to the lysines on the carrier.

In one embodiment step b) comprises reacting the carrier protein with an amount of agent bearing an N-Hydroxysuccinimide (NHS) moiety and an alkyne group that is about 1.5 molar equivalents to the lysines on the carrier.

In one embodiment step b) comprises reacting the carrier protein with an amount of agent bearing an N-Hydroxysuccinimide (NHS) moiety and an alkyne group that is about 1 molar equivalent to the lysines on the carrier.

In one embodiment step b) comprises reacting the carrier protein with an amount of agent bearing an N-Hydroxysuccinimide (NHS) moiety and an alkyne group that is about 0.5 molar equivalents to the lysines on the carrier.

In one embodiment step b) comprises reacting the carrier protein with an amount of agent bearing an N-Hydroxysuccinimide (NHS) moiety and an alkyne group that is about 0.1 molar equivalents to the lysines on the carrier.

In one embodiment the degree of activation of the activated carrier following step b) is between 1 and 50. The degree of activation of the activated carrier being defined as the number of lysine residues in the carrier protein that become linked to the agent bearing an N-Hydroxysuccinimide (NHS) moiety and an alkyne group.

In an embodiment, the carrier protein is $CRM_{197}$, which contains 39 lysine residues. In said embodiment the degree of activation of the activated carrier following step b) may be between 1 to 30. In another embodiment the degree of activation of the activated carrier ($CRM_{197}$) following step b) is between 5 to 20. In another embodiment the degree of activation of the activated carrier ($CRM_{197}$) following step b) is between 9 to 18. In another embodiment the degree of activation of the activated carrier ($CRM_{197}$) following step b) is between 8 to 11. In another embodiment the degree of activation of the activated carrier ($CRM_{197}$) following step b) is between 15 to 20. In another embodiment the degree of activation of the activated carrier ($CRM_{197}$) following step b) is about 5. In another embodiment the degree of activation of the activated carrier ($CRM_{197}$) following step b) is about 6. In another embodiment the degree of activation of the activated carrier ($CRM_{197}$) following step b) is about 7. In another embodiment the degree of activation of the activated carrier ($CRM_{197}$) following step b) is about 8. In another embodiment the degree of activation of the activated carrier ($CRM_{197}$) following step b) is about 9. In another embodiment the degree of activation of the activated carrier ($CRM_{197}$) following step b) is about 10. In another embodiment the degree of activation of the activated carrier ($CRM_{197}$) following step b) is about 11. In another embodiment the degree of activation of the activated carrier ($CRM_{197}$) following step b) is about 12. In another embodiment the degree of activation of the activated carrier ($CRM_{197}$) following step b) is about 13. In another embodiment the degree of activation of the activated carrier ($CRM_{197}$) following step b) is about 14. In another embodiment the degree of activation of the activated carrier ($CRM_{197}$) following step b) is about 15. In another embodiment the degree of activation of the activated carrier ($CRM_{197}$) following step b) is about 16. In another embodiment the degree of activation of the activated carrier ($CRM_{197}$) following step b) is about 17. In another embodiment the degree of activation of the activated carrier ($CRM_{197}$) following step b) is about 18. In another embodiment the degree of activation of the activated carrier ($CRM_{197}$) following step b) is about 19. In another embodiment the degree of activation of the activated carrier ($CRM_{197}$) following step b) is about 20. In another embodiment the degree of activation of the activated carrier ($CRM_{197}$) following step b) is about 21. In another embodiment the degree of activation of the activated carrier ($CRM_{197}$) following step b) is about 22. In another embodiment the degree of activation of the activated carrier ($CRM_{197}$) following step b) is about 23. In another embodiment the degree of activation of the activated carrier ($CRM_{197}$) following step b) is about 24. In another embodiment the degree of activation of the activated carrier ($CRM_{197}$) following step b) is about 25.

In an embodiment, the carrier protein is SCP or a fragment thereof. In said embodiment the degree of activation of the activated carrier following step b) may be between 1 to 50.

In another embodiment the degree of activation of the activated carrier (SCP) following step b) is between 5 to 50. In another embodiment the degree of activation of the activated carrier (SCP) following step b) is between 7 to 45. In another embodiment the degree of activation of the activated carrier (SCP) following step b) is between 5 to 15. In another embodiment the degree of activation of the activated carrier (SCP) following step b) is between 20 to 30. In another embodiment the degree of activation of the activated carrier (SCP) following step b) is between 30 to 50. In another embodiment the degree of activation of the activated carrier (SCP) following step b) is between 30 to 40. In another embodiment the degree of activation of the activated carrier (SCP) following step b) is between 10 to 40. In another embodiment the degree of activation of the activated carrier (SCP) following step b) is about 5. In another embodiment the degree of activation of the activated carrier (SCP) following step b) is about 7. In another embodiment the degree of activation of the activated carrier (SCP) following step b) is about 10. In another embodiment the degree of activation of the activated carrier (SCP) following step b) is about 13. In another embodiment the degree of activation of the activated carrier (SCP) following step b) is about 15. In another embodiment the degree of activation of the activated carrier (SCP) following step b) is about 20. In another embodiment the degree of activation of the activated carrier (SCP) following step b) is about 26. In another embodiment the degree of activation of the activated carrier (SCP) following step b) is about 30. In another embodiment the degree of activation of the activated carrier (SCP) following step b) is about 35. In another embodiment the degree of activation of the activated carrier (SCP) following step b) is about 37. In another embodiment the degree of activation of the activated carrier (SCP) following step b) is about 40. In another embodiment the degree of activation of the activated carrier (SCP) following step b) is about 45. In another embodiment the degree of activation of the activated carrier (SCP) following step b) is about 50.

In an embodiment, the carrier protein is TT or a fragment thereof. In said embodiment the degree of activation of the activated carrier following step b) may be between 1 to 30.

In another embodiment the degree of activation of the activated carrier (TT) following step b) is between 5 to 25. In another embodiment the degree of activation of the activated carrier (TT) following step b) is between 7 to 25. In another embodiment the degree of activation of the activated carrier (TT) following step b) is between 10 to 20. In another embodiment the degree of activation of the activated carrier (TT) following step b) is about 5. In another embodiment the degree of activation of the activated carrier (TT) following step b) is about 7. In another embodiment the degree of activation of the activated carrier (TT) following step b) is about 10. In another embodiment the degree of activation of the activated carrier (TT) following step b) is about 12. In another embodiment the degree of activation of the activated carrier (TT) following step b) is about 15. In another embodiment the degree of activation of the activated carrier (TT) following step b) is about 20. In another embodiment the degree of activation of the activated carrier (TT) following step b) is about 25. In another embodiment the degree of activation of the activated carrier (TT) following step b) is about 30.

In an embodiment, the conjugation reaction c) is carried out in aqueous buffer. In an embodiment, the conjugation reaction c) is carried out in aqueous buffer in the presence of copper (I) as catalyst. In an embodiment, the conjugation reaction c) is carried out in aqueous buffer in the presence an oxidant and of copper (I) as catalyst. In a preferred embodiment, the conjugation reaction c) is carried out in aqueous buffer in the presence of copper (I) as catalyst and ascorbate as oxidant. In an embodiment, THPTA (tris(3-hydroxypropyltriazolylmethyl)amine) and aminoguanidine may be further added to protect the protein from side reactions. Therefore, in a preferred embodiment, the conjugation reaction c) is carried out in aqueous buffer in the presence of copper (I) as catalyst and ascorbate as oxidant, wherein the reaction mixture further comprises THPTA (tris(3-hydroxypropyltriazolylmethyl)amine) and aminoguanidine.

In an embodiment the initial input ratio (weight by weight) of activated azido polysaccharide to activated alkyne-carrier at step c) is between 0.1 and 3. In an embodiment the initial input ratio (weight by weight) of activated azido polysaccharide to activated alkyne-carrier at step c) is between 0.5 and 2. In an embodiment the initial input ratio (weight by weight) of activated azido polysaccharide to activated alkyne-carrier at step c) is between 0.6 and 1.5. In a preferred embodiment the initial input ratio (weight by weight) of activated azido polysaccharide to activated alkyne-carrier at step c) is between 0.8 and 1. In an embodiment the initial input ratio (weight by weight) of activated azido polysaccharide to activated alkyne-carrier at step c) is about 0.5. In an embodiment the initial input ratio (weight by weight) of activated azido polysaccharide to activated alkyne-carrier at step c) is about 0.6. In an embodiment the initial input ratio (weight by weight) of activated azido polysaccharide to activated alkyne-carrier at step c) is about 0.7. In an embodiment the initial input ratio (weight by weight) of activated azido polysaccharide to activated alkyne-carrier at step c) is about 0.8. In an embodiment the initial input ratio (weight by weight) of activated azido polysaccharide to activated alkyne-carrier at step c) is about 0.9. In an embodiment the initial input ratio (weight by weight) of activated azido polysaccharide to activated alkyne-carrier at step c) is about 1. In an embodiment the initial input ratio (weight by weight) of activated azido polysaccharide to activated alkyne-carrier at step c) is about 1.1. In an embodiment the initial input ratio (weight by weight) of activated azido polysaccharide to activated alkyne-carrier at step c) is about 1.2. In an embodiment the initial input ratio (weight by weight) of activated azido polysaccharide to activated alkyne-carrier at step c) is about 1.3. In an embodiment the initial input ratio (weight by weight) of activated azido polysaccharide to activated alkyne-carrier at step c) is about 1.4. In an embodiment the initial input ratio (weight by weight) of activated azido polysaccharide to activated alkyne-carrier at step c) is about 1.5. In an embodiment the initial input ratio (weight by weight) of activated azido polysaccharide to activated alkyne-carrier at step c) is about 1.6. In an embodiment the initial input ratio (weight by weight) of activated azido polysaccharide to activated alkyne-carrier at step c) is about 1.7. In an embodiment the initial input ratio (weight by weight) of activated azido polysaccharide to activated alkyne-carrier at step c) is about 1.8. In an embodiment the initial input ratio (weight by weight) of activated azido polysaccharide to activated alkyne-carrier at step c) is about 1.9. In an embodiment the initial input ratio (weight by weight) of activated azido polysaccharide to activated alkyne-carrier at step c) is about 2.

Following the click conjugation reaction, there may remain unreacted azido groups in the conjugates, these may be capped using a suitable azido group capping agent. Therefore, in an embodiment, following step c), unreacted azido groups in the conjugates, are capped using a suitable azido group capping agent. In one embodiment this azido group capping agent is an agent bearing an alkyne group. In one embodiment this azido group capping agent is an agent bearing a terminal alkyne. In one embodiment this azido group capping agent is an agent bearing a cycloalkyne.

In an embodiment, said azido group capping agent is a compound of formula (V), $$\equiv\!—X—OH \qquad (V)$$

wherein X is $(CH_2)_n$ wherein n is selected from 1 to 15.

In one embodiment this azido group capping agent is propargyl alcohol.

Therefore, in an embodiment, following step (c) the process further comprises a step of capping the unreacted azido groups remained in the conjugates with an azido group capping agent.

In an embodiment the capping of the unreacted azido groups is performed with an amount of capping agent that is between 0.05 to 20 molar equivalents to the amount of polysaccharide repeat unit of the activated polysaccharide.

In an embodiment the capping of the unreacted azido groups is performed with an amount of capping agent that is between 0.1 to 15 molar equivalents to the amount of polysaccharide repeat unit of the activated polysaccharide.

In an embodiment the capping of the unreacted azido groups is performed with an amount of capping agent that is between 0.5 to 10 molar equivalents to the amount of polysaccharide repeat unit of the activated polysaccharide.

In an embodiment the capping of the unreacted azido groups is performed with an amount of capping agent that is between 0.5 to 5 molar equivalents to the amount of polysaccharide repeat unit of the activated polysaccharide.

In an embodiment the capping of the unreacted azido groups is performed with an amount of capping agent that is between 0.5 to 2 molar equivalents to the amount of polysaccharide repeat unit of the activated polysaccharide.

In an embodiment the capping of the unreacted azido groups is performed with an amount of capping agent that is between 0.5 to 1 molar equivalents to the amount of polysaccharide repeat unit of the activated polysaccharide.

In an embodiment the capping of the unreacted azido groups is performed with an amount of capping agent that is between 1 to 2 molar equivalents to the amount of polysaccharide repeat unit of the activated polysaccharide.

In an embodiment the capping of the unreacted azido groups is performed with an amount of capping agent that is between 0.75 to 1.5 molar equivalents to the amount of polysaccharide repeat unit of the activated polysaccharide.

In an embodiment the capping of the unreacted azido groups is performed with an amount of capping agent that is about 1 molar equivalent to the amount of polysaccharide repeat unit of the activated polysaccharide.

In an embodiment the capping of the unreacted azido groups is performed with an amount of capping agent that is about 1.5 molar equivalent to the amount of polysaccharide repeat unit of the activated polysaccharide.

In an embodiment the capping of the unreacted azido groups is performed with an amount of capping agent that is about 0.5 molar equivalent to the amount of polysaccharide repeat unit of the activated polysaccharide.

In an embodiment the capping of the unreacted azido groups is performed with an amount of capping agent that is about 2 molar equivalents to the amount of polysaccharide repeat unit of the activated polysaccharide.

Following the click conjugation reaction, unreacted alkyne groups may remain present in the conjugates, these may be capped using a suitable alkyne group capping agent. In one embodiment this alkyne group capping agent is an agent bearing an azido group.

In an embodiment, said alkyne group capping agent is a compound of formula (VI), $$N_3—X—OH \qquad (VI)$$

wherein X is $(CH_2)_n$ wherein n is selected from 1 to 15.

In one embodiment this alkyne group capping agent is 3-azido-1-propanol.

Therefore, in an embodiment, following step (c) the process further comprises a step of capping the unreacted alkyne groups remained in the conjugates with an alkyne group capping agent.

In an embodiment the capping of the unreacted alkyne groups is performed with an amount of capping agent that is between 0.05 to 20 molar equivalents to the amount of polysaccharide repeat unit of the activated polysaccharide.

In an embodiment the capping of the unreacted alkyne groups is performed with an amount of capping agent that is between 0.1 to 15 molar equivalents to the amount of polysaccharide repeat unit of the activated polysaccharide.

In an embodiment the capping of the unreacted alkyne groups is performed with an amount of capping agent that is between 0.5 to 10 molar equivalents to the amount of polysaccharide repeat unit of the activated polysaccharide.

In an embodiment the capping of the unreacted alkyne groups is performed with an amount of capping agent that is between 0.5 to 5 molar equivalents to the amount of polysaccharide repeat unit of the activated polysaccharide.

In an embodiment the capping of the unreacted alkyne groups is performed with an amount of capping agent that is between 0.5 to 2 molar equivalents to the amount of polysaccharide repeat unit of the activated polysaccharide.

In an embodiment the capping of the unreacted alkyne groups is performed with an amount of capping agent that is between 0.5 to 1 molar equivalents to the amount of polysaccharide repeat unit of the activated polysaccharide.

In an embodiment the capping of the unreacted alkyne groups is performed with an amount of capping agent that is between 1 to 5 molar equivalents to the amount of polysaccharide repeat unit of the activated polysaccharide.

In an embodiment the capping of the unreacted alkyne groups is performed with an amount of capping agent that is between 1 to 2 molar equivalents to the amount of polysaccharide repeat unit of the activated polysaccharide.

In an embodiment the capping of the unreacted alkyne groups is performed with an amount of capping agent that is between 1.5 to 2.5 molar equivalents to the amount of polysaccharide repeat unit of the activated polysaccharide.

In an embodiment the capping of the unreacted alkyne groups is performed with an amount of capping agent that about 0.5 molar equivalent to the amount of polysaccharide repeat unit of the activated polysaccharide.

In an embodiment the capping of the unreacted alkyne groups is performed with an amount of capping agent that about 1 molar equivalent to the amount of polysaccharide repeat unit of the activated polysaccharide.

In an embodiment the capping of the unreacted alkyne groups is performed with an amount of capping agent that about 1.5 molar equivalent to the amount of polysaccharide repeat unit of the activated polysaccharide.

In an embodiment the capping of the unreacted alkyne groups is performed with an amount of capping agent that about 2 molar equivalents to the amount of polysaccharide repeat unit of the activated polysaccharide.

In an embodiment the capping of the unreacted alkyne groups is performed with an amount of capping agent that about 2.5 molar equivalents to the amount of polysaccharide repeat unit of the activated polysaccharide.

In an embodiment the capping of the unreacted alkyne groups is performed with an amount of capping agent that about 5 molar equivalents to the amount of polysaccharide repeat unit of the activated polysaccharide.

Following conjugation to the carrier protein, the glycoconjugate can be purified (enriched with respect to the amount of saccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration. Therefore, in one embodiment the process for producing the glycoconjugate of the present invention comprises the step of purifying the glycoconjugate after it is produced.

In an aspect, the invention provides a serotype 3 glycoconjugate produced according to any of the methods disclosed herein.

In an aspect, the invention provides a serotype 3 glycoconjugate comprising a serotype 3 saccharide covalently conjugated to a carrier protein (CP) through a spacer and having the general formula (VII):

(VII)

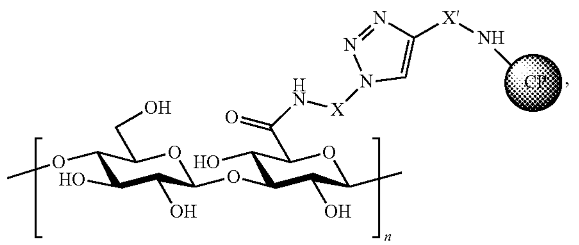

wherein X is selected from the group consisting of $CH_2(CH_2)_{n'}$, $(CH_2CH_2O)_mCH_2CH_2$, $NHCO(CH_2)_{n'}$, $NHCO(CH_2CH_2O)_mCH_2CH_2$, $OCH_2(CH_2)_{n'}$ and $O(CH_2CH_2O)_mCH_2CH_2$, where n' is selected from 1 to 10 and m is selected from 1 to 4, and wherein X is selected from the group consisting of $CH_2O(CH_2)_{n''}CH_2C{=}O$, $CH_2O(CH_2CH_2O)_{m'}(CH_2)_{n''}CH_2C{=}O$, where n" is selected from 0 to 10 and m' is selected from 0 to 4.

Formula (VII) is a schematic representation of serotype 3 glycoconjugates of the invention. It should not be understood that a linkage is present at every repeating unit of the saccharide. Rather, a majority of the *S. pneumoniae* serotype 3 saccharide repeating unit remains unmodified and covalent linkages between the carrier protein and the saccharide is for a minority of the saccharide repeat units. Additionally, an individual carrier protein (CP) molecule may be linked to more than one *S. pneumoniae* serotype 3 saccharide molecule and an individual *S. pneumoniae* serotype 3 saccharide molecule can be linked to more than one individual carrier protein (CP) molecule.

In a preferred embodiment, the invention provides a serotype 3 glycoconjugate comprising a serotype 3 saccharide covalently conjugated to a carrier protein (CP) through a spacer and having the general formula (VII), wherein X is $CH_2(CH_2)_{n'}$, where n' is 2 and wherein X is $CH_2O(CH_2)_{n''}CH_2C{=}O$ where n" is 1.

In an embodiment, the invention provides a serotype 3 glycoconjugate comprising a serotype 3 saccharide covalently conjugated to a carrier protein (CP) through a spacer and having the general formula (VII), wherein X is $CH_2(CH_2)_{n'}$, where n' is selected from 1 to 10 and wherein X is $CH_2O(CH_2)_{n''}CH_2C{=}O$ where n" is selected from 0 to 10. In an embodiment, n' is selected from 1 to 5 and n" is selected from 0 to 10. In an embodiment, n' is selected from 1 to 5 and n" is selected from 0 to 5. In an embodiment, n' is selected from 1 to 3 and n" is selected from 0 to 3. In an embodiment, n' is selected from 1 to 2 and n" is selected from 0 to 2. In a particular embodiment, n' is 1 and n" is 0. In another embodiment, n' is 2 and n" is 0. In yet another embodiment, n' is 3 and n" is 0. In yet a further embodiment, n' is 4 and n" is 0. In yet a further embodiment, n' is 5 and n" is 0. In yet a further embodiment, n' is 6 and n" is 0. In a particular embodiment, n' is 1 and n" is 1. In another embodiment, n' is 2 and n" is 1. In yet another embodiment, n' is 3 and n" is 1. In yet a further embodiment, n' is 4 and n" is 1. In yet a further embodiment, n' is 5 and n" is 1. In yet a further embodiment, n' is 6 and n" is 1. In a particular embodiment, n' is 1 and n" is 2. In another embodiment, n' is 2 and n" is 2. In yet another embodiment, n' is 3 and n" is 2. In yet a further embodiment, n' is 4 and n" is 2. In yet a further embodiment, n' is 5 and n" is 2. In yet a further embodiment, n' is 6 and n" is 2. In a particular embodiment, n' is 1 and n" is 3. In another embodiment, n' is 2 and n" is 3. In yet another embodiment, n' is 3 and n" is 3. In yet a further embodiment, n' is 4 and n" is 3. In yet a further embodiment, n' is 5 and n" is 3. In yet a further embodiment, n' is 6 and n" is 3. In a particular embodiment, n' is 1 and n" is 4. In another embodiment, n' is 2 and n" is 4. In yet another embodiment, n' is 3 and n" is 4. In yet a further embodiment, n' is 4 and n" is 4. In yet a further embodiment, n' is 5 and n" is 4. In yet a further embodiment, n' is 6 and n" is 4. In a particular embodiment, n' is 1 and n" is 5. In another embodiment, n' is 2 and n" is 5. In yet another embodiment, n' is 3 and n" is 5. In yet a further embodiment, n' is 4 and n" is 5. In yet a further embodiment, n' is 5 and n" is 5. In yet a further embodiment, n' is 6 and n" is 5. In a particular embodiment, n' is 1 and n" is 6. In another embodiment, n' is 2 and n" is 6. In yet another embodiment, n' is 3 and n" is 6.

In yet a further embodiment, n' is 4 and n" is 6. In yet a further embodiment, n' is 5 and n" is 6. In yet a further embodiment, n' is 6 and n" is 6.

In an embodiment, the invention provides a serotype 3 glycoconjugate comprising a serotype 3 saccharide covalently conjugated to a carrier protein (CP) through a spacer and having the general formula (VII), wherein X is $CH_2(CH_2)_{n'}$, where n' is selected from 1 to 10 and wherein $CH_2O(CH_2CH_2O)_{m'}(CH_2)_{n''}CH_2C{=}O$, where n" is selected from 0 to 10 and m' is selected from 0 to 4.

In an embodiment, n' is selected from 1 to 5, m' is selected from 0 to 4 and n" is selected from 0 to 10. In an embodiment, n' is selected from 1 to 5, m' is selected from 0 to 4 and n" is selected from 0 to 5. In an embodiment, n' is selected from 1 to 3, m' is selected from 0 to 2 and n" is selected from 0 to 3. In an embodiment, n' is selected from 1 to 2, m' is selected from 0 to 2 and n" is selected from 0 to 1.

In a particular embodiment, n' is 1, m' is 0 and n" is 0. In another embodiment, n' is 1, m' is 1 and n" is 0. In another embodiment, n' is 1, m' is 2 and n" is 0. In another embodiment, n' is 1, m' is 3 and n" is 0.

In another embodiment, n' is 2, m' is 0 and n" is 0. In another embodiment, n' is 2, m' is 1 and n" is 0. In another embodiment, n' is 2, m' is 2 and n" is 0. In another embodiment, n' is 2, m' is 3 and n" is 0.

In yet another embodiment, n' is 3, m' is 0 and n" is 0. In yet another embodiment, n' is 3, m' is 1 and n" is 0. In yet another embodiment, n' is 3, m' is 2 and n" is 0. In yet another embodiment, n' is 3, m' is 3 and n" is 0.

In yet a further embodiment, n' is 4, m' is 0 and n" is 0. In yet a further embodiment, n' is 4, m' is 1 and n" is 0. In yet a further embodiment, n' is 4, m' is 2 and n" is 0. In yet a further embodiment, n' is 4, m' is 3 and n" is 0.

In yet a further embodiment, n' is 5, m' is 0 and n" is 0. In yet a further embodiment, n' is 5, m' is 1 and n" is 0. In yet a further embodiment, n' is 5, m' is 2 and n" is 0. In yet a further embodiment, n' is 5, m' is 3 and n" is 0.

In a particular embodiment, n' is 1, m' is 0 and n" is 1. In a particular embodiment, n' is 1, m' is 1 and n" is 1. In a particular embodiment, n' is 1, m' is 2 and n" is 1. In a particular embodiment, n' is 1, m' is 3 and n" is 1.

In another embodiment, n' is 2, m' is 0 and n" is 1. In another embodiment, n' is 2, m' is 1 and n" is 1. In another embodiment, n' is 2, m' is 2 and n" is 1. In another embodiment, n' is 2, m' is 3 and n" is 1.

In yet another embodiment, n' is 3, m' is 0 and n" is 1. In yet another embodiment, n' is 3, m' is 1 and n" is 1. In yet another embodiment, n' is 3, m' is 2 and n" is 1. In yet another embodiment, n' is 3, m' is 3 and n" is 1.

In yet a further embodiment, n' is 4, m' is 0 and n" is 1. In yet a further embodiment, n' is 4, m' is 1 and n" is 1. In yet a further embodiment, n' is 4, m' is 2 and n" is 1. In yet a further embodiment, n' is 4, m' is 3 and n" is 1.

In yet a further embodiment, n' is 5, m' is 0 and n" is 1. In yet a further embodiment, n' is 5, m' is 1 and n" is 1. In yet a further embodiment, n' is 5, m' is 2 and n" is 1. In yet a further embodiment, n' is 5, m' is 3 and n" is 1.

In a particular embodiment, n' is 1, m' is 0 and n" is 2. In a particular embodiment, n' is 1, m' is 1 and n" is 2. In a particular embodiment, n' is 1, m' is 2 and n" is 2. In a particular embodiment, n' is 1, m' is 3 and n" is 2.

In another embodiment, n' is 2, m' is 0 and n" is 2. In another embodiment, n' is 2, m' is 1 and n" is 2. In another embodiment, n' is 2, m' is 2 and n" is 2. In another embodiment, n' is 2, m' is 3 and n" is 2.

In yet another embodiment, n' is 3, m' is 0 and n" is 2. In yet another embodiment, n' is 3, m' is 1 and n" is 2. In yet another embodiment, n' is 3, m' is 2 and n" is 2. In yet another embodiment, n' is 3, m' is 3 and n" is 2.

In yet a further embodiment, n' is 4, m' is 0 and n" is 2. In yet a further embodiment, n' is 4, m' is 1 and n" is 2. In yet a further embodiment, n' is 4, m' is 2 and n" is 2. In yet a further embodiment, n' is 4, m' is 3 and n" is 2.

In yet a further embodiment, n' is 5, m' is 0 and n" is 2. In yet a further embodiment, n' is 5, m' is 1 and n" is 2. In yet a further embodiment, n' is 5, m' is 2 and n" is 2. In yet a further embodiment, n' is 5, m' is 3 and n" is 2.

In a particular embodiment, n' is 1, m' is 0 and n" is 3. In a particular embodiment, n' is 1, m' is 1 and n" is 3. In a particular embodiment, n' is 1, m' is 2 and n" is 3. In a particular embodiment, n' is 1, m' is 3 and n" is 3.

In another embodiment, n' is 2, m' is 0 and n" is 3. In another embodiment, n' is 2, m' is 1 and n" is 3. In another embodiment, n' is 2, m' is 2 and n" is 3. In another embodiment, n' is 2, m' is 3 and n" is 3.

In yet another embodiment, n' is 3, m' is 0 and n" is 3. In yet another embodiment, n' is 3, m' is 1 and n" is 3. In yet another embodiment, n' is 3, m' is 2 and n" is 3. In yet another embodiment, n' is 3, m' is 3 and n" is 3.

In yet a further embodiment, n' is 4, m' is 0 and n" is 3. In yet a further embodiment, n' is 4, m' is 1 and n" is 3. In yet a further embodiment, n' is 4, m' is 2 and n" is 3. In yet a further embodiment, n' is 4, m' is 3 and n" is 3.

In yet a further embodiment, n' is 5, m' is 0 and n" is 3. In yet a further embodiment, n' is 5, m' is 1 and n" is 3. In yet a further embodiment, n' is 5, m' is 2 and n" is 3. In yet a further embodiment, n' is 5, m' is 3 and n" is 3.

In a particular embodiment, n' is 1, m' is 0 and n" is 4. In a particular embodiment, n' is 1, m' is 1 and n" is 4. In a particular embodiment, n' is 1, m' is 2 and n" is 4. In a particular embodiment, n' is 1, m' is 3 and n" is 4.

In another embodiment, n' is 2, m' is 0 and n" is 4. In another embodiment, n' is 2, m' is 1 and n" is 4. In another embodiment, n' is 2, m' is 2 and n" is 4. In another embodiment, n' is 2, m' is 3 and n" is 4.

In yet another embodiment, n' is 3, m' is 0 and n" is 4. In yet another embodiment, n' is 3, m' is 1 and n" is 4. In yet another embodiment, n' is 3, m' is 2 and n" is 4. In yet another embodiment, n' is 3, m' is 3 and n" is 4.

In yet a further embodiment, n' is 4, m' is 0 and n" is 4. In yet a further embodiment, n' is 4, m' is 1 and n" is 4. In yet a further embodiment, n' is 4, m' is 2 and n" is 4. In yet a further embodiment, n' is 4, m' is 3 and n" is 4.

In yet a further embodiment, n' is 5, m' is 0 and n" is 4. In yet a further embodiment, n' is 5, m' is 1 and n" is 4. In yet a further embodiment, n' is 5, m' is 2 and n" is 4. In yet a further embodiment, n' is 5, m' is 3 and n" is 4.

In a particular embodiment, n' is 1, m' is 0 and n" is 5. In a particular embodiment, n' is 1, m' is 1 and n" is 5. In a particular embodiment, n' is 1, m' is 2 and n" is 5. In a particular embodiment, n' is 1, m' is 3 and n" is 5.

In another embodiment, n' is 2, m' is 0 and n" is 5. In another embodiment, n' is 2, m' is 1 and n" is 5. In another embodiment, n' is 2, m' is 2 and n" is 5. In another embodiment, n' is 2, m' is 3 and n" is 5.

In yet another embodiment, n' is 3, m' is 0 and n" is 5. In yet another embodiment, n' is 3, m' is 1 and n" is 5. In yet another embodiment, n' is 3, m' is 2 and n" is 5. In yet another embodiment, n' is 3, m' is 3 and n" is 5.

In yet a further embodiment, n' is 4, m' is 0 and n" is 5. In yet a further embodiment, n' is 4, m' is 1 and n" is 5. In yet a further embodiment, n' is 4, m' is 2 and n" is 5. In yet a further embodiment, n' is 4, m' is 3 and n" is 5.

In yet a further embodiment, n' is 5, m' is 0 and n" is 5. In yet a further embodiment, n' is 5, m' is 1 and n" is 5. In yet a further embodiment, n' is 5, m' is 2 and n" is 5. In yet a further embodiment, n' is 5, m' is 3 and n" is 5.

In an embodiment, the invention provides a serotype 3 glycoconjugate comprising a serotype 3 saccharide covalently conjugated to a carrier protein (CP) through a spacer and having the general formula (VII), wherein X is $(CH_2CH_2O)_mCH_2CH_2$, where m is selected from 1 to 4 and wherein X is $CH_2O(CH_2)_{n''}CH_2C{=}O$, where n" is selected from 0 to 10. In an embodiment, m is selected from 1 to 3 and n" is selected from 0 to 10. In an embodiment, m is selected from 1 to 3 and n" is selected from 0 to 5. In an embodiment, m is selected from 1 to 2 and n" is selected from 0 to 3. In an embodiment, m is selected from 1 to 2 and n" is selected from 0 to 2. In a particular embodiment, m is 1 and n" is 0. In another embodiment, m is 2 and n" is 0. In yet another embodiment, m is 3 and n" is 0. In yet a further embodiment, m is 4 and n" is 0. In a particular embodiment, m is 1 and n'' is 1. In another embodiment, m is 2 and n'' is 1. In yet another embodiment, m is 3 and n'' is 1. In yet a further embodiment, m is 4 and n'' is 1. In a particular embodiment, m is 1 and n'' is 2. In another embodiment, m is 2 and n'' is 2. In yet another embodiment, m is 3 and n'' is 2. In yet a further embodiment, m is 4 and n'' is 2. In a particular embodiment, m is 1 and n'' is 3. In another embodiment, m is 2 and n'' is 3. In yet another embodiment, m is 3 and n'' is 3. In yet a further embodiment, m is 4 and n'' is 3. In a particular embodiment, m is 1 and n'' is 4. In another embodiment, m is 2 and n'' is 4. In yet another embodiment, m is 3 and n'' is 4. In yet a further embodiment, m is 4 and n'' is 4. In a particular embodiment, m is 1 and n'' is 5. In another embodiment, m is 2 and n'' is 5. In yet another embodiment, m is 3 and n'' is 5. In yet a further embodiment, m is 4 and n'' is 5. In a particular embodiment, m is 1 and n'' is 6. In another embodiment, m is 2 and n'' is 6. In yet another embodiment, m is 3 and n'' is 6. In yet a further embodiment, m is 4 and n'' is 6.

In an embodiment, the invention provides a serotype 3 glycoconjugate comprising a serotype 3 saccharide covalently conjugated to a carrier protein (CP) through a spacer and having the general formula (VII), wherein X is $(CH_2CH_2O)_mCH_2CH_2$, where m is selected from 1 to 4 and wherein X is $CH_2O(CH_2CH_2O)_{m'}(CH_2)_nCH_2C{=}O$, where n'' is selected from 0 to 10 and m' is selected from 0 to 4.

In an embodiment, m is selected from 1 to 3, m' is selected from 0 to 4 and n'' is selected from 0 to 10. In an embodiment, m is selected from 1 to 2, m' is selected from 0 to 4 and n'' is selected from 0 to 5. In an embodiment, m is selected from 1 to 2, m' is selected from 0 to 2 and n'' is selected from 0 to 3. In an embodiment, m is selected from 1 to 2, m' is selected from 0 to 2 and n'' is selected from 0 to 1.

In a particular embodiment, m is 1, m' is 0 and n'' is 0. In another embodiment, m is 1, m' is 1 and n'' is 0. In another embodiment, m is 1, m' is 2 and n'' is 0. In another embodiment, m is 1, m' is 3 and n'' is 0.

In another embodiment, m is 2, m' is 0 and n'' is 0. In another embodiment, m is 2, m' is 1 and n'' is 0. In another embodiment, m is 2, m' is 2 and n'' is 0. In another embodiment, m is 2, m' is 3 and n'' is 0.

In yet another embodiment, m is 3, m' is 0 and n'' is 0. In yet another embodiment, m is 3, m' is 1 and n'' is 0. In yet another embodiment, m is 3, m' is 2 and n'' is 0. In yet another embodiment, m is 3, m' is 3 and n'' is 0.

In yet a further embodiment, m is 4, m' is 0 and n'' is 0. In yet a further embodiment, m is 4, m' is 1 and n'' is 0. In yet a further embodiment, m is 4, m' is 2 and n'' is 0. In yet a further embodiment, m is 4, m' is 3 and n'' is 0.

In a particular embodiment, m is 1, m' is 0 and n'' is 1. In a particular embodiment, m is 1, m' is 1 and n'' is 1. In a particular embodiment, m is 1, m' is 2 and n'' is 1. In a particular embodiment, m is 1, m' is 3 and n'' is 1.

In another embodiment, m is 2, m' is 0 and n'' is 1. In another embodiment, m is 2, m' is 1 and n'' is 1. In another embodiment, m is 2, m' is 2 and n'' is 1. In another embodiment, m is 2, m' is 3 and n'' is 1.

In yet another embodiment, m is 3, m' is 0 and n'' is 1. In yet another embodiment, m is 3, m' is 1 and n'' is 1. In yet another embodiment, m is 3, m' is 2 and n'' is 1. In yet another embodiment, m is 3, m' is 3 and n'' is 1.

In yet a further embodiment, m is 4, m' is 0 and n'' is 1. In yet a further embodiment, m is 4, m' is 1 and n'' is 1. In yet a further embodiment, m is 4, m' is 2 and n'' is 1. In yet a further embodiment, m is 4, m' is 3 and n'' is 1.

In a particular embodiment, m is 1, m' is 0 and n'' is 2. In a particular embodiment, m is 1, m' is 1 and n'' is 2. In a particular embodiment, m is 1, m' is 2 and n'' is 2. In a particular embodiment, m is 1, m' is 3 and n'' is 2.

In another embodiment, m is 2, m' is 0 and n'' is 2. In another embodiment, m is 2, m' is 1 and n'' is 2. In another embodiment, m is 2, m' is 2 and n'' is 2. In another embodiment, m is 2, m' is 3 and n'' is 2.

In yet another embodiment, m is 3, m' is 0 and n'' is 2. In yet another embodiment, m is 3, m' is 1 and n'' is 2. In yet another embodiment, m is 3, m' is 2 and n'' is 2. In yet another embodiment, m is 3, m' is 3 and n'' is 2.

In yet a further embodiment, m is 4, m' is 0 and n'' is 2. In yet a further embodiment, m is 4, m' is 1 and n'' is 2. In yet a further embodiment, m is 4, m' is 2 and n'' is 2. In yet a further embodiment, m is 4, m' is 3 and n'' is 2.

In a particular embodiment, m is 1, m' is 0 and n'' is 3. In a particular embodiment, m is 1, m' is 1 and n'' is 3. In a particular embodiment, m is 1, m' is 2 and n'' is 3. In a particular embodiment, m is 1, m' is 3 and n'' is 3.

In another embodiment, m is 2, m' is 0 and n'' is 3. In another embodiment, m is 2, m' is 1 and n'' is 3. In another embodiment, m is 2, m' is 2 and n'' is 3. In another embodiment, m is 2, m' is 3 and n'' is 3.

In yet another embodiment, m is 3, m' is 0 and n'' is 3. In yet another embodiment, m is 3, m' is 1 and n'' is 3. In yet another embodiment, m is 3, m' is 2 and n'' is 3. In yet another embodiment, m is 3, m' is 3 and n'' is 3.

In yet a further embodiment, m is 4, m' is 0 and n'' is 3. In yet a further embodiment, m is 4, m' is 1 and n'' is 3. In yet a further embodiment, m is 4, m' is 2 and n'' is 3. In yet a further embodiment, m is 4, m' is 3 and n'' is 3.

In a particular embodiment, m is 1, m' is 0 and n'' is 4. In a particular embodiment, m is 1, m' is 1 and n'' is 4. In a particular embodiment, m is 1, m' is 2 and n'' is 4. In a particular embodiment, m is 1, m' is 3 and n'' is 4.

In another embodiment, m is 2, m' is 0 and n'' is 4. In another embodiment, m is 2, m' is 1 and n'' is 4. In another embodiment, m is 2, m' is 2 and n'' is 4. In another embodiment, m is 2, m' is 3 and n'' is 4.

In yet another embodiment, m is 3, m' is 0 and n'' is 4. In yet another embodiment, m is 3, m' is 1 and n'' is 4. In yet another embodiment, m is 3, m' is 2 and n'' is 4. In yet another embodiment, m is 3, m' is 3 and n'' is 4.

In yet a further embodiment, m is 4, m' is 0 and n'' is 4. In yet a further embodiment, m is 4, m' is 1 and n'' is 4. In yet a further embodiment, m is 4, m' is 2 and n'' is 4. In yet a further embodiment, m is 4, m' is 3 and n'' is 4.

In a particular embodiment, m is 1, m' is 0 and n'' is 5. In a particular embodiment, m is 1, m' is 1 and n'' is 5. In a particular embodiment, m is 1, m' is 2 and n'' is 5. In a particular embodiment, m is 1, m' is 3 and n'' is 5.

In another embodiment, m is 2, m' is 0 and n'' is 5. In another embodiment, m is 2, m' is 1 and n'' is 5. In another embodiment, m is 2, m' is 2 and n'' is 5. In another embodiment, m is 2, m' is 3 and n'' is 5.

In yet another embodiment, m is 3, m' is 0 and n'' is 5. In yet another embodiment, m is 3, m' is 1 and n'' is 5. In yet another embodiment, m is 3, m' is 2 and n'' is 5. In yet another embodiment, m is 3, m' is 3 and n'' is 5.

In yet a further embodiment, m is 4, m' is 0 and n'' is 5. In yet a further embodiment, m is 4, m' is 1 and n'' is 5. In yet a further embodiment, m is 4, m' is 2 and n'' is 5. In yet a further embodiment, m is 4, m' is 3 and n'' is 5.

In an embodiment, the invention provides a serotype 3 glycoconjugate comprising a serotype 3 saccharide covalently conjugated to a carrier protein (CP) through a spacer and having the general formula (VII), wherein X is NHCO $(CH_2)_{n'}$, where n' is selected from 1 to 10 and wherein X is $CH_2O(CH_2)_{n''}CH_2C{=}O$, where n" is selected from 0 to 10. In an embodiment, n' is selected from 1 to 5 and n" is selected from 0 to 10. In an embodiment, n' is selected from 1 to 5 and n" is selected from 0 to 5. In an embodiment, n' is selected from 1 to 3 and n" is selected from 0 to 3. In an embodiment, n' is selected from 1 to 2 and n" is selected from 0 to 2. In a particular embodiment, n' is 1 and n" is 0. In another embodiment, n' is 2 and n" is 0. In yet another embodiment, n' is 3 and n" is 0. In yet a further embodiment, n' is 4 and n" is 0. In yet a further embodiment, n' is 5 and n" is 0. In yet a further embodiment, n' is 6 and n" is 0. In a particular embodiment, n' is 1 and n" is 1. In another embodiment, n' is 2 and n" is 1. In yet another embodiment, n' is 3 and n" is 1. In yet a further embodiment, n' is 4 and n" is 1. In yet a further embodiment, n' is 5 and n" is 1. In yet a further embodiment, n' is 6 and n" is 1. In a particular embodiment, n' is 1 and n" is 2. In another embodiment, n' is 2 and n" is 2. In yet another embodiment, n' is 3 and n" is 2. In yet a further embodiment, n' is 4 and n" is 2. In yet a further embodiment, n' is 5 and n" is 2. In yet a further embodiment, n' is 6 and n" is 2. In a particular embodiment, n' is 1 and n" is 3. In another embodiment, n' is 2 and n" is 3. In yet another embodiment, n' is 3 and n" is 3. In yet a further embodiment, n' is 4 and n" is 3. In yet a further embodiment, n' is 5 and n" is 3. In yet a further embodiment, n' is 6 and n" is 3. In a particular embodiment, n' is 1 and n" is 4. In another embodiment, n' is 2 and n" is 4. In yet another embodiment, n' is 3 and n" is 4. In yet a further embodiment, n' is 4 and n" is 4. In yet a further embodiment, n' is 5 and n" is 4. In yet a further embodiment, n' is 6 and n" is 4. In a particular embodiment, n' is 1 and n" is 5. In another embodiment, n' is 2 and n" is 5. In yet another embodiment, n' is 3 and n" is 5. In yet a further embodiment, n' is 4 and n" is 5. In yet a further embodiment, n' is 5 and n" is 5. In yet a further embodiment, n' is 6 and n" is 5. In a particular embodiment, n' is 1 and n" is 6. In another embodiment, n' is 2 and n" is 6. In yet another embodiment, n' is 3 and n" is 6. In yet a further embodiment, n' is 4 and n" is 6. In yet a further embodiment, n' is 5 and n" is 6. In yet a further embodiment, n' is 6 and n" is 6.

In an embodiment, the invention provides a serotype 3 glycoconjugate comprising a serotype 3 saccharide covalently conjugated to a carrier protein (CP) through a spacer and having the general formula (VII), wherein X is NHCO $(CH_2)_{n'}$, where n' is selected from 1 to 10 and wherein X is $CH_2O(CH_2CH_2O)_{m'}(CH_2)_{n''}CH_2C{=}O$, where n" is selected from 0 to 10 and m' is selected from 0 to 4.

In an embodiment, n' is selected from 1 to 5, m' is selected from 0 to 4 and n" is selected from 0 to 10. In an embodiment, n' is selected from 1 to 5, m' is selected from 0 to 4 and n" is selected from 0 to 5. In an embodiment, n' is selected from 1 to 3, m' is selected from 0 to 2 and n" is selected from 0 to 3. In an embodiment, n' is selected from 1 to 2, m' is selected from 0 to 2 and n" is selected from 0 to 1.

In a particular embodiment, n' is 1, m' is 0 and n" is 0. In another embodiment, n' is 1, m' is 1 and n" is 0. In another embodiment, n' is 1, m' is 2 and n" is 0. In another embodiment, n' is 1, m' is 3 and n" is 0.

In another embodiment, n' is 2, m' is 0 and n" is 0. In another embodiment, n' is 2, m' is 1 and n" is 0. In another embodiment, n' is 2, m' is 2 and n" is 0. In another embodiment, n' is 2, m' is 3 and n" is 0.

In yet another embodiment, n' is 3, m' is 0 and n" is 0. In yet another embodiment, n' is 3, m' is 1 and n" is 0. In yet another embodiment, n' is 3, m' is 2 and n" is 0. In yet another embodiment, n' is 3, m' is 3 and n" is 0.

In yet a further embodiment, n' is 4, m' is 0 and n" is 0. In yet a further embodiment, n' is 4, m' is 1 and n" is 0. In yet a further embodiment, n' is 4, m' is 2 and n" is 0. In yet a further embodiment, n' is 4, m' is 3 and n" is 0.

In yet a further embodiment, n' is 5, m' is 0 and n" is 0. In yet a further embodiment, n' is 5, m' is 1 and n" is 0. In yet a further embodiment, n' is 5, m' is 2 and n" is 0. In yet a further embodiment, n' is 5, m' is 3 and n" is 0.

In a particular embodiment, n' is 1, m' is 0 and n" is 1. In a particular embodiment, n' is 1, m' is 1 and n" is 1. In a particular embodiment, n' is 1, m' is 2 and n" is 1. In a particular embodiment, n' is 1, m' is 3 and n" is 1.

In another embodiment, n' is 2, m' is 0 and n" is 1. In another embodiment, n' is 2, m' is 1 and n" is 1. In another embodiment, n' is 2, m' is 2 and n" is 1. In another embodiment, n' is 2, m' is 3 and n" is 1.

In yet another embodiment, n' is 3, m' is 0 and n" is 1. In yet another embodiment, n' is 3, m' is 1 and n" is 1. In yet another embodiment, n' is 3, m' is 2 and n" is 1. In yet another embodiment, n' is 3, m' is 3 and n" is 1.

In yet a further embodiment, n' is 4, m' is 0 and n" is 1. In yet a further embodiment, n' is 4, m' is 1 and n" is 1. In yet a further embodiment, n' is 4, m' is 2 and n" is 1. In yet a further embodiment, n' is 4, m' is 3 and n" is 1.

In yet a further embodiment, n' is 5, m' is 0 and n" is 1. In yet a further embodiment, n' is 5, m' is 1 and n" is 1. In yet a further embodiment, n' is 5, m' is 2 and n" is 1. In yet a further embodiment, n' is 5, m' is 3 and n" is 1.

In a particular embodiment, n' is 1, m' is 0 and n" is 2. In a particular embodiment, n' is 1, m' is 1 and n" is 2. In a particular embodiment, n' is 1, m' is 2 and n" is 2. In a particular embodiment, n' is 1, m' is 3 and n" is 2.

In another embodiment, n' is 2, m' is 0 and n" is 2. In another embodiment, n' is 2, m' is 1 and n" is 2. In another embodiment, n' is 2, m' is 2 and n" is 2. In another embodiment, n' is 2, m' is 3 and n" is 2.

In yet another embodiment, n' is 3, m' is 0 and n" is 2. In yet another embodiment, n' is 3, m' is 1 and n" is 2. In yet another embodiment, n' is 3, m' is 2 and n" is 2. In yet another embodiment, n' is 3, m' is 3 and n" is 2.

In yet a further embodiment, n' is 4, m' is 0 and n" is 2. In yet a further embodiment, n' is 4, m' is 1 and n" is 2. In yet a further embodiment, n' is 4, m' is 2 and n" is 2. In yet a further embodiment, n' is 4, m' is 3 and n" is 2.

In yet a further embodiment, n' is 5, m' is 0 and n" is 2. In yet a further embodiment, n' is 5, m' is 1 and n" is 2. In yet a further embodiment, n' is 5, m' is 2 and n" is 2. In yet a further embodiment, n' is 5, m' is 3 and n" is 2.

In a particular embodiment, n' is 1, m' is 0 and n" is 3. In a particular embodiment, n' is 1, m' is 1 and n" is 3. In a particular embodiment, n' is 1, m' is 2 and n" is 3. In a particular embodiment, n' is 1, m' is 3 and n" is 3.

In another embodiment, n' is 2, m' is 0 and n" is 3. In another embodiment, n' is 2, m' is 1 and n" is 3. In another embodiment, n' is 2, m' is 2 and n" is 3. In another embodiment, n' is 2, m' is 3 and n" is 3.

In yet another embodiment, n' is 3, m' is 0 and n" is 3. In yet another embodiment, n' is 3, m' is 1 and n" is 3. In yet another embodiment, n' is 3, m' is 2 and n" is 3. In yet another embodiment, n' is 3, m' is 3 and n" is 3.

In yet a further embodiment, n' is 4, m' is 0 and n" is 3. In yet a further embodiment, n' is 4, m' is 1 and n" is 3. In yet a further embodiment, n' is 4, m' is 2 and n" is 3. In yet a further embodiment, n' is 4, m' is 3 and n" is 3.

In yet a further embodiment, n' is 5, m' is 0 and n" is 3. In yet a further embodiment, n' is 5, m' is 1 and n" is 3. In yet a further embodiment, n' is 5, m' is 2 and n" is 3. In yet a further embodiment, n' is 5, m' is 3 and n" is 3.

In a particular embodiment, n' is 1, m' is 0 and n" is 4. In a particular embodiment, n' is 1, m' is 1 and n" is 4. In a particular embodiment, n' is 1, m' is 2 and n" is 4. In a particular embodiment, n' is 1, m' is 3 and n" is 4.

In another embodiment, n' is 2, m' is 0 and n" is 4. In another embodiment, n' is 2, m' is 1 and n" is 4. In another embodiment, n' is 2, m' is 2 and n" is 4. In another embodiment, n' is 2, m' is 3 and n" is 4.

In yet another embodiment, n' is 3, m' is 0 and n" is 4. In yet another embodiment, n' is 3, m' is 1 and n" is 4. In yet another embodiment, n' is 3, m' is 2 and n" is 4. In yet another embodiment, n' is 3, m' is 3 and n" is 4.

In yet a further embodiment, n' is 4, m' is 0 and n" is 4. In yet a further embodiment, n' is 4, m' is 1 and n" is 4. In yet a further embodiment, n' is 4, m' is 2 and n" is 4. In yet a further embodiment, n' is 4, m' is 3 and n" is 4.

In yet a further embodiment, n' is 5, m' is 0 and n" is 4. In yet a further embodiment, n' is 5, m' is 1 and n" is 4. In yet a further embodiment, n' is 5, m' is 2 and n" is 4. In yet a further embodiment, n' is 5, m' is 3 and n" is 4.

In a particular embodiment, n' is 1, m' is 0 and n" is 5. In a particular embodiment, n' is 1, m' is 1 and n" is 5. In a particular embodiment, n' is 1, m' is 2 and n" is 5. In a particular embodiment, n' is 1, m' is 3 and n" is 5.

In another embodiment, n' is 2, m' is 0 and n" is 5. In another embodiment, n' is 2, m' is 1 and n" is 5. In another embodiment, n' is 2, m' is 2 and n" is 5. In another embodiment, n' is 2, m' is 3 and n" is 5.

In yet another embodiment, n' is 3, m' is 0 and n" is 5. In yet another embodiment, n' is 3, m' is 1 and n" is 5. In yet another embodiment, n' is 3, m' is 2 and n" is 5. In yet another embodiment, n' is 3, m' is 3 and n" is 5.

In yet a further embodiment, n' is 4, m' is 0 and n" is 5. In yet a further embodiment, n' is 4, m' is 1 and n" is 5. In yet a further embodiment, n' is 4, m' is 2 and n" is 5. In yet a further embodiment, n' is 4, m' is 3 and n" is 5.

In yet a further embodiment, n' is 5, m' is 0 and n" is 5. In yet a further embodiment, n' is 5, m' is 1 and n" is 5. In yet a further embodiment, n' is 5, m' is 2 and n" is 5. In yet a further embodiment, n' is 5, m' is 3 and n" is 5.

In an embodiment, the invention provides a serotype 3 glycoconjugate comprising a serotype 3 saccharide covalently conjugated to a carrier protein (CP) through a spacer and having the general formula (VII), wherein X is $NHCO(CH_2CH_2O)_mCH_2CH_2$, where m is selected from 1 to 4 and wherein X is $CH_2O(CH_2)_{n''}CH_2C{=}O$, where n" is selected from 0 to 10. In an embodiment, m is selected from 1 to 3 and n" is selected from 0 to 10. In an embodiment, m is selected from 1 to 3 and n" is selected from 0 to 5. In an embodiment, m is selected from 1 to 2 and n" is selected from 0 to 3. In an embodiment, m is selected from 1 to 2 and n" is selected from 0 to 2. In a particular embodiment, m is 1 and n" is 0. In another embodiment, m is 2 and n" is 0. In yet another embodiment, m is 3 and n" is 0. In yet a further embodiment, m is 4 and n" is 0. In a particular embodiment, m is 1 and n" is 1. In another embodiment, m is 2 and n" is 1. In yet another embodiment, m is 3 and n" is 1. In yet a further embodiment, m is 4 and n" is 1. In a particular embodiment, m is 1 and n" is 2. In another embodiment, m is 2 and n" is 2. In yet another embodiment, m is 3 and n" is 2. In yet a further embodiment, m is 4 and n" is 2. In a particular embodiment, m is 1 and n" is 3. In another embodiment, m is 2 and n" is 3. In yet another embodiment, m is 3 and n" is 3. In yet a further embodiment, m is 4 and n" is 3. In a particular embodiment, m is 1 and n" is 4. In another embodiment, m is 2 and n" is 4. In yet another embodiment, m is 3 and n" is 4. In yet a further embodiment, m is 4 and n" is 4. In a particular embodiment, m is 1 and n" is 5. In another embodiment, m is 2 and n" is 5. In yet another embodiment, m is 3 and n" is 5. In yet a further embodiment, m is 4 and n" is 5. In a particular embodiment, m is 1 and n" is 6. In another embodiment, m is 2 and n" is 6. In yet another embodiment, m is 3 and n" is 6. In yet a further embodiment, m is 4 and n" is 6.

In an embodiment, the invention provides a serotype 3 glycoconjugate comprising a serotype 3 saccharide covalently conjugated to a carrier protein (CP) through a spacer and having the general formula (VII), wherein X is $NHCO(CH_2CH_2O)_mCH_2CH_2$, where m is selected from 1 to 4 and wherein X is $CH_2O(CH_2CH_2O)_{m'}(CH_2)_{n''}CH_2C{=}O$, where n" is selected from 0 to 10 and m' is selected from 0 to 4.

In an embodiment, m is selected from 1 to 3, m' is selected from 0 to 4 and n" is selected from 0 to 10. In an embodiment, m is selected from 1 to 2, m' is selected from 0 to 4 and n" is selected from 0 to 5. In an embodiment, m is selected from 1 to 2, m' is selected from 0 to 2 and n" is selected from 0 to 3. In an embodiment, m is selected from 1 to 2, m' is selected from 0 to 2 and n" is selected from 0 to 1.

In a particular embodiment, m is 1, m' is 0 and n" is 0. In another embodiment, m is 1, m' is 1 and n" is 0. In another embodiment, m is 1, m' is 2 and n" is 0. In another embodiment, m is 1, m' is 3 and n" is 0.

In another embodiment, m is 2, m' is 0 and n" is 0. In another embodiment, m is 2, m' is 1 and n" is 0. In another embodiment, m is 2, m' is 2 and n" is 0. In another embodiment, m is 2, m' is 3 and n" is 0.

In yet another embodiment, m is 3, m' is 0 and n" is 0. In yet another embodiment, m is 3, m' is 1 and n" is 0. In yet another embodiment, m is 3, m' is 2 and n" is 0. In yet another embodiment, m is 3, m' is 3 and n" is 0.

In yet a further embodiment, m is 4, m' is 0 and n" is 0. In yet a further embodiment, m is 4, m' is 1 and n" is 0. In yet a further embodiment, m is 4, m' is 2 and n" is 0. In yet a further embodiment, m is 4, m' is 3 and n" is 0.

In a particular embodiment, m is 1, m' is 0 and n" is 1. In a particular embodiment, m is 1, m' is 1 and n" is 1. In a particular embodiment, m is 1, m' is 2 and n" is 1. In a particular embodiment, m is 1, m' is 3 and n" is 1.

In another embodiment, m is 2, m' is 0 and n" is 1. In another embodiment, m is 2, m' is 1 and n" is 1. In another embodiment, m is 2, m' is 2 and n" is 1. In another embodiment, m is 2, m' is 3 and n" is 1.

In yet another embodiment, m is 3, m' is 0 and n" is 1. In yet another embodiment, m is 3, m' is 1 and n" is 1. In yet another embodiment, m is 3, m' is 2 and n" is 1. In yet another embodiment, m is 3, m' is 3 and n" is 1.

In yet a further embodiment, m is 4, m' is 0 and n" is 1. In yet a further embodiment, m is 4, m' is 1 and n" is 1. In yet a further embodiment, m is 4, m' is 2 and n" is 1. In yet a further embodiment, m is 4, m' is 3 and n" is 1.

In a particular embodiment, m is 1, m' is 0 and n" is 2. In a particular embodiment, m is 1, m' is 1 and n" is 2. In a particular embodiment, m is 1, m' is 2 and n" is 2. In a particular embodiment, m is 1, m' is 3 and n" is 2.

In another embodiment, m is 2, m' is 0 and n" is 2. In another embodiment, m is 2, m' is 1 and n" is 2. In another embodiment, m is 2, m' is 2 and n" is 2. In another embodiment, m is 2, m' is 3 and n" is 2.

In yet another embodiment, m is 3, m' is 0 and n" is 2. In yet another embodiment, m is 3, m' is 1 and n" is 2. In yet another embodiment, m is 3, m' is 2 and n" is 2. In yet another embodiment, m is 3, m' is 3 and n" is 2.

In yet a further embodiment, m is 4, m' is 0 and n" is 2. In yet a further embodiment, m is 4, m' is 1 and n" is 2. In yet a further embodiment, m is 4, m' is 2 and n" is 2. In yet a further embodiment, m is 4, m' is 3 and n" is 2.

In a particular embodiment, m is 1, m' is 0 and n" is 3. In a particular embodiment, m is 1, m' is 1 and n" is 3. In a particular embodiment, m is 1, m' is 2 and n" is 3. In a particular embodiment, m is 1, m' is 3 and n" is 3.

In another embodiment, m is 2, m' is 0 and n" is 3. In another embodiment, m is 2, m' is 1 and n" is 3. In another embodiment, m is 2, m' is 2 and n" is 3. In another embodiment, m is 2, m' is 3 and n" is 3.

In yet another embodiment, m is 3, m' is 0 and n" is 3. In yet another embodiment, m is 3, m' is 1 and n" is 3. In yet another embodiment, m is 3, m' is 2 and n" is 3. In yet another embodiment, m is 3, m' is 3 and n" is 3.

In yet a further embodiment, m is 4, m' is 0 and n" is 3. In yet a further embodiment, m is 4, m' is 1 and n" is 3. In yet a further embodiment, m is 4, m' is 2 and n" is 3. In yet a further embodiment, m is 4, m' is 3 and n" is 3.

In a particular embodiment, m is 1, m' is 0 and n" is 4. In a particular embodiment, m is 1, m' is 1 and n" is 4. In a particular embodiment, m is 1, m' is 2 and n" is 4. In a particular embodiment, m is 1, m' is 3 and n" is 4.

In another embodiment, m is 2, m' is 0 and n" is 4. In another embodiment, m is 2, m' is 1 and n" is 4. In another embodiment, m is 2, m' is 2 and n" is 4. In another embodiment, m is 2, m' is 3 and n" is 4.

In yet another embodiment, m is 3, m' is 0 and n" is 4. In yet another embodiment, m is 3, m' is 1 and n" is 4. In yet another embodiment, m is 3, m' is 2 and n" is 4. In yet another embodiment, m is 3, m' is 3 and n" is 4.

In yet a further embodiment, m is 4, m' is 0 and n" is 4. In yet a further embodiment, m is 4, m' is 1 and n" is 4. In yet a further embodiment, m is 4, m' is 2 and n" is 4. In yet a further embodiment, m is 4, m' is 3 and n" is 4.

In a particular embodiment, m is 1, m' is 0 and n" is 5. In a particular embodiment, m is 1, m' is 1 and n" is 5. In a particular embodiment, m is 1, m' is 2 and n" is 5. In a particular embodiment, m is 1, m' is 3 and n" is 5.

In another embodiment, m is 2, m' is 0 and n" is 5. In another embodiment, m is 2, m' is 1 and n" is 5. In another embodiment, m is 2, m' is 2 and n" is 5. In another embodiment, m is 2, m' is 3 and n" is 5.

In yet another embodiment, m is 3, m' is 0 and n" is 5. In yet another embodiment, m is 3, m' is 1 and n" is 5. In yet another embodiment, m is 3, m' is 2 and n" is 5. In yet another embodiment, m is 3, m' is 3 and n" is 5.

In yet a further embodiment, m is 4, m' is 0 and n" is 5. In yet a further embodiment, m is 4, m' is 1 and n" is 5. In yet a further embodiment, m is 4, m' is 2 and n" is 5. In yet a further embodiment, m is 4, m' is 3 and n" is 5.

In an embodiment, the invention provides a serotype 3 glycoconjugate comprising a serotype 3 saccharide covalently conjugated to a carrier protein (CP) through a spacer and having the general formula (VII), wherein X is $OCH_2(CH_2)_{n'}$, where n' is selected from 1 to 10 and wherein X is $CH_2O(CH_2)_{n''}CH_2C{=}O$, where n" is selected from 0 to 10.

In an embodiment, n' is selected from 1 to 5 and n" is selected from 0 to 10. In an embodiment, n' is selected from 1 to 5 and n" is selected from 0 to 5. In an embodiment, n' is selected from 1 to 3 and n" is selected from 0 to 3. In an embodiment, n' is selected from 1 to 2 and n" is selected from 0 to 2. In a particular embodiment, n' is 1 and n" is 0.

In another embodiment, n' is 2 and n" is 0. In yet another embodiment, n' is 3 and n" is 0. In yet a further embodiment, n' is 4 and n" is 0. In yet a further embodiment, n' is 5 and n" is 0. In yet a further embodiment, n' is 6 and n" is 0. In a particular embodiment, n' is 1 and n" is 1. In another embodiment, n' is 2 and n" is 1. In yet another embodiment, n' is 3 and n" is 1. In yet a further embodiment, n' is 4 and n" is 1. In yet a further embodiment, n' is 5 and n" is 1. In yet a further embodiment, n' is 6 and n" is 1. In a particular embodiment, n' is 1 and n" is 2. In another embodiment, n' is 2 and n" is 2. In yet another embodiment, n' is 3 and n" is 2. In yet a further embodiment, n' is 4 and n" is 2. In yet a further embodiment, n' is 5 and n" is 2. In yet a further embodiment, n' is 6 and n" is 2. In a particular embodiment, n' is 1 and n" is 3. In another embodiment, n' is 2 and n" is 3. In yet another embodiment, n' is 3 and n" is 3. In yet a further embodiment, n' is 4 and n" is 3. In yet a further embodiment, n' is 5 and n" is 3. In yet a further embodiment, n' is 6 and n" is 3. In a particular embodiment, n' is 1 and n" is 4. In another embodiment, n' is 2 and n" is 4. In yet another embodiment, n' is 3 and n" is 4. In yet a further embodiment, n' is 4 and n" is 4. In yet a further embodiment, n' is 5 and n" is 4. In yet a further embodiment, n' is 6 and n" is 4. In a particular embodiment, n' is 1 and n" is 5. In another embodiment, n' is 2 and n" is 5. In yet another embodiment, n' is 3 and n" is 5.

In yet a further embodiment, n' is 4 and n" is 5. In yet a further embodiment, n' is 5 and n" is 5. In yet a further embodiment, n' is 6 and n" is 5. In a particular embodiment, n' is 1 and n" is 6. In another embodiment, n' is 2 and n" is 6. In yet another embodiment, n' is 3 and n" is 6. In yet a further embodiment, n' is 4 and n" is 6. In yet a further embodiment, n' is 5 and n" is 6. In yet a further embodiment, n' is 6 and n" is 6.

In an embodiment, the invention provides a serotype 3 glycoconjugate comprising a serotype 3 saccharide covalently conjugated to a carrier protein (CP) through a spacer and having the general formula (VII), wherein X is $OCH_2(CH_2)_{n'}$, where n' is selected from 1 to 10 and wherein X is $CH_2O(CH_2CH_2O)_{m'}(CH_2)_{n''}CH_2C{=}O$, where n" is selected from 0 to 10 and m' is selected from 0 to 4.

In an embodiment, n' is selected from 1 to 5, m' is selected from 0 to 4 and n" is selected from 0 to 10. In an embodiment, n' is selected from 1 to 5, m' is selected from 0 to 4 and n" is selected from 0 to 5. In an embodiment, n' is selected from 1 to 3, m' is selected from 0 to 2 and n" is selected from 0 to 3. In an embodiment, n' is selected from 1 to 2, m' is selected from 0 to 2 and n" is selected from 0 to 1.

In a particular embodiment, n' is 1, m' is 0 and n" is 0. In another embodiment, n' is 1, m' is 1 and n" is 0. In another embodiment, n' is 1, m' is 2 and n" is 0. In another embodiment, n' is 1, m' is 3 and n" is 0.

In another embodiment, n' is 2, m' is 0 and n" is 0. In another embodiment, n' is 2, m' is 1 and n" is 0. In another embodiment, n' is 2, m' is 2 and n" is 0. In another embodiment, n' is 2, m' is 3 and n" is 0.

In yet another embodiment, n' is 3, m' is 0 and n" is 0. In yet another embodiment, n' is 3, m' is 1 and n" is 0. In yet another embodiment, n' is 3, m' is 2 and n" is 0. In yet another embodiment, n' is 3, m' is 3 and n" is 0.

In yet a further embodiment, n' is 4, m' is 0 and n" is 0. In yet a further embodiment, n' is 4, m' is 1 and n" is 0. In yet a further embodiment, n' is 4, m' is 2 and n" is 0. In yet a further embodiment, n' is 4, m' is 3 and n" is 0.

In yet a further embodiment, n' is 5, m' is 0 and n" is 0. In yet a further embodiment, n' is 5, m' is 1 and n" is 0. In yet a further embodiment, n' is 5, m' is 2 and n" is 0. In yet a further embodiment, n' is 5, m' is 3 and n" is 0.

In a particular embodiment, n' is 1, m' is 0 and n" is 1. In a particular embodiment, n' is 1, m' is 1 and n" is 1. In a particular embodiment, n' is 1, m' is 2 and n" is 1. In a particular embodiment, n' is 1, m' is 3 and n" is 1.

In another embodiment, n' is 2, m' is 0 and n" is 1. In another embodiment, n' is 2, m' is 1 and n" is 1. In another embodiment, n' is 2, m' is 2 and n" is 1. In another embodiment, n' is 2, m' is 3 and n" is 1.

In yet another embodiment, n' is 3, m' is 0 and n" is 1. In yet another embodiment, n' is 3, m' is 1 and n" is 1. In yet another embodiment, n' is 3, m' is 2 and n" is 1. In yet another embodiment, n' is 3, m' is 3 and n" is 1.

In yet a further embodiment, n' is 4, m' is 0 and n" is 1. In yet a further embodiment, n' is 4, m' is 1 and n" is 1. In yet a further embodiment, n' is 4, m' is 2 and n" is 1. In yet a further embodiment, n' is 4, m' is 3 and n" is 1.

In yet a further embodiment, n' is 5, m' is 0 and n" is 1. In yet a further embodiment, n' is 5, m' is 1 and n" is 1. In yet a further embodiment, n' is 5, m' is 2 and n" is 1. In yet a further embodiment, n' is 5, m' is 3 and n" is 1.

In a particular embodiment, n' is 1, m' is 0 and n" is 2. In a particular embodiment, n' is 1, m' is 1 and n" is 2. In a particular embodiment, n' is 1, m' is 2 and n" is 2. In a particular embodiment, n' is 1, m' is 3 and n" is 2.

In another embodiment, n' is 2, m' is 0 and n" is 2. In another embodiment, n' is 2, m' is 1 and n" is 2. In another embodiment, n' is 2, m' is 2 and n" is 2. In another embodiment, n' is 2, m' is 3 and n" is 2.

In yet another embodiment, n' is 3, m' is 0 and n" is 2. In yet another embodiment, n' is 3, m' is 1 and n" is 2. In yet another embodiment, n' is 3, m' is 2 and n" is 2. In yet another embodiment, n' is 3, m' is 3 and n" is 2.

In yet a further embodiment, n' is 4, m' is 0 and n" is 2. In yet a further embodiment, n' is 4, m' is 1 and n" is 2. In yet a further embodiment, n' is 4, m' is 2 and n" is 2. In yet a further embodiment, n' is 4, m' is 3 and n" is 2.

In yet a further embodiment, n' is 5, m' is 0 and n" is 2. In yet a further embodiment, n' is 5, m' is 1 and n" is 2. In yet a further embodiment, n' is 5, m' is 2 and n" is 2. In yet a further embodiment, n' is 5, m' is 3 and n" is 2.

In a particular embodiment, n' is 1, m' is 0 and n" is 3. In a particular embodiment, n' is 1, m' is 1 and n" is 3. In a particular embodiment, n' is 1, m' is 2 and n" is 3. In a particular embodiment, n' is 1, m' is 3 and n" is 3.

In another embodiment, n' is 2, m' is 0 and n" is 3. In another embodiment, n' is 2, m' is 1 and n" is 3. In another embodiment, n' is 2, m' is 2 and n" is 3. In another embodiment, n' is 2, m' is 3 and n" is 3.

In yet another embodiment, n' is 3, m' is 0 and n" is 3. In yet another embodiment, n' is 3, m' is 1 and n" is 3. In yet another embodiment, n' is 3, m' is 2 and n" is 3. In yet another embodiment, n' is 3, m' is 3 and n" is 3.

In yet a further embodiment, n' is 4, m' is 0 and n" is 3. In yet a further embodiment, n' is 4, m' is 1 and n" is 3. In yet a further embodiment, n' is 4, m' is 2 and n" is 3. In yet a further embodiment, n' is 4, m' is 3 and n" is 3.

In yet a further embodiment, n' is 5, m' is 0 and n" is 3. In yet a further embodiment, n' is 5, m' is 1 and n" is 3. In yet a further embodiment, n' is 5, m' is 2 and n" is 3. In yet a further embodiment, n' is 5, m' is 3 and n" is 3.

In a particular embodiment, n' is 1, m' is 0 and n" is 4. In a particular embodiment, n' is 1, m' is 1 and n" is 4. In a particular embodiment, n' is 1, m' is 2 and n" is 4. In a particular embodiment, n' is 1, m' is 3 and n" is 4.

In another embodiment, n' is 2, m' is 0 and n" is 4. In another embodiment, n' is 2, m' is 1 and n" is 4. In another embodiment, n' is 2, m' is 2 and n" is 4. In another embodiment, n' is 2, m' is 3 and n" is 4.

In yet another embodiment, n' is 3, m' is 0 and n" is 4. In yet another embodiment, n' is 3, m' is 1 and n" is 4. In yet another embodiment, n' is 3, m' is 2 and n" is 4. In yet another embodiment, n' is 3, m' is 3 and n" is 4.

In yet a further embodiment, n' is 4, m' is 0 and n" is 4. In yet a further embodiment, n' is 4, m' is 1 and n" is 4. In yet a further embodiment, n' is 4, m' is 2 and n" is 4. In yet a further embodiment, n' is 4, m' is 3 and n" is 4.

In yet a further embodiment, n' is 5, m' is 0 and n" is 4. In yet a further embodiment, n' is 5, m' is 1 and n" is 4. In yet a further embodiment, n' is 5, m' is 2 and n" is 4. In yet a further embodiment, n' is 5, m' is 3 and n" is 4.

In a particular embodiment, n' is 1, m' is 0 and n" is 5. In a particular embodiment, n' is 1, m' is 1 and n" is 5. In a particular embodiment, n' is 1, m' is 2 and n" is 5. In a particular embodiment, n' is 1, m' is 3 and n" is 5.

In another embodiment, n' is 2, m' is 0 and n" is 5. In another embodiment, n' is 2, m' is 1 and n" is 5. In another embodiment, n' is 2, m' is 2 and n" is 5. In another embodiment, n' is 2, m' is 3 and n" is 5.

In yet another embodiment, n' is 3, m' is 0 and n" is 5. In yet another embodiment, n' is 3, m' is 1 and n" is 5. In yet another embodiment, n' is 3, m' is 2 and n" is 5. In yet another embodiment, n' is 3, m' is 3 and n" is 5.

In yet a further embodiment, n' is 4, m' is 0 and n" is 5. In yet a further embodiment, n' is 4, m' is 1 and n" is 5. In yet a further embodiment, n' is 4, m' is 2 and n" is 5. In yet a further embodiment, n' is 4, m' is 3 and n" is 5.

In yet a further embodiment, n' is 5, m' is 0 and n" is 5. In yet a further embodiment, n' is 5, m' is 1 and n" is 5. In yet a further embodiment, n' is 5, m' is 2 and n" is 5. In yet a further embodiment, n' is 5, m' is 3 and n" is 5.

In an embodiment, the invention provides a serotype 3 glycoconjugate comprising a serotype 3 saccharide covalently conjugated to a carrier protein (CP) through a spacer and having the general formula (VII), wherein X is $O(CH_2CH_2O)_mCH_2CH_2$, where m is selected from 1 to 4 and wherein X is $CH_2O(CH_2)_{n''}CH_2C{=}O$, where n" is selected from 0 to 10.

In an embodiment, m is selected from 1 to 3 and n" is selected from 0 to 10. In an embodiment, m is selected from 1 to 3 and n" is selected from 0 to 5. In an embodiment, m is selected from 1 to 2 and n" is selected from 0 to 3. In an embodiment, m is selected from 1 to 2 and n" is selected from 0 to 2. In a particular embodiment, m is 1 and n" is 0. In another embodiment, m is 2 and n" is 0. In yet another embodiment, m is 3 and n" is 0. In yet a further embodiment, m is 4 and n" is 0. In a particular embodiment, m is 1 and n" is 1. In another embodiment, m is 2 and n" is 1. In yet another embodiment, m is 3 and n" is 1. In yet a further embodiment, m is 4 and n" is 1. In a particular embodiment, m is 1 and n" is 2. In another embodiment, m is 2 and n" is 2. In yet another embodiment, m is 3 and n" is 2. In yet a further embodiment, m is 4 and n" is 2. In a particular embodiment, m is 1 and n" is 3. In another embodiment, m is 2 and n" is 3. In yet another embodiment, m is 3 and n" is 3. In yet a further embodiment, m is 4 and n" is 3. In a particular embodiment, m is 1 and n" is 4. In another embodiment, m is 2 and n" is 4. In yet another embodiment, m is 3 and n" is 4. In yet a further embodiment, m is 4 and n" is 4. In a particular embodiment, m is 1 and n" is 5. In another embodiment, m is 2 and n" is 5. In yet another embodiment, m is 3 and n" is 5. In yet a further embodiment, m is 4 and n" is 5. In a particular embodiment, m is 1 and n" is 6. In another embodiment, m is 2 and n" is 6. In yet another embodiment, m is 3 and n" is 6. In yet a further embodiment, m is 4 and n" is 6.

In an embodiment, the invention provides a serotype 3 glycoconjugate comprising a serotype 3 saccharide covalently conjugated to a carrier protein (CP) through a spacer and having the general formula (VII), wherein X is $O(CH_2CH_2O)_mCH_2CH_2$, where m is selected from 1 to 4 and wherein X is $CH_2O(CH_2CH_2O)_{m'}(CH_2)_{n''}CH_2C{=}O$, where n" is selected from 0 to 10 and m' is selected from 0 to 4.

In an embodiment, m is selected from 1 to 3, m' is selected from 0 to 4 and n" is selected from 0 to 10. In an embodiment, m is selected from 1 to 2, m' is selected from 0 to 4 and n" is selected from 0 to 5. In an embodiment, m is selected from 1 to 2, m' is selected from 0 to 2 and n" is selected from 0 to 3. In an embodiment, m is selected from 1 to 2, m' is selected from 0 to 2 and n" is selected from 0 to 1.

In a particular embodiment, m is 1, m' is 0 and n" is 0. In another embodiment, m is 1, m' is 1 and n" is 0. In another embodiment, m is 1, m' is 2 and n" is 0. In another embodiment, m is 1, m' is 3 and n" is 0.

In another embodiment, m is 2, m' is 0 and n" is 0. In another embodiment, m is 2, m' is 1 and n" is 0. In another embodiment, m is 2, m' is 2 and n" is 0. In another embodiment, m is 2, m' is 3 and n" is 0.

In yet another embodiment, m is 3, m' is 0 and n" is 0. In yet another embodiment, m is 3, m' is 1 and n" is 0. In yet another embodiment, m is 3, m' is 2 and n" is 0. In yet another embodiment, m is 3, m' is 3 and n" is 0.

In yet a further embodiment, m is 4, m' is 0 and n" is 0. In yet a further embodiment, m is 4, m' is 1 and n" is 0. In yet a further embodiment, m is 4, m' is 2 and n" is 0. In yet a further embodiment, m is 4, m' is 3 and n" is 0.

In a particular embodiment, m is 1, m' is 0 and n" is 1. In a particular embodiment, m is 1, m' is 1 and n" is 1. In a particular embodiment, m is 1, m' is 2 and n" is 1. In a particular embodiment, m is 1, m' is 3 and n" is 1.

In another embodiment, m is 2, m' is 0 and n" is 1. In another embodiment, m is 2, m' is 1 and n" is 1. In another embodiment, m is 2, m' is 2 and n" is 1. In another embodiment, m is 2, m' is 3 and n" is 1.

In yet another embodiment, m is 3, m' is 0 and n" is 1. In yet another embodiment, m is 3, m' is 1 and n" is 1. In yet another embodiment, m is 3, m' is 2 and n" is 1. In yet another embodiment, m is 3, m' is 3 and n" is 1.

In yet a further embodiment, m is 4, m' is 0 and n" is 1. In yet a further embodiment, m is 4, m' is 1 and n" is 1. In yet a further embodiment, m is 4, m' is 2 and n" is 1. In yet a further embodiment, m is 4, m' is 3 and n" is 1.

In a particular embodiment, m is 1, m' is 0 and n" is 2. In a particular embodiment, m is 1, m' is 1 and n" is 2. In a particular embodiment, m is 1, m' is 2 and n" is 2. In a particular embodiment, m is 1, m' is 3 and n" is 2.

In another embodiment, m is 2, m' is 0 and n" is 2. In another embodiment, m is 2, m' is 1 and n" is 2. In another embodiment, m is 2, m' is 2 and n" is 2. In another embodiment, m is 2, m' is 3 and n" is 2.

In yet another embodiment, m is 3, m' is 0 and n" is 2. In yet another embodiment, m is 3, m' is 1 and n" is 2. In yet another embodiment, m is 3, m' is 2 and n" is 2. In yet another embodiment, m is 3, m' is 3 and n" is 2.

In yet a further embodiment, m is 4, m' is 0 and n" is 2. In yet a further embodiment, m is 4, m' is 1 and n" is 2. In yet a further embodiment, m is 4, m' is 2 and n" is 2. In yet a further embodiment, m is 4, m' is 3 and n" is 2.

In a particular embodiment, m is 1, m' is 0 and n" is 3. In a particular embodiment, m is 1, m' is 1 and n" is 3. In a particular embodiment, m is 1, m' is 2 and n" is 3. In a particular embodiment, m is 1, m' is 3 and n" is 3.

In another embodiment, m is 2, m' is 0 and n" is 3. In another embodiment, m is 2, m' is 1 and n" is 3. In another embodiment, m is 2, m' is 2 and n" is 3. In another embodiment, m is 2, m' is 3 and n" is 3.

In yet another embodiment, m is 3, m' is 0 and n" is 3. In yet another embodiment, m is 3, m' is 1 and n" is 3. In yet another embodiment, m is 3, m' is 2 and n" is 3. In yet another embodiment, m is 3, m' is 3 and n" is 3.

In yet a further embodiment, m is 4, m' is 0 and n" is 3. In yet a further embodiment, m is 4, m' is 1 and n" is 3. In yet a further embodiment, m is 4, m' is 2 and n" is 3. In yet a further embodiment, m is 4, m' is 3 and n" is 3.

In a particular embodiment, m is 1, m' is 0 and n" is 4. In a particular embodiment, m is 1, m' is 1 and n" is 4. In a particular embodiment, m is 1, m' is 2 and n" is 4. In a particular embodiment, m is 1, m' is 3 and n" is 4.

In another embodiment, m is 2, m' is 0 and n" is 4. In another embodiment, m is 2, m' is 1 and n" is 4. In another embodiment, m is 2, m' is 2 and n" is 4. In another embodiment, m is 2, m' is 3 and n" is 4.

In yet another embodiment, m is 3, m' is 0 and n" is 4. In yet another embodiment, m is 3, m' is 1 and n" is 4. In yet another embodiment, m is 3, m' is 2 and n" is 4. In yet another embodiment, m is 3, m' is 3 and n" is 4.

In yet a further embodiment, m is 4, m' is 0 and n" is 4. In yet a further embodiment, m is 4, m' is 1 and n" is 4. In yet a further embodiment, m is 4, m' is 2 and n" is 4. In yet a further embodiment, m is 4, m' is 3 and n" is 4.

In a particular embodiment, m is 1, m' is 0 and n" is 5. In a particular embodiment, m is 1, m' is 1 and n" is 5. In a particular embodiment, m is 1, m' is 2 and n" is 5. In a particular embodiment, m is 1, m' is 3 and n" is 5.

In another embodiment, m is 2, m' is 0 and n" is 5. In another embodiment, m is 2, m' is 1 and n" is 5. In another embodiment, m is 2, m' is 2 and n" is 5. In another embodiment, m is 2, m' is 3 and n" is 5.

In yet another embodiment, m is 3, m' is 0 and n" is 5. In yet another embodiment, m is 3, m' is 1 and n" is 5. In yet another embodiment, m is 3, m' is 2 and n" is 5. In yet another embodiment, m is 3, m' is 3 and n" is 5.

In yet a further embodiment, m is 4, m' is 0 and n" is 5. In yet a further embodiment, m is 4, m' is 1 and n" is 5. In yet a further embodiment, m is 4, m' is 2 and n" is 5. In yet a further embodiment, m is 4, m' is 3 and n" is 5.

1.6 Carrier Protein of the *Streptococcus pneumoniae* Serotype 3 Glycoconjugates of the Invention A component of the glycoconjugate is a carrier protein to which the purified polysaccharide is conjugated. The terms "protein carrier" or "carrier protein" or "carrier" may be used interchangeably herein. Carrier proteins should be amenable to standard conjugation procedures.

In a preferred embodiment, the carrier protein of the serotype 3 capsular polysaccharide glycoconjugate is selected in the group consisting of: DT (Diphtheria toxoid), TT (tetanus toxoid) or fragment C of TT, $CRM_{197}$ (a nontoxic but antigenically identical variant of diphtheria toxin), other DT mutants (such as $CRM_{176}$, $CRM_{228}$, $CRM_{45}$ (Uchida et al. (1973) J. Biol. Chem. 218:3838-3844), $CRM_9$, $CRM_{102}$, $CRM_{103}$ or $CRM_{107}$; and other mutations described by Nicholls and Youle in Genetically Engineered Toxins, Ed: Frankel, Maecel Dekker Inc. (1992); deletion or mutation of Glu-148 to Asp, Gln or Ser and/or Ala 158 to Gly and other mutations disclosed in U.S. Pat. Nos. 4,709,017 and 4,950,740; mutation of at least one or more residues Lys 516, Lys 526, Phe 530 and/or Lys 534 and other mutations disclosed in U.S. Pat. Nos. 5,917,017 and 6,455,673; or fragment disclosed in U.S. Pat. No. 5,843,711, pneumococcal pneumolysin (ply) (Kuo et al. (1995) Infect Immun 63:2706-2713) including ply detoxified in some fashion, for example dPLY-GMBS (WO 2004/081515, WO 2006/032499) or dPLY-formol, PhtX, including PhtA, PhtB, PhtD, PhtE (sequences of PhtA, PhtB, PhtD or PhtE are disclosed in WO 00/37105 and WO 00/39299) and fusions of Pht proteins, for example PhtDE fusions, PhtBE fusions, Pht A-E (WO 01/98334, WO 03/054007, WO 2009/000826), OMPC (meningococcal outer membrane protein), which is usually extracted from *Neisseria meningitidis* serogroup B (EP0372501), PorB (from *N. meningitidis*), PD (*Haemophilus influenzae* protein D; see, e.g., EP0594610 B), or immunologically functional equivalents thereof, synthetic peptides (EP0378881, EP0427347), heat shock proteins (WO 93/17712, WO 94/03208), pertussis proteins (WO 98/58668, EP0471177), cytokines, lymphokines, growth factors or hormones (WO 91/01146), artificial proteins comprising multiple human CD4+ T cell epitopes from various pathogen derived antigens (Falugi et al. (2001) Eur J Immunol 31:3816-3824) such as N19 protein (Baraldoi et al. (2004) Infect Immun 72:4884-4887) pneumococcal surface protein PspA (WO 02/091998), iron uptake proteins (WO 01/72337), toxin A or B of *Clostridium difficile* (WO 00/61761), transferrin binding proteins, pneumococcal adhesion protein (PsaA), recombinant *Pseudomonas aeruginosa* exotoxin A (in particular non-toxic mutants thereof (such as exotoxin A bearing a substation at glutamic acid 553 (Douglas et al. (1987) J. Bacteriol. 169(11):4967-4971)). Other proteins, such as ovalbumin, keyhole limpet hemocyanin (KLH), bovine serum albumin (BSA) or purified protein derivative of tuberculin (PPD) also can be used as carrier proteins. Other suitable carrier proteins include inactivated bacterial toxins such as cholera toxoid (e.g., as described in WO 2004/083251), *Escherichia coli* LT, *E. coli* ST, and exotoxin A from *P. aeruginosa*. Another suitable carrier protein is a C5a peptidase from *Streptococcus* (SCP).

In a preferred embodiment, the carrier protein of the serotype 3 capsular polysaccharide glycoconjugate of the invention is selected from the group consisting of TT, DT, DT mutants (such as $CRM_{197}$), and a C5a peptidase from *Streptococcus* (SCP).

In an embodiment, the carrier protein of the serotype 3 capsular polysaccharide glycoconjugate is DT (Diphtheria toxoid). In another embodiment, the carrier protein of the serotype 3 capsular polysaccharide glycoconjugate is TT (tetanus toxoid).

In another embodiment, the carrier protein of the serotype 3 capsular polysaccharide glycoconjugate is PD (*H. influenzae* protein D; see, e.g., EP0594610 B).

In a preferred embodiment, the carrier protein of the serotype 3 capsular polysaccharide glycoconjugate is $CRM_{197}$ or a C5a peptidase from *Streptococcus* (SCP).

In a preferred embodiment, the serotype 3 capsular polysaccharide is conjugated to $CRM_{197}$ protein. The $CRM_{197}$ protein is a nontoxic form of diphtheria toxin but is immunologically indistinguishable from the diphtheria toxin. $CRM_{197}$ is produced by *Corynebacterium diphtheriae* infected by the nontoxigenic phage $\beta 197^{tox-}$ created by nitrosoguanidine mutagenesis of the toxigenic corynephage beta (Uchida et al. (1971) Nature New Biology 233:8-11). The $CRM_{197}$ protein has the same molecular weight as the diphtheria toxin but differs therefrom by a single base change (guanine to adenine) in the structural gene. This single base change causes an amino acid substitution (glutamic acid for glycine) in the mature protein and eliminates the toxic properties of diphtheria toxin. The $CRM_{197}$ protein is a safe and effective T-cell dependent carrier for saccharides. Further details about $CRM_{197}$ and production thereof can be found, e.g., in U.S. Pat. No. 5,614,382.

In an embodiment, the serotype 3 capsular polysaccharide is conjugated to $CRM_{197}$ protein. In an embodiment, the serotype 3 capsular polysaccharide is conjugated to $CRM_{197}$ protein or the A chain of $CRM_{197}$ (see CN103495161). In an embodiment, the serotype 3 capsular polysaccharide is conjugated the A chain of $CRM_{197}$ obtained via expression by genetically recombinant *E. coli* (see CN103495161).

In other preferred embodiments, the carrier protein of the serotype 3 capsular polysaccharide glycoconjugate of the invention is SCP (Streptococcal C5a Peptidase).

Two important species of β-hemolytic streptococci, *Streptococcus pyogenes* (group A *Streptococcus*, GAS) and *Streptococcus agalactiae* (group B *Streptococcus*, GBS), which cause a variety of serious human infections that range from mild cases of pharyngitis and impetigo to serious invasive diseases such as necrotizing fasciitis (GAS) and neonatal sepsis (GBS) have developed a way to defeat this immune response. All human isolates of β-hemolytic streptococci, including GAS and GBS, produce a highly conserved cell-wall protein SCP (Streptococcal C5a Peptidase) that specifically inactivates C5a. The scp genes from GAS and GBS encode a polypeptide containing between 1,134 and 1,181 amino acids (Brown et al., PNAS, 2005, vol. 102, no. 51 pages 18391-18396). The first 31 residues are the export signal presequence and are removed upon passing through the cytoplasmic membrane. The next 68 residues serve as a pro-sequence and must be removed to produce active SCP. The next 10 residues can be removed without loss of protease activity. At the other end, starting with Lys-1034, are four consecutive 17-residue motifs followed by a cell sorting and cell-wall attachment signal. This combined signal is composed of a 20-residue hydrophilic sequence containing an LPTTND sequence, a 17-residue hydrophobic sequence, and a short basic carboxyl terminus.

SCP can be divided in domains (see FIG. 1B of Brown et al., PNAS, 2005, vol. 102, no. 51 pages 18391-18396). These domains are the Pre/Pro domain (which comprises the export signal presequence (commonly the first 31 residues) and the pro-sequence (commonly the next 68 residues)), the protease domain (which is splitted in two part (protease part 1 commonly residues 89-333/334 and protease domain part 2 and commonly residues 467/468-583/584), the protease-associated domain (PA domain) (commonly residues 333/334-467/468), three fibronectin type III (Fn) domains (Fn1, commonly residues 583/584-712/713; Fn2, commonly residues 712/713-928/929/930; commonly Fn3, residues 929/930-1029/1030/1031) and a cell wall anchor domain (commonly residues 1029/1030/1031 to the C-terminus).

In an embodiment, the carrier protein of the serotype 3 capsular polysaccharide glycoconjugate of the invention is an SCP from GBS (SCPB). An example of SCPB is provided at SEQ. ID. NO: 3 of WO97/26008. See also SEQ ID NO: 3 of WO00/34487.

In another preferred embodiments, the carrier protein of the serotype 3 capsular polysaccharide glycoconjugate of the invention is an SCP from GAS (SCPA).

Examples of SCPA can be found at SEQ.ID.No.1 and SEQ.ID.No.2 of WO97/26008. See also SEQ ID NO: 1, 2 and 23 of WO00/34487.

In a preferred embodiment, the carrier protein of the serotype 3 capsular polysaccharide glycoconjugate of the invention is an enzymatically inactive SCP.

In other preferred embodiments, the carrier protein of the serotype 3 capsular polysaccharide glycoconjugate of the invention is an enzymatically inactive SCP from GBS (SCPB).

In another preferred embodiments, the carrier protein of the serotype 3 capsular polysaccharide glycoconjugate of the invention is an enzymatically inactive SCP from GAS (SCPA).

In an embodiment, the carrier protein of the serotype 3 capsular polysaccharide glycoconjugate of the invention is a fragment of an SCP. In an embodiment, the carrier protein of the serotype 3 capsular polysaccharide glycoconjugate of the invention is a fragment of an SCPA. Preferably, the carrier protein of the serotype 3 capsular polysaccharide glycoconjugate of the invention is a fragment of an SCPB.

In an embodiment, the carrier protein of the serotype 3 capsular polysaccharide glycoconjugate of the invention is a fragment of an SCP which comprises the protease domain, the protease-associated domain (PA domain) and the three fibronectin type Ill (Fn) domains but does not comprise the export signal presequence, the pro-sequence and the cell wall anchor domain.

In an embodiment, the carrier protein of the serotype 3 capsular polysaccharide glycoconjugate of the invention is a fragment of an SCP which comprises the protease domain, the protease-associated domain (PA domain) and the three fibronectin type Ill (Fn) domains but does not comprise the export signal presequence, the pro-sequence and the cell wall anchor domain.

In an embodiment, the carrier protein of the serotype 3 capsular polysaccharide glycoconjugate of the invention is an enzymatically inactive fragment of an SCP which comprises the protease domain, the protease-associated domain (PA domain) and two of the three fibronectin type III (Fn) domains but does not comprise the export signal presequence, the pro-sequence and the cell wall anchor domain.

In an embodiment, the carrier protein of the serotype 3 capsular polysaccharide glycoconjugate of the invention is an enzymatically inactive fragment of an SCP. In an embodiment, said enzymatically inactive fragment of SCP comprises the protease domain, the protease-associated domain (PA domain) and the three fibronectin type Ill (Fn) domains but does not comprise the export signal presequence, the pro-sequence and the cell wall anchor domain.

In an embodiment, the carrier protein of the serotype 3 capsular polysaccharide glycoconjugate of the invention is an enzymatically inactive fragment of an SCPA. In an embodiment, said enzymatically inactive fragment of an SCPA comprises the protease domain, the protease-associated domain (PA domain) and the three fibronectin type Ill (Fn) domains but does not comprise the export signal presequence, the pro-sequence and the cell wall anchor domain.

In a preferred embodiment, the carrier protein of the serotype 3 capsular polysaccharide glycoconjugate of the invention is an enzymatically inactive fragment of SCPB.

Preferably, said enzymatically inactive fragment of SCPB comprises the protease domain, the protease-associated domain (PA domain) and the three fibronectin type Ill (Fn) domains but does not comprise the export signal presequence, the pro-sequence and the cell wall anchor domain.

In an embodiment, the enzymatic activity of SCP is inactivated by replacing at least one amino acid of the wild type sequence. In an embodiment, said replacement is selected from the group consisting of D130A, H193A, N295A and S512A. The numbers indicate the amino acid residue position in the peptidase according to the numbering of SEQ ID NO: 1 of WO00/34487.

Therefore, in an embodiment, the carrier protein of the serotype 3 capsular polysaccharide glycoconjugate of the invention is an enzymatically inactive SCP where said inactivation is accomplished by replacing at least one amino acid of the wild type sequence. Preferably, said replacement of at least one amino acid is in the protease domain. In an embodiment, said replacement of at least one amino acid is in part 1 of the protease domain. In an embodiment, said replacement of at least one amino acid is in part 2 of the protease domain. In an embodiment, said replacement is selected from the group consisting of D130A, H193A, N295A and S512A. In an embodiment, said replacement is D130A. In another embodiment, said replacement is H193A. In another embodiment, said replacement is N295A. In yet another embodiment, said replacement is S512A.

In an embodiment, the carrier protein of the serotype 3 capsular polysaccharide glycoconjugate of the invention is an enzymatically inactive SCPA where said inactivation is accomplished by replacing at least one amino acid of the wild type sequence.

Preferably, said replacement of at least one amino acid is in the protease domain. In an embodiment, said replacement of at least one amino acid is in part 1 of the protease domain. In an embodiment, said replacement of at least one amino acid is in part 2 of the protease domain. In an embodiment, said replacement is selected from the group consisting of D130A, H193A, N295A and S512A. In an embodiment, said replacement is D130A. In another embodiment, said replacement is H193A. In another embodiment, said replacement is N295A. In yet another embodiment, said replacement is S512A.

In an embodiment, the carrier protein of the serotype 3 capsular polysaccharide glycoconjugate of the invention is an enzymatically inactive SCPB where said inactivation is accomplished by replacing at least one amino acid of the wild type sequence.

Preferably, said replacement of at least one amino acid is in the protease domain. In an embodiment, said replacement of at least one amino acid is in part 1 of the protease domain. In an embodiment, said replacement of at least one amino acid is in part 2 of the protease domain. In an embodiment, said replacement is selected from the group consisting of D130A, H193A, N295A and S512A. In an embodiment, said replacement is D130A. In another embodiment, said replacement is H193A. In another embodiment, said replacement is N295A. In yet another embodiment, said replacement is S512A.

In an embodiment, the carrier protein of the serotype 3 capsular polysaccharide glycoconjugate of the invention is an enzymatically inactive fragment of an SCP where said inactivation is accomplished by replacing at least one amino acid of the wild type sequence. Preferably, said replacement of at least one amino acid is in the protease domain. In an embodiment, said replacement of at least one amino acid is in part 1 of the protease domain. In an embodiment, said replacement of at least one amino acid is in part 2 of the protease domain. In an embodiment, said replacement is selected from the group consisting of D130A, H193A, N295A and S512A. In an embodiment, said replacement is D130A. In another embodiment, said replacement is H193A. In another embodiment, said replacement is N295A. In yet another embodiment, said replacement is S512A.

In an embodiment, the carrier protein of the serotype 3 capsular polysaccharide glycoconjugate of the invention is an enzymatically inactive fragment of SCP which comprises the protease domain, the protease-associated domain (PA domain) and the three fibronectin type III (Fn) domains but does not comprise the export signal presequence, the pro-sequence and the cell wall anchor domain, where said inactivation is accomplished by replacing at least one amino acid of the wild type sequence.

Preferably, said replacement of at least one amino acid is in the protease domain. In an embodiment, said replacement of at least one amino acid is in part 1 of the protease domain. In an embodiment, said replacement of at least one amino acid is in part 2 of the protease domain. In an embodiment, said replacement is selected from the group consisting of D130A, H193A, N295A and S512A. In an embodiment, said replacement is D130A. In another embodiment, said replacement is H193A. In another embodiment, said replacement is N295A. In yet another embodiment, said replacement is S512A.

In an embodiment, the carrier protein of the serotype 3 capsular polysaccharide glycoconjugate of the invention is an enzymatically inactive fragment of SCPA which comprises the protease domain, the protease-associated domain (PA domain) and the three fibronectin type III (Fn) domains but does not comprise the export signal presequence, the pro-sequence and the cell wall anchor domain, where said inactivation is accomplished by replacing at least one amino acid of the wild type sequence.

Preferably, said replacement of at least one amino acid is in the protease domain. In an embodiment, said replacement of at least one amino acid is in part 1 of the protease domain. In an embodiment, said replacement of at least one amino acid is in part 2 of the protease domain. In an embodiment, said replacement is selected from the group consisting of D130A, H193A, N295A and S512A. In an embodiment, said replacement is D130A. In another embodiment, said replacement is H193A. In another embodiment, said replacement is N295A. In yet another embodiment, said replacement is S512A.

In an embodiment, the carrier protein of the serotype 3 capsular polysaccharide glycoconjugate of the invention is an enzymatically inactive fragment of SCPB which comprises the protease domain, the protease-associated domain (PA domain) and the three fibronectin type III (Fn) domains but does not comprise the export signal presequence, the pro-sequence and the cell wall anchor domain, where said inactivation is accomplished by replacing at least one amino acid of the wild type sequence.

Preferably, said replacement of at least one amino acid is in the protease domain. In an embodiment, said replacement of at least one amino acid is in part 1 of the protease domain. In an embodiment, said replacement of at least one amino acid is in part 2 of the protease domain. In an embodiment, said replacement is selected from the group consisting of D130A, H193A, N295A and S512A. In an embodiment, said replacement is D130A. In another embodiment, said replacement is H193A. In another embodiment, said replacement is N295A. In yet another embodiment, said replacement is S512A.

In an embodiment, the enzymatic activity of SCP is inactivated by replacing at least two amino acids of the wild type sequence. In an embodiment, said at least two amino acids replacements are selected from the group consisting of D130A, H193A, N295A and S512A. In an embodiment, said at least two amino acids replacements are D130A and H193A. In an embodiment, said at least two amino acids replacements are D130A and N295A. In an embodiment, said at least two amino acids replacements are D130A and S512A. In an embodiment, said at least two amino acids replacements are H193A and N295A. In an embodiment, said at least two amino acids replacements are H193A and S512A. In an embodiment, said at least two amino acids replacements are N295A and S512A.

Therefore, in an embodiment, the carrier protein of the serotype 3 capsular polysaccharide glycoconjugate of the invention is an enzymatically inactive SCP where said inactivation is accomplished by replacing at least two amino acids of the wild type sequence. Preferably, said replacement of at least two amino acids is in the protease domain. In an embodiment, said replacement of at least two amino acid is in part 1 of the protease domain. In an embodiment, said replacement of at least two amino acid is in part 2 of the protease domain. In an embodiment, said at least two amino acids replacements are selected from the group consisting of D130A, H193A, N295A and S512A. In an embodiment, said at least two amino acids replacements are D130A and H193A. In an embodiment, said at least two amino acids replacements are D130A and N295A. Preferably, said at least two amino acids replacements are D130A and S512A.

In an embodiment, said at least two amino acids replacements are H193A and N295A. In an embodiment, said at least two amino acids replacements are H193A and S512A. In an embodiment, said at least two amino acids replacements are N295A and S512A.

In an embodiment, the carrier protein of the serotype 3 capsular polysaccharide glycoconjugate of the invention is an enzymatically inactive SCPA where said inactivation is accomplished by replacing at least two amino acids of the wild type sequence.

Preferably, said replacement of at least two amino acids is in the protease domain. In an embodiment, said replacement of at least two amino acids is in part 1 of the protease domain. In an embodiment, said replacement of at least two amino acid is in part 2 of the protease domain. In an embodiment, said at least two amino acids replacements are selected from the group consisting of D130A, H193A, N295A and S512A. In an embodiment, said at least two amino acids replacements are D130A and H193A. In an embodiment, said at least two amino acids replacements are D130A and N295A.

Preferably, said at least two amino acids replacements are D130A and S512A. In an embodiment, said at least two amino acids replacements are H193A and N295A. In an embodiment, said at least two amino acids replacements are H193A and S512A. In an embodiment, said at least two amino acids replacements are N295A and S512A.

In an embodiment, the carrier protein of the serotype 3 capsular polysaccharide glycoconjugate of the invention is an enzymatically inactive SCPB where said inactivation is accomplished by replacing at least two amino acids of the wild type sequence.

Preferably, said replacement of at least two amino acids is in the protease domain. In an embodiment, said replacement of at least two amino acids is in part 1 of the protease domain. In an embodiment, said replacement of at least two amino acid is in part 2 of the protease domain. In an embodiment, said at least two amino acids replacements are selected from the group consisting of D130A, H193A, N295A and S512A. In an embodiment, said at least two amino acids replacements are D130A and H193A. In an embodiment, said at least two amino acids replacements are D130A and N295A.

Preferably, said at least two amino acids replacements are D130A and S512A. In an embodiment, said at least two amino acids replacements are H193A and N295A. In an embodiment, said at least two amino acids replacements are H193A and S512A. In an embodiment, said at least two amino acids replacements are N295A and S512A.

In an embodiment, the carrier protein of the serotype 3 capsular polysaccharide glycoconjugate of the invention is an enzymatically inactive fragment of an SCP where said inactivation is accomplished by replacing at least two amino acids of the wild type sequence. Preferably, said replacement of at least two amino acids is in the protease domain. In an embodiment, said replacement of at least two amino acids is in part 1 of the protease domain. In an embodiment, said replacement of at least two amino acid is in part 2 of the protease domain. In an embodiment, said at least two amino acids replacements are selected from the group consisting of D130A, H193A, N295A and S512A. In an embodiment, said at least two amino acids replacements are D130A and H193A. In an embodiment, said at least two amino acids replacements are D130A and N295A. Preferably, said at least two amino acids replacements are D130A and S512A.

In an embodiment, said at least two amino acids replacements are H193A and N295A. In an embodiment, said at least two amino acids replacements are H193A and S512A. In an embodiment, said at least two amino acids replacements are N295A and S512A.

In an embodiment, the carrier protein of the serotype 3 capsular polysaccharide glycoconjugate of the invention is an enzymatically inactive fragment of SCP which comprises the protease domain, the protease-associated domain (PA domain) and the three fibronectin type III (Fn) domains but does not comprise the export signal presequence, the pro-sequence and the cell wall anchor domain, where said inactivation is accomplished by replacing at least two amino acids of the wild type sequence.

Preferably, said replacement of at least two amino acids is in the protease domain. In an embodiment, said replacement of at least two amino acids is in part 1 of the protease domain. In an embodiment, said replacement of at least two amino acid is in part 2 of the protease domain. In an embodiment, said at least two amino acids replacements are selected from the group consisting of D130A, H193A, N295A and S512A. In an embodiment, said at least two amino acids replacements are D130A and H193A. In an embodiment, said at least two amino acids replacements are D130A and N295A.

Preferably, said at least two amino acids replacements are D130A and S512A. In an embodiment, said at least two amino acids replacements are H193A and N295A. In an embodiment, said at least two amino acids replacements are H193A and S512A. In an embodiment, said at least two amino acids replacements are N295A and S512A.

In an embodiment, the carrier protein of the serotype 3 capsular polysaccharide glycoconjugate of the invention is an enzymatically inactive fragment of SCPA which comprises the protease domain, the protease-associated domain (PA domain) and the three fibronectin type III (Fn) domains but does not comprise the export signal presequence, the pro-sequence and the cell wall anchor domain, where said inactivation is accomplished by replacing at least two amino acids of the wild type sequence.

Preferably, said replacement of at least two amino acids is in the protease domain. In an embodiment, said replacement of at least two amino acids is in part 1 of the protease domain. In an embodiment, said replacement of at least one amino acids is in part 2 of the protease domain. In an embodiment, said at least two amino acids replacements are selected from the group consisting of D130A, H193A, N295A and S512A. In an embodiment, said at least two amino acids replacements are D130A and H193A. In an embodiment, said at least two amino acids replacements are D130A and N295A.

Preferably, said at least two amino acids replacements are D130A and S512A. In an embodiment, said at least two amino acids replacements are H193A and N295A. In an embodiment, said at least two amino acids replacements are H193A and S512A. In an embodiment, said at least two amino acids replacements are N295A and S512A.

In an embodiment, the carrier protein of the serotype 3 capsular polysaccharide glycoconjugate of the invention is an enzymatically inactive fragment of SCPB which comprises the protease domain, the protease-associated domain (PA domain) and the three fibronectin type III (Fn) domains but does not comprise the export signal presequence, the pro-sequence and the cell wall anchor domain, where said inactivation is accomplished by replacing at least two amino acids of the wild type sequence.

Preferably, said replacement of at least two amino acids is in the protease domain. In an embodiment, said replacement of at least two amino acids is in part 1 of the protease domain. In an embodiment, said replacement of at least two amino acids is in part 2 of the protease domain. In an embodiment, said at least two amino acids replacements are selected from the group consisting of D130A, H193A, N295A and S512A. In an embodiment, said at least two amino acids replacements are D130A and H193A. In an embodiment, said at least two amino acids replacements are D130A and N295A.

Preferably, said at least two amino acids replacements are D130A and S512A. In an embodiment, said at least two amino acids replacements are H193A and N295A. In an embodiment, said at least two amino acids replacements are H193A and S512A. In an embodiment, said at least two amino acids replacements are N295A and S512A.

In an embodiment, the enzymatic activity of SCP is inactivated by replacing at least three amino acids of the wild type sequence. In an embodiment, said at least three amino acids replacements are selected from the group consisting of D130A, H193A, N295A and S512A. In an embodiment, said at least three amino acids replacements are D130A, H193A and N295A. In an embodiment, said at least three amino acids replacements are D130A, H193A and S512A. In an embodiment, said at least three amino acids replacements are D130A, N295A and S512A. In an embodiment, said at least three amino acids replacements are H193A, N295A and S512A.

Therefore, in an embodiment, the carrier protein of the serotype 3 capsular polysaccharide glycoconjugate of the invention is an enzymatically inactive SCP where said inactivation is accomplished by replacing at least three amino acids of the wild type sequence. Preferably, said replacement of at least three amino acids is in the protease domain. In an embodiment, said replacement of at least three amino acid is in part 1 of the protease domain. In an embodiment, said replacement of at least three amino acid is in part 2 of the protease domain. In an embodiment, said at least three amino acids replacements are selected from the group consisting of D130A, H193A, N295A and S512A. In an embodiment, said at least three amino acids replacements are D130A, H193A and N295A. In an embodiment, said at least three amino acids replacements are D130A, H193A and S512A. In an embodiment, said at least three amino acids replacements are D130A, N295A and S512A. In an embodiment, said at least three amino acids replacements are H193A, N295A and S512A.

In an embodiment, the carrier protein of the serotype 3 capsular polysaccharide glycoconjugate of the invention is an enzymatically inactive SCPA where said inactivation is accomplished by replacing at least three amino acids of the wild type sequence.

Preferably, said replacement of at least three amino acids is in the protease domain. In an embodiment, said replacement of at least three amino acids is in part 1 of the protease domain. In an embodiment, said replacement of at least three amino acid is in part 2 of the protease domain. In an embodiment, said at least three amino acids replacements are selected from the group consisting of D130A, H193A, N295A and S512A. In an embodiment, said at least three amino acids replacements are D130A, H193A and N295A. In an embodiment, said at least three amino acids replacements are D130A, H193A and S512A. In an embodiment, said at least three amino acids replacements are D130A, N295A and S512A. In an embodiment, said at least three amino acids replacements are H193A, N295A and S512A.

In an embodiment, the carrier protein of the serotype 3 capsular polysaccharide glycoconjugate of the invention is an enzymatically inactive SCPB where said inactivation is accomplished by replacing at least three amino acids of the wild type sequence.

Preferably, said replacement of at least three amino acids is in the protease domain. In an embodiment, said replacement of at least three amino acids is in part 1 of the protease domain. In an embodiment, said replacement of at least three amino acid is in part 2 of the protease domain. In an embodiment, said at least three amino acids replacements are selected from the group consisting of D130A, H193A, N295A and S512A. In an embodiment, said at least three amino acids replacements are D130A, H193A and N295A. In an embodiment, said at least three amino acids replacements are D130A, H193A and S512A. In an embodiment, said at least three amino acids replacements are D130A, N295A and S512A. In an embodiment, said at least three amino acids replacements are H193A, N295A and S512A.

In an embodiment, the carrier protein of the serotype 3 capsular polysaccharide glycoconjugate of the invention is an enzymatically inactive fragment of an SCP where said inactivation is accomplished by replacing at least three amino acids of the wild type sequence. Preferably, said replacement of at least three amino acids is in the protease domain. In an embodiment, said replacement of at least three amino acids is in part 1 of the protease domain. In an embodiment, said replacement of at least three amino acid is in part 2 of the protease domain. In an embodiment, said at least three amino acids replacements are selected from the group consisting of D130A, H193A, N295A and S512A. In an embodiment, said at least three amino acids replacements are D130A, H193A and N295A. In an embodiment, said at least three amino acids replacements are D130A, H193A and S512A. In an embodiment, said at least three amino acids replacements are D130A, N295A and S512A. In an embodiment, said at least three amino acids replacements are H193A, N295A and S512A.

In an embodiment, the carrier protein of the serotype 3 capsular polysaccharide glycoconjugate of the invention is an enzymatically inactive fragment of SCP which comprises the protease domain, the protease-associated domain (PA domain) and the three fibronectin type III (Fn) domains but does not comprise the export signal presequence, the pro-sequence and the cell wall anchor domain, where said inactivation is accomplished by replacing at least three amino acids of the wild type sequence.

Preferably, said replacement of at least three amino acids is in the protease domain. In an embodiment, said replacement of at least three amino acids is in part 1 of the protease domain. In an embodiment, said replacement of at least three amino acid is in part 2 of the protease domain. In an embodiment, said at least three amino acids replacements are selected from the group consisting of D130A, H193A, N295A and S512A. In an embodiment, said at least three amino acids replacements are D130A, H193A and N295A. In an embodiment, said at least three amino acids replacements are D130A, H193A and S512A. In an embodiment, said at least three amino acids replacements are D130A, N295A and S512A. In an embodiment, said at least three amino acids replacements are H193A, N295A and S512A.

In an embodiment, the carrier protein of the serotype 3 capsular polysaccharide glycoconjugate of the invention is an enzymatically inactive fragment of SCPA which comprises the protease domain, the protease-associated domain (PA domain) and the three fibronectin type III (Fn) domains but does not comprise the export signal presequence, the pro-sequence and the cell wall anchor domain, where said inactivation is accomplished by replacing at least three amino acids of the wild type sequence.

Preferably, said replacement of at least three amino acids is in the protease domain. In an embodiment, said replacement of at least three amino acids is in part 1 of the protease domain. In an embodiment, said replacement of at least three amino acids is in part 2 of the protease domain. In an embodiment, said at least three amino acids replacements are selected from the group consisting of D130A, H193A, N295A and S512A. In an embodiment, said at least three amino acids replacements are D130A, H193A and N295A. In an embodiment, said at least three amino acids replacements are D130A, H193A and S512A. In an embodiment, said at least three amino acids replacements are D130A, N295A and S512A. In an embodiment, said at least three amino acids replacements are H193A, N295A and S512A.

In an embodiment, the carrier protein of the serotype 3 capsular polysaccharide glycoconjugate of the invention is an enzymatically inactive fragment of SCPB which comprises the protease domain, the protease-associated domain (PA domain) and the three fibronectin type III (Fn) domains but does not comprise the export signal presequence, the pro-sequence and the cell wall anchor domain, where said inactivation is accomplished by replacing at least three amino acids of the wild type sequence.

Preferably, said replacement of at least three amino acids is in the protease domain. In an embodiment, said replacement of at least three amino acids is in part 1 of the protease domain. In an embodiment, said replacement of at least three amino acids is in part 2 of the protease domain. In an embodiment, said at least three amino acids replacements are selected from the group consisting of D130A, H193A, N295A and S512A. In an embodiment, said at least three amino acids replacements are D130A, H193A and N295A. In an embodiment, said at least three amino acids replacements are D130A, H193A and S512A. In an embodiment, said at least three amino acids replacements are D130A, N295A and S512A. In an embodiment, said at least three amino acids replacements are H193A, N295A and S512A.

In an embodiment, the enzymatic activity of SCP is inactivated by replacing at least four amino acids of the wild type sequence. In an embodiment, said at least four amino acids replacements are D130A, H193A, N295A and S512A.

Therefore, in an embodiment, the carrier protein of the serotype 3 capsular polysaccharide glycoconjugate of the invention is an enzymatically inactive SCP where said inactivation is accomplished by replacing at least four amino acids of the wild type sequence. Preferably, said replacement of at least four amino acids is in the protease domain. In an embodiment, said replacement of at least four amino acid is in part 1 of the protease domain. In an embodiment, said replacement of at least four amino acid is in part 2 of the protease domain. In an embodiment, said at least four amino acids replacements are D130A, H193A, N295A and S512A In an embodiment, the carrier protein of the serotype 3 capsular polysaccharide glycoconjugate of the invention is an enzymatically inactive SCPA where said inactivation is accomplished by replacing at least four amino acids of the wild type sequence.

Preferably, said replacement of at least four amino acids is in the protease domain. In an embodiment, said replacement of at least four amino acids is in part 1 of the protease domain. In an embodiment, said replacement of at least four amino acid is in part 2 of the protease domain. In an embodiment, said at least four amino acids replacements are D130A, H193A, N295A and S512A In an embodiment, the carrier protein of the serotype 3 capsular polysaccharide glycoconjugate of the invention is an enzymatically inactive SCPB where said inactivation is accomplished by replacing at least four amino acids of the wild type sequence.

Preferably, said replacement of at least four amino acids is in the protease domain. In an embodiment, said replacement of at least four amino acids is in part 1 of the protease domain. In an embodiment, said replacement of at least four amino acid is in part 2 of the protease domain. In an embodiment, said at least four amino acids replacements are D130A, H193A, N295A and S512A In an embodiment, the carrier protein of the serotype 3 capsular polysaccharide glycoconjugate of the invention is an enzymatically inactive fragment of an SCP where said inactivation is accomplished by replacing at least four amino acids of the wild type sequence. Preferably, said replacement of at least four amino acids is in the protease domain. In an embodiment, said replacement of at least four amino acids is in part 1 of the protease domain. In an embodiment, said replacement of at least four amino acid is in part 2 of the protease domain. In an embodiment, said at least four amino acids replacements are D130A, H193A, N295A and S512A In an embodiment, the carrier protein of the serotype 3 capsular polysaccharide glycoconjugate of the invention is an enzymatically inactive fragment of SCP which comprises the protease domain, the protease-associated domain (PA domain) and the three fibronectin type III (Fn) domains but does not comprise the export signal presequence, the pro-sequence and the cell wall anchor domain, where said inactivation is accomplished by replacing at least four amino acids of the wild type sequence.

Preferably, said replacement of at least four amino acids is in the protease domain. In an embodiment, said replacement of at least four amino acids is in part 1 of the protease domain. In an embodiment, said replacement of at least four amino acid is in part 2 of the protease domain. In an embodiment, said at least four amino acids replacements are D130A, H193A, N295A and S512A In an embodiment, the carrier protein of the serotype 3 capsular polysaccharide glycoconjugate of the invention is an enzymatically inactive fragment of SCPA which comprises the protease domain, the protease-associated domain (PA domain) and the three fibronectin type III (Fn) domains but does not comprise the export signal presequence, the pro-sequence and the cell wall anchor domain, where said inactivation is accomplished by replacing at least four amino acids of the wild type sequence.

Preferably, said replacement of at least four amino acids is in the protease domain. In an embodiment, said replacement of at least four amino acids is in part 1 of the protease domain. In an embodiment, said replacement of at least one amino acids is in part 2 of the protease domain. In an embodiment, said at least four amino acids replacements are D130A, H193A, N295A and S512A In an embodiment, the carrier protein of the serotype 3 capsular polysaccharide glycoconjugate of the invention is an enzymatically inactive fragment of SCPB which comprises the protease domain, the protease-associated domain (PA domain) and the three fibronectin type III (Fn) domains but does not comprise the export signal presequence, the pro-sequence and the cell wall anchor domain, where said inactivation is accomplished by replacing at least four amino acids of the wild type sequence.

Preferably, said replacement of at least four amino acids is in the protease domain. In an embodiment, said replacement of at least four amino acids is in part 1 of the protease domain. In an embodiment, said replacement of at least four amino acids is in part 2 of the protease domain. In an embodiment, said at least four amino acids replacements are D130A, H193A, N295A and S512A In a particular embodiment, the carrier protein of the serotype 3 capsular polysaccharide glycoconjugate of the invention is an enzymatically inactive fragment of SCP which consists of SEQ ID NO: 41.

In a particular embodiment, the carrier protein of the serotype 3 capsular polysaccharide glycoconjugate of the invention is an enzymatically inactive fragment of SCP which consists of SEQ ID NO: 42.

SEQ ID NO: 41:
MAKTADTPATSKATIRDLNDPSQVKTLQEKAGKGA

GTVVAVIAAGFDKNHEAWRLTDKAKARYQSKEDLE

KAKKEHGITYGEWVNDKVAYYHDYSKDGKTAVDQE

HGTHVSGILSGNAPSETKEPYRLEGAMPEAQLLLM

RVEIVNGLADYARNYAQAIRDAINLGAKVINMSFG

NAALAYANLPDETKKAFDYAKSKGVSIVTSAGNDS

SFGGKTRLPLADHPDYGVVGTPAAADSTLTVASYS

PDKQLTETVTVKTADQQDKEMPVLSTNRFEPNKAY

DYAYANRGTKEDDFKDVKGKIALIERGDIDFKDKI

AKAKKAGAVGVLIYDNQDKGFPIELPNVDQMPAAF

ISRKDGLLLKDNPQKTITFNATPKVLPTASGTKLS

RFSSWGLTADGNIKPDIAAPGQDILSSVANNKYAK

LSGTAMSAPLVAGIMGLLQEQYETQYPDMTPSERL

DLAKKVLMSSATALYDEDEKAYFSPRQQGAGAVDA

KKASAATMYVTDKDNTSSKVHLNNVSDKFEVTVTV

HNKSDKPQELYYQATVQTDKVDGKHFALAPKALYE

-continued

TSWQKITIPANSSKQVTVPIDASRFSKDLLAQMKN

GYFLEGFVRFKQDPKKEELMSIPYIGFRGDFGNLS

ALEKPIYDSKDGSSYYHEANSDAKDQLDGDGLQFY

ALKNNFTALTTESNPWTIIKAVKEGVENIEDIESS

EITETIFAGTFAKQDDDSHYYIHRHANGKPYAAIS

PNGDGNRDYVQFQGTFLRNAKNLVAEVLDKEGNVV

WTSEVTEQVVKNYNNDLASTLGSTRFEKTRWDGKD

KDGKVVANGTYTYRVRYTPISSGAKEQHTDFDVIV

DNTTPEVATSATFSTEDRRLTLASKPKTSQPVYRE

RIAYTYMDEDLPTTEYISPNEDGTFTLPEEAETME

GATVPLKMSDFTYWEDMAGNITYTPVTKLLEGHSN

KPEQ

SEQ ID NO: 41 is 950 amino acids long.

SEQ ID NO: 42:
AKTADTPATSKATIRDLNDPSQVKTLQEKAGKGAG

TVVAVIAAGFDKNHEAWRLTDKAKARYQSKEDLEK

AKKEHGITYGEWVNDKVAYYHDYSKDGKTAVDQEH

GTHVSGILSGNAPSETKEPYRLEGAMPEAQLLLMR

VEIVNGLADYARNYAQAIRDAINLGAKVINMSFGN

AALAYANLPDETKKAFDYAKSKGVSIVTSAGNDSS

FGGKTRLPLADHPDYGVVGTPAAADSTLTVASYSP

DKQLTETVTVKTADQQDKEMPVLSTNRFEPNKAYD

YAYANRGTKEDDFKDVKGKIALIERGDIDFKDKIA

KAKKAGAVGVLIYDNQDKGFPIELPNVDQMPAAFI

SRKDGLLLKDNPQKTITFNATPKVLPTASGTKLSR

FSSWGLTADGNIKPDIAAPGQDILSSVANNKYAKL

SGTAMSAPLVAGIMGLLQEQYETQYPDMTPSERLD

LAKKVLMSSATALYDEDEKAYFSPRQQGAGAVDAK

KASAATMYVTDKDNTSSKVHLNNVSDKFEVTVTVH

NKSDKPQELYYQATVQTDKVDGKHFALAPKALYET

SWQKITIPANSSKQVTVPIDASRFSKDLLAQMKNG

YFLEGFVRFKQDPKKEELMSIPYIGFRGDFGNLSA

LEKPIYDSKDGSSYYHEANSDAKDQLDGDGLQFYA

LKNNFTALTTESNPWTIIKAVKEGVENIEDIESSE

ITETIFAGTFAKQDDDSHYYIHRHANGKPYAAISP

NGDGNRDYVQFQGTFLRNAKNLVAEVLDKEGNVVW

TSEVTEQVVKNYNNDLASTLGSTRFEKTRWDGKDK

DGKVVANGTYTYRVRYTPISSGAKEQHTDFDVIVD

NTTPEVATSATFSTEDRRLTLASKPKTSQPVYRER

IAYTYMDEDLPTTEYISPNEDGTFTLPEEAETMEG

ATVPLKMSDFTYWEDMAGNITYTPVTKLLEGHSNK

-continued

PEQ

SEQ ID NO: 42 is 949 amino acids long.

In a particular embodiment, the carrier protein of the serotype 3 capsular polysaccharide glycoconjugate of the invention is an enzymatically inactive fragment of SCP consisting of a polypeptide having at least 90% identity with SEQ ID NO: 41.

In a particular embodiment, the carrier protein of the serotype 3 capsular polysaccharide glycoconjugate of the invention is an enzymatically inactive fragment of SCP consisting of a polypeptide having at least 95% identity with SEQ ID NO: 41.

In a particular embodiment, the carrier protein of the serotype 3 capsular polysaccharide glycoconjugate of the invention is an enzymatically inactive fragment of SCP consisting of a polypeptide having at least 99% identity with SEQ ID NO: 41.

In a particular embodiment, the carrier protein of the serotype 3 capsular polysaccharide glycoconjugate of the invention is an enzymatically inactive fragment of SCP consisting of a polypeptide having at least 99.5% identity with SEQ ID NO: 41.

In a particular embodiment, the carrier protein of the serotype 3 capsular polysaccharide glycoconjugate of the invention is an enzymatically inactive fragment of SCP consisting of a polypeptide having at least 99.8% identity with SEQ ID NO: 41.

In a particular embodiment, the carrier protein of the serotype 3 capsular polysaccharide glycoconjugate of the invention is an enzymatically inactive fragment of SCP consisting of a polypeptide having at least 99.85% identity with SEQ ID NO: 41.

In a particular embodiment, the carrier protein of the serotype 3 capsular polysaccharide glycoconjugate of the invention is an enzymatically inactive fragment of SCP consisting of a polypeptide having at least 90% identity with SEQ ID NO: 42.

In a particular embodiment, the carrier protein of the serotype 3 capsular polysaccharide glycoconjugate of the invention is an enzymatically inactive fragment of SCP consisting of a polypeptide having at least 95% identity with SEQ ID NO: 42.

In a particular embodiment, the carrier protein of the serotype 3 capsular polysaccharide glycoconjugate of the invention is an enzymatically inactive fragment of SCP consisting of a polypeptide having at least 99% identity with SEQ ID NO: 42.

In a particular embodiment, the carrier protein of the serotype 3 capsular polysaccharide glycoconjugate of the invention is an enzymatically inactive fragment of SCP consisting of a polypeptide having at least 99.5% identity with SEQ ID NO: 42.

In a particular embodiment, the carrier protein of the serotype 3 capsular polysaccharide glycoconjugate of the invention is an enzymatically inactive fragment of SCP consisting of a polypeptide having at least 99.8% identity with SEQ ID NO: 42.

In a particular embodiment, the carrier protein of the serotype 3 capsular polysaccharide glycoconjugate of the invention is an enzymatically inactive fragment of SCP consisting of a polypeptide having at least 99.85% identity with SEQ ID NO: 42.

2 IMMUNOGENIC COMPOSITIONS

2.1 Combinations of Glycoconjugates of the Invention

In an embodiment the invention relates to an immunogenic composition comprising a *Streptococcus pneumoniae* serotype 3 glycoconjugate of the invention.

In an embodiment the invention relates to an immunogenic composition comprising a *Streptococcus pneumoniae* serotype 3 glycoconjugate of the invention and comprising from 1 to 25 different glycoconjugates.

In an embodiment the invention relates to an immunogenic composition comprising a *Streptococcus pneumoniae* serotype 3 glycoconjugate of the invention and comprising from 1 to 25 glycoconjugates from different serotypes of *S. pneumoniae* (1 to 25 pneumococcal conjugates). In one embodiment the invention relates to an immunogenic composition comprising glycoconjugates from 7, 8, 9, 10, 11, 12, 13, 14, 15, 16, 17, 18, 19, 20, 21, 22, 23, 24 or 25 different serotypes of *S. pneumoniae*. In one embodiment the immunogenic composition comprises glycoconjugates from 16 or 20 different serotypes of *S. pneumoniae*. In an embodiment the immunogenic composition is a 7, 8, 9, 10, 11, 12, 13, 14, 15, 16, 17, 18, 19 or 20-valent pneumococcal conjugate compositions. In an embodiment the immunogenic composition is a 14, 15, 16, 17, 18 or 19-valent pneumococcal conjugate compositions. In an embodiment the immunogenic composition is a 16-valent pneumococcal conjugate composition. In an embodiment the immunogenic composition is a 19-valent pneumococcal conjugate composition. In an embodiment the immunogenic composition is a 20-valent pneumococcal conjugate composition.

In an embodiment the immunogenic composition is a 21, 22, 23, 24 or 25-valent pneumococcal conjugate compositions. In an embodiment the immunogenic composition is a 21-valent pneumococcal conjugate composition. In an embodiment the immunogenic composition is a 22-valent pneumococcal conjugate composition. In an embodiment the immunogenic composition is a 23-valent pneumococcal conjugate composition. In an embodiment the immunogenic composition is a 24-valent pneumococcal conjugate composition. In an embodiment the immunogenic composition is a 25-valent pneumococcal conjugate composition.

In an embodiment the invention relates to an immunogenic composition comprising a *Streptococcus pneumoniae* serotype 3 glycoconjugate of the invention and further comprising glycoconjugates from *S. pneumoniae* serotypes 4.6B, 9V, 14, 18C, 19F and 23F.

In an embodiment said immunogenic composition comprises in addition glycoconjugates from *S. pneumoniae* serotypes 1, 5 and 7F.

In an embodiment any of the immunogenic compositions above comprises in addition glycoconjugates from *S. pneumoniae* serotypes 6A and 19A.

In an embodiment any of the immunogenic compositions above comprise in addition a glycoconjugates from *S. pneumoniae* serotype 22F and 33F.

In an embodiment any of the immunogenic compositions above comprise in addition a glycoconjugates from *S. pneumoniae* serotypes 8.10A, 11A, 12F and 15B.

In an embodiment any of the immunogenic compositions above comprise in addition a glycoconjugates from *S. pneumoniae* serotype 2.

In an embodiment any of the immunogenic compositions above comprise in addition a glycoconjugates from *S. pneumoniae* serotypes 9N.

In an embodiment any of the immunogenic compositions above comprise in addition a glycoconjugates from *S. pneumoniae* serotypes 17F.

In an embodiment any of the immunogenic compositions above comprise in addition a glycoconjugates from *S. pneumoniae* serotypes 20.

In an embodiment the invention relates to an immunogenic composition comprising a *Streptococcus pneumoniae* serotype 3 glycoconjugate of the invention and further comprising glycoconjugates from *S. pneumoniae* serotypes 4.6B, 9V, 14, 18C, 19F and 23F. In an embodiment the immunogenic composition is an 8-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6B, 7F, 9V, 14, 18C, 19F and 23F. In an embodiment the immunogenic composition is an 11-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 9V, 14, 18C, 19A, 19F and 23F. In an embodiment the immunogenic composition is a 13-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 9V, 14, 18C, 19A, 19F, 22F, 23F and 33F. In an embodiment the immunogenic composition is a 15-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23F and 33F. In an embodiment the immunogenic composition is a 20-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 2, 4, 5, 6A, 6B, 7F, 8, 9V, 10A, 11A, 12F, 14, 15B, 18C, 19A, 19F, 22F, 23F and 33F. In an embodiment the immunogenic composition is a 21-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 9N, 10A, 11A, 12F, 14, 15B, 18C, 19A, 19F, 22F, 23F and 33F. In an embodiment the immunogenic composition is a 21-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 2, 4, 5, 6A, 6B, 7F, 8, 9V, 9N, 10A, 11A, 12F, 14, 15B, 18C, 19A, 19F, 22F, 23F and 33F. In an embodiment the immunogenic composition is a 22-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 2, 4, 5, 6A, 6B, 7F, 8, 9V, 9N, 10A, 11A, 12F, 14, 15B, 17F, 18C, 19A, 19F, 22F, 23F and 33F. In an embodiment the immunogenic composition is a 23-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 2, 4, 5, 6A, 6B, 7F, 8, 9V, 9N, 10A, 11A, 12F, 14, 15B, 17F, 18C, 19A, 19F, 20, 22F, 23F and 33F. In an embodiment the immunogenic composition is a 24-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23F and 33F. In an embodiment the immunogenic composition is a 21-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23A, 23F and 33F. In an embodiment the immunogenic composition is a 21-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23B, 23F and 33F. In an embodiment the immunogenic composition is a 21-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23F, 24F and 33F. In an embodiment the immunogenic composition is a 21-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23F, 33F and 35B. In an embodiment the immunogenic composition is a 21-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23A, 23F and 33F. In an embodiment the immunogenic composition is a 22-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23B, 23F and 33F. In an embodiment the immunogenic composition is a 22-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23F, 24F and 33F. In an embodiment the immunogenic composition is a 22-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23F, 33F and 35B. In an embodiment the immunogenic composition is a 22-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23A, 23B, 23F and 33F. In an embodiment the immunogenic composition is a 22-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23A, 23F, 24F and 33F. In an embodiment the immunogenic composition is a 22-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23A, 23F, 33F and 35B. In an embodiment the immunogenic composition is a 22-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23B, 23F, 24F and 33F. In an embodiment the immunogenic composition is a 22-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23B, 23F, 33F and 35B. In an embodiment the immunogenic composition is a 22-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23F, 24F, 33F and 35B. In an embodiment the immunogenic composition is a 22-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23A, 23B, 23F and 33F. In an embodiment the immunogenic composition is a 23-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23A, 23F, 24F and 33F. In an embodiment the immunogenic composition is a 23-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23A, 23F, 33F and 35B. In an embodiment the immunogenic composition is a 23-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23B, 23F, 24F and 33F. In an embodiment the immunogenic composition is a 23-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23B, 23F, 33F and 35B. In an embodiment the immunogenic composition is a 23-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23F, 24F, 33F and 35B. In an embodiment the immunogenic composition is a 23-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23A, 23B, 23F, 33F and 35B. In an embodiment the immunogenic composition is a 23-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23A, 23B, 23F, 24F and 33F. In an embodiment the immunogenic composition is a 23-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23A, 23F, 24F, 33F and 35B. In an embodiment the immunogenic composition is a 23-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23B, 23F, 24F, 33F and 35B. In an embodiment the immunogenic composition is a 23-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23A, 23B, 23F, 24F and 33F. In an embodiment the immunogenic composition is a 24-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23A, 23B, 23F, 33F and 35B. In an embodiment the immunogenic composition is a 24-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23A, 23F, 24F, 33F and 35B. In an embodiment the immunogenic composition is a 24-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23B, 23F, 24F, 33F and 35B. In an embodiment the immunogenic composition is a 24-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23A, 23B, 23F, 24F, 33F and 35B. In an embodiment the immunogenic composition is a 24-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23A, 23B, 23F, 24F, 33F and 35B. In an embodiment the immunogenic composition is a 25-valent pneumococcal conjugate compositions.

In an embodiment the invention relates to an immunogenic composition comprising a *Streptococcus pneumoniae* serotype 3 glycoconjugate of the invention and further comprising at least one glycoconjugate selected from the group consisting of glycoconjugates from *S. pneumoniae* serotypes 2, 7C, 9N, 10B, 15A, 16F, 17F, 20, 21, 22A, 23A, 23B, 24B, 24F, 27, 29, 31, 33B, 34, 35B, 35F and 38.

In an embodiment the invention relates to an immunogenic composition comprising a *Streptococcus pneumoniae* serotype 3 glycoconjugate of the invention and further comprising twenty glycoconjugates selected from the group consisting of glycoconjugates from *S. pneumoniae* serotypes 2, 7C, 9N, 10B, 15A, 16F, 17F, 20, 21, 22A, 23A, 23B, 24B, 24F, 27, 29, 31, 33B, 34, 35B, 35F and 38. In an embodiment the immunogenic composition is a 21-valent pneumococcal conjugate compositions.

In an embodiment the invention relates to an immunogenic composition comprising a *Streptococcus pneumoniae* serotype 3 glycoconjugate of the invention and further comprising twenty one glycoconjugates selected from the group consisting of glycoconjugates from *S. pneumoniae* serotypes 2, 7C, 9N, 10B, 15A, 16F, 17F, 20, 21, 22A, 23A, 23B, 24B, 24F, 27, 29, 31, 33B, 34, 35B, 35F and 38. In an embodiment the immunogenic composition is a 22-valent pneumococcal conjugate compositions.

In an embodiment the invention relates to an immunogenic composition comprising a *Streptococcus pneumoniae* serotype 3 glycoconjugate of the invention and further comprising at least one glycoconjugate selected from the group consisting of glycoconjugates from *S. pneumoniae* serotypes 2, 7C, 9N, 10B, 15A, 16F, 17F, 19A, 19F, 20, 21, 22A, 23A, 23B, 24B, 24F, 27, 29, 31, 33B, 34, 35B, 35F and 38.

In an embodiment the invention relates to an immunogenic composition comprising a *Streptococcus pneumoniae* serotype 3 glycoconjugate of the invention and further comprising twenty two glycoconjugates selected from the group consisting of glycoconjugates from *S. pneumoniae* serotypes 2, 7C, 9N, 10B, 15A, 16F, 17F, 19A, 19F, 20, 21, 22A, 23A, 23B, 24B, 24F, 27, 29, 31, 33B, 34, 35B, 35F and 38. In an embodiment the immunogenic composition is a 23-valent pneumococcal conjugate compositions.

In an embodiment the invention relates to an immunogenic composition comprising a *Streptococcus pneumoniae* serotype 3 glycoconjugate of the invention and further comprising twenty three glycoconjugates selected from the group consisting of glycoconjugates from *S. pneumoniae* serotypes 2, 7C, 9N, 10B, 15A, 16F, 17F, 19A, 19F, 20, 21, 22A, 23A, 23B, 24B, 24F, 27, 29, 31, 33B, 34, 35B, 35F and 38. In an embodiment the immunogenic composition is a 24-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 2, 9N, 15A, 17F, 20, 23A, 23B, 24F and 35B. In an embodiment the immunogenic composition is a 10-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 2, 9N, 15A, 17F, 19A, 19F, 20, 23A, 23B, 24F and 35B. In an embodiment the immunogenic composition is a 12-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 2, 7C, 9N, 10B, 15A, 16F, 17F, 20, 21, 22A, 23A, 23B, 24B, 24F, 27, 29, 31, 33B, 34, 35B, 35F and 38. In an embodiment the immunogenic composition is a 23-valent pneumococcal conjugate compositions.

In an embodiment the invention relates to an immunogenic composition comprising a *Streptococcus pneumoniae* serotype 3 glycoconjugate of the invention and further comprising glycoconjugates from *S. pneumoniae* serotypes 2, 7C, 9N, 10B, 15A, 16F, 17F, 19A, 19F, 20, 21, 22A, 23A, 23B, 24B, 24F, 27, 29, 31, 33B, 34, 35B, 35F and 38.

In an embodiment the immunogenic composition is a 25-valent pneumococcal conjugate compositions.

In a preferred embodiment, the saccharides are each individually conjugated to different molecules of the protein carrier (each molecule of protein carrier only having one type of saccharide conjugated to it). In said embodiment, the capsular saccharides are said to be individually conjugated to the carrier protein. Preferably, all the glycoconjugates of the above immunogenic compositions are individually conjugated to the carrier protein.

In an embodiment of any of the above immunogenic compositions, the glycoconjugate from *S. pneumoniae* serotype 3 is conjugated to $CRM_{197}$. In an embodiment of any of the above immunogenic compositions, the glycoconjugate from *S. pneumoniae* serotype 3 is conjugated to SCP.

In an embodiment of any of the above immunogenic compositions, the glycoconjugate from *S. pneumoniae* serotype 22F is conjugated to $CRM_{197}$. In an embodiment of any of the above immunogenic compositions, the glycoconjugate from *S. pneumoniae* serotype 33F is conjugated to $CRM_{197}$. In an embodiment of any of the above immunogenic compositions, the glycoconjugate from *S. pneumoniae* serotype 15B is conjugated to CRM197. In an embodiment of any of the above immunogenic compositions, the glycoconjugate from *S. pneumoniae* serotype 12F is conjugated to $CRM_{197}$. In an embodiment of any of the above immunogenic compositions, the glycoconjugate from *S. pneumoniae* serotype 10A is conjugated to CRM197. In an embodiment of any of the above immunogenic compositions, the glycoconjugate from *S. pneumoniae* serotype 11A is conjugated to $CRM_{197}$. In an embodiment of any of the above immunogenic compositions, the glycoconjugate from *S. pneumoniae* serotype 8 is conjugated to $CRM_{197}$. In an embodiment of any of the above immunogenic compositions, the glycoconjugates from *S. pneumoniae* serotypes 4, 6B, 9V, 14, 18C, 19F and 23F are conjugated to $CRM_{197}$. In an embodiment of any of the above immunogenic compositions, the glycoconjugates from *S. pneumoniae* serotypes 1, 5 and 7F are conjugated to $CRM_{197}$. In an embodiment of any of the above immunogenic compositions, the glycoconjugates from *S. pneumoniae* serotypes 6A and 19A are conjugated to $CRM_{197}$.

In an embodiment of any of the above immunogenic compositions, the glycoconjugates of any of the above immunogenic compositions are all individually conjugated to $CRM_{197}$.

In an embodiment of any of the above immunogenic compositions, the glycoconjugate from *S. pneumoniae* serotype 3 is conjugated to SCP and the other glycoconjugate(s) is/are all individually conjugated to $CRM_{197}$.

In an embodiment, the glycoconjugates from *S. pneumoniae* serotypes 1, 4, 5, 6B, 7F, 9V, 14 and/or 23F of any of the above immunogenic compositions are individually conjugated to PD.

In an embodiment, the glycoconjugate from *S. pneumoniae* serotype 18C of any of the above immunogenic compositions is conjugated to TT.

In an embodiment, the glycoconjugate from *S. pneumoniae* serotype 19F of any of the above immunogenic compositions is conjugated to DT.

In an embodiment, the glycoconjugates from *S. pneumoniae* serotypes 1, 4, 5, 6B, 7F, 9V, 14 and/or 23F of any of the above immunogenic compositions are individually conjugated to PD, the glycoconjugate from *S. pneumoniae* serotype 18C is conjugated to TT and the glycoconjugate from *S. pneumoniae* serotype 19F is conjugated to DT.

In an embodiment the above immunogenic compositions comprise from 8 to 20 different serotypes of *S. pneumoniae.*

In an embodiment of any of the above immunogenic compositions, the glycoconjugate from *S. pneumoniae* serotype 3 is conjugated to SCP, at least one other glycoconjugate is conjugated to TT and the other glycoconjugate(s) is/are all individually conjugated to CRM197.

In an embodiment of any of the above immunogenic compositions, the glycoconjugate from *S. pneumoniae* serotype 3 is conjugated to SCP, one other glycoconjugate is conjugated to TT and the other glycoconjugate(s) is/are all individually conjugated to $CRM_{197}$.

In an embodiment of any of the above immunogenic compositions, the glycoconjugate from *S. pneumoniae* serotype 3 is conjugated to SCP, at least two other glycoconjugates are conjugated to TT and the other glycoconjugate(s) is/are all individually conjugated to $CRM_{197}$.

In an embodiment of any of the above immunogenic compositions, the glycoconjugate from *S. pneumoniae* serotype 3 is conjugated to SCP, two other glycoconjugates are conjugated to TT and the other glycoconjugate(s) is/are all individually conjugated to $CRM_{197}$.

In an embodiment of any of the above immunogenic compositions, the glycoconjugate from *S. pneumoniae* serotype 3 is conjugated to SCP, at least three other glycoconjugates are conjugated to TT and the other glycoconjugate(s) is/are all individually conjugated to $CRM_{197}$.

In an embodiment of any of the above immunogenic compositions, the glycoconjugate from *S. pneumoniae* serotype 3 is conjugated to SCP, three other glycoconjugates are conjugated to TT and the other glycoconjugate(s) is/are all individually conjugated to $CRM_{197}$.

In an embodiment of any of the above immunogenic compositions, the glycoconjugate from *S. pneumoniae* serotype 3 is conjugated to SCP, at least four other glycoconjugates are conjugated to TT and the other glycoconjugate(s) is/are all individually conjugated to $CRM_{197}$.

In an embodiment of any of the above immunogenic compositions, the glycoconjugate from *S. pneumoniae* serotype 3 is conjugated to SCP, four other glycoconjugates are conjugated to TT and the other glycoconjugate(s) is/are all individually conjugated to $CRM_{197}$.

In an embodiment of any of the above immunogenic compositions, the glycoconjugate from *S. pneumoniae* serotype 3 is conjugated to SCP, at least five other glycoconjugates are conjugated to TT and the other glycoconjugate(s) is/are all individually conjugated to CRM197.

In an embodiment of any of the above immunogenic compositions, the glycoconjugate from *S. pneumoniae* serotype 3 is conjugated to SCP, five other glycoconjugates are conjugated to TT and the other glycoconjugate(s) is/are all individually conjugated to $CRM_{197}$.

In an embodiment of any of the above immunogenic compositions, the glycoconjugate from *S. pneumoniae* serotype 3 is conjugated to SCP, at least one other glycoconjugate is conjugated to SCP and the other glycoconjugate(s) is/are all individually conjugated to $CRM_{197}$.

In an embodiment of any of the above immunogenic compositions, the glycoconjugate from *S. pneumoniae* serotype 3 is conjugated to SCP, one other glycoconjugate is conjugated to SCP and the other glycoconjugate(s) is/are all individually conjugated to $CRM_{197}$.

In an embodiment of any of the above immunogenic compositions, the glycoconjugate from *S. pneumoniae* serotype 3 is conjugated to SCP, at least two other glycoconjugates are conjugated to SCP and the other glycoconjugate(s) is/are all individually conjugated to $CRM_{197}$.

In an embodiment of any of the above immunogenic compositions, the glycoconjugate from *S. pneumoniae* serotype 3 is conjugated to SCP, two other glycoconjugates are conjugated to SCP and the other glycoconjugate(s) is/are all individually conjugated to $CRM_{197}$.

In an embodiment of any of the above immunogenic compositions, the glycoconjugate from *S. pneumoniae* serotype 3 is conjugated to SCP, at least three other glycoconjugates are conjugated to SCP and the other glycoconjugate (s) is/are all individually conjugated to $CRM_{197}$.

In an embodiment of any of the above immunogenic compositions, the glycoconjugate from *S. pneumoniae* serotype 3 is conjugated to SCP, three other glycoconjugates are conjugated to SCP and the other glycoconjugate(s) is/are all individually conjugated to $CRM_{197}$.

In an embodiment of any of the above immunogenic compositions, the glycoconjugate from *S. pneumoniae* serotype 3 is conjugated to SCP, at least four other glycoconjugates are conjugated to SCP and the other glycoconjugate(s) is/are all individually conjugated to $CRM_{197}$.

In an embodiment of any of the above immunogenic compositions, the glycoconjugate from *S. pneumoniae* serotype 3 is conjugated to SCP, four other glycoconjugates are conjugated to SCP and the other glycoconjugate(s) is/are all individually conjugated to $CRM_{197}$.

In an embodiment of any of the above immunogenic compositions, the glycoconjugate from *S. pneumoniae* serotype 3 is conjugated to SCP, at least five other glycoconjugates are conjugated to SCP and the other glycoconjugate(s) is/are all individually conjugated to $CRM_{197}$.

In an embodiment of any of the above immunogenic compositions, the glycoconjugate from *S. pneumoniae* serotype 3 is conjugated to SCP, five other glycoconjugates are conjugated to SCP and the other glycoconjugate(s) is/are all individually conjugated to $CRM_{197}$.

Compositions of the invention may include a small amount of free carrier. When a given carrier protein is present in both free and conjugated form in a composition of the invention, the unconjugated form is preferably no more than 5% of the total amount of the carrier protein in the composition as a whole, and more preferably present at less than 2% by weight.

2.2 Dosage of the Immunogenic Compositions of the Invention

The amount of glycoconjugate(s) in each dose is selected as an amount which induces an immunoprotective response without significant, adverse side effects in typical vaccinees. Such amount will vary depending upon which specific immunogen is employed and how it is presented.

The amount of a particular glycoconjugate in an immunogenic composition can be calculated based on total polysaccharide for that conjugate (conjugated and non-conjugated). For example, a glycoconjugate with 20% free polysaccharide will have about 80 μg of conjugated polysaccharide and about 20 μg of nonconjugated polysaccharide in a 100 μg polysaccharide dose. The amount of glycoconjugate can vary depending upon the pneumococcal serotype. The saccharide concentration can be determined by the uronic acid assay.

The "immunogenic amount" of the different polysaccharide components in the immunogenic composition, may diverge and each may comprise about 0.5 μg, about 0.75 μg, about 1 μg, about 2 μg, about 3 μg, about 4 μg, about 5 μg, about 6 μg, about 7 μg, about 8 μg, about 9 μg, about 10 μg, about 15 μg, about 20 μg, about 30 μg, about 40 μg, about 50 μg, about 60 μg, about 70 μg, about 80 μg, about 90 μg, or about 100 μg of any particular polysaccharide antigen.

Generally, each dose will comprise 0.1 μg to 100 μg of serotype 3 polysaccharide. In an embodiment each dose will comprise 0.1 μg to 100 μg of serotype 3 polysaccharide. In a preferred embodiment each dose will comprise 0.5 μg to 20 μg. In a preferred embodiment each dose will comprise 1.0 μg to 10 μg. In an even preferred embodiment, each dose will comprise 2.0 μg to 5.0 μg of serotype 3 polysaccharide. Any whole number integer within any of the above ranges is contemplated as an embodiment of the disclosure.

In an embodiment, each dose will comprise about 0.5 μg of serotype 3 polysaccharide.

In an embodiment, each dose will comprise about 0.55 μg of serotype 3 polysaccharide.

In an embodiment, each dose will comprise about 0.75 μg of serotype 3 polysaccharide.

In an embodiment, each dose will comprise about 1.0 μg of serotype 3 polysaccharide.

In an embodiment, each dose will comprise about 1.1 μg of serotype 3 polysaccharide.

In an embodiment, each dose will comprise about 1.5 μg of serotype 3 polysaccharide.

In an embodiment, each dose will comprise about 2.0 μg of serotype 3 polysaccharide.

In an embodiment, each dose will comprise about 2.2 μg of serotype 3 polysaccharide.

In an embodiment, each dose will comprise about 2.5 μg of serotype 3 polysaccharide.

In an embodiment, each dose will comprise about 3.0 μg of serotype 3 polysaccharide.

In an embodiment, each dose will comprise about 3.5 μg of serotype 3 polysaccharide.

In an embodiment, each dose will comprise about 4.0 μg of serotype 3 polysaccharide.

In an embodiment, each dose will comprise about 4.4 μg of serotype 3 polysaccharide.

In an embodiment, each dose will comprise about 5.0 μg of serotype 3 polysaccharide.

In an embodiment, each dose will comprise about 5.5 μg of serotype 3 polysaccharide.

In an embodiment, each dose will comprise about 6.0 μg of serotype 3 polysaccharide.

Generally, each dose will comprise 0.1 μg to 100 μg of polysaccharide for a given serotype. In an embodiment each dose will comprise 0.1 μg to 100 μg of polysaccharide for a given serotype. In a preferred embodiment each dose will comprise 0.5 μg to 20 μg.

In a preferred embodiment each dose will comprise 1.0 μg to 10 μg. In an even preferred embodiment, each dose will comprise 2.0 μg to 5.0 μg of polysaccharide for a given serotype. Any whole number integer within any of the above ranges is contemplated as an embodiment of the disclosure.

In an embodiment, each dose will comprise about 0.5 μg of polysaccharide for each particular glycoconjugate. In an embodiment, each dose will comprise about 0.55 μg of polysaccharide for each particular glycoconjugate. In an embodiment, each dose will comprise about 0.75 μg of polysaccharide for each particular glycoconjugate. In an embodiment, each dose will comprise about 1.0 μg of polysaccharide for each particular glycoconjugate. In an embodiment, each dose will comprise about 1.1 μg of polysaccharide for each particular glycoconjugate. In an embodiment, each dose will comprise about 1.5 μg of polysaccharide for each particular glycoconjugate. In an embodiment, each dose will comprise about 2.0 μg of polysaccharide for each particular glycoconjugate. In an embodiment, each dose will comprise about 2.2 μg of polysaccharide for each particular glycoconjugate. In an embodiment, each dose will comprise about 2.5 μg of polysaccharide for each particular glycoconjugate. In an embodiment, each dose will comprise about 3.0 μg of polysaccharide for each particular glycoconjugate. In an embodiment, each dose will comprise about 3.5 μg of polysaccharide for each particular glycoconjugate. In an embodiment, each dose will comprise about 4.0 μg of polysaccharide for each particular glycoconjugate. In an embodiment, each dose will comprise about 4.4 μg of polysaccharide for each particular glycoconjugate. In an embodiment, each dose will comprise about 5.0 μg of polysaccharide for each particular glycoconjugate. In an embodiment, each dose will comprise about 5.5 μg of polysaccharide for each particular glycoconjugate. In an embodiment, each dose will comprise about 6.0 μg of polysaccharide for each particular glycoconjugate.

In an embodiment, each dose will comprise about 1.1 μg, about 1.2 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.6 μg, about 2.7 μg, about 2.8 μg, about 2.9 μg, or about 3.0 μg of polysaccharide for glycoconjugates from *S. pneumoniae* serotype 1, 3, 4, 5, 6A, 7F, 8, 9V, 10A, 11A, 12F, 14, 15B, 18C, 19A, 19F, 22F, 23F and/or 33F.

In an embodiment, each dose will comprise about 1.1 μg, about 1.2 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.6 μg, about 2.7 μg, about 2.8 μg, about 2.9 μg, or about 3.0 μg of polysaccharide for glycoconjugates from *S. pneumoniae* serotype 1, 4, 5, 6A, 7F, 8, 9V, 10A, 11A, 12F, 14, 15B, 18C, 19A, 19F, 22F, 23F and/or 33F.

In an embodiment, each dose will comprise about 2.0 μg, about 2.2 μg, about 2.4 μg, about 2.6 μg, about 2.8 μg, about 3.0 μg, about 3.2 μg, about 3.4 μg, about 3.6 μg, about 3.8 μg, about 4.0 μg, about 4.2 μg, about 4.4 μg, about 4.6 μg, about 4.8 μg, about 5.0, about 5.2 μg, about 5.4 μg, about 5.6 μg, about 5.8 μg or about 6.0 μg of polysaccharide for glycoconjugates from *S. pneumoniae* serotype 6B.

In an embodiment, each dose will comprise about 0.5 μg, about 0.55 μg, about 0.75 μg, about 1.1 μg, about 1.2 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.6 μg, about 2.7 μg, about 2.8 μg, about 2.9 μg, or about 3.0 μg of polysaccharide for glycoconjugates from *S. pneumoniae* serotype 1, 3, 4, 5, 6A, 7F, 8, 9V, 10A, 11A, 12F, 14, 15B, 18C, 19A, 19F, 22F, 23F and/or 33F.

In an embodiment, each dose will comprise about 0.5 μg, about 0.55 μg, about 0.75 μg, about 1.1 μg, about 1.2 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.6 μg, about 2.7 μg, about 2.8 μg, about 2.9 μg, or about 3.0 μg of polysaccharide for glycoconjugates from *S. pneumoniae* serotype 1, 4, 5, 6A, 7F, 8, 9V, 10A, 11A, 12F, 14, 15B, 18C, 19A, 19F, 22F, 23F and/or 33F.

In an embodiment, each dose will comprise about 1.0 μg, about 1.1 μg, about 2.0 μg, about 2.2 μg, about 2.4 μg, about 2.6 μg, about 2.8 μg, about 3.0 μg, about 3.2 μg, about 3.4 μg, about 3.6 μg, about 3.8 μg, about 4.0 μg, about 4.2 μg, about 4.4 μg, about 4.6 μg, about 4.8 μg, about 5.0, about 5.2 μg, about 5.4 μg, about 5.6 μg, about 5.8 μg or about 6.0 μg of polysaccharide for glycoconjugates from *S. pneumoniae* serotype 6B.

In an embodiment, each dose will comprise about 0.5 μg to about 1.0 μg of polysaccharide for each glycoconjugate from *S. pneumoniae* serotype 1, 3, 4, 5, 6A, 7F, 8, 9V, 10A, 11A, 12F, 14, 15B, 18C, 19A, 19F, 22F, 23F and 33F, and about 1.0 μg to about 2.0 μg of polysaccharide for glycoconjugate from *S. pneumoniae* serotype 6B.

In an embodiment, each dose will comprise about 1.5 μg to about 3.0 μg of polysaccharide for each glycoconjugate from *S. pneumoniae* serotype 1, 3, 4, 5, 6A, 7F, 8, 9V, 10A, 11A, 12F, 14, 15B, 18C, 19A, 19F, 22F, 23F and 33F, and about 3.0 μg to about 6.0 μg of polysaccharide for glycoconjugate from *S. pneumoniae* serotype 6B.

In an embodiment, each dose will comprise about 2.0 μg to about 2.5 μg of polysaccharide for each glycoconjugate from *S. pneumoniae* serotype 1, 3, 4, 5, 6A, 7F, 8, 9V, 10A, 11A, 12F, 14, 15B, 18C, 19A, 19F, 22F, 23F and 33F, and about 4.0 μg to about 4.8 μg of polysaccharide for glycoconjugate from *S. pneumoniae* serotype 6B.

In an embodiment, each dose will comprise about 2.2 μg of polysaccharide from each glycoconjugate from *S. pneumoniae* serotype 1, 3, 4, 5, 6A, 7F, 8, 9V, 10A, 11A, 12F, 14, 15B, 18C, 19A, 19F, 22F, 23F and 33F, and about 4.4 μg of polysaccharide for glycoconjugate from *S. pneumoniae* serotype 6B.

In an embodiment, each dose will comprise about 0.5 μg to about 1.0 μg of polysaccharide for each glycoconjugate from *S. pneumoniae* serotype 1, 3, 4, 5, 6A, 7F, 9V, 14, 15B, 18C, 19A, 19F, 22F, 23F and 33F, and about 1.0 μg to about 2.0 μg of polysaccharide for glycoconjugate from *S. pneumoniae* serotype 6B.

In an embodiment, each dose will comprise about 1.5 μg to about 3.0 μg of polysaccharide for each glycoconjugate from *S. pneumoniae* serotype 1, 3, 4, 5, 6A, 7F, 9V, 14, 15B, 18C, 19A, 19F, 22F, 23F and 33F, and about 3 μg to about 6 μg of polysaccharide for glycoconjugate from *S. pneumoniae* serotype 6B.

In an embodiment, each dose will comprise about 2.0 μg to about 2.5 μg of polysaccharide for each glycoconjugate from *S. pneumoniae* serotype 1, 3, 4, 5, 6A, 7F, 9V, 14, 15B, 18C, 19A, 19F, 22F, 23F and 33F, and about 4.0 μg to about 4.8 μg of polysaccharide for glycoconjugate from *S. pneumoniae* serotype 6B.

In an embodiment, each dose will comprise about 2.0 μg of polysaccharide from each glycoconjugate from *S. pneumoniae* serotype 1, 3, 4, 5, 6A, 7F, 9V, 14, 18C, 19A, 19F, 22F, 23F and 33F, and about 4.0 μg of polysaccharide for glycoconjugate from *S. pneumoniae* serotype 6B.

In an embodiment, each dose will comprise about 2.2 μg of polysaccharide from each glycoconjugate from *S. pneumoniae* serotype 1, 3, 4, 5, 6A, 7F, 9V, 14, 15B, 18C, 19A, 19F, 22F, 23F and 33F, and about 4.4 μg of polysaccharide for glycoconjugate from *S. pneumoniae* serotype 6B.

In an embodiment, each dose will comprise about 0.5 μg to about 1.0 μg of polysaccharide for each glycoconjugate from *S. pneumoniae* serotype 1, 4, 5, 6A, 7F, 8, 9V, 10A, 11A, 12F, 14, 15B, 18C, 19A, 19F, 22F, 23F and 33F, and about 1.0 μg to about 2.0 μg of polysaccharide for glycoconjugate from *S. pneumoniae* serotype 6B.

In an embodiment, each dose will comprise about 1.5 μg to about 3.0 μg of polysaccharide for each glycoconjugate from *S. pneumoniae* serotype 1, 4, 5, 6A, 7F, 8, 9V, 10A, 11A, 12F, 14, 15B, 18C, 19A, 19F, 22F, 23F and 33F, and about 3.0 μg to about 6.0 μg of polysaccharide for glycoconjugate from *S. pneumoniae* serotype 6B.

In an embodiment, each dose will comprise about 2.0 μg to about 2.5 μg of polysaccharide for each glycoconjugate from *S. pneumoniae* serotype 1, 4, 5, 6A, 7F, 8, 9V, 10A, 11A, 12F, 14, 15B, 18C, 19A, 19F, 22F, 23F and 33F, and about 4.0 μg to about 4.8 μg of polysaccharide for glycoconjugate from *S. pneumoniae* serotype 6B.

In an embodiment, each dose will comprise about 2.2 μg of polysaccharide from each glycoconjugate from *S. pneumoniae* serotype 1, 4, 5, 6A, 7F, 8, 9V, 10A, 11A, 12F, 14, 15B, 18C, 19A, 19F, 22F, 23F and 33F, and about 4.4 μg of polysaccharide for glycoconjugate from *S. pneumoniae* serotype 6B.

In an embodiment, each dose will comprise about 0.5 μg to about 1.0 μg of polysaccharide for each glycoconjugate from *S. pneumoniae* serotype 1, 4, 5, 6A, 7F, 9V, 14, 15B, 18C, 19A, 19F, 22F, 23F and 33F, and about 1.0 μg to about 2.0 μg of polysaccharide for glycoconjugate from *S. pneumoniae* serotype 6B.

In an embodiment, each dose will comprise about 1.5 μg to about 3.0 μg of polysaccharide for each glycoconjugate from *S. pneumoniae* serotype 1, 4, 5, 6A, 7F, 9V, 14, 15B, 18C, 19A, 19F, 22F, 23F and 33F, and about 3.0 μg to about 6.0 μg of polysaccharide for glycoconjugate from *S. pneumoniae* serotype 6B.

In an embodiment, each dose will comprise about 2.0 μg to about 2.5 μg of polysaccharide for each glycoconjugate from *S. pneumoniae* serotype 1, 4, 5, 6A, 7F, 9V, 14, 15B, 18C, 19A, 19F, 22F, 23F and 33F, and about 4.0 μg to about 4.8 μg of polysaccharide for glycoconjugate from *S. pneumoniae* serotype 6B.

In an embodiment, each dose will comprise about 2.2 μg of polysaccharide from each glycoconjugate from *S. pneumoniae* serotype 1, 4, 5, 6A, 7F, 9V, 14, 15B, 18C, 19A, 19F, 22F, 23F and 33F, and about 4.4 μg of polysaccharide for glycoconjugate from *S. pneumoniae* serotype 6B.

In an embodiment, each dose will comprise about 0.5 μg, about 0.55 μg, about 0.75 μg, about 1.1 μg, about 1.2 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.6 μg, about 2.7 μg, about 2.8 μg, about 2.9 μg, or about 3.0 μg of polysaccharide for glycoconjugates from *S. pneumoniae* serotypes 1, 3, 4, 5, 6A, 7F, 8, 9V, 10A, 11A, 12F, 14, 15A, 15B, 18C, 19A, 19F, 22F, 23A, 23B, 23F, 24F, 33F and/or 35B.

In an embodiment, each dose will comprise about 0.5 μg, about 0.55 μg, about 0.75 μg, about 1.1 μg, about 1.2 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.6 μg, about 2.7 μg, about 2.8 μg, about 2.9 μg, or about 3.0 μg of polysaccharide for glycoconjugates from *S. pneumoniae* serotypes 1, 3, 4, 5, 6A, 7F, 8, 9V, 10A, 11A, 12F, 14, 15A, 15B, 18C, 19A, 19F, 22F, 23A, 23B, 23F, 24F, 33F and/or 35B.

In an embodiment, each dose will comprise about 1.0 μg, about 1.1 μg, about 2.0 μg, about 2.2 μg, about 2.4 μg, about 2.6 μg, about 2.8 μg, about 3.0 μg, about 3.2 μg, about 3.4 μg, about 3.6 μg, about 3.8 μg, about 4.0 μg, about 4.2 μg, about 4.4 μg, about 4.6 μg, about 4.8 μg, about 5.0, about 5.2 μg, about 5.4 μg, about 5.6 μg, about 5.8 μg or about 6.0 μg of polysaccharide for glycoconjugates from *S. pneumoniae* serotype 6B.

In an embodiment, each dose will comprise about 1.5 μg to about 3.0 μg of polysaccharide for each glycoconjugate from *S. pneumoniae* serotypes 1, 3, 4, 5, 6A, 7F, 8, 9V, 10A, 11A, 12F, 14, 15A, 15B, 18C, 19A, 19F, 22F, 23A, 23B, 23F, 24F, 33F and 35B, and about 3.0 μg to about 6.0 μg of polysaccharide for glycoconjugate from *S. pneumoniae* serotype 6B.

In an embodiment, each dose will comprise about 2.0 μg to about 2.5 μg of polysaccharide for each glycoconjugate from *S. pneumoniae* serotypes 1, 3, 4, 5, 6A, 7F, 8, 9V, 10A, 11A, 12F, 14, 15A, 15B, 18C, 19A, 19F, 22F, 23A, 23B, 23F, 24F, 33F and 35B, and about 4.0 μg to about 4.8 μg of polysaccharide for glycoconjugate from *S. pneumoniae* serotype 6B.

In an embodiment, each dose will comprise about 2.2 μg of polysaccharide from each glycoconjugate from *S. pneumoniae* serotypes 1, 3, 4, 5, 6A, 7F, 8, 9V, 10A, 11A, 12F, 14, 15A, 15B, 18C, 19A, 19F, 22F, 23A, 23B, 23F, 24F, 33F and 35B, and about 4.4 μg of polysaccharide for glycoconjugate from *S. pneumoniae* serotype 6B.

In an embodiment, each dose will comprise about 0.5 μg to about 1.0 μg of polysaccharide for each glycoconjugate from *S. pneumoniae* serotypes 1, 4, 5, 6A, 7F, 8, 9V, 10A, 11A, 12F, 14, 15B, 18C, 19A, 19F, 22F, 23F and 33F, and about 1.0 μg to about 2.0 μg of polysaccharide for glycoconjugate from *S. pneumoniae* serotype 6B.

In an embodiment, each dose will comprise about 1.5 μg to about 3.0 μg of polysaccharide for each glycoconjugate from *S. pneumoniae* serotypes 1, 4, 5, 6A, 7F, 8, 9V, 10A, 11A, 12F, 14, 15B, 18C, 19A, 19F, 22F, 23F and 33F, and about 3.0 μg to about 6.0 μg of polysaccharide for glycoconjugate from *S. pneumoniae* serotype 6B.

In an embodiment, each dose will comprise about 2.0 μg to about 2.5 μg of polysaccharide for each glycoconjugate from *S. pneumoniae* serotypes 1, 4, 5, 6A, 7F, 8, 9V, 10A, 11A, 12F, 14, 15B, 18C, 19A, 19F, 22F, 23F and 33F, and about 4.0 μg to about 4.8 μg of polysaccharide for glycoconjugate from *S. pneumoniae* serotype 6B.

In an embodiment, each dose will comprise about 2.2 μg of polysaccharide from each glycoconjugate from *S. pneumoniae* serotypes 1, 4, 5, 6A, 7F, 8, 9V, 10A, 11A, 12F, 14, 15B, 18C, 19A, 19F, 22F, 23F and 33F, and about 4.4 μg of polysaccharide for glycoconjugate from *S. pneumoniae* serotype 6B.

In an embodiment, each dose will comprise about 0.5 μg, about 0.55 μg, about 0.75 μg, about 1.1 μg, about 1.2 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.6 μg, about 2.7 μg, about 2.8 μg, about 2.9 μg, or about 3.0 μg of polysaccharide for glycoconjugates from *S. pneumoniae* serotypes 2, 7C, 9N, 10B, 15A, 16F, 17F, 20, 21, 22A, 23A, 23B, 24B, 24F, 27, 29, 31, 33B, 34, 35B, 35F and/or 38.

In an embodiment, each dose will comprise about 0.5 μg, about 0.55 μg, about 0.75 μg, about 1.1 μg, about 1.2 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.6 μg, about 2.7 μg, about 2.8 μg, about 2.9 μg, or about 3.0 μg of polysaccharide for glycoconjugates from *S. pneumoniae* serotypes 2, 3, 7C, 9N, 10B, 15A, 16F, 17F, 20, 21, 22A, 23A, 23B, 24B, 24F, 27, 29, 31, 33B, 34, 35B, 35F and/or 38.

In an embodiment, each dose will comprise about 0.5 μg, about 0.55 μg, about 0.75 μg, about 1.1 μg, about 1.2 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.6 μg, about 2.7 μg, about 2.8 μg, about 2.9 μg, or about 3.0 μg of polysaccharide for glycoconjugates from *S. pneumoniae* serotypes 2, 3, 7C, 9N, 10B, 15A, 16F, 17F, 19A, 19F, 20, 21, 22A, 23A, 23B, 24B, 24F, 27, 29, 31, 33B, 34, 35B, 35F and/or 38.

In an embodiment, each dose will comprise about 0.5 μg, about 0.55 μg, about 0.75 μg, about 1.1 μg, about 1.2 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.6 μg, about 2.7 μg, about 2.8 μg, about 2.9 μg, or about 3.0 μg of polysaccharide for glycoconjugates from *S. pneumoniae* serotypes 2, 7C, 9N, 10B, 15A, 16F, 17F, 20, 21, 22A, 23A, 23B, 24B, 24F, 27, 29, 31, 33B, 34, 35B, 35F and 38.

In an embodiment, each dose will comprise about 0.5 μg, about 0.55 μg, about 0.75 μg, about 1.1 μg, about 1.2 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.6 μg, about 2.7 μg, about 2.8 μg, about 2.9 μg, or about 3.0 μg of polysaccharide for glycoconjugates from *S. pneumoniae* serotypes 2, 3, 7C, 9N, 10B, 15A, 16F, 17F, 20, 21, 22A, 23A, 23B, 24B, 24F, 27, 29, 31, 33B, 34, 35B, 35F and 38.

In an embodiment, each dose will comprise about 0.5 μg, about 0.55 μg, about 0.75 μg, about 1.1 μg, about 1.2 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.6 μg, about 2.7 μg, about 2.8 μg, about 2.9 μg, or about 3.0 μg of polysaccharide for glycoconjugates from *S. pneumoniae* serotypes 2, 3, 7C, 9N, 10B, 15A, 16F, 17F, 19A, 19F, 20, 21, 22A, 23A, 23B, 24B, 24F, 27, 29, 31, 33B, 34, 35B, 35F and 38.

In an embodiment, each dose will comprise about 0.5 μg to about 1.0 μg of polysaccharide for each glycoconjugate from *S. pneumoniae* serotypes 2, 7C, 9N, 10B, 15A, 16F, 17F, 20, 21, 22A, 23A, 23B, 24B, 24F, 27, 29, 31, 33B, 34, 35B, 35F and 38.

In an embodiment, each dose will comprise about 1.5 μg to about 3.0 μg of polysaccharide for each glycoconjugate from *S. pneumoniae* serotypes 2, 7C, 9N, 10B, 15A, 16F, 17F, 20, 21, 22A, 23A, 23B, 24B, 24F, 27, 29, 31, 33B, 34, 35B, 35F and 38.

In an embodiment, each dose will comprise about 2.0 μg to about 2.5 μg of polysaccharide for each glycoconjugate from *S. pneumoniae* serotypes 2, 7C, 9N, 10B, 15A, 16F, 17F, 20, 21, 22A, 23A, 23B, 24B, 24F, 27, 29, 31, 33B, 34, 35B, 35F and 38.

In an embodiment, each dose will comprise about 2.0 μg of polysaccharide from each glycoconjugate from *S. pneumoniae* serotypes 2, 7C, 9N, 10B, 15A, 16F, 17F, 20, 21, 22A, 23A, 23B, 24B, 24F, 27, 29, 31, 33B, 34, 35B, 35F and 38.

In an embodiment, each dose will comprise about 2.2 μg of polysaccharide from each glycoconjugate from *S. pneu-*

*moniae* serotypes 2, 7C, 9N, 10B, 15A, 16F, 17F, 20, 21, 22A, 23A, 23B, 24B, 24F, 27, 29, 31, 33B, 34, 35B, 35F and 38.

In an embodiment, each dose will comprise about 0.5 μg to about 1.0 μg of polysaccharide for each glycoconjugate from *S. pneumoniae* serotypes 2, 3, 7C, 9N, 10B, 15A, 16F, 17F, 20, 21, 22A, 23A, 23B, 24B, 24F, 27, 29, 31, 33B, 34, 35B, 35F and 38.

In an embodiment, each dose will comprise about 1.5 μg to about 3.0 μg of polysaccharide for each glycoconjugate from *S. pneumoniae* serotypes 2, 3, 7C, 9N, 10B, 15A, 16F, 17F, 20, 21, 22A, 23A, 23B, 24B, 24F, 27, 29, 31, 33B, 34, 35B, 35F and 38.

In an embodiment, each dose will comprise about 2.0 μg to about 2.5 μg of polysaccharide for each glycoconjugate from *S. pneumoniae* serotypes 2, 3, 7C, 9N, 10B, 15A, 16F, 17F, 20, 21, 22A, 23A, 23B, 24B, 24F, 27, 29, 31, 33B, 34, 35B, 35F and 38.

In an embodiment, each dose will comprise about 2.0 μg of polysaccharide from each glycoconjugate from *S. pneumoniae* serotypes 2, 3, 7C, 9N, 10B, 15A, 16F, 17F, 20, 21, 22A, 23A, 23B, 24B, 24F, 27, 29, 31, 33B, 34, 35B, 35F and 38.

In an embodiment, each dose will comprise about 2.2 μg of polysaccharide from each glycoconjugate from *S. pneumoniae* serotypes 2, 3, 7C, 9N, 10B, 15A, 16F, 17F, 20, 21, 22A, 23A, 23B, 24B, 24F, 27, 29, 31, 33B, 34, 35B, 35F and 38.

In an embodiment, each dose will comprise about 0.5 μg to about 1.0 μg of polysaccharide for each glycoconjugate from *S. pneumoniae* serotypes 2, 3, 7C, 9N, 10B, 15A, 16F, 17F, 19A, 19F, 20, 21, 22A, 23A, 23B, 24B, 24F, 27, 29, 31, 33B, 34, 35B, 35F and 38.

In an embodiment, each dose will comprise about 1.5 μg to about 3.0 μg of polysaccharide for each glycoconjugate from *S. pneumoniae* serotypes 2, 3, 7C, 9N, 10B, 15A, 16F, 17F, 19A, 19F, 20, 21, 22A, 23A, 23B, 24B, 24F, 27, 29, 31, 33B, 34, 35B, 35F and 38.

In an embodiment, each dose will comprise about 2.0 μg to about 2.5 μg of polysaccharide for each glycoconjugate from *S. pneumoniae* serotypes 2, 3, 7C, 9N, 10B, 15A, 16F, 17F, 19A, 19F, 20, 21, 22A, 23A, 23B, 24B, 24F, 27, 29, 31, 33B, 34, 35B, 35F and 38.

In an embodiment, each dose will comprise about 2.0 μg of polysaccharide from each glycoconjugate from *S. pneumoniae* serotypes 2, 3, 7C, 9N, 10B, 15A, 16F, 17F, 19A, 19F, 20, 21, 22A, 23A, 23B, 24B, 24F, 27, 29, 31, 33B, 34, 35B, 35F and 38.

In an embodiment, each dose will comprise about 2.2 μg of polysaccharide from each glycoconjugate from *S. pneumoniae* serotypes 2, 3, 7C, 9N, 10B, 15A, 16F, 17F, 19A, 19F, 20, 21, 22A, 23A, 23B, 24B, 24F, 27, 29, 31, 33B, 34, 35B, 35F and 38.

2.3 Carrier Amount

Generally, each dose will comprise 10 μg to 150 μg of carrier protein, particularly 15 μg to 100 μg of carrier protein, more particularly 25 μg to 75 μg of carrier protein, and even more particularly 40 μg to 60 μg of carrier protein. In an embodiment, said carrier protein is $CRM_{197}$. In an embodiment, said carrier protein is SCP.

In an embodiment, each dose will comprise about 10 μg, about 15 μg, about 20 μg, about 25 μg, about 26 μg, about 27 μg, about 28 μg, about 29 μg, about 30 μg, about 31 μg, about 32 μg, about 33 μg, about 34 μg, about 35 μg, about 36 μg, about 37 μg, about 38 μg, about 39 μg, about 40 μg, about 41 μg, about 42 μg, about 43 μg, about 44 μg, about 45 μg, about 46 μg, about 47 μg, about 48 μg, about 49 μg, about 50 μg, about 51 μg, about 52 μg, about 53 μg, about 54 μg, about 55 μg, about 56 μg, about 57 μg, about 58 μg, about 59 μg, about 60 μg, about 61 μg, about 62 μg, about 63 μg, about 64 μg, about 65 μg, about 66 μg, about 67 μg, about 68 μg, about 69 μg, about 70 μg, about 71 μg, about 72 μg, about 73 μg, about 74 μg or about 75 μg of carrier protein.

In an embodiment, each dose will comprise about 25 μg, about 26 μg, about 27 μg, about 28 μg, about 29 μg, about 30 μg, about 31 μg, about 32 μg, about 33 μg, about 34 μg, about 35 μg, about 36 μg, about 37 μg, about 38 μg, about 39 μg, about 40 μg, about 41 μg, about 42 μg, about 43 μg, about 44 μg, about 45 μg, about 46 μg, about 47 μg, about 48 μg, about 49 μg, about 50 μg, about 51 μg, about 52 μg, about 53 μg, about 54 μg, about 55 μg, about 56 μg, about 57 μg, about 58 μg, about 59 μg, about 60 μg, about 61 μg, about 62 μg, about 63 μg, about 64 μg, about 65 μg, about 66 μg, about 67 μg, about 68 μg, about 69 μg, about 70 μg, about 71 μg, about 72 μg, about 73 μg, about 74 μg or about 75 μg of carrier protein.

In an embodiment, each dose will comprise about 30 μg of carrier protein. In an embodiment, each dose will comprise about 31 μg of carrier protein. In an embodiment, each dose will comprise about 32 μg of carrier protein. In an embodiment, each dose will comprise about 33 μg of carrier protein. In an embodiment, each dose will comprise about 34 μg of carrier protein. In an embodiment, each dose will comprise about 45 μg of carrier protein.

In an embodiment, each dose will comprise about 40 μg of carrier protein. In an embodiment, each dose will comprise about 41 μg of carrier protein. In an embodiment, each dose will comprise about 42 μg of carrier protein. In an embodiment, each dose will comprise about 43 μg of carrier protein. In an embodiment, each dose will comprise about 44 μg of carrier protein. In an embodiment, each dose will comprise about 45 μg of carrier protein.

In an embodiment, each dose will comprise about 48 μg of carrier protein. In an embodiment, each dose will comprise about 49 μg of carrier protein. In an embodiment, each dose will comprise about 50 μg of carrier protein. In an embodiment, each dose will comprise about 51 μg of carrier protein. In an embodiment, each dose will comprise about 52 μg of carrier protein. In an embodiment, each dose will comprise about 53 μg of carrier protein.

In an embodiment, said carrier protein is $CRM_{197}$.

In an embodiment, said carrier protein is SCP.

2.4 Further Antigens

Immunogenic compositions of the invention comprise conjugated *S. pneumoniae* saccharide antigen(s) (glycoconjugate(s)). They may also further include antigen(s) from other pathogen(s), particularly from bacteria and/or viruses. Preferred further antigens are selected from: a diphtheria toxoid (D), a tetanus toxoid (T), a pertussis antigen (P), which is typically acellular (Pa), a hepatitis B virus (HBV) surface antigen (HBsAg), a hepatitis A virus (HAV) antigen, a conjugated *Haemophilus influenzae* type b capsular saccharide (Hib), inactivated poliovirus vaccine (IPV).

In an embodiment, the immunogenic compositions of the invention comprise D-T-Pa. In an embodiment, the immunogenic compositions of the invention comprise D-T-Pa-Hib, D-T-Pa-IPV or D-T-Pa-HBsAg. In an embodiment, the immunogenic compositions of the invention comprise D-T-Pa-HBsAg-IPV or D-T-Pa-HBsAg-Hib. In an embodiment, the immunogenic compositions of the invention comprise D-T-Pa-HBsAg-IPV-Hib.

Pertussis antigens: *Bordetella pertussis* causes whooping cough. Pertussis antigens in vaccines are either cellular (whole cell, in the form of inactivated *B. pertussis* cells) or acellular. Preparation of cellular pertussis antigens is well documented (e.g., it may be obtained by heat inactivation of phase I culture of *B. pertussis*). Preferably, however, the invention uses acellular antigens. Where acellular antigens are used, it is preferred to use one, two or (preferably) three of the following antigens: (1) detoxified pertussis toxin (pertussis toxoid, or PT); (2) filamentous hemagglutinin (FHA); (3) pertactin (also known as the 69 kilodalton outer membrane protein). FHA and pertactin may be treated with formaldehyde prior to use according to the invention. PT is preferably detoxified by treatment with formaldehyde and/or glutaraldehyde. Acellular pertussis antigens are preferably adsorbed onto one or more aluminum salt adjuvants. As an alternative, they may be added in an unadsorbed state. Where pertactin is added then it is preferably already adsorbed onto an aluminum hydroxide adjuvant. PT and FHA may be adsorbed onto an aluminum hydroxide adjuvant or an aluminum phosphate. Adsorption of all of PT, FHA and pertactin to aluminum hydroxide is most preferred.

Inactivated poliovirus vaccine: Poliovirus causes poliomyelitis. Rather than use oral poliovirus vaccine, preferred embodiments of the invention use IPV. Prior to administration to patients, polioviruses must be inactivated, and this can be achieved by treatment with formaldehyde. Poliomyelitis can be caused by one of three types of poliovirus. The three types are similar and cause identical symptoms, but they are antigenically different and infection by one type does not protect against infection by others. It is therefore preferred to use three poliovirus antigens in the invention: poliovirus Type 1 (e.g., Mahoney strain), poliovirus Type 2 (e.g., MEF-1 strain), and poliovirus Type 3 (e.g., Saukett strain). The viruses are preferably grown, purified and inactivated individually, and are then combined to give a bulk trivalent mixture for use with the invention.

Diphtheria toxoid: *Corynebacterium diphtheriae* causes diphtheria. Diphtheria toxin can be treated (e.g., using formalin or formaldehyde) to remove toxicity while retaining the ability to induce specific anti-toxin antibodies after injection. These diphtheria toxoids are used in diphtheria vaccines. Preferred diphtheria toxoids are those prepared by formaldehyde treatment. The diphtheria toxoid can be obtained by growing *C. diphtheriae* in growth medium, followed by formaldehyde treatment, ultrafiltration and precipitation.

The toxoided material may then be treated by a process comprising sterile filtration and/or dialysis. The diphtheria toxoid is preferably adsorbed onto an aluminum hydroxide adjuvant.

Tetanus toxoid: *Clostridium tetani* causes tetanus. Tetanus toxin can be treated to give a protective toxoid. The toxoids are used in tetanus vaccines. Preferred tetanus toxoids are those prepared by formaldehyde treatment. The tetanus toxoid can be obtained by growing *C. tetani* in growth medium, followed by formaldehyde treatment, ultrafiltration and precipitation. The material may then be treated by a process comprising sterile filtration and/or dialysis.

Hepatitis A virus antigens: Hepatitis A virus (HAV) is one of the known agents which causes viral hepatitis. A preferred HAV component is based on inactivated virus, and inactivation can be achieved by formalin treatment.

Hepatitis B virus (HBV) is one of the known agents which causes viral hepatitis. The major component of the capsid is a protein known as HBV surface antigen or, more commonly, HBsAg, which is typically a 226-amino acid polypeptide with a molecular weight of ~24 kDa. All existing hepatitis B vaccines contain HBsAg, and when this antigen is administered to a normal vaccinee it stimulates the production of anti-HBsAg antibodies which protect against HBV infection.

For vaccine manufacture, HBsAg has been made in two ways: purification of the antigen in particulate form from the plasma of chronic hepatitis B carriers or expression of the protein by recombinant DNA methods (e.g., recombinant expression in yeast cells).

Unlike native HBsAg (i.e., as in the plasma-purified product), yeast-expressed HBsAg is generally non-glycosylated, and this is the most preferred form of HBsAg for use with the invention.

Conjugated *Haemophilus influenzae* type b antigens: *Haemophilus influenzae* type b (Hib) causes bacterial meningitis. Hib vaccines are typically based on the capsular saccharide antigen, the preparation of which is well documented. The Hib saccharide can be conjugated to a carrier protein in order to enhance its immunogenicity, especially in children. Typical carrier proteins are tetanus toxoid, diphtheria toxoid, $CRM_{197}$, *H. influenzae* protein D, and an outer membrane protein complex from serogroup B meningococcus. The saccharide moiety of the conjugate may comprise full-length polyribosylribitol phosphate (PRP) as prepared from Hib bacteria, and/or fragments of full-length PRP. Hib conjugates may or may not be adsorbed to an aluminum salt adjuvant.

In an embodiment the immunogenic compositions of the invention further include a conjugated *N. meningitidis* serogroup Y capsular saccharide (MenY), and/or a conjugated *N. meningitidis* serogroup C capsular saccharide (MenC).

In an embodiment the immunogenic compositions of the invention further include a conjugated *N. meningitidis* serogroup A capsular saccharide (MenA), a conjugated *N. meningitidis* serogroup W135 capsular saccharide (MenW135), a conjugated *N. meningitidis* serogroup Y capsular saccharide (MenY), and/or a conjugated *N. meningitidis* serogroup C capsular saccharide (MenC).

In an embodiment the immunogenic compositions of the invention further include a conjugated *N. meningitidis* serogroup W135 capsular saccharide (MenW135), a conjugated *N. meningitidis* serogroup Y capsular saccharide (MenY), and/or a conjugated *N. meningitidis* serogroup C capsular saccharide (MenC).

2.5 Adjuvant(s)

In some embodiments, the immunogenic compositions disclosed herein may further comprise at least one, two or three adjuvants. In some embodiments, the immunogenic compositions disclosed herein may further comprise at least one adjuvant. In some embodiments, the immunogenic compositions disclosed herein may further comprise one adjuvant. In some embodiments, the immunogenic compositions disclosed herein may further comprise two adjuvants. The term “adjuvant” refers to a compound or mixture that enhances the immune response to an antigen. Antigens may act primarily as a delivery system, primarily as an immune modulator or have strong features of both. Suitable adjuvants include those suitable for use in mammals, including humans.

Examples of known suitable delivery-system type adjuvants that can be used in humans include, but are not limited to, alum (e.g., aluminum phosphate, aluminum sulfate or aluminum hydroxide), calcium phosphate, liposomes, oil-in-water emulsions such as MF59 (4.3% w/v squalene, 0.5% w/v polysorbate 80 (Tween 80), 0.5% w/v sorbitan trioleate (Span 85)), water-in-oil emulsions such as Montanide, and poly(D,L-lactide-co-glycolide) (PLG) microparticles or nanoparticles.

In an embodiment, the immunogenic compositions disclosed herein comprise aluminum salts (alum) as adjuvant (e.g., aluminum phosphate, aluminum sulfate or aluminum hydroxide). In a preferred embodiment, the immunogenic compositions disclosed herein comprise aluminum phosphate or aluminum hydroxide as adjuvant. In a preferred embodiment, the immunogenic compositions disclosed herein comprise aluminum phosphate as adjuvant.

Further exemplary adjuvants to enhance effectiveness of the immunogenic compositions as disclosed herein include, but are not limited to: (1) oil-in-water emulsion formulations (with or without other specific immunostimulating agents such as muramyl peptides (see below) or bacterial cell wall components), such as for example (a) SAF, containing 10% Squalene, 0.4% Tween 80, 5% pluronic-blocked polymer L121, and thr-MDP either microfluidized into a submicron emulsion or vortexed to generate a larger particle size emulsion, and (b) RIBI™ adjuvant system (RAS), (Ribi Immunochem, Hamilton, MT) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21, STIMULON™ (Cambridge Bioscience, Worcester, MA), ABISCO® (Isconova, Sweden), or ISCOMATRIX@ (Commonwealth Serum Laboratories, Australia), may be used or particles generated therefrom such as ISCOMs (immunostimulating complexes), which ISCOMS may be devoid of additional detergent (e.g., WO 00/07621); (3) Complete Freund's Adjuvant (CFA) and Incomplete Freund's Adjuvant (IFA); (4) cytokines, such as interleukins (e.g., IL-1, IL-2, IL-4, IL-5, IL-6, IL-7, IL-12 (e.g., WO 99/44636)), interferons (e.g., gamma interferon), macrophage colony stimulating factor (M-CSF), tumor necrosis factor (TNF), etc.; (5) monophosphoryl lipid A (MPL) or 3-O-deacylated MPL (3dMPL) (see, e.g., GB-2220221, EP0689454), optionally in the substantial absence of alum when used with pneumococcal saccharides (see, e.g., WO 00/56358); (6) combinations of 3dMPL with, for example, QS21 and/or oil-in-water emulsions (see, e.g., EP0835318, EP0735898, EP0761231); (7) a polyoxyethylene ether or a polyoxyethylene ester (see, e.g., WO 99/52549); (8) a polyoxyethylene sorbitan ester surfactant in combination with an octoxynol (e.g., WO 01/21207) or a polyoxyethylene alkyl ether or ester surfactant in combination with at least one additional non-ionic surfactant such as an octoxynol (e.g., WO 01/21152); (9) a saponin and an immunostimulatory oligonucleotide (e.g., a CpG oligonucleotide) (e.g., WO 00/62800); (10) an immunostimulant and a particle of metal salt (see, e.g., WO 00/23105); (11) a saponin and an oil-in-water emulsion (e.g., WO 99/11241); (12) a saponin (e.g., QS21)+3dMPL+IM2 (optionally+a sterol) (e.g., WO 98/57659); (13) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc.

In an embodiment of the present invention, the immunogenic compositions as disclosed herein comprise a CpG Oligonucleotide as adjuvant. A CpG oligonucleotide as used herein refers to an immunostimulatory CpG oligodeoxynucleotide (CpG ODN), and accordingly these terms are used interchangeably unless otherwise indicated. Immunostimulatory CpG oligodeoxynucleotides contain one or more immunostimulatory CpG motifs that are unmethylated cytosine-guanine dinucleotides, optionally within certain preferred base contexts. The methylation status of the CpG immunostimulatory motif generally refers to the cytosine residue in the dinucleotide. An immunostimulatory oligonucleotide containing at least one unmethylated CpG dinucleotide is an oligonucleotide which contains a 5' unmethylated cytosine linked by a phosphate bond to a 3' guanine, and which activates the immune system through binding to Toll-like receptor 9 (TLR-9). In another embodiment the immunostimulatory oligonucleotide may contain one or more methylated CpG dinucleotides, which will activate the immune system through TLR9 but not as strongly as if the CpG motif(s) was/were unmethylated. CpG immunostimulatory oligonucleotides may comprise one or more palindromes that in turn may encompass the CpG dinucleotide. CpG oligonucleotides have been described in a number of issued patents, published patent applications, and other publications, including U.S. Pat. Nos. 6,194,388; 6,207,646; 6,214,806; 6,218,371; 6,239,116; and 6,339,068.

In an embodiment of the present invention, the immunogenic compositions as disclosed herein comprise any of the CpG Oligonucleotide described at page 3, line 22, to page 12, line 36, of WO 2010/125480.

Different classes of CpG immunostimulatory oligonucleotides have been identified. These are referred to as A, B, C and P class, and are described in greater detail at page 3, line 22, to page 12, line 36, of WO 2010/125480. Methods of the invention embrace the use of these different classes of CpG immunostimulatory oligonucleotides.

In an embodiment of the present invention, the immunogenic compositions as disclosed herein comprise an A class CpG oligonucleotide. Preferably, the "A class" CpG oligonucleotide of the invention has the following nucleic acid sequence: 5' GGGGACGACGTCGTGGGGGGG 3' (SEQ ID NO: 1). Some non-limiting examples of A-Class oligonucleotides include: 5' G*G*G_G_A_C_G_A_C_G_T_C_G_T_G_G*G*G*G*G*G 3' (SEQ ID NO: 2); wherein refers to a phosphorothioate bond and "_" refers to a phosphodiester bond.

In an embodiment of the present invention, the immunogenic compositions as disclosed herein comprise a B class CpG Oligonucleotide. In one embodiment, the CpG oligonucleotide for use in the present invention is a B class CpG oligonucleotide represented by at least the formula:

5' $X_1X_2CGX_3X_4$ 3', wherein $X_1$, $X_2$, $X_3$, and $X_4$ are nucleotides. In one embodiment, $X_2$ is adenine, guanine, or thymine. In another embodiment, $X_3$ is cytosine, adenine, or thymine.

The B class CpG oligonucleotide sequences of the invention are those broadly described above as well as disclosed in WO 96/02555, WO 98/18810 and U.S. Pat. Nos. 6,194,388; 6,207,646; 6,214,806; 6,218,371; 6,239,116 and 6,339,068. Exemplary sequences include but are not limited to those disclosed in these latter applications and patents.

In an embodiment, the "B class" CpG oligonucleotide of the invention has the following nucleic acid sequence:

```
                                        (SEQ ID NO: 3)
5' TCGTCGTTTTTCGGTGCTTTT 3',
or

                                        (SEQ ID NO: 4)
5' TCGTCGTTTTTCGGTCGTTTT 3',
or
```

-continued (SEQ ID NO: 5)
5' TCGTCGTTTTGTCGTTTTGTCGTT 3',
or (SEQ ID NO: 6)
5' TCGTCGTTTCGTCGTTTTGTCGTT 3',
or (SEQ ID NO: 7)
5' TCGTCGTTTTGTCGTTTTTTTCGA 3'.

In any of these sequences, all of the linkages may be all phosphorothioate bonds. In another embodiment, in any of these sequences, one or more of the linkages may be phosphodiester, preferably between the "C" and the "G" of the CpG motif making a semi-soft CpG oligonucleotide. In any of these sequences, an ethyl-uridine or a halogen may substitute for the 5' T; examples of halogen substitutions include but are not limited to bromo-uridine or iodo-uridine substitutions.

Some non-limiting examples of B-Class oligonucleotides include:

(SEQ ID NO: 8)
5' T*C*G*T*C*G*T*T*T*T*C*G*
G*T*G*C*T*T*T*T 3',
or (SEQ ID NO: 9)
5' T*C*G*T*C*G*T*T*T*T*C*G*
G*T*C*G*T*T*T*T 3',
or (SEQ ID NO: 10)
5' T*C*G*T*C*G*T*T*T*T*G*T*C*
G*T*T*T*T*G*T*C*G*T*T 3',
or (SEQ ID NO: 11)
5' T*C*G*T*C*G*T*T*T*C*G*T*C*
G*T*T*T*T*G*T*C*G*T*T 3',
or (SEQ ID NO: 12)
5' T*C*G*T*C*G*T*T*T*T*G*T*C*
G*T*T*T*T*T*T*T*C*G*A 3'.

wherein "*" refers to a phosphorothioate bond.

In an embodiment of the present invention, the immunogenic compositions as disclosed herein comprise a C class CpG Oligonucleotide. In an embodiment, the "C class" CpG oligonucleotides of the invention have the following nucleic acid sequence:

(SEQ ID NO: 13)
5' TCGCGTCGTTCGGCGCGCGCCG 3',
or (SEQ ID NO: 14)
5' TCGTCGACGTTCGGCGCGCGCCG 3',
or (SEQ ID NO: 15)
5' TCGGACGTTCGGCGCGCGCCG 3',
or (SEQ ID NO: 16)
5' TCGGACGTTCGGCGCGCCG 3',
or (SEQ ID NO: 17)
5' TCGCGTCGTTCGGCGCGCCG 3',
or (SEQ ID NO: 18)
5' TCGACGTTCGGCGCGCGCCG 3',
or (SEQ ID NO: 19)
5' TCGACGTTCGGCGCGCCG 3',
or (SEQ ID NO: 20)
5' TCGCGTCGTTCGGCGCCG 3',
or (SEQ ID NO: 21)
5' TCGCGACGTTCGGCGCGCGCCG 3',
or (SEQ ID NO: 22)
5' TCGTCGTTTTCGGCGCGCGCCG 3',
or (SEQ ID NO: 23)
5' TCGTCGTTTTCGGCGGCCGCCG 3',
or (SEQ ID NO: 24)
5' TCGTCGTTTTACGGCGCCGTGCCG 3',
or (SEQ ID NO: 25)
5' TCGTCGTTTTCGGCGCGCGCCGT 3'.

In any of these sequences, all of the linkages may be all phosphorothioate bonds. In another embodiment, in any of these sequences, one or more of the linkages may be phosphodiester, preferably between the "C" and the "G" of the CpG motif making a semi-soft CpG oligonucleotide.

Some non-limiting examples of C-Class oligonucleotides include:

(SEQ ID NO: 26)
5' T*C_G*C_G*T*C_G*T*T*C_G*G*
C*G*C_G*C*G*C*C*G 3',
or (SEQ ID NO: 27)
5' T*C_G*T*C_G*A*C_G*T*T*
C_G*G*C*G*C_G*C*G*C*C*G 3',
or (SEQ ID NO: 28)
5' T*C_G*G*A*C_G*T*T*C_G*
G*C*G*C_G*C*G*C*C*G 3',
or (SEQ ID NO: 29)
5' T*C_G*G*A*C_G*T*T*C_G*
G*C*G*C*G*C*C*G 3',
or (SEQ ID NO: 30)
5' T*C_G*C_G*T*C_G*T*T*C_G*
G*C*G*C*G*C*C*G 3',
or (SEQ ID NO: 31)
5' T*C_G*A*C_G*T*T*C_G*G*C*
G*C_G*C*G*C*C*G 3',

-continued or (SEQ ID NO: 32)
5' T*C_G*A*C_G*T*T*C_G*G*C*
G*C*G*C*C*G 3', or (SEQ ID NO: 33)
5' T*C_G*C_G*T*C_G*T*T*C_G*
G*C*G*C*C*G 3', or (SEQ ID NO: 34)
5' T*C_G*C_G*A*C_G*T*T*C_G*
G*C*G*C_G*C*G*C*C*G 3', or (SEQ ID NO: 35)
5' T*C*G*T*C*G*T*T*T*T*C*G*
G*C*G*C*G*C*G*C*C*G 3', or (SEQ ID NO: 36)
5' T*C*G*T*C*G*T*T*T*T*C*G*
G*C*G*G*C*C*G*C*C*G 3', or (SEQ ID NO: 37)
5' T*C*G*T*C_G*T*T*T*T*A*C_G*
G*C*G*C*C_G*T*G*C*C*G 3', or (SEQ ID NO: 38)
5' T*C_G*T*C*G*T*T*T*T*C*G*G*
C*G*C*G*C*G*C*C*G*T 3' wherein "*" refers to a phosphorothioate bond and "_" refers to a phosphodiester bond.

In any of these sequences, an ethyl-uridine or a halogen may substitute for the 5' T, examples of halogen substitutions include but are not limited to bromo-uridine or iodo-uridine substitutions.

In an embodiment of the present invention, the immunogenic compositions as disclosed herein comprise a P class CpG Oligonucleotide. In an embodiment, the CpG oligonucleotide for use in the present invention is a P class CpG oligonucleotide containing a 5' TLR activation domain and at least two palindromic regions, one palindromic region being a 5' palindromic region of at least 6 nucleotides in length and connected to a 3' palindromic region of at least 8 nucleotides in length either directly or through a spacer, wherein the oligonucleotide includes at least one YpR dinucleotide. In an embodiment, said oligonucleotide is not T*C_G*T*C_G*A*C_G*T*T*C_G*G*C*G*C_G*C*G*C*C*G (SEQ ID NO: 27). In one embodiment the P class CpG oligonucleotide includes at least one unmethylated CpG dinucleotide. In another embodiment the TLR activation domain is TCG, TTCG, TTTCG, TYpR, TTYpR, TTTYpR, UCG, UUCG, UUUCG, TTT, or TTTT. In yet another embodiment the TLR activation domain is within the 5' palindromic region. In another embodiment the TLR activation domain is immediately 5' to the 5' palindromic region.

In an embodiment, the "P class" CpG oligonucleotides of the invention have the following nucleic acid sequence: 5' TCGTCGACGATCGGCGCGCGCCG 3' (SEQ ID NO: 39).

In said sequences, all of the linkages may be all phosphorothioate bonds. In another embodiment, one or more of the linkages may be phosphodiester, preferably between the "C" and the "G" of the CpG motif making a semi-soft CpG oligonucleotide. In any of these sequences, an ethyl-uridine or a halogen may substitute for the 5' T; examples of halogen substitutions include but are not limited to bromo-uridine or iodo-uridine substitutions.

A non-limiting example of P-Class oligonucleotides include:

(SEQ ID NO: 40)
5' T*C_G*T*C_G*A*C_G*A*T*C_G*
G*C*G*C_G*C*G*C*C*G 3' wherein "*" refers to a phosphorothioate bond and "_" refers to a phosphodiester bond.

In one embodiment the oligonucleotide includes at least one phosphorothioate linkage.

In another embodiment all internucleotide linkages of the oligonucleotide are phosphorothioate linkages. In another embodiment the oligonucleotide includes at least one phosphodiester-like linkage. In another embodiment the phosphodiester-like linkage is a phosphodiester linkage. In another embodiment a lipophilic group is conjugated to the oligonucleotide. In one embodiment the lipophilic group is cholesterol.

In an embodiment, all the internucleotide linkages of the CpG oligonucleotides disclosed herein are phosphodiester bonds ("soft" oligonucleotides, as described in WO 2007/026190). In another embodiment, CpG oligonucleotides of the invention are rendered resistant to degradation (e.g., are stabilized). A "stabilized oligonucleotide" refers to an oligonucleotide that is relatively resistant to in vivo degradation (e.g., via an exo- or endo-nuclease). Nucleic acid stabilization can be accomplished via backbone modifications. Oligonucleotides having phosphorothioate linkages provide maximal activity and protect the oligonucleotide from degradation by intracellular exo- and endo-nucleases.

The immunostimulatory oligonucleotides may have a chimeric backbone, which have combinations of phosphodiester and phosphorothioate linkages. For purposes of the instant invention, a chimeric backbone refers to a partially stabilized backbone, wherein at least one internucleotide linkage is phosphodiester or phosphodiester-like, and wherein at least one other internucleotide linkage is a stabilized internucleotide linkage, wherein the at least one phosphodiester or phosphodiester-like linkage and the at least one stabilized linkage are different. When the phosphodiester linkage is preferentially located within the CpG motif such molecules are called "semi-soft" as described in WO 2007/026190.

Other modified oligonucleotides include combinations of phosphodiester, phosphorothioate, methylphosphonate, methylphosphorothioate, phosphorodithioate, and/or p-ethoxy linkages.

Mixed backbone modified ODN may be synthesized as described in WO 2007/026190.

The size of the CpG oligonucleotide (i.e., the number of nucleotide residues along the length of the oligonucleotide) also may contribute to the stimulatory activity of the oligonucleotide. For facilitating uptake into cells, CpG oligonucleotide of the invention preferably have a minimum length of 6 nucleotide residues. Oligonucleotides of any size greater than 6 nucleotides (even many kb long) are capable of inducing an immune response if sufficient immunostimulatory motifs are present, because larger oligonucleotides are degraded inside cells. In certain embodiments, the CpG oligonucleotides are 6 to 100 nucleotides long, preferentially 8 to 30 nucleotides long. In important embodiments, nucleic acids and oligonucleotides of the invention are not plasmids or expression vectors.

In an embodiment, the CpG oligonucleotide disclosed herein comprise substitutions or modifications, such as in the bases and/or sugars as described at paragraphs 134 to 147 of WO 2007/026190.

In an embodiment, the CpG oligonucleotide of the present invention is chemically modified. Examples of chemical modifications are known to the skilled person and are described, for example in Uhlmann et al. (1990) Chem. Rev. 90:543; S. Agrawal, Ed., Humana Press, Totowa, USA 1993; Crooke et al. (1996) Annu. Rev. Pharmacol. Toxicol. 36:107-129; and Hunziker et al. (1995) Mod. Synth. Methods 7:331-417. An oligonucleotide according to the invention may have one or more modifications, wherein each modification is located at a particular phosphodiester internucleoside bridge and/or at a particular R-D-ribose unit and/or at a particular natural nucleoside base position in comparison to an oligonucleotide of the same sequence which is composed of natural DNA or RNA.

In some embodiments of the invention, CpG-containing nucleic acids might be simply mixed with immunogenic carriers according to methods known to those skilled in the art (see, e.g., WO 03/024480).

In a particular embodiment of the present invention, any of the immunogenic compositions disclosed herein comprise from 2 μg to 100 mg of CpG oligonucleotide. In a particular embodiment of the present invention, the immunogenic composition of the invention comprises 0.1 mg to 50 mg of CpG oligonucleotide, preferably from 0.2 mg to 10 mg CpG oligonucleotide, more preferably from 0.3 mg to 5 mg CpG oligonucleotide. In a particular embodiment of the present invention, the immunogenic composition of the invention comprises from 0.3 mg to 5 mg CpG oligonucleotide. Even preferably, the immunogenic composition of the invention may comprise from 0.5 to 2 mg CpG oligonucleotide. Most preferably, the immunogenic composition of the invention may comprise from 0.75 to 1.5 mg CpG oligonucleotide. In a preferred embodiment, any of the immunogenic composition disclosed herein may comprise about 1 mg CpG oligonucleotide.

3 FORMULATION

The immunogenic compositions of the invention may be formulated in liquid form (i.e., solutions or suspensions) or in a lyophilized form. In an embodiment, the immunogenic composition of the invention is formulated in a liquid form. In an embodiment, the immunogenic composition of the invention is formulated in a lyophilized form. Liquid formulations may advantageously be administered directly from their packaged form and are thus ideal for injection without the need for reconstitution in aqueous medium as otherwise required for lyophilized compositions of the invention.

Formulation of the immunogenic composition of the present disclosure can be accomplished using art-recognized methods. For instance, the individual polysaccharides and/or conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

The present disclosure provides an immunogenic composition comprising any of combination of glycoconjugates disclosed herein and a pharmaceutically acceptable excipient, carrier, or diluent.

In an embodiment, the immunogenic composition of the disclosure is in liquid form, preferably in aqueous liquid form.

Immunogenic compositions of the disclosure may comprise one or more of a buffer, a salt, a divalent cation, a non-ionic detergent, a cryoprotectant such as a sugar, and an anti-oxidant such as a free radical scavenger or chelating agent, or any multiple combinations thereof.

In an embodiment, the immunogenic compositions of the disclosure comprise a buffer. In an embodiment, said buffer has a pKa of about 3.5 to about 7.5. In some embodiments, the buffer is phosphate, succinate, histidine or citrate. In some embodiments, the buffer is succinate. In some embodiments, the buffer is histidine. In certain embodiments, the buffer is succinate at a final concentration of 1 mM to 10 mM. In one particular embodiment, the final concentration of the succinate buffer is about 5 mM.

In an embodiment, the immunogenic compositions of the disclosure comprise a salt. In some embodiments, the salt is selected from the groups consisting of magnesium chloride, potassium chloride, sodium chloride and a combination thereof. In one particular embodiment, the salt is sodium chloride. In one particular embodiment, the immunogenic compositions of the invention comprise sodium chloride at 150 mM.

In an embodiment, the immunogenic compositions of the disclosure comprise a surfactant. In an embodiment, the surfactant is selected from the group consisting of polysorbate 20 (TWEEN™20), polysorbate 40 (TWEEN™40), polysorbate 60 (TWEEN™60), polysorbate 65 (TWEEN™65), polysorbate 80 (TWEEN™80), polysorbate 85 (TWEEN™85), TRITON™ N-101, TRITON™ X-100, oxtoxynol 40, nonoxynol-9, triethanolamine, triethanolamine polypeptide oleate, polyoxyethylene-660 hydroxystearate (PEG-15, Solutol H 15), polyoxyethylene-35-ricinoleate (CREMOPHOR® EL), soy lecithin and a poloxamer. In one particular embodiment, the surfactant is polysorbate 80. In some said embodiment, the final concentration of polysorbate 80 in the formulation is at least 0.0001% to 10% polysorbate 80 weight to weight (w/w). In some said embodiments, the final concentration of polysorbate 80 in the formulation is at least 0.001% to 1% polysorbate 80 weight to weight (w/w). In some said embodiments, the final concentration of polysorbate 80 in the formulation is at least 0.01% to 1% polysorbate 80 weight to weight (w/w). In other embodiments, the final concentration of polysorbate 80 in the formulation is 0.01%, 0.02%, 0.03%, 0.04%, 0.05%, 0.06%, 0.07%, 0.08%, 0.09% or 0.1% polysorbate 80 (w/w). In another embodiment, the final concentration of the polysorbate 80 in the formulation is 0.02% polysorbate 80 (w/w). In another embodiment, the final concentration of the polysorbate 80 in the formulation is 0.01% polysorbate 80 (w/w). In another embodiment, the final concentration of the polysorbate 80 in the formulation is 0.03% polysorbate 80 (w/w). In another embodiment, the final concentration of the polysorbate 80 in the formulation is 0.04% polysorbate 80 (w/w). In another embodiment, the final concentration of the polysorbate 80 in the formulation is 0.05% polysorbate 80 (w/w). In another embodiment, the final concentration of the polysorbate 80 in the formulation is 1% polysorbate 80 (w/w). In one particular embodiment, the surfactant is polysorbate 20. In some said embodiment, the final concentration of polysorbate 20 in the formulation is at least 0.0001% to 10% polysorbate 20 weight to weight (w/w). In some said embodiments, the final concentration of polysorbate 20 in the formulation is at least 0.001% to 1% polysorbate 20 weight to weight (w/w). In some said embodiments, the final concentration of polysorbate 20 in the formulation is at least 0.01% to 1% polysorbate 20 weight to weight (w/w). In other embodiments, the final concentration of polysorbate 20 in the formulation is 0.01%, 0.02%, 0.03%, 0.04%, 0.05%, 0.06%, 0.07%, 0.08%, 0.09% or 0.1% polysorbate 20 (w/w). In another embodiment, the final concentration of the polysorbate 20 in the formulation is 0.02% polysorbate 20 (w/w). In another embodiment, the final concentration of the polysorbate 20 in the formulation is 0.01% polysorbate 20 (w/w). In another embodiment, the final concentration of the polysorbate 20 in the formulation is 0.03% polysorbate 20 (w/w). In another embodiment, the final concentration of the polysorbate 20 in the formulation is 0.04% polysorbate 80 (w/w). In another embodiment, the final concentration of the polysorbate 20 in the formulation is 0.05% polysorbate 20 (w/w). In another embodiment, the final concentration of the polysorbate 20 in the formulation is 1% polysorbate 20 (w/w).

In one particular embodiment, the surfactant is polysorbate 40. In some said embodiment, the final concentration of polysorbate 40 in the formulation is at least 0.0001% to 10% polysorbate 40 weight to weight (w/w). In some said embodiments, the final concentration of polysorbate 40 in the formulation is at least 0.001% to 1% polysorbate 40 weight to weight (w/w). In some said embodiments, the final concentration of polysorbate 40 in the formulation is at least 0.01% to 1% polysorbate 40 weight to weight (w/w). In other embodiments, the final concentration of polysorbate 40 in the formulation is 0.01%, 0.02%, 0.03%, 0.04%, 0.05%, 0.06%, 0.07%, 0.08%, 0.09% or 0.1% polysorbate 40 (w/w). In another embodiment, the final concentration of the polysorbate 40 in the formulation is 1% polysorbate 40 (w/w).

In one particular embodiment, the surfactant is polysorbate 60. In some said embodiment, the final concentration of polysorbate 60 in the formulation is at least 0.0001% to 10% polysorbate 60 weight to weight (w/w). In some said embodiments, the final concentration of polysorbate 60 in the formulation is at least 0.001% to 1% polysorbate 60 weight to weight (w/w). In some said embodiments, the final concentration of polysorbate 60 in the formulation is at least 0.01% to 1% polysorbate 60 weight to weight (w/w). In other embodiments, the final concentration of polysorbate 60 in the formulation is 0.01%, 0.02%, 0.03%, 0.04%, 0.05%, 0.06%, 0.07%, 0.08%, 0.09% or 0.1% polysorbate 60 (w/w). In another embodiment, the final concentration of the polysorbate 60 in the formulation is 1% polysorbate 60 (w/w).

In one particular embodiment, the surfactant is polysorbate 65. In some said embodiment, the final concentration of polysorbate 65 in the formulation is at least 0.0001% to 10% polysorbate 65 weight to weight (w/w). In some said embodiments, the final concentration of polysorbate 65 in the formulation is at least 0.001% to 1% polysorbate 65 weight to weight (w/w). In some said embodiments, the final concentration of polysorbate 65 in the formulation is at least 0.01% to 1% polysorbate 65 weight to weight (w/w). In other embodiments, the final concentration of polysorbate 65 in the formulation is 0.01%, 0.02%, 0.03%, 0.04%, 0.05%, 0.06%, 0.07%, 0.08%, 0.09% or 0.1% polysorbate 65 (w/w). In another embodiment, the final concentration of the polysorbate 65 in the formulation is 1% polysorbate 65 (w/w).

In one particular embodiment, the surfactant is polysorbate 85. In some said embodiment, the final concentration of polysorbate 85 in the formulation is at least 0.0001% to 10% polysorbate 85 weight to weight (w/w). In some said embodiments, the final concentration of polysorbate 85 in the formulation is at least 0.001% to 1% polysorbate 85 weight to weight (w/w). In some said embodiments, the final concentration of polysorbate 85 in the formulation is at least 0.01% to 1% polysorbate 85 weight to weight (w/w). In other embodiments, the final concentration of polysorbate 85 in the formulation is 0.01%, 0.02%, 0.03%, 0.04%, 0.05%, 0.06%, 0.07%, 0.08%, 0.09% or 0.1% polysorbate 85 (w/w). In another embodiment, the final concentration of the polysorbate 85 in the formulation is 1% polysorbate 85 (w/w).

In certain embodiments, the immunogenic composition of the disclosure has a pH of 5.5 to 7.5, more preferably a pH of 5.6 to 7.0, even more preferably a pH of 5.8 to 6.0.

In one embodiment, the present disclosure provides a container filled with any of the immunogenic compositions disclosed herein. In one embodiment, the container is selected from the group consisting of a vial, a syringe, a flask, a fermentor, a bioreactor, a bag, a jar, an ampoule, a cartridge and a disposable pen. In certain embodiments, the container is siliconized.

In an embodiment, the container of the present disclosure is made of glass, metals (e.g., steel, stainless steel, aluminum, etc.) and/or polymers (e.g., thermoplastics, elastomers, thermoplastic-elastomers). In an embodiment, the container of the present disclosure is made of glass.

In one embodiment, the present disclosure provides a syringe filled with any of the immunogenic compositions disclosed herein. In certain embodiments, the syringe is siliconized and/or is made of glass.

A typical dose of the immunogenic composition of the invention for injection has a volume of 0.1 mL to 2 mL. In an embodiment, the immunogenic composition of the invention for injection has a volume of 0.2 mL to 1 mL, even more preferably a volume of about 0.5 mL.

4 USES OF THE GLYCOCONJUGATE AND IMMUNOGENIC COMPOSITIONS OF THE INVENTION

The glycoconjugates disclosed herein may be use as antigens. For example, they may be part of a vaccine.

Therefore, in an embodiment, the immunogenic compositions of the invention are for use as a medicament.

In an embodiment, the immunogenic compositions of the invention are for use as a vaccine.

Therefore, in an embodiment, the immunogenic compositions described herein are for use in generating an immune response in a subject. In one aspect, the subject is a mammal, such as a human, non-human primate, cat, sheep, pig, horse, bovine or dog. In one aspect, the subject is a human.

The immunogenic compositions described herein may be used in therapeutic or prophylactic methods for preventing, treating or ameliorating a bacterial infection, disease or condition in a subject. In particular, immunogenic compositions described herein may be used to prevent, treat or ameliorate a *S. pneumoniae* serotype 3 infection, disease or condition in a subject.

Thus, in one aspect, the disclosure provides a method of preventing, treating or ameliorating an infection, disease or condition associated with *S. pneumoniae* serotype 3 in a subject, comprising administering to the subject an immunologically effective amount of an immunogenic composition of the disclosure.

In some such embodiments, the infection, disease or condition is selected from the group consisting of pneumonia, sinusitis, otitis media, acute otitis media, meningitis, bacteremia, sepsis, pleural empyema, conjunctivitis, osteomyelitis, septic arthritis, endocarditis, peritonitis, pericarditis, mastoiditis, cellulitis, soft tissue infection and brain abscess.

In an embodiment, the disclosure provides a method of inducing an immune response to *S. pneumoniae* serotype 3 in a subject comprising administering to the subject an immunologically effective amount of an immunogenic composition of the invention. In one aspect, the subject is a mammal, such as a human, cat, sheep, pig, horse, bovine or dog.

In one aspect, the subject is a human.

In an embodiment, the immunogenic compositions disclosed herein are for use as a vaccine. In such embodiments the immunogenic compositions described herein may be used to prevent *S. pneumoniae* serotype 3 infection in a subject. Thus, in one aspect, the invention provides a method of preventing an infection by *S. pneumoniae* serotype 3 in a subject comprising administering to the subject an immunologically effective amount of an immunogenic composition of the disclosure. In some such embodiments, the infection is selected from the group consisting of pneumonia, sinusitis, otitis media, acute otitis media, meningitis, bacteremia, sepsis, pleural empyema, conjunctivitis, osteomyelitis, septic arthritis, endocarditis, peritonitis, pericarditis, mastoiditis, cellulitis, soft tissue infection and brain abscess. In one aspect, the subject is a mammal, such as a human, cat, sheep, pig, horse, bovine or dog. In one aspect, the subject is a human. The immunogenic composition of the present disclosure can be used to protect or treat a human susceptible to a *S. pneumoniae* serotype 3 infection, by means of administering the immunogenic composition via a systemic or mucosal route. In an embodiment, the immunogenic composition of the invention is administered by intramuscular, intraperitoneal, intradermal or subcutaneous routes. In an embodiment, the immunogenic composition of the invention is administered by intramuscular, intraperitoneal, intradermal or subcutaneous injection. In an embodiment, the immunogenic composition of the invention is administered by intramuscular or subcutaneous injection. In an embodiment, the immunogenic composition of the invention is administered by intramuscular injection. In an embodiment, the immunogenic composition of the invention is administered by subcutaneous injection.

5 SUBJECT TO BE TREATED WITH THE IMMUNOGENIC COMPOSITIONS OF THE INVENTION

As disclosed herein, the immunogenic compositions described herein may be used in various therapeutic or prophylactic methods for preventing, treating or ameliorating a bacterial infection, disease or condition in a subject.

In a preferred embodiment, said subject is a human. In a most preferred embodiment, said subject is a newborn (i.e., under three months of age), an infant (i.e., from 3 months to one year of age) or a toddler (i.e., from one year to four years of age).

In an embodiment, the immunogenic compositions disclosed herein are for use as a vaccine.

In such embodiment, the subject to be vaccinated may be less than 1 year of age. For example, the subject to be vaccinated can be about 1, about 2, about 3, about 4, about 5, about 6, about 7, about 8, about 9, about 10, about 11 or about 12 months of age. In an embodiment, the subject to be vaccinated is about 2, about 4 or about 6 months of age. In another embodiment, the subject to be vaccinated is less than 2 years of age. For example, the subject to be vaccinated can be about 12 to about 15 months of age. In some cases, as little as one dose of the immunogenic composition according to the invention is needed, but under some circumstances, a second, third or fourth dose may be given (see section 8 below).

In an embodiment of the present invention, the subject to be vaccinated is a human adult 50 years of age or older, more preferably a human adult 55 years of age or older. In an embodiment, the subject to be vaccinated is a human adult 65 years of age or older, 70 years of age or older, 75 years of age or older or 80 years of age or older.

In an embodiment the subject to be vaccinated is an immunocompromised individual, in particular a human. An immunocompromised individual is generally defined as a person who exhibits an attenuated or reduced ability to mount a normal humoral or cellular defense to challenge by infectious agents.

In an embodiment of the present invention, the immunocompromised subject to be vaccinated suffers from a disease or condition that impairs the immune system and results in an antibody response that is insufficient to protect against or treat pneumococcal disease.

In an embodiment, said disease is a primary immunodeficiency disorder. Preferably, said primary immunodeficiency disorder is selected from the group consisting of: combined T- and B-cell immunodeficiencies, antibody deficiencies, well-defined syndromes, immune dysregulation diseases, phagocyte disorders, innate immunity deficiencies, autoinflammatory disorders, and complement deficiencies. In an embodiment, said primary immunodeficiency disorder is selected from the one disclosed on page 24, line 11, to page 25, line 19, of WO 2010/125480.

In a particular embodiment of the present invention, the immunocompromised subject to be vaccinated suffers from a disease selected from the groups consisting of: HIV-infection, acquired immunodeficiency syndrome (AIDS), cancer, chronic heart or lung disorders, congestive heart failure, diabetes mellitus, chronic liver disease, alcoholism, cirrhosis, spinal fluid leaks, cardiomyopathy, chronic bronchitis, emphysema, chronic obstructive pulmonary disease (COPD), spleen dysfunction (such as sickle cell disease), lack of spleen function (asplenia), blood malignancy, leukemia, multiple myeloma, Hodgkin's disease, lymphoma, kidney failure, nephrotic syndrome and asthma.

In an embodiment of the present invention, the immunocompromised subject to be vaccinated suffers from malnutrition.

In a particular embodiment of the present invention, the immunocompromised subject to be vaccinated is taking a drug or treatment that lowers the body's resistance to infection.

In an embodiment, said drug is selected from the one disclosed on page 26, line 33, to page 26, line 4, of WO 2010/125480.

In a particular embodiment of the present invention, the immunocompromised subject to be vaccinated is a smoker.

In a particular embodiment of the present invention, the immunocompromised subject to be vaccinated has a white blood cell count (leukocyte count) below $5\times10^9$ cells per liter, or below $4\times10^9$ cells per liter, or below $3\times10^9$ cells per liter, or below $2\times10^9$ cells per liter, or below $1\times10^9$ cells per liter, or below $0.5\times10^9$ cells per liter, or below $0.3\times10^9$ cells per liter, or below $0.1\times10^9$ cells per liter.

White blood cell count (leukocyte count): The number of white blood cells (WBC) in the blood. The WBC is usually measured as part of the CBC (complete blood count). White blood cells are the infection-fighting cells in the blood and are distinct from the red (oxygen-carrying) blood cells known as erythrocytes. There are different types of white blood cells, including neutrophils (polymorphonuclear leukocytes; PMN), band cells (slightly immature neutrophils), T-type lymphocytes (T-cells), B-type lymphocytes (B-cells), monocytes, eosinophils, and basophils. All the types of white blood cells are reflected in the white blood cell count. The normal range for the white blood cell count is usually between 4,300 and 10,800 cells per cubic millimeter of blood. This can also be referred to as the leukocyte count and can be expressed in international units as $4.3\text{-}10.8\times10^9$ cells per liter.

In a particular embodiment of the present invention, the immunocompromised subject to be vaccinated suffers from neutropenia. In a particular embodiment of the present invention, the immunocompromised subject to be vaccinated has a neutrophil count below $2\times10^9$ cells per liter, or below $1\times10^9$ cells per liter, or below $0.5\times10^9$ cells per liter, or below $0.1\times10^9$ cells per liter, or below $0.05\times10^9$ cells per liter.

A low white blood cell count or "neutropenia" is a condition characterized by abnormally low levels of neutrophils in the circulating blood. Neutrophils are a specific kind of white blood cell that help to prevent and fight infections. The most common reason that cancer patients experience neutropenia is as a side effect of chemotherapy. Chemotherapy-induced neutropenia increases a patient's risk of infection and disrupts cancer treatment.

In a particular embodiment of the present invention, the immunocompromised subject to be vaccinated has a CD4+ cell count below $500/mm^3$, or CD4+ cell count below $300/mm^3$, or CD4+ cell count below $200/mm^3$, CD4+ cell count below $100/mm^3$, CD4+ cell count below $75/mm^3$, or CD4+ cell count below $50/mm^3$.

CD4 cell tests are normally reported as the number of cells in $mm^3$. Normal CD4 counts are between 500 and 1,600, and CD8 counts are between 375 and 1,100. CD4 counts drop dramatically in people with HIV.

In an embodiment of the invention, any of the immunocompromised subjects disclosed herein is a human male or a human female.

6 REGIMEN

In some cases, as little as one dose of the immunogenic composition according to the invention is needed, but under some circumstances, such as conditions of greater immune deficiency, a second, third or fourth dose may be given. Following an initial vaccination, subjects can receive one or several booster immunizations adequately spaced.

In an embodiment, the schedule of vaccination of the immunogenic composition according to the invention is a single dose. In a particular embodiment, said single dose schedule is for healthy persons being at least 2 years of age.

In an embodiment, the schedule of vaccination of the immunogenic composition according to the invention is a multiple dose schedule. In a particular embodiment, said multiple dose schedule consists of a series of 2 doses separated by an interval of about 1 month to about 2 months.

In a particular embodiment, said multiple dose schedule consists of a series of 2 doses separated by an interval of about 1 month, or a series of 2 doses separated by an interval of about 2 months.

In another embodiment, said multiple dose schedule consists of a series of 3 doses separated by an interval of about 1 month to about 2 months. In another embodiment, said multiple dose schedule consists of a series of 3 doses separated by an interval of about 1 month, or a series of 3 doses separated by an interval of about 2 months.

In another embodiment, said multiple dose schedule consists of a series of 3 doses separated by an interval of about 1 month to about 2 months followed by a fourth dose about 10 months to about 13 months after the first dose. In another embodiment, said multiple dose schedule consists of a series of 3 doses separated by an interval of about 1 month followed by a fourth dose about 10 months to about 13 months after the first dose, or a series of 3 doses separated by an interval of about 2 months followed by a fourth dose about 10 months to about 13 months after the first dose.

In an embodiment, the multiple dose schedule consists of at least one dose (e.g., 1, 2 or 3 doses) in the first year of age followed by at least one toddler dose.

In an embodiment, the multiple dose schedule consists of a series of 2 or 3 doses separated by an interval of about 1 month to about 2 months (for example 28-56 days between doses), starting at 2 months of age, and followed by a toddler dose at 12-18 months of age. In an embodiment, said multiple dose schedule consists of a series of 3 doses separated by an interval of about 1 month to about 2 months (for example 28-56 days between doses), starting at 2 months of age, and followed by a toddler dose at 12-15 months of age. In another embodiment, said multiple dose schedule consists of a series of 2 doses separated by an interval of about 2 months, starting at 2 months of age, and followed by a toddler dose at 12-18 months of age.

In an embodiment, the multiple dose schedule consists of a 4-dose series of vaccine at 2, 4, 6, and 12-15 months of age.

In an embodiment, a prime dose is given at day 0 and one or more boosts are given at intervals that range from about 2 to about 24 weeks, preferably with a dosing interval of 4-8 weeks.

In an embodiment, a prime dose is given at day 0 and a boost is given about 3 months later.

7. THE INVENTION ALSO PROVIDES THE FOLLOWING EMBODIMENTS AS DEFINED IN THE FOLLOWING NUMBERED PARAGRAPHS 1 TO 84

1. A method of making a *Streptococcus pneumoniae* serotype 3 glycoconjugate, comprising the steps of:
   (a) reacting an isolated *Streptococcus pneumoniae* serotype 3 capsular polysaccharide with a carbonic acid derivative and an azido linker in an aprotic solvent to produce an activated azido polysaccharide,
   (b) reacting a carrier protein with an agent bearing an N-Hydroxysuccinimide (NHS) moiety and an alkyne group where the NHS moiety reacts with the amino groups to form an amide linkage thereby obtaining an alkyne functionalized carrier protein,
   (c) reacting the activated azido polysaccharide of step (a) with the activated alkyne-carrier protein of step (b) by $Cu^{+1}$ mediated azide-alkyne cycloaddition reaction to form a glycoconjugate.

2. The method of paragraph 1 wherein, the isolated polysaccharide is sized before the activation step (a).
3. The method of paragraph 2 wherein, the isolated serotype 3 capsular polysaccharide is sized to a weight average molecular weight between 100 kDa and 200 kDa.
4. The method of any one of paragraphs 1-3 wherein, said carbonic acid derivative is selected from the group consisting of 1,1'-carbonyldiimidazole (CDI), 1,1'-carbonyl-di-(1,2,4-triazole) (CDT), disuccinimidyl carbonate (DSC) and N-hydroxysuccinimidyl chloroformate.
5. The method of any one of paragraphs 1-3 wherein, said carbonic acid derivative is 1,1'-carbonyldiimidazole (CDI).
6. The method of any one of paragraphs 1-3 wherein, said carbonic acid derivative is 1,1'-Carbonyl-di-(1,2,4-triazole) (CDT).
7. The method of any one of paragraphs 1-6 wherein said azido linker is a compound of formula (I), $H_2N—X—N_3$ (I)

wherein X is selected from the group consisting of $CH_2(CH_2)_n$, $(CH_2CH_2O)_mCH_2CH_2$, $NHCO(CH_2)_n$, $NHCO(CH_2CH_2O)_mCH_2CH_2$, $OCH_2(CH_2)_n$ and $O(CH_2CH_2O)_mCH_2CH_2$, where n is selected from 1 to 10 and m is selected from 1 to 4.

8. The method of any one of paragraphs 1-6 wherein said azido linker is a compound of formula (II), (II)

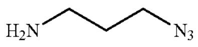

9. The method of any one of paragraphs 1-8 wherein, said agent bearing an N-Hydroxysuccinimide (NHS) moiety and an alkyne group is an agent bearing an N-Hydroxysuccinimide (NHS) moiety and a terminal alkyne.
10. The method of any one of paragraphs 1-8 wherein, said agent bearing an N-Hydroxysuccinimide (NHS) moiety and an alkyne group is an agent bearing an N-Hydroxysuccinimide (NHS) moiety and a cycloalkyne.
11. The method of any one of paragraphs 1-8 wherein, said agent bearing an N-Hydroxysuccinimide (NHS) moiety and an alkyne group is a compound of formula (III), (III)

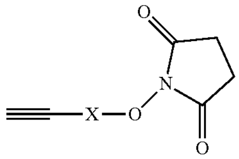

where X is selected from the group consisting of $CH_2O(CH_2)_nCH_2C{=}O$ and $CH_2O(CH_2CH_2O)_m(CH_2)_nCH_2C{=}O$, where n is selected from 0 to 10 and m is selected from 0 to 4.

12. The method of any one of paragraphs 1-8 wherein, said agent bearing an N-Hydroxysuccinimide (NHS) moiety and an alkyne group is a compound of formula (IV):

(IV)

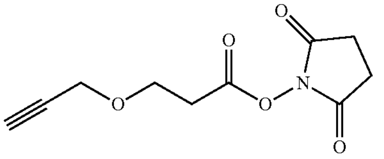

13. The method of any one of paragraphs 1-12 wherein, step a) comprises reacting the polysaccharide with a carbonic acid derivative followed by reacting the carbonic acid derivative-activated polysaccharide with an azido linker in an aprotic solvent to produce an activated azido polysaccharide.
14. The method of any one of paragraphs 1-13 wherein, at step a) the isolated polysaccharide is reacted with said carbonic acid derivative in an aprotic solvent.
15. The method of any one of paragraphs 1-13 wherein, at step a) the isolated polysaccharide is reacted with a carbonic acid derivative in a solution consisting essentially of dimethylsulphoxide (DMSO).
16. The method of any one of paragraphs 1-14 wherein, at step a) the isolated polysaccharide is reacted with CDI in an aprotic solvent comprising 0.1% to 1% (v/v) water.
17. The method of any one of paragraphs 1-14 wherein, at step a) the isolated polysaccharide is reacted with CDI in DMSO comprising 0.1% to 1% (v/v) water.
18. The method of any one of paragraphs 1-17 wherein at step a) carbonic acid derivative activation is followed by the addition of water.
19. The method of paragraph 18 wherein water is added to bring the total water content in the mixture to between about 1% to about 10% (v/v).
20. The method of any one of paragraphs 1-19 wherein step a) further comprises reacting the carbonic acid derivative-activated polysaccharide with an amount of azido linker that is between 0.01-10 molar equivalent to the amount of polysaccharide Repeat Unit of the activated polysaccharide.
21. The method of any on of paragraphs 1-20 wherein the degree of activation of the activated polysaccharide following step a) is between 0.5 to 50%.
22. The method of any one of paragraphs 1-21 wherein step b) comprises reacting the carrier protein with an amount of agent bearing an N-Hydroxysuccinimide (NHS) moiety and an alkyne group that is 0.1-10 molar equivalents to the lysines on the carrier.
23. The method of any one of paragraphs 1-22 wherein the degree of activation of the activated carrier following step b) is between 1 and 50.
24. The method of any one of paragraphs 1-23 wherein the conjugation reaction c) is carried out in aqueous buffer in the presence of copper (I) as catalyst.
25. The method of any one of paragraphs 1-23 wherein the conjugation reaction c) is carried out in aqueous buffer in the presence an oxidant and of copper (1) as catalyst.
26. The method of any one of paragraphs 1-23 wherein the conjugation reaction c) is carried out in aqueous buffer in the presence of copper (1) as catalyst and ascorbate as oxidant, wherein the reaction mixture further comprises THPTA (tris(3-hydroxypropyltriazolylmethyl) amine) and aminoguanidine.
27. The method of any one of paragraphs 1-26 wherein the initial input ratio (weight by weight) of activated azido polysaccharide to activated alkyne-carrier at step c) is between 0.1 and 3.

28. The method of any one of paragraphs 1-27 wherein following step c), the method further comprises a step of capping the unreacted azido groups remained in the conjugate with an azido group capping agent.

29. The method of paragraph 28 wherein, said azido group capping agent is a compound of formula (V), $$\equiv\!-X-OH \qquad (V)$$

wherein X is $(CH_2)_n$ wherein n is selected from 1 to 15.

30. The method of paragraph 28 wherein, said azido group capping agent is propargyl alcohol.

31. The method of any one of paragraphs 28-30 wherein the capping of the unreacted azido groups is performed with an amount of capping agent that is between 0.05 to 20 molar equivalents to the amount of polysaccharide repeat unit of the activated polysaccharide.

32. The method of any one of paragraphs 1-31 wherein following step c), the method further comprises a step of capping the unreacted alkyne groups remained in the conjugate with an alkyne group capping agent.

33. The method of paragraph 32 wherein said alkyne group capping agent is an agent bearing an azido group.

34. The method of paragraph 33 wherein said alkyne group capping agent is a compound of formula (VI), $$N_3-X-OH \qquad (VI)$$

wherein X is $(CH_2)_n$ wherein n is selected from 1 to 15.

35. The method of paragraph 32 wherein said alkyne group capping agent is 3-azido-1-propanol.

36. The method of any one of paragraphs 32-35 wherein the capping of the unreacted alkyne groups is performed with an amount of capping agent that is between 0.05 to 20 molar equivalents to the amount of polysaccharide repeat unit of the activated polysaccharide.

37. The method of any one of paragraphs 1-36 wherein the method further comprises the step of purifying the glycoconjugate after it is produced.

38. A *Streptococcus pneumoniae* serotype 3 glycoconjugate produced according to any one of the methods of paragraphs 1 to 37.

39. A *Streptococcus pneumoniae* serotype 3 glycoconjugate comprising a *Streptococcus pneumoniae* serotype 3 saccharide covalently conjugated to a carrier protein (CP) through a spacer and having the general formula (VII):

(VII)

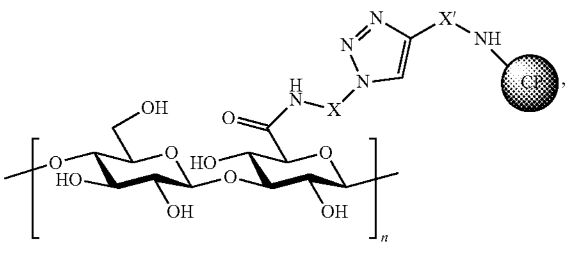

wherein X is selected from the group consisting of $CH_2(CH_2)_{n'}$, $(CH_2CH_2O)_mCH_2CH_2$, $NHCO(CH_2)_{n'}$, $NHCO(CH_2CH_2O)_mCH_2CH_2$, $OCH_2(CH_2)_{n'}$ and $O(CH_2CH_2O)_mCH_2CH_2$, where n' is selected from 1 to 10 and m is selected from 1 to 4, and wherein X is selected from the group consisting of $CH_2O(CH_2)_{n''}CH_2C{=}O$, $CH_2O(CH_2CH_2O)_{m'}(CH_2)_{n''}CH_2C{=}O$, where n" is selected from 0 to 10 and m' is selected from 0 to 4.

40. A *Streptococcus pneumoniae* serotype 3 glycoconjugate comprising a *Streptococcus pneumoniae* serotype 3 saccharide covalently conjugated to a carrier protein (CP) through a spacer and having the general formula (VII), wherein X is $CH_2(CH_2)_{n'}$, where n' is 2 and wherein X is $CH_2O(CH_2)_{n''}CH_2C{=}O$ where n" is 1.

41. The serotype 3 glycoconjugate of any one of paragraphs 38 to 40 comprising a serotype 3 capsular polysaccharide wherein the weight average molecular weight (Mw) of said polysaccharide before conjugation is between 10 kDa and 2,000 kDa.

42. The serotype 3 glycoconjugate of any one of paragraphs 38 to 40 comprising a serotype 3 capsular polysaccharide wherein the weight average molecular weight (Mw) of said polysaccharide before conjugation is between 50 kDa and 300 kDa.

43. The serotype 3 glycoconjugate of any one of paragraphs 38 to 40 comprising a serotype 3 capsular polysaccharide wherein the weight average molecular weight (Mw) of said polysaccharide before conjugation is between 75 kDa and 200 kDa.

44. The serotype 3 glycoconjugate of any one of paragraphs 38 to 40 comprising a serotype 3 capsular polysaccharide wherein the weight average molecular weight (Mw) of said polysaccharide before conjugation is between 100 kDa and 200 kDa.

45. The serotype 3 glycoconjugate of any one of paragraphs 38 to 40 comprising a serotype 3 capsular polysaccharide wherein the weight average molecular weight (Mw) of said polysaccharide before conjugation is between 125 kDa and 200 kDa.

46. The serotype 3 glycoconjugate of any one of paragraphs 38 to 40 comprising a serotype 3 capsular polysaccharide wherein the weight average molecular weight (Mw) of said polysaccharide before conjugation is about 200 kDa.

47. The serotype 3 glycoconjugate of any one of paragraphs 38 to 40 comprising a serotype 3 capsular polysaccharide wherein the weight average molecular weight (Mw) of said polysaccharide before conjugation is about 150 kDa.

48. The serotype 3 glycoconjugate of any one of paragraphs 38 to 47 having a weight average molecular weight (Mw) of between 250 kDa and 20,000 kDa.

49. The serotype 3 glycoconjugate of any one of paragraphs 38 to 47 having a weight average molecular weight (Mw) of between 500 kDa and 5,000 kDa.

50. The serotype 3 glycoconjugate of any one of paragraphs 38 to 47 having a weight average molecular weight (Mw) of between 750 kDa and 2,000 kDa.

51. The serotype 3 glycoconjugate of any one of paragraphs 38 to 47 having a weight average molecular weight (Mw) of between 1,000 kDa and 4,000 kDa.

52. The serotype 3 glycoconjugate of any one of paragraphs 38 to 51 wherein, the degree of conjugation of the serotype 3 glycoconjugate is between 2 and 15.

53. The serotype 3 glycoconjugate of any one of paragraphs 38 to 52 wherein the ratio of serotype 3 polysaccharide to carrier protein in the glycoconjugate (w/w) is between 0.5 and 3.0.

54. The serotype 3 glycoconjugate of any one of paragraphs 38 to 52 wherein the said serotype 3 glycoconjugate comprises at least one covalent linkage between the carrier protein and the polysaccharide for every 4 saccharide repeat units of the polysaccharide.

55. The serotype 3 glycoconjugate of any one of paragraphs 38 to 52 wherein the said serotype 3 glycoconjugate comprises at least one covalent linkage between the carrier protein and the polysaccharide for every 25 saccharide repeat units of the polysaccharide.

56. The serotype 3 glycoconjugate of any one of paragraphs 38 to 52 wherein the said serotype 3 glycoconjugate comprises at least one covalent linkage between the carrier protein and the polysaccharide for every 5 to 10 saccharide repeat units of the polysaccharide.

57. The serotype 3 glycoconjugate of any one of paragraphs 38 to 56 wherein said carrier protein is $CRM_{197}$.

58. The serotype 3 glycoconjugate of any one of paragraphs 38 to 56 wherein said carrier protein is SCP.

59. The serotype 3 glycoconjugate of any one of paragraphs 38 to 56 wherein said carrier protein is an enzymatically inactive SCP.

60. The serotype 3 glycoconjugate of any one of paragraphs 38 to 56 wherein said carrier protein is an enzymatically inactive SCP from GBS (SCPB).

61. The serotype 3 glycoconjugate of any one of paragraphs 38 to 56 wherein said carrier protein is a fragment of an SCPB.

62. The serotype 3 glycoconjugate of any one of paragraphs 38 to 56 wherein said carrier protein is a fragment of an SCP which comprises the protease domain, the protease-associated domain (PA domain) and the three fibronectin type III (Fn) domains but does not comprise the export signal presequence, the prosequence and the cell wall anchor domain.

63. The serotype 3 glycoconjugate of any one of paragraphs 38 to 56 wherein said carrier protein is an enzymatically inactive fragment of an SCP. In an embodiment, said enzymatically inactive fragment of SCP comprises the protease domain, the protease-associated domain (PA domain) and the three fibronectin type III (Fn) domains but does not comprise the export signal presequence, the pro-sequence and the cell wall anchor domain.

64. The serotype 3 glycoconjugate of any one of paragraphs 38 to 56 wherein said carrier protein is an enzymatically inactive fragment of SCP which comprises the protease domain, the protease-associated domain (PA domain) and the three fibronectin type Ill (Fn) domains but does not comprise the export signal presequence, the pro-sequence and the cell wall anchor domain, where said inactivation is accomplished by replacing at least one amino acid of the wild type sequence and wherein said replacement is selected from the group consisting of D130A, H193A, N295A and S512A where the numbers indicate the amino acid residue position in the peptidase according to the numbering of SEQ ID NO: 1 of WO00/34487.

65. The serotype 3 glycoconjugate of any one of paragraphs 38 to 56 wherein said carrier protein is an enzymatically inactive fragment of SCP which comprises the protease domain, the protease-associated domain (PA domain) and the three fibronectin type III (Fn) domains but does not comprise the export signal presequence, the pro-sequence and the cell wall anchor domain, where said inactivation is accomplished by replacing at least two amino acids of the wild type sequence wherein said at least two amino acids replacements are D130A and S512A where the numbers indicate the amino acid residue position in the peptidase according to the numbering of SEQ ID NO: 1 of WO00/34487.

66. The serotype 3 glycoconjugate of any one of paragraphs 38 to 56 wherein said carrier protein is an enzymatically inactive fragment of SCP consisting of a polypeptide having at least 95% identity with SEQ ID NO: 41.

67. The serotype 3 glycoconjugate of any one of paragraphs 38 to 56 wherein said carrier protein is an enzymatically inactive fragment of SCP consisting of a polypeptide having at least 95% identity with SEQ ID NO: 42.

68. The serotype 3 glycoconjugate of any one of paragraphs 38 to 56 wherein said carrier protein is an enzymatically inactive fragment of SCP which consists of SEQ ID NO: 41.

69. The serotype 3 glycoconjugate of any one of paragraphs 38 to 56 wherein said carrier protein is an enzymatically inactive fragment of SCP which consists of SEQ ID NO: 42.

70. An immunogenic composition comprising a *Streptococcus pneumoniae* serotype 3 glycoconjugate of any one of paragraphs 38 to 69.

71. The immunogenic composition of paragraph 70 comprising from 1 to 25 glycoconjugates from different serotypes of *S. pneumoniae*.

72. The immunogenic composition of paragraph 70 comprising glycoconjugates from 7, 8, 9, 10, 11, 12, 13, 14, 15, 16, 17, 18, 19, 20, 21, 22, 23, 24 or 25 different serotypes of *S. pneumoniae*.

73. The immunogenic composition of paragraph 70 which is a 15-valent pneumococcal conjugate composition.

74. The immunogenic composition of paragraph 70 which is a 20-valent pneumococcal conjugate composition.

75. The immunogenic composition of any one of paragraphs 70-74 comprising glycoconjugates from *S. pneumoniae* serotypes 4, 6B, 9V, 14, 18C, 19F and 23F.

76. The immunogenic composition of paragraph 75 comprising in addition glycoconjugates from *S. pneumoniae* serotypes 1, 5 and 7F.

77. The immunogenic composition of paragraph 76 comprising in addition glycoconjugates from *S. pneumoniae* serotypes 6A and 19A.

78. The immunogenic composition of paragraph 77 comprising in addition glycoconjugates from *S. pneumoniae* serotype 22F and 33F.

79. The immunogenic composition of paragraph 78 comprising in addition glycoconjugates from *S. pneumoniae* serotypes 8, 10A, 11A, 12F and 15B.

80. The immunogenic composition of paragraph 70 further comprising glycoconjugates from *S. pneumoniae* serotypes 1, 4, 5, 6A, 6B, 7F, 9V, 14, 18C, 19A, 19F and 23F, wherein said immunogenic composition is a 13-valent pneumococcal conjugate composition.

81. The immunogenic composition of paragraph 70 further comprising glycoconjugates from *S. pneumoniae* serotypes 1, 4, 5, 6A, 6B, 7F, 9V, 14, 18C, 19A, 19F, 22F, 23F and 33F wherein said immunogenic composition is a 15-valent pneumococcal conjugate composition.

82. The immunogenic composition of paragraph 70 further comprising glycoconjugates from *S. pneumoniae* serotypes 1, 4, 5, 6A, 6B, 7F, 8, 9V, 10A, 11A, 12F, 14, 15B, 18C, 19A, 19F, 22F, 23F and 33F, wherein said immunogenic composition is a 20-valent pneumococcal conjugate composition.

83. The immunogenic composition of paragraph 70 further comprising glycoconjugates from *S. pneumoniae* serotypes 1, 4, 5, 6A, 6B, 7F, 8, 9V, 10A, 11A, 12F, 14, 15A, 15B, 18C, 19A, 19F, 22F, 23A, 23B, 23F, 24F, 33F and 35B, wherein said immunogenic composition is a 25-valent pneumococcal conjugate composition.
84. The immunogenic composition of paragraph 70 further comprising glycoconjugates from *S. pneumoniae* serotypes 2, 7C, 9N, 10B, 15A, 16F, 17F, 19A, 19F, 20, 21, 22A, 23A, 23B, 24B, 24F, 27, 29, 31, 33B, 34, 35B, 35F and 38, wherein said immunogenic composition is a 25-valent pneumococcal conjugate composition.

As used herein, the term "about" means within a statistically meaningful range of a value, such as a stated concentration range, time frame, molecular weight, temperature or pH.

Such a range can be within an order of magnitude, typically within 20%, more typically within 10%, and even more typically within 5% or within 1% of a given value or range.

Sometimes, such a range can be within the experimental error typical of standard methods used for the measurement and/or determination of a given value or range. The allowable variation encompassed by the term "about" will depend upon the particular system under study, and can be readily appreciated by one of ordinary skill in the art.

Whenever a range is recited within this application, every number within the range is also contemplated as an embodiment of the disclosure.

The terms "comprising", "comprise" and "comprises" herein are intended by the inventors to be optionally substitutable with the terms "consisting essentially of", "consist essentially of", "consists essentially of", "consisting of", "consist of" and "consists of", respectively, in every instance.

An "immunogenic amount", an "immunologically effective amount", a "therapeutically effective amount", a "prophylactically effective amount", or "dose", each of which is used interchangeably herein, generally refers to the amount of antigen or immunogenic composition sufficient to elicit an immune response, either a cellular (T cell) or humoral (B cell or antibody) response, or both, as measured by standard assays known to one skilled in the art.

Any whole number integer within any of the ranges of the present document is contemplated as an embodiment of the disclosure.

All references or patent applications cited within this patent specification are incorporated by reference herein.

The invention is illustrated in the accompanying examples. The examples below are carried out using standard techniques, which are well known and routine to those of skill in the art, except where otherwise described in detail. The examples are illustrative, but do not limit the invention.

EXAMPLE

Example 1. Preparation of Serotype 3 Glycoconjugate Using Reductive Amination in Aqueous Buffer (RAC/Aq.)

1. Hydrolysis

The native polysaccharide was hydrolyzed to reduce the molecular weight prior to activation. A calculated volume of 2M acetic acid was added to the polysaccharide solution to achieve a final polysaccharide concentration of 2.0±0.2 g/L and a final acetic acid concentration of 0.2M. The diluted polysaccharide solution was heated to 85±5° C. The hydrolysis reaction was maintained for certain time depending on the target polysaccharide Mw. At the end of reaction, the mixture was cooled to 23±2° C.

2. Oxidation

For the oxidation reaction, 1 M magnesium chloride was added to the reaction solution to a final concentration of 0.10M. Periodic acid was then added to the polysaccharide solution to initiate the oxidation reaction (added as a 50 mg/mL solution in WFI). The required molar equivalent of periodic acid was selected based on the target Degree of Oxidation (DO). The target range for the DO was 5.0±3.0. The oxidation reaction time was 20±4 hours, at 23±2° C.

3. Purification of the Activated Polysaccharide

The activated polysaccharide was purified by tangential flow filtration against WFI. The diafiltration was performed using polyethersulfone (PES) flat sheet membranes with a molecular weight cut-off (MWCO) of 100 kDa. Once the diafiltration was complete, the activated polysaccharide was characterized, by (i) saccharide concentration by colorimetric assay; (ii) aldehyde concentration by colorimetric assay; (iii) degree of oxidation; and (iv) molecular weight by SEC-MALLS. The pH of purified saccharide was adjusted to 6.3±0.3. Protein ($CRM_{197}$, TT or SCP) was then added to a predetermined ratio. The mixture was then shell frozen and lyophilized to dry.

4. Conjugation Reaction

The lyophilized activated polysaccharide and protein were reconstituted in 0.1M sodium phosphate buffer. After the reconstitution was complete, the pH was adjusted to a final pH of 6.5±0.2 using 1 N hydrochloric acid or 1 N sodium hydroxide. To initiate the conjugation reaction, predetermined molar equivalent of sodium cyanoborohydride was added to the reaction mixture. The conjugation proceeded for a period of 40±4 hours at 30±2° C. with continuous mixing at 100±10 rpm.

5. Dilution and Capping Reaction

After the conjugation reaction time was complete, the reaction solution was cooled to 23±2° C. and diluted by a factor of 0.5-1.0 times the reaction volume with 0.9% NaCl buffer, 1 molar equivalent of sodium borohydride was then added to the mixture. The capping reaction proceeded for a period of 3-6 hours at 23±2° C. with continuous mixing at 100±10 rpm.

6. Purification of Conjugate

The diluted conjugate solution was passed through a 5 µm filter, and diafiltration was performed using 5 mM succinate/0.9% saline (pH 6.0) as the medium. After the diafiltration was completed, the conjugate retentate was filtered through a 0.45 um/0.22 µm filter.

Example 2. Preparation of Serotype 3 Glycoconjugate Using Reductive Amination in Dimethylsulfoxide (RAC/DMSO)

1. Hydrolysis and Oxidation

Polysaccharide hydrolysis, activation and diafiltration were performed in the same manner as described for above aqueous based conjugation. The required molar equivalent of sodium periodate was selected based on the target DO. The target range for the DO is 15.0±4.0. The oxidation reaction time is 20±4 hours, at 23±2° C.

2. Compounding and Lyophilization

The activated polysaccharide was compounded with sucrose to a ratio of 25-100 grams of sucrose per gram of activated polysaccharide, preferably at a ratio of 40-60 grams of sucrose per gram of activated polysaccharide. The compounded mixture was then lyophilized. Calculated amount of carrier proteins ($CRM_{197}$, TT or SCP) were shell-frozen and lyophilized separately.

3. Conjugating and Capping

Lyophilized activated polysaccharide was reconstituted in anhydrous dimethyl sulfoxide (DMSO), an equal amount of anhydrous DMSO was used to reconstitute the carrier protein.

Reconstituted activated polysaccharide was combined with reconstituted carrier protein in the reaction vessel, followed by mixing thoroughly to obtain a clear solution before initiating the conjugation with sodium cyanoborohydride. The final polysaccharide concentration in reaction solution was approximately 1 g/L. Conjugation was initiated by adding 0.5-2.0 MEq of sodium cyanoborohydride to the reaction mixture and incubating at 23±2° C. for 20-48 hrs. The conjugation reaction was terminated by adding 2 MEq of sodium borohydride (NaBH4) to cap unreacted aldehydes. This capping reaction continued at 23±2° C. for 3±1 hrs.

4. Purification

The conjugate solution was diluted 1:10 with chilled 5 mM succinate-0.9% saline (pH 6.0) in preparation for purification by tangential flow filtration using 100-300K MWCO membranes. The diafiltration was then performed using 5 mM succinate/0.9% saline (pH 6.0) as the medium. After the diafiltration was completed, the conjugate retentate was transferred through a 0.22 μm filter. The conjugate was diluted further with 5 mM succinate/0.9% saline (pH 6), to a target saccharide concentration of approximately 0.5 mg/mL. Alternatively, the conjugate was purified using 20 mM Histidine-0.9% saline (pH 6.5) by tangential flow filtration using 100-300K MWCO membranes. Final 0.22 μm filtration step was completed to obtain the immunogenic conjugate.

TABLE 1 summarizes the results from some of the conjugates obtained using both conjugations (reductive amination in DMSO or aqueous buffer)

| | RAC/ DMSO Protein: CRM | RAC/ DMSO Protein: TT | RAC/ DMSO Protein: SCP | RAC/ Aqueous Protein: CRM |
|---|---|---|---|---|
| Poly MW (kDa) | 166 | 199 | 199 | 140 |
| Degree of Oxidation (DO) | 14 | 14 | 14 | 5 |
| Saccharide/Protein Ratio | 0.9 | 0.9 | 1.0 | 1.0 |
| % Free Saccharide | <5% | <5% | <5% | 8.5% |
| Conjugate MW by SEC-MALLS, kDa | 2670 | 3962 | 4760 | 1530 |

Example 3. Effect of the Size of the Polysaccharide for Serotype 3 Glycoconjugate The opsonophagocytic activity (OPA) titers for Serotype 3-$CRM_{197}$ conjugates in mice comprising polysaccharide of different size were determined under standard conditions.

Sized Serotype 3 polysaccharides (~25, 150, or 250 kDa) conjugated to $CRM_{197}$ using the either RAC/Aqueous (see example 1) or RAC/DMSO (see example 2) conjugation to –$CRM_{197}$ was used to vaccinate animals in the presence of adjuvant (see attributes of the tested conjugates at Table 2).

TABLE 2

Attributes of Pn3 Conjugates for evaluation of effect size of the Polysaccharide

| | RAC/ Aq. High MW | RAC/ Aq. Medium MW | RAC/ Aq. Low MW | RAC/ DMSO High MW | RAC/ DMSO Medium MW | RAC/ DMSO Low MW |
|---|---|---|---|---|---|---|
| Activated Polysaccharide MW, kDa | 250 | 150 | 25 | 250 | 150 | 25 |
| Conjugate MW (kDa) | 2467 | 1278 | 1972 | 3123 | 2670 | 1790 |
| Degree of Activation | 3.9 | 10 | 7 | 14 | 14 | 13 |
| SPR Ratio | 0.9 | 0.8 | 1.1 | 1 | 0.94 | 0.9 |
| Free Saccharide, % | <5 | 9 | <5 | 4.5 | 7 | 13 |

MW: molecular weight;
SPR: Saccharide to protein ratio

Groups of twenty-five 6-8 weeks old female Swiss Webster mice were immunized (250 μL) with 0.01 μg/ml, 0.1 μg/ml, or 1 μg/ml of test conjugates via the subcutaneous route on week 0. The mice were boosted with the same dose of conjugate on week 3 and then bled at week 5. Each vaccination was formulated with 100 μg/dose of $AlPO_4$ as an adjuvant. All preclinical immunogenicity studies were powered to detect a 4 to 5-fold difference in OPA titers using 25 mice per group. Whole blood was collected from mice two weeks after the second vaccination (Week 5, PD 2) and sera used for analyses. Serotype-specific OPAs were performed on week 5 sera samples.

Opsonophagocytic activity (OPA) assays are used to measure functional antibodies in murine sera specific for *S. pneumonia* serotype 3. Test serum is set up in assay reactions that measure the ability of capsular polysaccharide specific immunoglobulin to opsonize bacteria, trigger complement deposition, thereby facilitating phagocytosis and killing of bacteria by phagocytes. The OPA titer is defined as the reciprocal dilution that results in a 50% reduction in bacterial count over control wells without test serum. The OPA titer is interpolated from the two dilutions that encompass this 50% killing cut-off.

OPA procedures were based on methods described in Hu et al. (2005) Clin Diagn Lab Immunol 12 (2):287-295 with the following modifications. Test serum was serially diluted 2.5-fold and added to microtiter assay plates. Live serotype 3 target bacterial strains were added to the wells and the plates were shaken at 25° C. for 30 minutes. Differentiated HL-60 cells (phagocytes) and baby rabbit serum (3- to 4-week old, PEL-FREEZ®, 12% final concentration) were added to the wells, and the plates were shaken at 37° C. for 45 minutes. To terminate the reaction, 80 μL of 0.9% NaCl was added to all wells, mixed, and a 10 μL aliquot were transferred to the wells of MULTISCREEN® HTS HV filter plates (MILLIPORE®) containing 200 μL of water. Liquid was filtered through the plates under vacuum, and 150 μL of HYSOY® medium was added to each well and filtered through. The filter plates were then incubated at 37° C., 5% $CO_2$ overnight and were then fixed with Destain Solution (Bio-Rad Laboratories, Inc., Hercules, CA). The plates were then stained with Coomassie Blue and destained once. Colonies were imaged and enumerated on a Cellular Technology Limited (CTL) (Shaker Heights, OH) IMMUNOSPOT® Analyzer. Raw colony counts were used to plot kill curves and calculate OPA titers.

OPA titers (geometric mean titer (GMT) with 95% confidence interval (Cl)) at five weeks at different doses are shown in Table 3. The results are presented in FIG. 3.

TABLE 3

OPA titers following vaccination with sized Serotype 3 polysaccharide conjugated to -$CRM_{197}$. Sized (~25, 150, or 250 kDa) Serotype 3 conjugated to $CRM_{197}$ using the either Rac/aqueous or RAC/DMSO was used to vaccinate animals in the presence of adjuvant. Female Swiss-Webster mice, 6-8 weeks old; Doses: 0.01; 0.1 and 1 μg/ml + $AIPO_4$; Vaccinate: 0 and 3 wk.; exsang wk. 5 Readout: OPA

| | | 0.01 | 0.1 | 1 |
|---|---|---|---|---|
| 250 kDa (RAC/Aq.) | Mean | 49 | 663 | 1909 |
| | Total # of mice | 47 | 49 | 49 |
| | # of non-responders | 19 | 1 | 0 |
| | % of non-responders | 40 | 2 | 0 |
| 150 kDa (RAC/Aq.) | Mean | 117 | 1286 | 3679 |
| | Total # of mice | 44 | 49 | 49 |
| | # of non-responders | 6 | 0 | 0 |
| | % of non-responders | 14 | 0 | 0 |
| 25 kDa (RAC/Aq.) | Mean | 158 | 1677 | 5644 |
| | Total # of mice | 25 | 25 | 25 |
| | # of non-responders | 4 | 0 | 0 |
| | % of non-responders | 16 | 0 | 0 |
| 250 kDa (RAC/DMSO) | Mean | 46 | 360 | 3271 |
| | Total # of mice | 40 | 39 | 40 |
| | # of non-responders | 16 | 3 | 0 |
| | % of non-responders | 40 | 8 | 0 |
| 150 kDa (RAC/DMSO) | Mean | 19 | 626 | 1285 |
| | Total # of mice | 47 | 40 | 47 |
| | # of non-responders | 29 | 1 | 0 |
| | % of non-responders | 62 | 3 | 0 |
| 25 kDa (RAC/DMSO) | Mean | 93 | 319 | 3560 |
| | Total # of mice | 25 | 25 | 25 |
| | # of non-responders | 6 | 3 | 0 |
| | % of non-responders | 24 | 12 | 0 |

Figure 3:
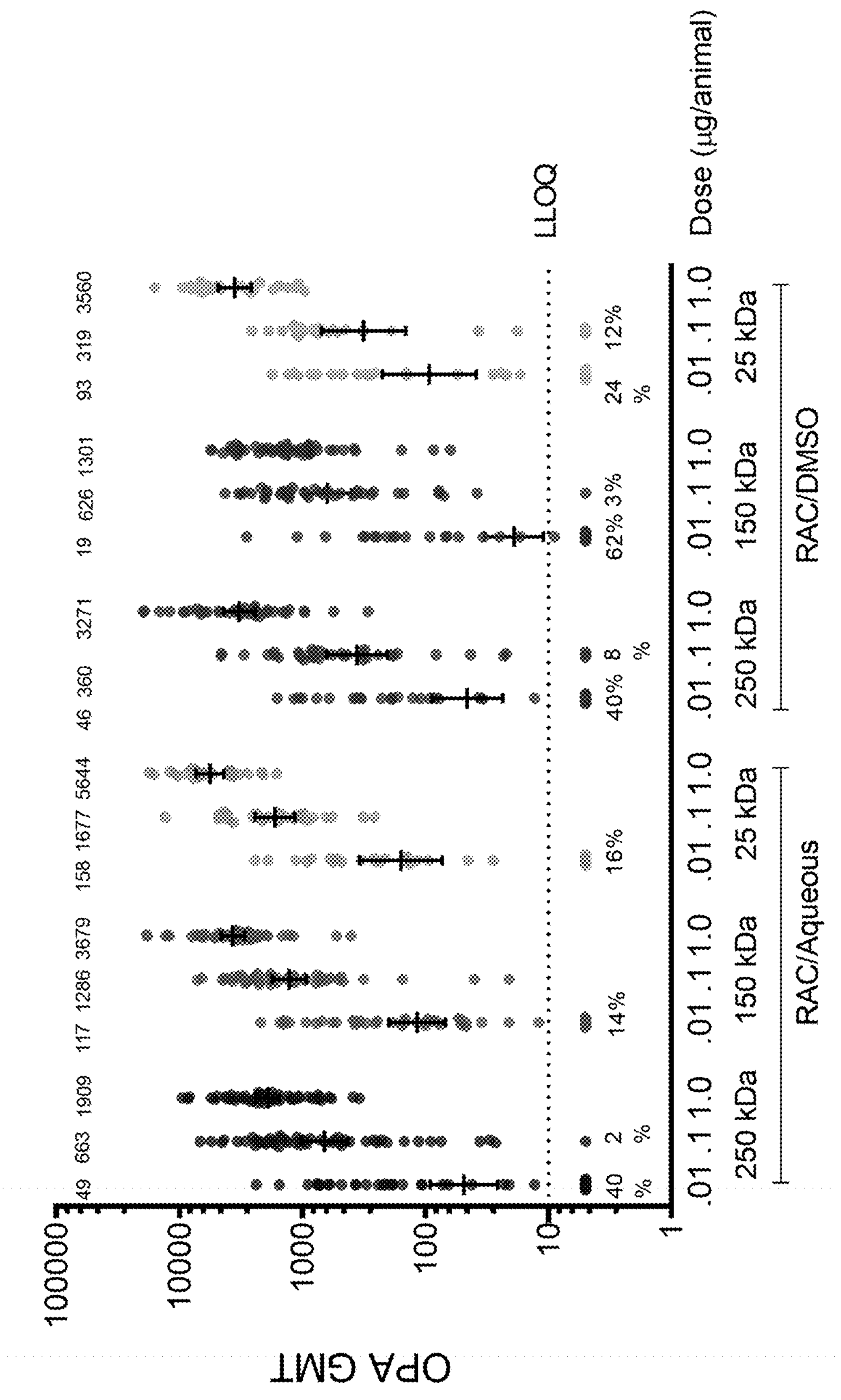
FIG. 3 shows opsonophagocytic activity (OPA) geometric mean titers (GMT) for Serotype 3-$CRM_{197}$ conjugates in mice comprising polysaccharide of different size. Sized Serotype 3 polysaccharides (~25, 150, or 250 kDa) conjugated to $CRM_{197}$ using either RAC/Aqueous or RAC/DMSO conjugation was used to vaccinate mice.

The data of Table 3 and FIG. 3 indicate that the serotype 3 conjugates elicited dose dependent OPA titers in a murine immunogenicity model. As shown in Table 3, serotype 3 conjugates with RAC/Aqueous chemistry induced higher OPA GMT at all doses as the polysaccharide size decreased. For the RAC/DMSO chemistry there were less non responders at the 0.01 μg dose with the small polysaccharide size.

Example 4. Effect of Degree of Oxidation (DO)/Degree of Activation (DoA) of the Polysaccharide for Serotype 3 Glycoconjugate The opsonophagocytic activity (OPA) titers for Serotype 3-$CRM_{197}$ conjugates in mice generated using different degree of oxidation were determined under standard conditions.

Sized Serotype 3 polysaccharides (~120-170 kDa) conjugated to $CRM_{197}$ using the either RAC/Aqueous (see example 1) or RAC/DMSO (see example 2) conjugation to –$CRM_{197}$ was used to vaccinate animals in the presence of adjuvant (see attributes of the tested conjugates at Table 4).

TABLE 4

Attributes of Pn3 Conjugates for Evaluation of Degree of Oxidation

| | RAC/ DMSO Low DO | RAC/ DMSO High DO | RAC/ Aqueous Low DO | RAC/ Aqueous High DO |
|---|---|---|---|---|
| Activated Polysaccharide MW, kDa | 156 | 166 | 140 | 123 |
| Conjugate MW (kDa) | 1580 | 2670 | 1530 | 1278 |
| Degree of Activation (DoA) | 7 | 14 | 5 | 10 |
| SPR Ratio | 1 | 0.94 | 1 | 0.8 |
| Free Saccharide, % | <5 | 7 | 8.5 | 9 |

MW: molecular weight;
SPR: Saccharide to protein ratio

Groups of twenty-five 6-8 weeks old female Swiss Webster mice were immunized (250 μL) with 0.01 μg/ml, 0.1 μg/ml, or 1 μg/ml of test conjugates via the subcutaneous route on week 0. The mice were boosted with the same dose of conjugate on week 3 and then bled at week 5. Serotype-specific OPAs were performed on week 5 sera samples.

OPA was conducted as described at Example 3. The results are presented at table 5 and FIG. 4.

TABLE 5

OPA titers following vaccination with Serotype 3 antigen with variable degree of oxidation (DO) - conjugated to -CRM. Serotype 3 conjugated to CRM was used to vaccinate animals in the presence of adjuvant. Female Swiss-Webster mice, 6-8 weeks old; Doses: 0.01; 0.1 and 1 μg/ml + $AIPO_4$; Vaccinate: 0 and 3 wk.; exsang wk. 5 Readout: OPA

| | | 0.01 | 0.1 | 1 |
|---|---|---|---|---|
| DO 7 (RAC/DMSO) | Mean | 14 | 113 | 963 |
| | Total # of mice | 19 | 17 | 25 |
| | # of non-responders | 12 | 4 | 0 |
| | % of non-responders | 63 | 24 | 0 |
| DO 14 (RAC/DMSO) | Mean | 19 | 626 | 1301 |
| | Total # of mice | 47 | 40 | 48 |
| | # of non-responders | 29 | 1 | 0 |
| | % of non-responders | 62 | 3 | 0 |
| DO 5 (RAC/Aq.) | Mean | 38 | 383 | 1478 |
| | Total # of mice | 22 | 21 | 24 |
| | # of non-responders | 10 | 1 | 0 |
| | %of non-responders | 45 | 5 | 0 |
| DO 10 (RAC/Aq.) | Mean | 117 | 1286 | 3679 |
| | Total # of mice | 44 | 49 | 49 |
| | # of non-responders | 6 | 0 | 0 |
| | % of non-responders | 14 | 0 | 0 |

Figure 4:
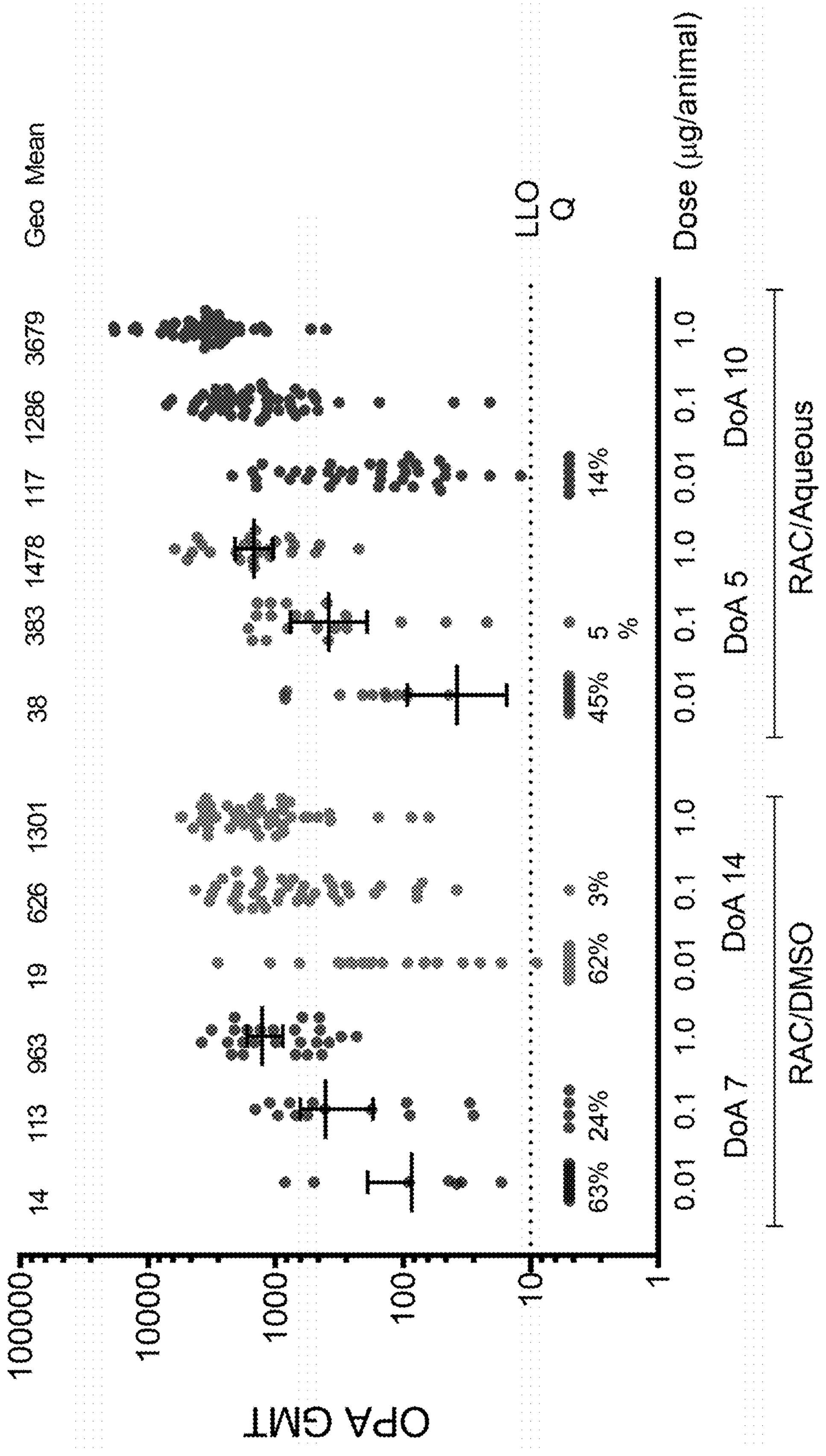
FIG. 4 shows opsonophagocytic activity (OPA) geometric mean titers (GMT) for Serotype 3-$CRM_{197}$ conjugates in mice with different Degree of Activation (DoA). Sized Serotype 3 polysaccharides conjugated to $CRM_{197}$ using the either RAC/Aqueous or RAC/DMSO conjugation were used to vaccinate mice.

The data of Table 5 and FIG. 4 indicate that the serotype 3 conjugates elicited dose dependent OPA titers in a murine immunogenicity model. As shown in Table 5, serotype 3 conjugates with RAC/Aqueous or RAC/DMSO chemistry induced higher OPA GMT at all doses with a higher DO.

Figure 2:
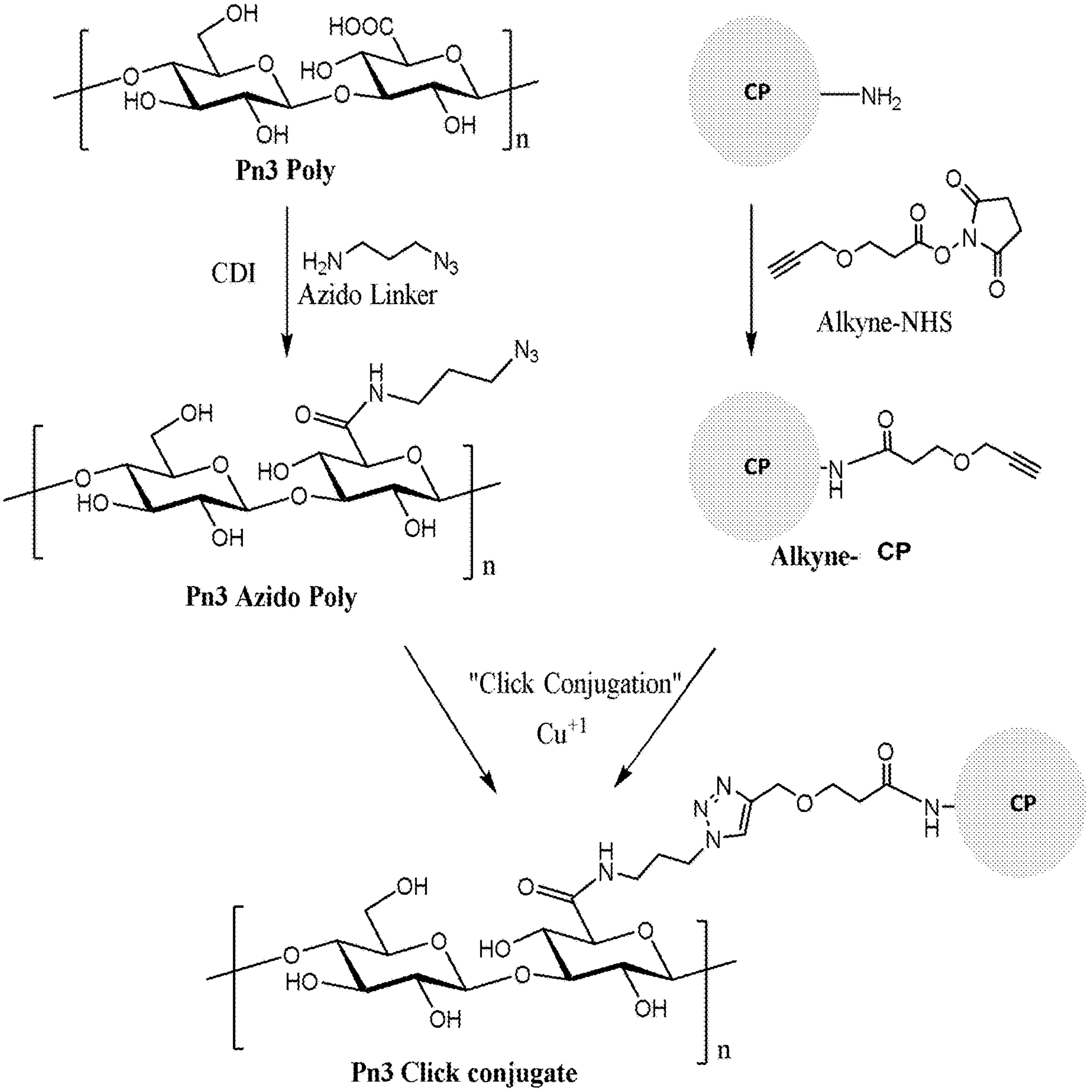

Example 5: Conjugation of Serotype 3 Capsular Polysaccharide Using Click Chemistry (See FIG. 2)

1. Activation of Serotype 3 Capsular Polysaccharide with Azido Linker

Serotype 3 capsular polysaccharide was mixed with imidazole (3×, w/w) and pH was adjusted to 3.5 with 1 M-HCl then frozen and lyophilized.

After 3 days lyophilization, the lyophilized polysaccharide is reconstituted with anhydrous DMSO (4 mg/mL). The reaction mixture was then warmed to 35° C., and CDI (0.2 MEq) was added. The reaction mixture was stirred at 35° C. for 3 hrs. After the reaction mixture was cooled to 23° C., WFI (2% v/v) was added to quench free CDI and then stirred further for 30 min at 23° C. To the reaction mixture 3-azido-propylamine (2 MEq) is added. After 20 hrs reaction at 23° C., the reaction mixture was diluted to chilled (at 5° C.) 10 mM NaH2PO4 buffer (5×, v/v). The diluted reaction mixture was then purified by UF/DF using 10K MWCO PES membrane against WFI (30×, v/v).

2. Activation of $CRM_{197}$ to Alkyne-$CRM_{197}$ with Alkyne NHS Ester

To the $CRM_{197}$ solution (1000 mg) WFI 57 mL and 0.5 M sodium phosphate buffer (pH 8.3) 50 mL were added. After cooled to 8° C., 3-Propargyloxy-propanoic acid NHS ester (POPS) (20 mg/mL in DMSO) 18 mL (2.4 MEq to lysine on $CRM_{197}$) was added to the reaction mixture dropwise maintaining the reaction temperature at 8±3° C. After the reaction mixture was stirred for 2 hrs at 8° C., purified by UF/DF using 10K MWCO PES membrane (Millipore Pellicon 2 Mini) against 100 mM sodium phosphate buffer in saline (pH 7.0) (30× diavolume). After UF/DF, sucrose 23 g (15% v/v) was added.

3. Click Conjugation: Activated Azido Poly and Alkyne CRM is Conjugated by Cu+1 Mediated Azide-Alkyne Cycloaddition Reaction, Referred as "Click Reaction The mixture of 5 mM copper sulfate ($CuSO_4$) (1 mL) and 25 mM Tris(3-hydroxypropyltriazolylmethyl)amine (THPTA) (1 mL) were added to the mixture of Serotype 3 Capsular Polysaccharide activated with azido linker (see step 1 above) and alkyne-$CRM_{197}$ (see step 2 above) (in 100 mM Sodium Phosphate Buffer (SPB) in saline, pH 7.0) at 23° C. and followed by the addition of 100 mM aminoguanidine (2 mL) and 100 mM sodium ascorbate (2 mL). After the reaction mixture was stirred for 2 hours at 23° C., the unreacted azido group was capped by propargyl alcohol (1 MEq) for 2 hours at 23° C. and after the first capping, subsequently the unreacted alkyne group was capped by 3-azido-1-propanol (2 MEq) for 2 hours at 23° C. Then, the reaction mixture was purified by UF/DF using 100K MWCO PES membrane against 10 mM EDTA+10 mM SPB in saline (pH 7.0) (30× diavolume) and then followed by 5 mM succinate in saline (pH 6.0) (30× diavolume).

Example 6. Effect of the Carrier Protein on Immunogenicity for Serotype 3 Glycoconjugates The opsonophagocytic activity (OPA) titers for Serotype 3 conjugates to -$CRM_{197}$, -SCP, or Tetanus toxoid in mice were determined under standard conditions. Reductive Amination in DMSO (RAC/DMSO) was used (see example 2).

Sized Serotype 3 polysaccharides (~160-250 kDa) conjugated to different protein carrier was used to vaccinate animals in the presence of adjuvant (see attributes of the tested conjugates at Table 6).

TABLE 6

Attributes of Pn3 Conjugates for Chemistry Evaluation (RAC/DMSO)

| | $CRM_{197}$ | TT | SCP |
|---|---|---|---|
| Activated Polysaccharide MW, kDa | 166 | 199 | 199 |
| Conjugate MW (kDa) | 2670 | 3962 | 4760 |
| Degree of Activation | 14 | 14 | 14 |

TABLE 6-continued

Attributes of Pn3 Conjugates for Chemistry Evaluation (RAC/DMSO)

| | $CRM_{197}$ | TT | SCP |
|---|---|---|---|
| SPR Ratio | 0.94 | 0.92 | 1 |
| Free Saccharide, % | 7 | <5 | <5 |

MW: molecular weight;
SPR: Saccharide to protein ratio

Groups of twenty-five 6-8 weeks old female Swiss Webster mice were immunized (250 μL) with 0.01 μg/m, 0.1 μg/m, or 1 μg/ml of test conjugates via the subcutaneous route on week 0. The mice were boosted with the same dose of conjugate on week 3 and then bled at week 5. Serotype-specific OPAs were performed on week 5 sera samples.

Figure 5:
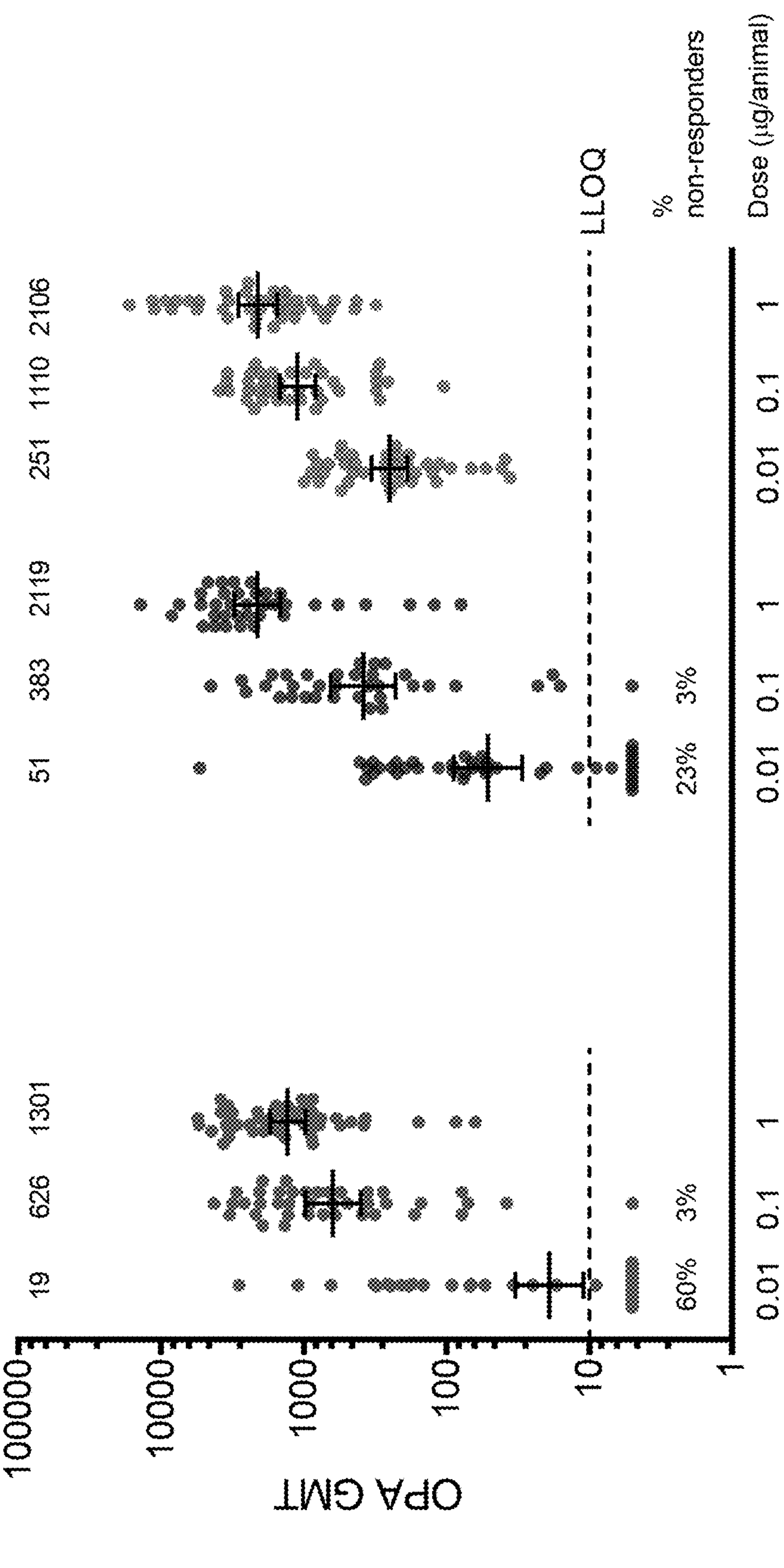
FIG. 5 shows the opsonophagocytic activity (OPA) geometric mean titers (GMT) for Serotype 3 conjugates to -$CRM_{197}$, -SCP, or Tetanus toxoid (TT) in mice. Reductive Amination in DMSO (RAC/DMSO) was used.

The results are presented at table 7 and FIG. 5.

TABLE 7

OPA titers following vaccination Serotype 3 antigen conjugate to -$CRM_{197}$, -SCP, or Tetanus toxoid. Conjugated Serotype 3 was used to vaccinate animals in the presence of adjuvant. Female Swiss-Webster mice, 6-8 weeks old; Doses: 0.01; 0.1 and 1 μg/ml + $AlPO_4$; Vaccinate: 0 and 3 wk.; exsang wk. 5 Readout: OPA

| | | 0.01 | 0.1 | 1 |
|---|---|---|---|---|
| Tetanus Toxoid (RAC/DMSO) | Mean | 51 | 383 | 2119 |
| | Total # of mice | 40 | 35 | 37 |
| | # of none responders | 9 | 1 | 0 |
| | % of none responders | 23 | 3 | 0 |
| SCP (RAC/DMSO) | Mean | 251 | 1110 | 2106 |
| | Total # of mice | 40 | 38 | 40 |
| | # of none responders | 0 | 0 | 0 |
| | % of none responders | 0 | 0 | 0 |
| CRM197 (RAC/DMSO) | Mean | 19 | 626 | 1301 |
| | Total # of mice | 47 | 40 | 48 |
| | # of none responders | 28 | 1 | 0 |
| | % of none responders | 60 | 3 | 0 |

The data of Table 7 and FIG. 5 indicate that the serotype 3 conjugates elicited dose dependent OPA titers in a murine immunogenicity model. As shown in Table 7, serotype 3 conjugated to SCP induced higher OPA GMT and all mice responded with measurable OPA titiers (0% non-responders) even at the low dose.

As depicted here, only SCP truly enhanced the percentage of mice responding to vaccination at the 0.01 ug/ml dose. TT elicited responses generally lower than $CRM_{197}$.

Example 7. Effect of Chemistry on Immunogenicity for Serotype 3 Glycoconjugates The opsonophagocytic activity (OPA) titers for Serotype 3 conjugates to -$CRM_{197}$ in mice were determined under standard conditions. Different chemistries (Reductive Amination in aqueous (RAC/Aq.) see example 1, Reductive Amination in DMSO (RAC/DMSO) see example 2, eTEC linked glycoconjugates (eTEC) see WO2014/027302 or click chemistry (Click) see example 5) were used to evaluate changes in OPA responses in mice.

Sized Serotype 3 polysaccharides (~160-1100 kDa) conjugated to $CRM_{197}$ using different chemistries were used to vaccinate animals in the presence of adjuvant (see attributes of the tested conjugates at Table 8).

TABLE 8

Attribtues of Pn3 Conjugates for evaluation of conjugation chemistry

| | RAC/Aq. | RAC/DMSO | eTEC | Click |
|---|---|---|---|---|
| Activated Polysaccharide MW, kDa | 250 | 234 | 1131 | 470 |
| Conjugate MW (kDa) | 2467 | 3123 | 2278 | 598 |
| Degree of Activation | 3.9 | 14 | 19 | 12 |
| SPR Ratio | 0.9 | 1 | 1.1 | 0.4 |
| Free Saccharide, % | <5 | 4.5 | 3 | 9 |

MW: molecular weight;
SPR: Saccharide to protein ratio

Groups of twenty-five 6-8 weeks old female Swiss Webster mice were immunized (250 μL) with 0.01 μg/ml, 0.1 μg/ml, or 1 μg/ml of test conjugates via the subcutaneous route on week 0. The mice were boosted with the same dose of conjugate on week 3 and then bled at week 5. Serotype-specific OPAs were performed on week 5 sera samples.

Figure 6:
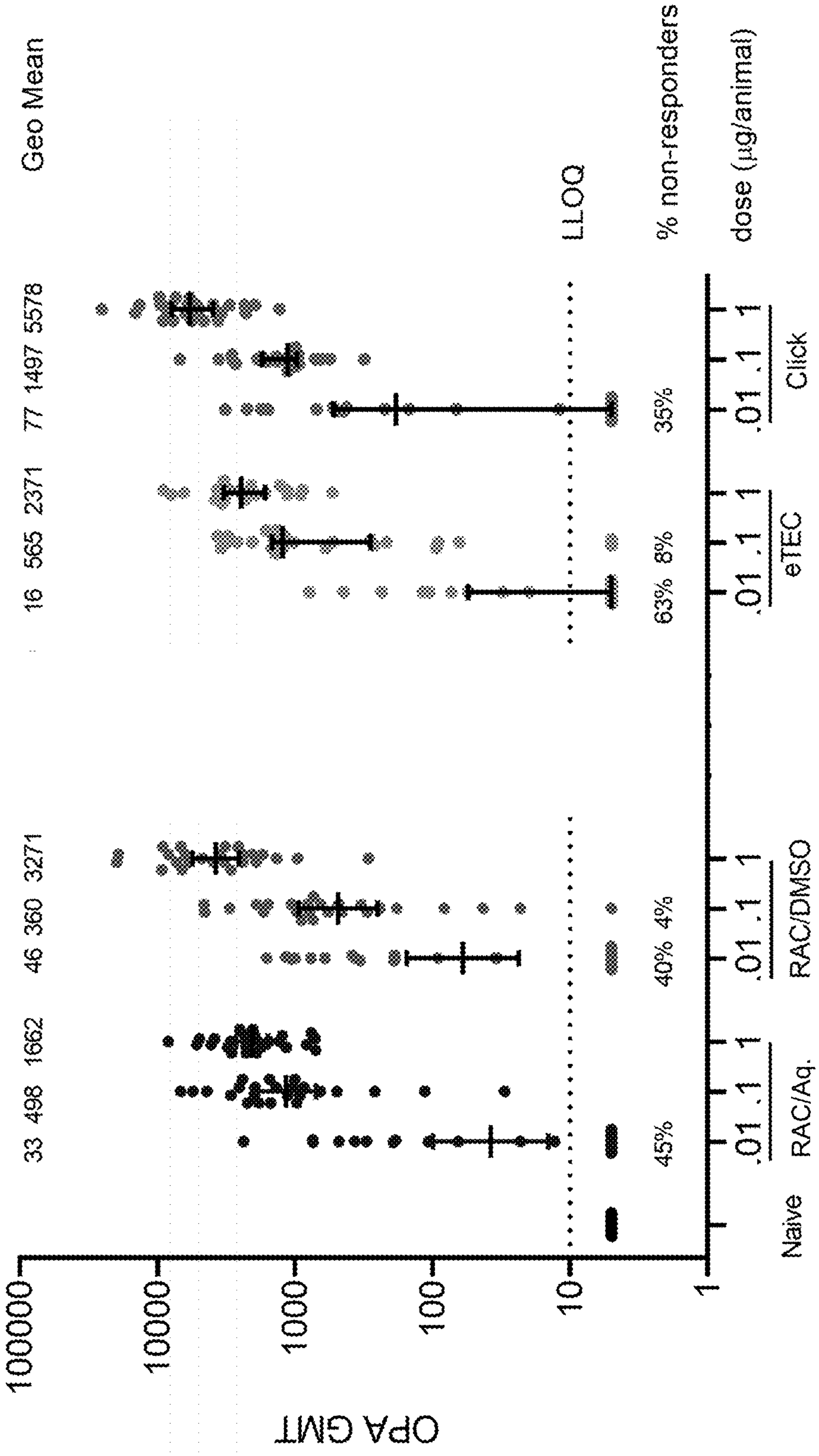
FIG. 6 shows opsonophagocytic activity (OPA) geometric mean titers (GMT) for Serotype 3-$CRM_{197}$ conjugates in mice. Different chemistries have been used (Reductive Amination in aqueous (RAC/Aq.), Reductive Amination in DMSO (RAC/DMSO), eTEC linked glycoconjugates (eTEC) or click chemistry (Click).

The results are presented at table 9 and FIG. 6.

TABLE 9

OPA titers following vaccination Serotype 3 antigen conjugate to -$CRM_{197}$, using different chemistries: RAC/Aq., RAC/DMSO, eTEC or Click. Conjugated Serotype 3 was used to vaccinate animals in the presence of adjuvant. Female Swiss-Webster mice, 6-8 weeks old; Doses: 0.01; 0.1 and 1 μg/ml + $AlPO_4$; Vaccinate: 0 and 3 wk.; exsang wk. 5 Readout: OPA

| | | 0.01 | 0.1 | 1 |
|---|---|---|---|---|
| $CRM_{197}$ (RAC/Aq.) | Mean | 38 | 1165 | 2049 |
| | Total # of mice | 22 | 24 | 25 |
| | # of non-responders | 10 | 0 | 0 |
| | % of non-responders | 45 | 0 | 0 |
| $CRM_{197}$ (RAC/DMSO) | Mean | 60 | 486 | 3766 |
| | Total # of mice | 25 | 25 | 25 |
| | # of non-responders | 10 | 1 | 0 |
| | % of non-responders | 40 | 4 | 0 |
| $CRM_{197}$ (eTEC) | Mean | 16 | 565 | 2371 |
| | Total # of mice | 24 | 25 | 24 |
| | # of non-responders | 15 | 2 | 0 |
| | % of non-responders | 63 | 8 | 0 |
| $CRM_{197}$ (Click) | Mean | 91 | 1308 | 5578 |
| | Total # of mice | 20 | 24 | 25 |
| | # of non-responders | 7 | 0 | 0 |
| | % of non-responders | 35 | 0 | 0 |

The data of Table 9 and FIG. 6 indicate that all serotype 3 conjugates elicited dose dependent OPA titers in a murine immunogenicity model. As shown in Table 9 and FIG. 6 serotype 3 using Click chemistry induced higher OPA GMT indicative of measurable OPA responses in all mice as compared with other chemistries.

Example 8: *S. pneumoniae* Serotype 3 Glycoconjugates with $CRM_{197}$ as Carrier Protein Using Click Chemistry Conjugates with different attributes have been generated using a process similar to the one of Example 5 (click chemistry) and $CRM_{197}$ as carrier (see Table 10). Pn3 Click conjugation with azido poly (Degree of Activation (DoA) 12%) and Alkyne $CRM_{197}$ (DoA 18) generated conjugates #1 and #2 resulted in low yield, low MW and low Saccharide Protein Ratio (SPR). The process has been optimized to increase conjugate yield and target conjugate SPR ~1 by lowering the DoA of azido polysaccharide and alkyne $CRM_{197}$. Conjugate #3 with SPR 1.1 and higher yield was produced with azido polysaccharide (DoA 5%) and alkyne $CRM_{197}$ (DoA 11).

Later this process was used, and yield was increased up to 76%. Most of these parameters have generated conjugates in free saccharide less than 20%.

TABLE 10

Pn3-$CRM_{197}$ Click Conjugates

| | Conjugate # | | | | |
|---|---|---|---|---|---|
| | 1 | 2 | 3 | 4 | 5 |
| Poly Mw (kDa) | 130 | 250 | 134 | 124 | 116 |
| Azido Poly DoA (%) per Poly RU | 12 | 12 | 5 | 6 | 4 |
| Azido Poly Mw (kDa) | 150 | 470 | 224 | 207 | 226 |
| Alkyne-$CRM_{197}$ Mw (kDa) | 63 | 63 | 59 | 59 | 58 |
| Alkyne-$CRM_{197}$ DoA (AAA), alkynes/$CRM_{197}$ | 18 | 18 | 11 | 9 | 10 |
| Conjugation | | | | | |
| Conjugates Yield (%) | 18 | 20 | 41 | 76 | 70 |
| Conjugate Output SPR | 0.4 | 0.4 | 1.1 | 1 | 1.1 |
| Free Saccharide (%) | 8 | 9 | 20 | 6 | 7 |
| Free Protein (%) | <1 | <1 | <1 | <1 | <1 |
| Conjugate Mw (kDa) | 702 | 598 | 1477 | 1757 | 1089 |

Example 9: *S. pneumoniae* Serotype 3 Glycoconjugates with SCP as Carrier Protein Using Click Chemistry Conjugates with different attributes have been generated using a process similar to the one of Example 5 (click chemistry) and SCP as carrier. Click conjugation with azido poly (DOA 5%) and alkyne SCP (DOA 26) generated conjugate #1 with moderate yield and SPR. However, during optimization azido poly with 4 and 13% DOA and alkyne SCP DOA 13, 26 and 37 generated conjugates #2 to #7. As shown from the table below (Table 11) alkyne SCP with DOA 26 generated conjugates #2 and #3 with high yield, SPR ~1 and higher MW. Conjugates prepared with alkyne SCP with DOA 13 and 37 generated conjugate #4 to #6 in lower yield, MW and SPR as compared to conjugates #2 and 3.

TABLE 11

Click Pn3-SCP Click Conjugates

| | Conjugate # | | | | | | |
|---|---|---|---|---|---|---|---|
| | 1 | 2 | 3 | 4 | 5 | 6 | 7 |
| Poly Mw (kDa) | 134 | 116 | 116 | 116 | 116 | 116 | 116 |
| Azido Poly DoA (%) | 5 | 4 | 13 | 4 | 13 | 4 | 13 |
| Azido Poly Mw (kDa) | 224 | 226 | 249 | 226 | 249 | 226 | 249 |
| Alkyne-SCP Mw (kDa) | 103 | 103 | 103 | 101 | 101 | 105 | 105 |
| Alkyne-SCP DOA (AAA) | 26 | 26 | 26 | 13 | 13 | 37 | 37 |
| Conjugation | | | | | | | |
| Conjugates Yield (%) | 51 | 72 | 79 | 29 | 36 | 41 | 63 |
| Conjugate | 0.7 | 0.91 | 0.9 | 0.57 | 0.52 | 0.64 | 0.72 |

TABLE 11-continued

Click Pn3-SCP Click Conjugates

| | Conjugate # | | | | | | |
|---|---|---|---|---|---|---|---|
| | 1 | 2 | 3 | 4 | 5 | 6 | 7 |
| Output SPR | | | | | | | |
| Free Saccharide (%) | 9 | <5 | <5 | <5 | <5 | <5 | <5 |
| Free Protein (%) | <1 | <1 | <1 | <1 | <1 | <1 | <1 |
| Conjugate Mw (kDa) | 1075 | 1696 | 3128 | 746 | 877 | 711 | 1778 |

Example 10: *S. pneumoniae* Serotype 3 Glycoconjugates with TT as Carrier Protein Using Click Chemistry Conjugates with different attributes have been generated using a process similar to the one of Example 5 (click chemistry) and TT as carrier.

Click conjugation with azido poly (DOA ~5%) and alkyne TT (DOA ~10, 15 and 20) generated conjugates #1-4 with higher free saccharide level. However, during process optimization azido poly with DOA ~10% and alkyne TT with DOA ~20, generated conjugate #5 with low free saccharide (see Table 12).

TABLE 12

Pn3-TT Conjugates

| | Conj# | | | | |
|---|---|---|---|---|---|
| | 1 | 2 | 3 | 4 | 5 |
| Poly Mw (kDa) | 134 | 182 | 182 | 182 | 182 |
| Azido Poly DoA (%) | ~5 | ~5 | ~5 | ~10 | ~10 |
| Azido Poly Mw (kDa) | | | | | |
| Alkyne-TT Mw (kDa) | 230 | 287 | 259 | 287 | 259 |
| Alkyne-TT DOA (AAA) | ~15 | ~10 | ~20 | ~10 | ~20 |
| Conjugation | | | | | |
| Conjugates Yield (%) | 30 | 33 | 36 | 37 | 47 |
| Conjugate SPR | 0.59 | 0.56 | 0.51 | 0.53 | 0.54 |
| Free Saccharide (%) | 36 | 35 | 25 | 18 | 12 |

TABLE 12-continued

Pn3-TT Conjugates

| | Conj# | | | | |
|---|---|---|---|---|---|
| | 1 | 2 | 3 | 4 | 5 |
| Free Protein (%) | <1 | <1 | <1 | <1 | <1 |
| Conjugate Mw (kDa) | 1119 | 1773 | 1126 | 1483 | 1186 |

Example 11: Evaluation of Immunogenicity of *S. pneumoniae* Serotype 3 Glycoconjugates Using Different Chemistry and Different Carriers Infant rhesus macaques, were vaccinated with *Streptococcus pneumoniae* serotype 3 conjugated to either of 2 carrier proteins ($CRM_{197}$ or SCP) using either RAC/Aq. or Click chemistry.

1. Infant Rhesus Monkey Studies

Age and sex matched Infant Rhesus Macaques (IRM) (3-6 months old) were randomly assigned into 3 groups (see Study design table 13).

Infants were vaccinated intramuscular (either with Click polysaccharide chemistry (Click-SCP, Click-CRM; all with poly size of about 130 kDa) or with ST3 RAC-aqueous CRM conjugates (poly size of about 250 kDa). Pre-bleeds to assess baseline ST3-specific sera titers were collected 1 week (wk=−1) before primary vaccination (DO). Two repeat vaccinations were administered at week 8 and week 16 following primary vaccination. Whole blood for sera was collected at 4- and 8-weeks post-dose 1 (PD1); 1, 4 and 8 weeks PD2 and 1, 4 16 and 36 weeks PD3.

2. Opsonophagocytosis Assay

Microcolony opsonophagocytic assay (mcOPA) was performed.

For the Pn3 mcOPA, reaction mixtures composed of target bacterial cells and heat-inactivated test serum are incubated for 30 minutes at 25° C. in an environmental shaker. Differentiated HL-60 tissue culture cells (effector cells) and baby rabbit complement are then added to the reaction mixture, and incubated for 45 minutes at 37° C. in an environmental shaker. Functional anti-*S. pneumoniae* antibody titers are determined by measuring bacterial survival in mcOPA reactions containing the test serum. The assay mixture is plated and grown overnight.

On day 2, the number of non-phagocytosed live bacteria is determined. The mcOPA antibody titer is the reciprocal of the serum dilution resulting in 50% reduction in the number of bacterial colonies when compared to the bacteria-effector cell-complement control wells that do not contain serum.

TABLE 13

| Pn3 conjugate type | Chemistry | Carrier | Poly size (kDa) | Degree of activation | Antigen dose (µg) | Adjuvant | #IRM | Male/ Female |
|---|---|---|---|---|---|---|---|---|
| CRM/RAC Aq. | RAC/Aq. | CRM | 250 | 3.9 | 2.2 | $AIPO_4$ | 13 | 5/8 |
| CRM-Click | Click | CRM | 130 | 11 | 2.2 | $AIPO_4$ | 9 | 4/5 |
| SCP-Click | Click | SCP | 130 | 11 | 2.2 | $AIPO_4$ | 11 | 7/4 |

3. Results 3.1. Click-SCP Chemistry Significantly Improved Serotype 3 Specific OPA Titers in Infant Rhesus Macaques Post Dose 1:

We evaluated the OPA response after primary vaccination of infant rhesus macaques with pneumo serotype 3 click chemistry (Click-SCP, Click-CRM) compared to RAC/Aq-CRM chemistry. All constructs were adjuvanted with $AlPO_4$ as described (Table 13). Interestingly, Click-SCP chemistry/carrier combination significantly improved serotype 3 specific OPA (>8 fold) compared to RAC/Aq-CRM (FIG. 7; Table 14).

TABLE 14

Week 4 Post Dose 1 OPA titers in Infant Rhesus Macaques

| Pn3 conjugate type | Geometric mean OPA | Lower 95% CI | Upper 95% CI | N | Fold increase over-CRM RAC/Aq | p values* compared to-CRM RAC/Aq |
|---|---|---|---|---|---|---|
| CRM/RAC Aq. | 33.78 | 13.9 | 81.6 | 13 | | |
| CRM-Click | 48.78 | 13.0 | 181.9 | 9 | 1.4 | 0.65 |
| SCP-Click | 283.9 | 190.3 | 423.6 | 11 | 8.4 | 0.0001 |

*one way ANOVA with Tukey's multiple comparison's test 3.2 Click-SCP Chemistry Induced Highest OPA Titers in Infant Rhesus Macaques Post Dose 2 (PD2)

We further tested whether a second dose at month 2 induced an increase in OPA titers in infant rhesus macaques. Vaccinations with conjugates of all different chemistries induced a higher OPA titer PD2 compared corresponding PD1 titers (FIG. 8). Click-SOP vaccination induced the highest geomean titers about 4.5-fold more than RAO/Aq-ORM chemistry (Table 15). Moreover, Click-SOP induced titers were with a narrow confidence interval indicating a uniform immune response generated in all monkeys of that group (FIG. 8). Click-CRM vaccination improved the OPA titers PD2 compared to RAC/Aq-CRM at respective doses but with a wider confidence interval (FIG. 8).

TABLE 15

Week 4 Post Dose 2 OPA titers in Infant Rhesus Macaques

| Pn3 conjugate type | Geometric mean OPA | Lower 95% CI | Upper 95% CI | N | Fold increase over-CRM RAC/Aq | p values* compared to-CRM RAC/Aq |
|---|---|---|---|---|---|---|
| CRM/RAC Aq. | 76.04 | 26.38 | 219.2 | 13 | | |
| CRM-Click | 134.5 | 35.11 | 514.9 | 9 | 1.7 | 0.65 |
| SCP-Click | 349 | 229.2 | 531.4 | 11 | 4.5 | 0.06 |

*one way ANOVA with Tukey's multiple comparison's test

Vaccination with Click-SOP conjugate induced significantly higher serotype 3 specific OPA/IgG titers in infant rhesus macaques compared to RAC/Aq-CRM conjugate with a single dose and the higher responses were maintained PD2. Click-CRM vaccination induced higher average titers in infant rhesus macaques than RAC/Aq-CRM conjugate.

All publications and patent applications mentioned in the specification are indicative of the level of those skilled in the art to which this invention pertains. All publications and patent applications are hereby incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

The invention claimed is:

1. An immunogenic glycoconjugate capable of inducing a humoral immune response to *Streptococcus pneumoniae* (*S. pneumoniae*) serotype 3 capsular polysaccharide comprising a *S. pneumoniae* serotype 3 capsular polysaccharide covalently conjugated to a carrier protein (CP) through a spacer and having the general formula:

(VII)

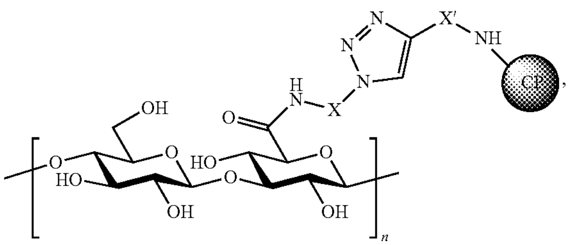

wherein X is selected from the group consisting of $CH_2(CH_2)_{n'}$, $(CH_2CH_2O)_mCH_2CH_2$, $NHCO(CH_2)_{n'}$, $NHCO(CH_2CH_2O)_mCH_2CH_2$, $OCH_2(CH_2)_{n'}$ and $O(CH_2CH_2O)_mCH_2CH_2$; where n' is selected from 1 to 10 and m is selected from 1 to 4, and wherein X' is selected from the group consisting of $CH_2O(CH_2)_{n''}CH_2C{=}O$ and $CH_2O(CH_2CH_2O)_{m'}(CH_2)_{n''}CH_2C{=}O$, where n'' is selected from 0 to 10 and m' is selected from 0 to 4, and wherein said carrier protein is Cross-Reacting Material 197 (CRM197), C5a peptidase from *Streptococcus* (SCP), diphtheria toxoid (DT), tetanus toxoid (TT), or *Haemophilus influenzae* protein D (PD).

2. The immunogenic glycoconjugate of claim 1, wherein X is $CH_2(CH_2)_{n'}$, where n' is 2 and wherein X' is $CH_2O(CH_2)_{n''}CH_2C{=}O$ where n'' is 1.

3. The immunogenic glycoconjugate of claim 2, wherein said carrier protein is $CRM_{197}$.

4. The immunogenic glycoconjugate of claim 2, wherein said carrier protein is SCP.

5. The immunogenic glycoconjugate of claim 2, wherein said carrier protein is TT.

6. The immunogenic glycoconjugate of claim 1, wherein the weight average molecular weight (Mw) of said polysaccharide before conjugation is between 75 kDa and 500 kDa.

7. The immunogenic glycoconjugate of claim 6, wherein the Mw of said polysaccharide before conjugation is between 100 kDa and 300 kDa.

8. The immunogenic glycoconjugate of claim 7, wherein the Mw of said polysaccharide before conjugation is between 100 kDa and 200 kDa.

9. The immunogenic glycoconjugate of claim 1, wherein the weight average molecular weight (Mw) of said glycoconjugate is between 500 kDa and 4,000 kDa.

10. The immunogenic glycoconjugate of claim 1, wherein the saccharide to protein ratio (SPR) of said glycoconjugate is 0.5 to 1.5.

11. The immunogenic glycoconjugate of claim 1, wherein the degree of conjugation of said glycoconjugate is 2 to 15.

12. The immunogenic glycoconjugate of claim 1, wherein said glycoconjugate comprises at least one covalent linkage between the carrier protein and the polysaccharide for every 5 to 10 saccharide repeat units of the polysaccharide.

13. The immunogenic glycoconjugate of claim 1, wherein said carrier protein is $CRM_{197}$.

14. The immunogenic glycoconjugate of claim 13, wherein the Mw of said polysaccharide before conjugation is 100 kDa to 500 kDa, wherein the Mw of said glycoconjugate is 500 kDa to 4000 kDa, wherein SPR of said glycoconjugate is 0.5 to 1.5, wherein the degree of conjugation of said glycoconjugate is 2 to 15, and wherein said glycoconjugate comprises at least one covalent linkage between the carrier protein and the polysaccharide for every 5 to 10 saccharide repeat units of the polysaccharide.

15. The glycoconjugate of claim 13, wherein said glycoconjugate is a first glycoconjugate, and said first glycoconjugate elicits higher opsonophagocytic activity titers against *S. pneumoniae* serotype 3 capsular polysaccharide than a second glycoconjugate comprising a *S. pneumoniae* serotype 3 capsular polysaccharide covalently conjugated to the same type of carrier protein comprised by said first glycoconjugate, wherein the polysaccharide and carrier protein of said second glycoconjugate are conjugated by reductive amination.

16. The immunogenic glycoconjugate of claim 1, wherein said carrier protein is SCP.

17. The immunogenic glycoconjugate of claim 16, wherein the Mw of said polysaccharide before conjugation is 100 kDa to 500 kDa, wherein the Mw of said glycoconjugate is 500 kDa to 4000 kDa, wherein SPR of said glycoconjugate is 0.5 to 1.5, wherein the degree of conjugation of said glycoconjugate is 2 to 15, and wherein said glycoconjugate comprises at least one covalent linkage between the carrier protein and the polysaccharide for every 5 to 10 saccharide repeat units of the polysaccharide.

18. The glycoconjugate of claim 16, wherein said glycoconjugate is a first glycoconjugate, and said first glycoconjugate elicits higher opsonophagocytic activity titers against *S. pneumoniae* serotype 3 capsular polysaccharide than a second glycoconjugate comprising a *S. pneumoniae* serotype 3 capsular polysaccharide covalently conjugated to the same type of carrier protein comprised by said first glycoconjugate, wherein the polysaccharide and carrier protein of said second glycoconjugate are conjugated by reductive amination.

19. The immunogenic glycoconjugate of claim 1, wherein said carrier protein is TT.

20. The immunogenic glycoconjugate of claim 19, wherein the Mw of said polysaccharide before conjugation is 100 kDa to 500 kDa, wherein the Mw of said glycoconjugate is 500 kDa to 4000 kDa, wherein SPR of said glycoconjugate is 0.5 to 1.5, wherein the degree of conjugation of said glycoconjugate is 2 to 15, and wherein said glycoconjugate comprises at least one covalent linkage between the carrier protein and the polysaccharide for every 5 to 10 saccharide repeat units of the polysaccharide.

21. The glycoconjugate of claim 19, wherein said glycoconjugate is a first glycoconjugate, and said first glycoconjugate elicits higher opsonophagocytic activity titers against *S. pneumoniae* serotype 3 capsular polysaccharide than a second glycoconjugate comprising a *S. pneumoniae* serotype 3 capsular polysaccharide covalently conjugated to the same type of carrier protein comprised by said first glycoconjugate, wherein the polysaccharide and carrier protein of said second glycoconjugate are conjugated by reductive amination.

22. The immunogenic glycoconjugate of claim 1, wherein said carrier protein is DT or PD, wherein the Mw of said polysaccharide before conjugation is 100 kDa to 500 kDa, wherein the Mw of said glycoconjugate is 500 kDa to 4000 kDa, wherein SPR of said glycoconjugate is 0.5 to 1.5, wherein the degree of conjugation of said glycoconjugate is 2 to 15, and wherein said glycoconjugate comprises at least one covalent linkage between the carrier protein and the polysaccharide for every 5 to 10 saccharide repeat units of the polysaccharide.

* * * * *